(12) United States Patent
Whitlock et al.

(10) Patent No.: US 12,091,652 B2
(45) Date of Patent: *Sep. 17, 2024

(54) **AMMONIA-OXIDIZING *NITROSOMONAS EUTROPHA* STRAIN D23**

(71) Applicant: AOBIOME LLC, Cambridge, MA (US)

(72) Inventors: David R. Whitlock, Cambridge, MA (US); Spiros Jamas, Cambridge, MA (US); Larry Weiss, San Francisco, CA (US); Ioannis Gryllos, Brookline, MA (US)

(73) Assignee: AOBIOME LLC, Cambridge, MA (US)

( * ) Notice: Subject to any disclaimer, the term of this patent is extended or adjusted under 35 U.S.C. 154(b) by 202 days.

This patent is subject to a terminal disclaimer.

(21) Appl. No.: 17/101,871

(22) Filed: Nov. 23, 2020

(65) Prior Publication Data

US 2022/0002662 A1    Jan. 6, 2022

Related U.S. Application Data

(63) Continuation of application No. 16/856,789, filed on Apr. 23, 2020, now abandoned, which is a continuation of application No. 16/596,694, filed on Oct. 8, 2019, now abandoned, which is a continuation of application No. 15/304,151, filed as application No. PCT/US2015/025909 on Apr. 15, 2015, now abandoned.

(60) Provisional application No. 62/053,588, filed on Sep. 22, 2014, provisional application No. 62/012,811, filed on Jun. 16, 2014, provisional application No. 62/002,084, filed on May 22, 2014.

(30) Foreign Application Priority Data

Apr. 15, 2014    (GR) ............................... 20140100217
Mar. 13, 2015   (GR) ............................... 20150100115

(51) Int. Cl.
| | | |
|---|---|---|
| *C12N 1/20* | (2006.01) | |
| *A61K 8/99* | (2017.01) | |
| *A61K 9/00* | (2006.01) | |
| *A61K 35/74* | (2015.01) | |
| *A61K 35/744* | (2015.01) | |
| *A61K 35/745* | (2015.01) | |
| *A61K 35/747* | (2015.01) | |
| *A61K 48/00* | (2006.01) | |
| *A61L 15/36* | (2006.01) | |
| *A61Q 15/00* | (2006.01) | |
| *A61Q 17/04* | (2006.01) | |
| *A61Q 19/00* | (2006.01) | |
| *C07K 14/195* | (2006.01) | |
| *C12N 1/00* | (2006.01) | |
| *C12Q 1/02* | (2006.01) | |
| *C12Q 1/689* | (2018.01) | |
| *A61Q 19/02* | (2006.01) | |
| *A61Q 19/04* | (2006.01) | |
| *C12R 1/01* | (2006.01) | |

(52) U.S. Cl.
CPC .................. *C12N 1/20* (2013.01); *A61K 8/99* (2013.01); *A61K 9/0014* (2013.01); *A61K 35/74* (2013.01); *A61K 35/744* (2013.01); *A61K 35/745* (2013.01); *A61K 35/747* (2013.01); *A61K 48/00* (2013.01); *A61L 15/36* (2013.01); *A61Q 15/00* (2013.01); *A61Q 17/04* (2013.01); *A61Q 19/00* (2013.01); *C07K 14/195* (2013.01); *C12N 1/00* (2013.01); *C12N 1/205* (2021.05); *C12Q 1/02* (2013.01); *C12Q 1/689* (2013.01); *A61Q 19/02* (2013.01); *A61Q 19/04* (2013.01); *C12R 2001/01* (2021.05)

(58) Field of Classification Search
CPC ............... C12N 1/20; A61P 17/10; A61P 9/00
See application file for complete search history.

(56) References Cited

U.S. PATENT DOCUMENTS

| | | |
|---|---|---|
| 3,984,575 A | 10/1976 | Farr |
| 4,147,807 A | 4/1979 | Gryczka et al. |
| 4,335,107 A | 6/1982 | Snoeyenbos et al. |
| 4,689,226 A | 8/1987 | Nurmi et al. |
| 4,720,344 A | 1/1988 | Ganczarczyk et al. |

(Continued)

FOREIGN PATENT DOCUMENTS

| | | |
|---|---|---|
| CN | 1446128 A | 10/2003 |
| EP | 0761607 A1 | 3/1997 |

(Continued)

OTHER PUBLICATIONS

Minniti et al., "Topical Sodium Nitrite Is Effective In Reducing Leg Ulcer-Associated Pain In Patients With Sickle Cell Disease", Blood 122:2236, 2013, 4 pages (Year: 2013).*

(Continued)

*Primary Examiner* — David Steadman
(74) *Attorney, Agent, or Firm* — Lando & Anastasi, LLP

(57) ABSTRACT

This disclosure provides, inter alia, an optimized strain of *Nitrosomonas eutropha* (*N. eutropha*) designated D23, D23-100, or AOB D23-100. *N. eutropha* bacteria disclosed in this application have desirable properties, e.g., optimized properties, such as the ability to suppress growth of pathogenic bacteria, and an enhanced ability to produce nitric oxide and nitric oxide precursors. The *N. eutropha* herein may be used, for instance, to treat diseases associated with low nitrite levels, skin diseases, and diseases caused by pathogenic bacteria.

12 Claims, 82 Drawing Sheets

Specification includes a Sequence Listing.

(56) References Cited

U.S. PATENT DOCUMENTS

| | | |
|---|---|---|
| 5,139,792 A | 8/1992 | Ware et al. |
| 5,176,911 A | 1/1993 | Tosi et al. |
| 5,278,192 A | 1/1994 | Fung et al. |
| 5,314,542 A | 5/1994 | Cassidy et al. |
| 5,322,686 A | 6/1994 | Grahn et al. |
| 5,380,758 A | 1/1995 | Stamler et al. |
| 5,385,940 A | 1/1995 | Moskowitz |
| 5,396,882 A | 3/1995 | Zapol |
| 5,427,797 A | 6/1995 | Frostell et al. |
| 5,451,400 A | 9/1995 | Stern et al. |
| 5,519,020 A | 5/1996 | Smith et al. |
| 5,534,253 A | 7/1996 | Casas et al. |
| 5,570,683 A | 11/1996 | Zapol |
| 5,574,068 A | 11/1996 | Stamler et al. |
| 5,595,753 A | 1/1997 | Hechtman |
| 5,604,127 A | 2/1997 | Nisbet et al. |
| 5,632,981 A | 5/1997 | Saavedra et al. |
| 5,645,839 A | 7/1997 | Chobanian et al. |
| 5,646,181 A | 7/1997 | Fung et al. |
| 5,648,101 A | 7/1997 | Tawashi |
| 5,648,393 A | 7/1997 | Stamler et al. |
| 5,650,447 A | 7/1997 | Keefer et al. |
| 5,665,077 A | 9/1997 | Rosen et al. |
| 5,693,676 A | 12/1997 | Gorfine |
| 5,713,349 A | 2/1998 | Keaney |
| 5,714,511 A | 2/1998 | Saavedra et al. |
| 5,721,278 A | 2/1998 | Garfield et al. |
| 5,725,492 A | 3/1998 | Igo et al. |
| 5,728,705 A | 3/1998 | Lawson et al. |
| 5,765,548 A | 6/1998 | Perry |
| 5,767,160 A | 6/1998 | Kaesemeyer |
| 5,789,447 A | 8/1998 | Wink, Jr. et al. |
| 5,800,385 A | 9/1998 | Demopulos et al. |
| 5,801,203 A | 9/1998 | Lipton |
| 5,807,546 A | 9/1998 | Stern et al. |
| 5,814,656 A | 9/1998 | Saavedra et al. |
| 5,814,666 A | 9/1998 | Green et al. |
| 5,821,112 A | 10/1998 | Botto et al. |
| 5,824,669 A | 10/1998 | Garvey et al. |
| 5,834,030 A | 11/1998 | Bolton |
| 5,839,433 A | 11/1998 | Higenbottam et al. |
| 5,849,180 A | 12/1998 | Sumino et al. |
| 5,849,192 A | 12/1998 | Jagush et al. |
| 5,858,017 A | 1/1999 | Demopulos et al. |
| 5,861,168 A | 1/1999 | Cooke et al. |
| 5,873,359 A | 2/1999 | Zapol et al. |
| 5,891,472 A | 4/1999 | Russell |
| 5,892,658 A | 4/1999 | Urda et al. |
| 5,900,433 A | 5/1999 | Igo et al. |
| 5,904,938 A | 5/1999 | Zapol et al. |
| 5,910,316 A | 6/1999 | Keefer et al. |
| 5,910,482 A | 6/1999 | Yallampalli et al. |
| 5,912,019 A | 6/1999 | Singh |
| 5,958,427 A | 9/1999 | Salzman et al. |
| 5,994,444 A | 11/1999 | Trescony et al. |
| 7,267,816 B2 | 9/2007 | Hovanec |
| 7,314,748 B1 | 1/2008 | Fredenburgh et al. |
| 7,544,501 B2 | 6/2009 | Hovanec et al. |
| 7,820,420 B2 | 10/2010 | Whitlock |
| 9,738,870 B2 * | 8/2017 | Whitlock ............ A61P 17/10 |
| 10,017,731 B2 * | 7/2018 | Whitlock ............ A61P 37/08 |
| 10,131,871 B2 * | 11/2018 | Whitlock ............ A61P 9/10 |
| 11,225,640 B2 * | 1/2022 | Whitlock ............ A61P 17/10 |
| 2004/0014188 A1 | 1/2004 | Whitlock |
| 2005/0036996 A1 | 2/2005 | Roussel et al. |
| 2005/0244382 A9 | 11/2005 | Whitlock |
| 2021/0052672 A1 * | 2/2021 | Whitlock ............ A61K 9/0014 |
| 2022/0347230 A1 * | 11/2022 | Whitlock ............ A61K 35/74 |
| 2022/0370516 A1 * | 11/2022 | Krueger ............ A61K 9/0014 |

FOREIGN PATENT DOCUMENTS

| | | |
|---|---|---|
| EP | 0780419 A1 | 6/1997 |
| EP | 0987000 A1 | 3/2000 |
| FR | 2682296 A1 | 4/1993 |
| GB | 2020174 A | 11/1979 |
| JP | 59-135845 A | 8/1984 |
| JP | S63227515 A | 9/1988 |
| JP | 02-121665 A | 5/1990 |
| JP | 02-169092 A | 6/1990 |
| JP | 03-289957 A | 12/1991 |
| JP | 09-075984 A | 3/1997 |
| WO | 09827991 A1 | 7/1998 |
| WO | 0213982 A1 | 2/2002 |
| WO | 03057380 A2 | 7/2003 |
| WO | 2005030147 A2 | 4/2005 |

OTHER PUBLICATIONS

Whitlock et al., "The Hygiene Hypothesis and Darwinian Medicine: Soil bacteria, nitrite and the skin", pp. 103-115, 2009 (Year: 2009).*

Vajrala et al., International Conference on Nitrification (and Related Processes): Poster Abstracts, [EG-2], 2015, 1 page (Year: 2015).*

Maura et al., "The ammonia oxidizing bacterium Nitrosomonas eutropha blocks T helper 2 cell polarization via the anti-inflammatory cytokine IL-10", Scientific Reports 11:14162, 2021, 10 pages (Year: 2021).*

Norton et al., "Diversity of ammonia monooxygenase operon in autotrophic ammonia-oxidizing bacteria," Archives of Microbiology, vol. 177, No. 2, pp. 139-149 (Feb. 2002).

Stein et al., "Whole-genome analysis of the ammonia-oxidizing bacterium, Nitrosomonas eutrophra C91: implications for niche adaption," Environmental Microbiology, vol. 9, No. 12, pp. 2993-3007 (Dec. 2007).

Suwa et al., "Phylogenetic relationships of activated sludge isolates of ammonia oxidizers with different sensitivities to ammonium sulfate," Journal of General and Applied Microbiology, vol. 43, pp. 373-379 (Jan. 1, 1997).

atcc.orglcommonlcatalog/wordSearch/results.cfm, total of 4 pages, (2006).

Air Products 2004, MSDS, Version 1.4, Revision Date Apr. 4, 2004, pp. 1-6.

Brochures for Ultra Bac from ABI, Inc., Cleveland, OH, undated.

Bock et al., "Oxidation of Inorganic Nitrogen Compounds as Energy Source," In: The Prokaryotes. A Handbook on the Biology of Bacteria: Ecophysiology, Isolation, Identification, Applications. Edited by Balows et al. Springer-Verlag. Second Edition. 1992, vol. 1. Chapter 17, pp. 414-417.

Catalogue of Bacteria and Phages. 1989. American Type Culture Collection. p. 152, col. 2.

Head et al., 1993, The Phylogeny of Autotrophic Ammonia-Oxidizing Bacteria as Determined by Analysis of 16s Ribosomal RNA Gene Sequences. Journal of General Microbiology, vol. 139, pp. 1147-1153.

Ida et al., 2004, Identification of Genus Nitrosovibrio, Ammonia-Oxidizing Bacteria by Comparison of N-Terminal Amino Acid Sequences of Phosphoglycerate Kinase, Journal of Bioscience and Bioengineering, vol. 98, No. 5, pp. 380-383.

Koops et al., Classification of eight new species of ammonia-oxidizing bacteria: Nitrosomonas communis sp. nov., Nitrosomonas ureae sp. nov., Nitrosomonas aestuarii sp. nov., Nitrosomonas marina sp. nov., Nitrosomonas nitrosa sp. nov., Nitrosomonas eutropha sp. nov., Nitrosomonas oligotropha sp. nov. and Nitrosomonas halophila sp. nov., Jounal of General Microbiology, 137, pp. 1689-1699 (1991).

Scott, "My No-Soap, No-Shampoo, Bacteria-Rich Hygiene Experiment", nytimes.com/2014/05/25/magazine/my-no-soap-no-shampoo-bacteria-rich-hygien-experiment.html. (May 22, 2014).

Gryllos et al., "Oral 2011-2-Ammonia-oxidizing bacteria accelerate wound closure in diabetic mice", Nitric Oxide, vol. 42, pp. 111-112 (Nov. 15, 2014).

Gryllos et al., "P129—Ammonia-oxidizing bacteria for generation and delivery of acidified nitrite and nitric oxide", Nitric Oxide, vol. 42, p. 124 (Nov. 15, 2014).

* cited by examiner

FIG. 5I
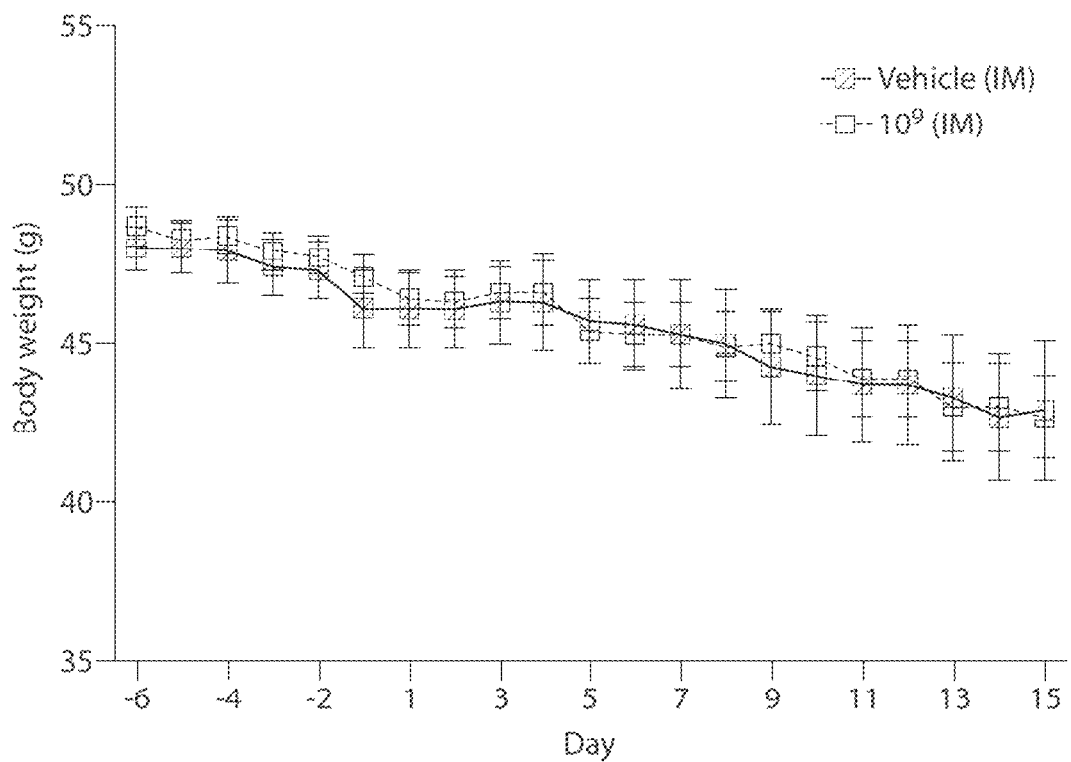
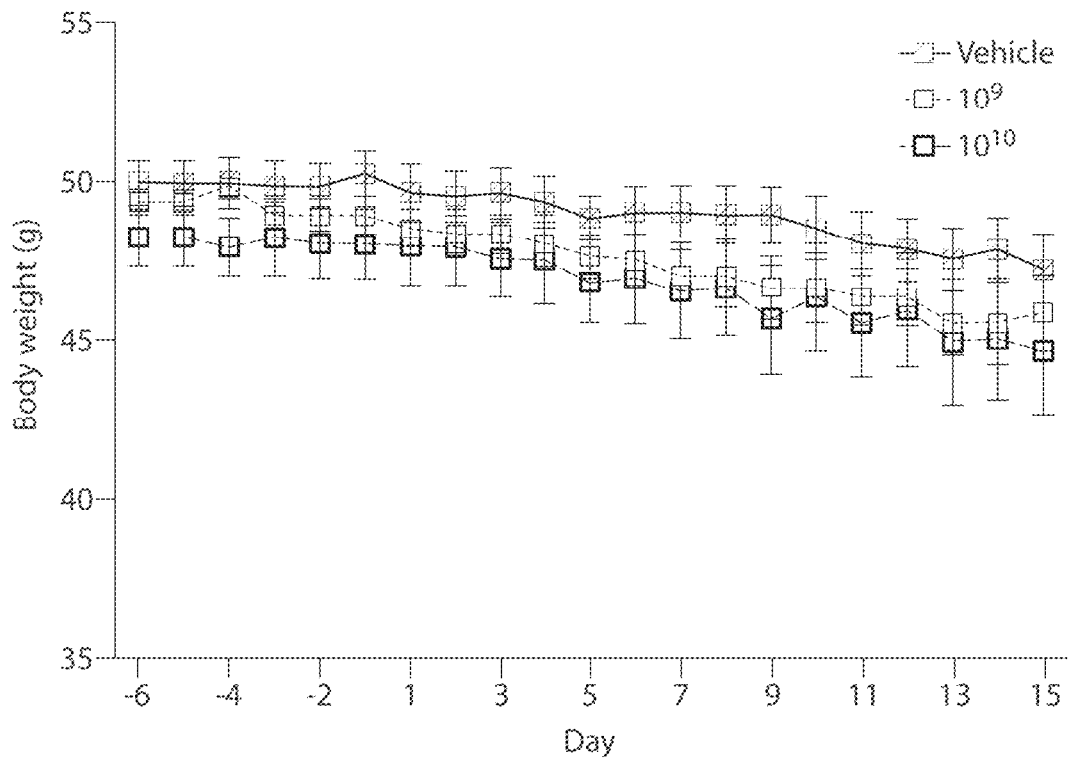

FIG. 6A

Unique D23 genes with assigned ORF number and function, or hypothetical above 200 base pairs: 162 genes

| Feature.ID | Type | Start | Stop | Frame | Strand | Length (bp) | Function | Subsystem | D23Gbkid |
|---|---|---|---|---|---|---|---|---|---|
| fig\|6666666.609 66.peg.23 | CDS | 29060 | 28851 | -2 | - | 210 | Death on curing protein, Doc toxin | Phd-Doc, YdcE-YdcD toxin-antitoxin (programmed cell death) systems | D23_1c0025 |
| fig\|6666666.609 66.peg.33 | CDS | 34044 | 34424 | 3 | + | 381 | hypothetical protein | - none - | D23_1c0034 |
| fig\|6666666.609 66.peg.41 | CDS | 42537 | 43733 | 3 | + | 1197 | glycosyl transferase, group 1/2 family protein | - none - | D23_1c0042 |
| fig\|6666666.609 66.peg.47 | CDS | 47082 | 46804 | -3 | - | 279 | hypothetical protein | - none - | D23_1c0047 |
| fig\|6666666.609 66.peg.55 | CDS | 51293 | 50880 | -2 | - | 414 | Mobile element protein | - none - | D23_1c0056 |
| fig\|6666666.609 66.peg.69 | CDS | 64515 | 66023 | 3 | + | 1509 | CBSS-498211.3.peg.1514: hypothetical protein | - none - | D23_1c0070 |

FIG. 6B

| | | | | | | |
|---|---|---|---|---|---|---|
| fig\|6666666.609 66.peg.70 | CDS | 66074 | 66751 | 2 | + | 678 | FIG039767: hypothetical protein | - none - | D23_1c0071 |
| fig\|6666666.609 66.peg.71 | CDS | 66741 | 70157 | 3 | + | 3417 | FIG007317: hypothetical protein | - none - | D23_1c0072 |
| fig\|6666666.609 66.peg.158 | CDS | 157584 | 157859 | 3 | + | 276 | DNA-3-methyladenine glycosylase II (EC 3.2.2.21) | DNA Repair Base Excision | D23_1c0165 |
| fig\|6666666.609 66.peg.207 | CDS | 198088 | 198819 | 1 | + | 732 | Mobile element protein | - none - | D23_1c0213 |
| fig\|6666666.609 66.peg.215 | CDS | 203592 | 203461 | -3 | - | 132 | Phage Rha protein | - none - | D23_1c0220 |
| fig\|6666666.609 66.peg.235 | CDS | 219960 | 219271 | -3 | - | 690 | InterPro IPR001687 | - none - | D23_1c0239 |
| fig\|6666666.609 66.peg.281 | CDS | 259254 | 259123 | -3 | - | 132 | cAMP-binding proteins - catabolite gene activator and regulatory subunit of cAMP-dependent protein kinases | cAMP signaling in bacteria | D23_1c0289 |
| fig\|6666666.609 66.peg.282 | CDS | 259543 | 260031 | 1 | + | 489 | Cytochrome c' | - none - | D23_1c0291 |
| fig\|6666666.609 66.peg.289 | CDS | 263106 | 264041 | 3 | + | 936 | hypothetical protein | - none - | D23_1c0297 |
| fig\|6666666.609 66.peg.290 | CDS | 264137 | 265633 | 2 | + | 1497 | Sll1503 protein | - none - | D23_1c0298 |
| fig\|6666666.609 66.peg.302 | CDS | 273758 | 274108 | 2 | + | 351 | hypothetical protein | - none - | D23_1c0307 |
| fig\|6666666.609 66.peg.471 | CDS | 440180 | 438420 | -2 | - | 1761 | Gluconate 2-dehydrogenase (EC 1.1.99.3), membrane- | D-glucorate and ketogluconates metabolism | D23_1c0475 |

FIG. 6C

| | | | | | | | | |
|---|---|---|---|---|---|---|---|---|
| fig\|6666666.609 66.peg.474 | CDS | 441829 | 441158 | -1 | - | 672 | Gluconate 2-dehydrogenase (EC 1.1.99.3), membrane-bound, gamma subunit bound, flavoprotein | D-gluconate and ketogluconates metabolism | D23_1c0478 |
| fig\|6666666.609 66.peg.487 | CDS | 455203 | 454049 | -1 | - | 1155 | hypothetical protein | - none - | D23_1c0491 |
| fig\|6666666.609 66.peg.493 | CDS | 462292 | 461345 | -1 | - | 948 | Putative DNA-binding protein in cluster with Type I restriction-modification system | Restriction-Modification System | D23_1c0497 |
| fig\|6666666.609 66.peg.508 | CDS | 474111 | 474269 | 3 | + | 159 | Mobile element protein | - none - | D23_1c0513 |
| fig\|6666666.609 66.peg.510 | CDS | 474450 | 474653 | 3 | + | 204 | hypothetical protein | - none - | D23_1c0514 |
| fig\|6666666.609 66.peg.577 | CDS | 535028 | 535240 | 2 | + | 213 | hypothetical protein | - none - | D23_1c0578 |
| fig\|6666666.609 66.peg.579 | CDS | 537497 | 536616 | -2 | - | 882 | hypothetical protein | - none - | D23_1c0581 |
| fig\|6666666.609 66.peg.580 | CDS | 538547 | 537726 | -2 | - | 822 | hypothetical protein | - none - | D23_1c0582 |
| fig\|6666666.609 66.peg.581 | CDS | 539856 | 538789 | -3 | - | 1068 | Conserved domain protein | - none - | D23_1c0583 |
| fig\|6666666.609 66.peg.582 | CDS | 540712 | 539849 | -1 | - | 864 | Conserved domain protein | - none - | D23_1c0584 |
| fig\|6666666.609 66.peg.615 | CDS | 565168 | 564959 | -1 | - | 210 | hypothetical protein | - none - | D23_1c0618 |
| fig\|6666666.609 66.peg.677 | CDS | 626009 | 625605 | -2 | - | 405 | hypothetical protein | - none - | D23_1c0682 |

FIG. 6D

| | | | | | | | | | |
|---|---|---|---|---|---|---|---|---|---|
| fig\|6666666.609 66.peg.688 | CDS | 639034 | 639930 | 1 | + | 897 | Quinolinate phosphoribosyltransferase [decarboxylating] (EC 2.4.2.19) | Mycobacterium virulence operon possibly involved in quinolinate biosynthesis; NAD and NADP cofactor biosynthesis global | D23_1c0695 |
| fig\|6666666.609 66.peg.741 | CDS | 687933 | 687400 | -3 | - | 534 | Adenylate kinase (EC 2.7.4.3) | Purine conversions | D23_1c0748 |
| fig\|6666666.609 66.peg.756 | CDS | 696806 | 696934 | 2 | + | 129 | Mobile element protein | - none - | D23_1c0761 |
| fig\|6666666.609 66.peg.783 | CDS | 723822 | 723676 | -3 | - | 147 | Mobile element protein | - none - | D23_1c0788 |
| fig\|6666666.609 66.peg.785 | CDS | 724125 | 724304 | 3 | + | 180 | Rubisco activation protein CbbO | CO2 uptake, carboxysome | D23_1c0791 |
| fig\|6666666.609 66.peg.850 | CDS | 781999 | 782385 | 1 | + | 387 | hypothetical protein | - none - | D23_1c0856 |
| fig\|6666666.609 66.peg.851 | CDS | 782415 | 782747 | 3 | + | 333 | Mobile element protein | - none - | D23_1c0857 |
| fig\|6666666.609 66.peg.855 | CDS | 785041 | 784757 | -1 | - | 285 | Mobile element protein | - none - | D23_1c0861 |
| fig\|6666666.609 66.peg.887 | CDS | 814624 | 815706 | 1 | + | 1083 | glycosyltransferase | - none - | D23_1c0891 |
| fig\|6666666.609 66.peg.888 | CDS | 817016 | 816339 | -2 | - | 678 | hypothetical protein | - none - | D23_1c0892 |
| fig\|6666666.609 66.peg.988 | CDS | 919358 | 918504 | -2 | - | 855 | DNA-directed RNA polymerase alpha subunit (EC 2.7.7.6) | RNA polymerase bacterial | D23_1c0998 |

FIG. 6E

| | | | | | | | | |
|---|---|---|---|---|---|---|---|---|
| fig\|6666666.609 66.peg.1077 | CDS | 1005165 | 1004962 | -3 | - | 204 | hypothetical protein | - none - | D23_1ci1090 |
| fig\|6666666.609 66.peg.1169 | CDS | 1094042 | 1093413 | -2 | - | 630 | Nicotinamidase family protein YcaC | NAD and NADP cofactor biosynthesis global | D23_1ci1176 |
| fig\|6666666.609 66.peg.1172 | CDS | 1095334 | 1094984 | -1 | - | 351 | hypothetical protein | - none - | D23_1ci1180 |
| fig\|6666666.609 66.peg.1201 | CDS | 1124005 | 1124823 | 1 | + | 819 | Cytochrome c family protein | - none - | D23_1ci1207 |
| fig\|6666666.609 66.peg.1217 | CDS | 1137576 | 1138703 | 3 | + | 1128 | Catalase (EC 1.11.1.6) | Oxidative stress; Photorespiration (oxidative C2 cycle); Protection from Reactive Oxygen Species | D23_1ci1222 |
| fig\|6666666.609 66.peg.1225 | CDS | 1144087 | 1143419 | -1 | - | 669 | hypothetical protein | - none - | D23_1ci1230 |
| fig\|6666666.609 66.peg.1226 | CDS | 1144326 | 1144078 | -3 | - | 252 | ABC-type antimicrobial peptide transport system, permease component | | D23_1ci1231 |
| fig\|6666666.609 66.peg.1233 | CDS | 1150719 | 1150507 | -3 | - | 213 | hypothetical protein | - none - | D23_1ci1238 |
| fig\|6666666.609 66.peg.1237 | CDS | 1151916 | 1152278 | 3 | + | 363 | hypothetical protein | - none - | D23_1ci1242 |
| fig\|6666666.609 66.peg.1272 | CDS | 1181355 | 1181558 | 3 | + | 204 | hypothetical protein | - none - | D23_1ci1279 |
| fig\|6666666.609 66.peg.1274 | CDS | 1181748 | 1181981 | 3 | + | 234 | Mobile element protein | - none - | D23_1ci1281 |
| fig\|6666666.609 66.peg.1303 | CDS | 1209139 | 1208375 | -1 | - | 765 | Mobile element protein | - none - | D23_1ci1311 |

FIG. 6F

| | | | | | | | | |
|---|---|---|---|---|---|---|---|---|
| fig\|6666666.609 66.peg.1305 | CDS | 1210466 | 1210134 | -2 | - | 333 | hypothetical protein | - none - | D23_1c1313 |
| fig\|6666666.609 66.peg.1321 | CDS | 1223815 | 1224054 | 1 | + | 240 | hypothetical protein | - none - | D23_1c1328 |
| fig\|6666666.609 66.peg.1341 | CDS | 1244736 | 1243531 | -3 | - | 1206 | Catalase (EC 1.11.1.6) | Oxidative stress; Photorespiration (oxidative C2 cycle); Protection from Reactive Oxygen Species | D23_1c1348 |
| fig\|6666666.609 66.peg.1342 | CDS | 1246268 | 1244739 | -2 | - | 1530 | Peroxidase (EC 1.11.1.7) | Oxidative stress; Protection from Reactive Oxygen Species | D23_1c1349 |
| fig\|6666666.609 66.peg.1343 | CDS | 1247585 | 1246281 | -2 | - | 1305 | Peroxidase (EC 1.11.1.7) | Oxidative stress; Protection from Reactive Oxygen Species | D23_1c1350 |
| fig\|6666666.609 66.peg.1344 | CDS | 1248078 | 1247623 | -3 | - | 456 | hypothetical protein | - none - | D23_1c1351 |
| fig\|6666666.609 66.peg.1346 | CDS | 1251218 | 1253155 | 2 | + | 1938 | Choline dehydrogenase (EC 1.1.99.1) | - none - | D23_1c1353 |
| fig\|6666666.609 66.peg.1347 | CDS | 1256051 | 1253184 | -2 | - | 2868 | Peroxidase (EC 1.11.1.8) | - none - | D23_1c1354 |

FIG. 6G

| | | | | | | | |
|---|---|---|---|---|---|---|---|
| fig\|6666666.609 66.peg.1348 | CDS | 1257505 | 1256081 | -1 | 1425 | Hemagglutinin | - none - | D23_1c1355 |
| fig\|6666666.609 66.peg.1349 | CDS | 1258257 | 1257547 | -3 | 711 | hypothetical protein | - none - | D23_1c1356 |
| fig\|6666666.609 66.peg.1350 | CDS | 1259233 | 1258262 | -1 | 972 | hypothetical protein | - none - | D23_1c1357 |
| fig\|6666666.609 66.peg.1351 | CDS | 1261078 | 1259246 | -1 | 1833 | hypothetical protein | - none - | D23_1c1358 |
| fig\|6666666.609 66.peg.1352 | CDS | 1262776 | 1261109 | -1 | 1668 | Arachidonate 15-lipoxygenase (EC 1.13.11.33) | - none - | D23_1c1359 |
| fig\|6666666.609 66.peg.1353 | CDS | 1264449 | 1262845 | -3 | 1605 | putative cyclooxygenase-2 | - none - | D23_1c1360 |
| fig\|6666666.609 66.peg.1354 | CDS | 1266134 | 1264638 | -2 | 1497 | hypothetical protein | - none - | D23_1c1361 |
| fig\|6666666.609 66.peg.1355 | CDS | 1266382 | 1266167 | -1 | 216 | hypothetical protein | - none - | D23_1c1362 |
| fig\|6666666.609 66.peg.1356 | CDS | 1266702 | 1266444 | -2 | 261 | hypothetical protein | - none - | D23_1c1363 |
| fig\|6666666.609 66.peg.1357 | CDS | 1267804 | 1266983 | -1 | 822 | Kazal-type serine protease inhibitor domain | - none - | D23_1c1364 |

FIG. 6H

| | | | | | | | |
|---|---|---|---|---|---|---|---|
| fig\|666666.609 66.peg.1358 | CDS | 1268650 | 1267970 | -1 | - | 681 | Kazal-type serine protease inhibitor domain | - none - | D23_1c1365 |
| fig\|666666.609 66.peg.1363 | CDS | 1271332 | 1270409 | -1 | - | 924 | alpha/beta hydrolase fold | - none - | D23_1c1370 |
| fig\|666666.609 66.peg.1364 | CDS | 1271721 | 1271329 | -3 | - | 393 | hypothetical protein | - none - | D23_1c1371 |
| fig\|666666.609 66.peg.1371 | CDS | 1279031 | 1278027 | -2 | - | 1005 | Putative DNA-binding protein in cluster with Type I restriction-modification system | Restriction-Modification System | D23_1c1378 |
| fig\|666666.609 66.peg.1373 | CDS | 1283272 | 1282982 | -1 | - | 291 | Type I restriction-modification system, restriction subunit R (EC 3.1.21.3) | Restriction-Modification System; Type I Restriction-Modification | D23_1c1380 |
| fig\|666666.609 66.peg.1405 | CDS | 1318192 | 1317827 | -1 | - | 366 | Putative metal chaperone, involved in Zn homeostasis, GTPase of COG0523 family | G3E family of P-loop GTPases (metallocenter biosynthesis); Zinc regulated enzymes | D23_1c1412 |
| fig\|666666.609 66.peg.1408 | CDS | 1320314 | 1321651 | 2 | + | 1338 | DNA modification methyltransferase | - none - | D23_1c1415 |
| fig\|666666.609 66.peg.1409 | CDS | 1321654 | 1322532 | 1 | + | 879 | hypothetical protein | - none - | D23_1c1416 |
| fig\|666666.609 66.peg.1410 | CDS | 1322666 | 1322882 | 1 | + | 216 | hypothetical protein | - none - | D23_1c1417 |

FIG. 6I

| | | | | | | | |
|---|---|---|---|---|---|---|---|
| fig\|666666.609. peg.1410 | CDS | 5 | 1323475 | 1324150 | 3 | + | 681 | ThiJ/PfpI family protein | - none - | D23_1c1418 |
| fig\|666666.609. peg.1411 | | | | | | | | | | |
| fig\|666666.609. peg.1415 | CDS | | 1326558 | 1328531 | 3 | + | 1974 | Monoamine oxidase (1.4.3.4) | Auxin biosynthesis; Glycine and Serine Utilization; Threonine degradation | D23_1c1421 |
| fig\|666666.609. peg.1420 | CDS | | 1330200 | 1329892 | -3 | - | 309 | Death on curing protein, Doc toxin | Phd-Doc, YdcE-YdcD toxin-antitoxin (programmed cell death) systems | D23_1c1425 |
| fig\|666666.609. peg.1421 | CDS | | 1330677 | 1330231 | -3 | - | 447 | Prevent host death protein, Phd antitoxin | Phd-Doc, YdcE-YdcD toxin-antitoxin (programmed cell death) systems | D23_1c1426 |
| fig\|666666.609. peg.1454 | CDS | | 1363397 | 1365250 | 2 | + | 1854 | hypothetical protein | - none - | D23_1c1461 |
| fig\|666666.609. peg.1471 | CDS | | 1384401 | 1384814 | 3 | + | 414 | ABC-type multidrug transport system, permease component | CBSS-196164.1.peg.1690 | D23_1c1478 |
| fig\|666666.609. peg.1472 | CDS | | 1384811 | 1385149 | 2 | + | 339 | ABC-type multidrug transport system, | CBSS-196164.1.peg.1690 | D23_1c1479 |

FIG. 6J

| | | | | | | permease component | | |
|---|---|---|---|---|---|---|---|---|
| fig\|6666666.609 66.peg.1554 | CDS | 1456740 | 1456501 | -3 | - | hypothetical protein | - none - | D23_1c1561 |
| fig\|6666666.609 66.peg.1557 | CDS | 1457678 | 1457277 | -2 | - | hypothetical protein | - none - | D23_1c1564 |
| fig\|6666666.609 66.peg.1558 | CDS | 1458137 | 1458478 | 2 | + | hypothetical protein | - none - | D23_1c1565 |
| fig\|6666666.609 66.peg.1559 | CDS | 1458868 | 1459158 | 1 | + | hypothetical protein | - none - | D23_1c1566 |
| fig\|6666666.609 66.peg.1569 | CDS | 1464806 | 1463826 | -2 | - | Abortive infection bacteriophage resistance protein | - none - | D23_1c1573 |
| fig\|6666666.609 66.peg.1648 | CDS | 1532787 | 1530136 | -3 | - | Malto-oligosyltrehalose synthase (EC 5.4.99.15) | - none - | D23_1c1646 |
| fig\|6666666.609 66.peg.1651 | CDS | 1535327 | 1534896 | -2 | - | Trehalose synthase, nucleoside diphosphate glucose dependent | - none - | D23_1c1649 |
| fig\|6666666.609 66.peg.1689 | CDS | 1573320 | 1573129 | -3 | - | FIG00859257: hypothetical protein | - none - | D23_1c1687 |
| fig\|6666666.609 66.peg.1694 | CDS | 1575572 | 1575369 | -2 | - | hypothetical protein | - none - | D23_1c1693 |
| fig\|6666666.609 66.peg.1725 | CDS | 1608741 | 1606597 | -3 | - | hypothetical protein | - none - | D23_1c1723 |
| fig\|6666666.609 66.peg.1725 | CDS | 1610071 | 1608737 | -2 | - | hypothetical protein | - none - | D23_1c1724 |

FIG. 6K

| | | | | | | | |
|---|---|---|---|---|---|---|---|
| fig\|6666666.609 66.peg.1726 | CDS | 2 | 8 | -2 | - | 474 | Mobile element protein | - none - | D23_1c1783 |
| fig\|6666666.609 66.peg.1788 | CDS | 166717 | 166664 | -2 | - | 474 | Mobile element protein | - none - | D23_1c1783 |
| fig\|6666666.609 66.peg.1854 | CDS | 1727880 | 172881 | 3 | + | 939 | Major facilitator family transporter | - none - | D23_1c1857 |
| fig\|6666666.609 66.peg.1863 | CDS | 173757 | 173784 | 2 | + | 267 | Mobile element protein | - none - | D23_1c1866 |
| fig\|6666666.609 66.peg.1864 | CDS | 173783 | 173797 | 1 | + | 141 | Mobile element protein | - none - | D23_1c1867 |
| fig\|6666666.609 66.peg.1878 | CDS | 175230 | 175313 | 3 | + | 831 | Potassium efflux system KefA protein / Small-conductance mechanosensitive channel | Potassium homeostasis | D23_1c1880 |
| fig\|6666666.609 66.peg.1879 | CDS | 175372 | 175315 | -3 | - | 570 | hypothetical protein | - none - | D23_1c1881 |
| fig\|6666666.609 66.peg.1943 | CDS | 182184 | 182198 | 2 | + | 138 | Prevent host death protein, Phd antitoxin | Phd-Doc, YdcE-YdcD toxin-antitoxin (programmed cell death) systems | D23_1c1953 |
| fig\|6666666.609 66.peg.1944 | CDS | 182198 | 182227 | 1 | + | 297 | Death on curing protein, Doc toxin | Phd-Doc, YdcE-YdcD toxin-antitoxin (programmed cell death) systems | D23_1c1954 |
| fig\|6666666.609 66.peg.1947 | CDS | 182349 | 182315 | -1 | - | 342 | Predicted transcriptional regulator | - none - | D23_1c1957 |
| fig\|6666666.609 66.peg.1948 | CDS | 182370 | 182348 | -2 | - | 225 | Phage-related protein | - none - | D23_1c1958 |

FIG. 6L

| fig ID | type | start | end | | ± | length | product | subsystem | D23 ID |
|---|---|---|---|---|---|---|---|---|---|
| fig\|6666666.609 66.peg.2001 | CDS | 1866618 | 1866328 | -3 | - | 291 | hypothetical protein | - none - | D23_ic2004 |
| fig\|6666666.609 66.peg.2097 | CDS | 1949252 | 1949386 | 2 | + | 135 | Type I restriction-modification system, restriction subunit R (EC 3.1.21.3) | Restriction-Modification System; Type I Restriction-Modification | D23_ic2099 |
| fig\|6666666.609 66.peg.2111 | CDS | 1961191 | 1961517 | 1 | + | 327 | hypothetical protein | - none - | D23_ic2112 |
| fig\|6666666.609 66.peg.2127 | CDS | 1976514 | 1974985 | -3 | - | 1530 | Capsular polysaccharide biosynthesis protein WcbQ | Capsular Polysaccharides Biosynthesis and Assembly | D23_ic2128 |
| fig\|6666666.609 66.peg.2132 | CDS | 1982214 | 1981231 | -3 | - | 984 | hypothetical protein | - none - | D23_ic2133 |
| fig\|6666666.609 66.peg.2133 | CDS | 1982778 | 1982218 | -3 | - | 561 | hypothetical protein | - none - | D23_ic2134 |
| fig\|6666666.609 66.peg.2137 | CDS | 1985076 | 1984852 | -3 | - | 225 | hypothetical protein | - none - | D23_ic2138 |
| fig\|6666666.609 66.peg.2156 | CDS | 1997890 | 1998093 | 1 | + | 204 | Mobile element protein | - none - | D23_ic2154 |
| fig\|6666666.609 66.peg.2157 | CDS | 1998565 | 1998266 | -1 | - | 300 | VapC toxin protein | Toxin-antitoxin replicon stabilization systems | D23_ic2155 |
| fig\|6666666.609 66.peg.2158 | CDS | 1998899 | 1998666 | -2 | - | 234 | VapB protein (antitoxin to VapC) | Toxin-antitoxin replicon stabilization systems | D23_ic2156 |
| fig\|6666666.609 66.peg.2160 | CDS | 1999629 | 1999339 | -3 | - | 291 | transcriptional regulator, XRE family | - none - | D23_ic2158 |

FIG. 6M

| | | | | | | | | | |
|---|---|---|---|---|---|---|---|---|---|
| fig\|666666.609 66.peg.2161 | CDS | 1999997 | 1999969 2 | -2 | - | 306 | Phage-related protein | - none - | D23_1c2159 |
| fig\|666666.609 66.peg.2163 | CDS | 2000220 | 2000048 6 | 3 | + | 267 | Mobile element protein | - none - | D23_1c2161 |
| fig\|666666.609 66.peg.2164 | CDS | 2000507 | 2000099 5 | 2 | + | 489 | Mobile element protein | - none - | D23_1c2162 |
| fig\|666666.609 66.peg.2167 | CDS | 2002011 | 2002328 | 3 | + | 318 | Mobile element protein | - none - | D23_1c2165 |
| fig\|666666.609 66.peg.2168 | CDS | 2003529 | 2002369 | -3 | - | 1161 | CDP-4-dehydro-6-deoxy-D-glucose 3-dehydratase (EC 4.2.1.-) | - none - | D23_1c2166 |
| fig\|666666.609 66.peg.2169 | CDS | 2004426 | 2003539 | -3 | - | 888 | NAD-dependent epimerase/dehydratase family protein | CBSS-296591.1.peg.2330 | D23_1c2167 |
| fig\|666666.609 66.peg.2171 | CDS | 2007467 | 2005632 | -2 | - | 1836 | hypothetical protein | - none - | D23_1c2169 |
| fig\|666666.609 66.peg.2172 | CDS | 2010563 | 2007473 | -1 | - | 3096 | Minor teichoic acid biosynthesis protein GgaB | - none - | D23_1c2170 |
| fig\|666666.609 66.peg.2173 | CDS | 2012163 | 2010694 | -3 | - | 1470 | InterPro IPR001173 COGs COG0463 | - none - | D23_1c2171 |
| fig\|666666.609 66.peg.2174 | CDS | 2015828 | 2012172 | -2 | - | 3657 | Beta-1,3-glucosyltransferase | - none - | D23_1c2172 |
| fig\|666666.609 66.peg.2175 | CDS | 2017307 | 2016147 | -2 | - | 1161 | Capsular polysaccharide export system inner membrane protein KpsE | Capsular Polysaccharides Biosynthesis and Assembly | D23_1c2173 |

FIG. 6N

| | | | | | | | | |
|---|---|---|---|---|---|---|---|---|
| fig\|6666666.609 66.peg.2177 | CDS | 2018757 | 2017963 | -3 | - | 795 | Capsular polysaccharide ABC transporter, permease protein KpsM | Capsular Polysaccharides Biosynthesis and Assembly; Rhamnose containing glycans | D23_1c2175 |
| fig\|6666666.609 66.peg.2180 | CDS | 2025121 | 2021276 | -1 | - | 3846 | Capsular polysaccharide biosynthesis fatty acid synthase WcbR | - none - | D23_1c2178 |
| fig\|6666666.609 66.peg.2225 | CDS | 2067907 | 2068395 | 1 | + | 489 | Zinc uptake regulation protein ZUR | Glycyl-tRNA synthetase containing cluster; Oxidative stress; Zinc regulated enzymes | D23_1c2222 |
| fig\|6666666.609 66.peg.2228 | CDS | 2068811 | 2069020 | 2 | + | 210 | hypothetical protein | - none - | D23_1c2224 |
| fig\|6666666.609 66.peg.2320 | CDS | 2153132 | 2151816 | -2 | - | 1317 | hypothetical protein | - none - | D23_1c2315 |
| fig\|6666666.609 66.peg.2418 | CDS | 2240239 | 2240093 | -1 | - | 147 | Aconitate hydratase (EC 4.2.1.3) | TCA Cycle | D23_1c2410 |
| fig\|6666666.609 66.peg.2421 | CDS | 2241835 | 2241987 | 1 | + | 153 | Mobile element protein | - none - | D23_1c2413 |
| fig\|6666666.609 66.peg.2422 | CDS | 2242232 | 2242522 | 2 | + | 291 | hypothetical protein | - none - | D23_1c2414 |
| fig\|6666666.609 66.peg.2457 | CDS | 2275758 | 2274997 | -3 | - | 762 | hypothetical protein | - none - | D23_1c2447 |
| fig\|6666666.609 66.peg.2465 | CDS | 2282716 | 2281352 | -1 | - | 1365 | hypothetical protein | - none - | D23_1c2455 |
| fig\|6666666.609 66.peg. | CDS | 2285016 | 2284021 | -2 | - | 996 | hypothetical protein | - none - | D23_1c2459 |

FIG. 60

| | | | | | | | | |
|---|---|---|---|---|---|---|---|---|
| fig\|6666666.609.peg.2459 66.peg.2470 | CDS | 228530 5 | 228504 8 | -1 | - | 258 | hypothetical protein | - none - | D23_1c2460 |
| fig\|6666666.609 66.peg.2553 | CDS | 236155 1 | 236138 4 | -2 | - | 168 | protein of unknown function DUF1328 | - none - | D23_1c2543 |
| fig\|6666666.609 66.peg.2576 | CDS | 237876 5 | 237834 0 | -2 | - | 426 | hypothetical protein | - none - | D23_1c2565 |
| fig\|6666666.609 66.peg.2594 | CDS | 239214 5 | 239256 7 | 2 | + | 423 | Putative TEGT family carrier/transport protein | CBSS-326442.4.peg.1852 | D23_1c2580 |
| fig\|6666666.609 66.peg.2652 | CDS | 245799 8 | 245748 0 | -2 | - | 519 | HrgA protein | - none - | D23_1c2641 |
| fig\|6666666.609 66.peg.2653 | CDS | 245935 0 | 245801 3 | -1 | - | 1338 | hypothetical protein | - none - | D23_1c2642 |
| fig\|6666666.609 66.peg.2654 | CDS | 246024 9 | 245934 7 | -3 | - | 903 | hypothetical protein | - none - | D23_1c2643 |
| fig\|6666666.609 66.peg.2655 | CDS | 246330 5 | 246026 4 | -2 | - | 3042 | Type I restriction-modification system, restriction subunit R (EC 3.1.21.3) | Restriction-Modification System; Type I Restriction-Modification | D23_1c2644 |
| fig\|6666666.609 66.peg.2656 | CDS | 246394 3 | 246334 1 | -1 | - | 603 | hypothetical protein | - none - | D23_1c2645 |
| fig\|6666666.609 66.peg.2657 | CDS | 246534 8 | 246396 0 | -2 | - | 1389 | Type I restriction modification system, specificity subunit S (EC 3.1.21.3) | Restriction-Modification System; Type I Restriction-Modification | D23_1c2646 |
| fig\|6666666.609 66.peg.2685 | CDS | 249923 0 | 249952 0 | 2 | + | 291 | hypothetical protein | - none - | D23_1c2677 |

FIG. 6P

| | | | | | | | |
|---|---|---|---|---|---|---|---|
| fig\|6666666.609 66.peg.2687 | CDS | 2501402 | 2500767 | -2 | - | 636 | FIG01057587: hypothetical protein | - none - | D23_1c2679 |
| fig\|6666666.609 66.peg.2692 | CDS | 2503893 | 2504105 | 3 | + | 213 | hypothetical protein | - none - | D23_1c2683 |
| fig\|6666666.609 66.peg.2693 | CDS | 2505239 | 2504595 | -2 | - | 645 | hypothetical protein | - none - | D23_1c2685 |
| fig\|6666666.609 66.peg.2696 | CDS | 2506924 | 2506445 | -1 | - | 480 | DNA primase/helicase, phage-associated | Phage replication | D23_1c2688 |
| fig\|6666666.609 66.peg.2697 | CDS | 2507166 | 2506921 | -3 | - | 246 | hypothetical protein | - none - | D23_1c2689 |
| fig\|6666666.609 66.peg.2698 | CDS | 2507393 | 2507166 | -2 | - | 228 | hypothetical protein | - none - | D23_1c2690 |
| fig\|6666666.609 66.peg.2699 | CDS | 2507735 | 2508577 | 2 | + | 843 | hypothetical protein | - none - | D23_1c2691 |
| fig\|6666666.609 66.peg.2700 | CDS | 2508650 | 2509111 | 2 | + | 462 | Putative bacteriophage-related protein | - none - | D23_1c2692 |
| fig\|6666666.609 66.peg.2702 | CDS | 2510478 | 2510897 | 3 | + | 420 | elements of external origin; phage-related functions and prophages | - none - | D23_1c2694 |
| fig\|6666666.609 66.peg.2733 | CDS | 2537388 | 2537077 | -3 | - | 312 | hypothetical protein | - none - | D23_1c2724 |

FIG. 7A

Unique D23 genes below 200 base pairs with assigned ORF number: 164

| Feature.ID | Type | Start | Stop | Frame | Strand | Length (bp) | Function | Subsystem | D23Gbkid |
|---|---|---|---|---|---|---|---|---|---|
| fig\|6666666.609 66.peg.22 | CDS | 28682 | 28867 | 2 | + | 186 | hypothetical protein | - none - | D23_1c0024 |
| fig\|6666666.609 66.peg.29 | CDS | 31959 | 32078 | 3 | + | 120 | hypothetical protein | - none - | D23_1c0030 |
| fig\|6666666.609 66.peg.38 | CDS | 36580 | 36750 | 1 | + | 171 | hypothetical protein | - none - | D23_1c0039 |
| fig\|6666666.609 66.peg.52 | CDS | 49615 | 49502 | -1 | - | 114 | hypothetical protein | - none - | D23_1c0052 |
| fig\|6666666.609 66.peg.64 | CDS | 56874 | 56746 | -3 | - | 129 | hypothetical protein | - none - | D23_1c0065 |
| fig\|6666666.609 66.peg.66 | CDS | 60633 | 60755 | 3 | + | 123 | hypothetical protein | - none - | D23_1c0067 |
| fig\|6666666.609 66.peg.92 | CDS | 89253 | 89375 | 3 | + | 123 | hypothetical protein | - none - | D23_1c0091 |
| fig\|6666666.609 66.peg.93 | CDS | 89433 | 89579 | 3 | + | 147 | hypothetical protein | - none - | D23_1c0092 |
| fig\|6666666.609 66.peg.119 | CDS | 120193 | 120056 | -1 | - | 138 | hypothetical protein | - none - | D23_1c0120 |
| fig\|6666666.609 66.peg.121 | CDS | 122376 | 122495 | 3 | + | 120 | hypothetical protein | - none - | D23_1c0124 |
| fig\|6666666.609 66.peg.120 | CDS | 121863 | 121994 | 3 | + | 132 | hypothetical protein | - none - | D23_1c0124 |

FIG. 7B

| | | | | | | | |
|---|---|---|---|---|---|---|---|
| fig\|6666666.609 66.peg.123 | CDS | | 124878 | 124708 | -3 | - | 171 | hypothetical protein | - none - | D23_1c0127 |
| fig\|6666666.609 66.peg.132 | CDS | 132190 | 132312 | 1 | + | 123 | hypothetical protein | - none - | D23_1c0137 |
| fig\|6666666.609 66.peg.210 | CDS | 200398 | 200210 | -1 | - | 189 | hypothetical protein | - none - | D23_1c0215 |
| fig\|6666666.609 66.peg.231 | CDS | 215510 | 215623 | 2 | + | 114 | hypothetical protein | - none - | D23_1c0235 |
| fig\|6666666.609 66.peg.246 | CDS | 231229 | 231411 | 1 | + | 183 | hypothetical protein | - none - | D23_1c0253 |
| fig\|6666666.609 66.peg.249 | CDS | 232767 | 232585 | -3 | - | 183 | hypothetical protein | - none - | D23_1c0256 |
| fig\|6666666.609 66.peg.256 | CDS | 237299 | 237415 | 2 | + | 117 | hypothetical protein | - none - | D23_1c0264 |
| fig\|6666666.609 66.peg.294 | CDS | 266897 | 266760 | -2 | - | 138 | hypothetical protein | - none - | D23_1c0300 |
| fig\|6666666.609 66.peg.304 | CDS | 274944 | 274792 | -3 | - | 153 | hypothetical protein | - none - | D23_1c0309 |
| fig\|6666666.609 66.peg.313 | CDS | 284258 | 284401 | 2 | + | 144 | hypothetical protein | - none - | D23_1c0317 |
| fig\|6666666.609 66.peg.315 | CDS | 286328 | 286191 | -2 | - | 138 | hypothetical protein | - none - | D23_1c0321 |
| fig\|6666666.609 66.peg.330 | CDS | 302493 | 302368 | -3 | - | 126 | hypothetical protein | - none - | D23_1c0338 |
| fig\|6666666.609 66.peg.334 | CDS | 306026 | 305904 | -2 | - | 123 | hypothetical protein | - none - | D23_1c0342 |
| fig\|6666666.609 66.peg.349 | CDS | 322196 | 322363 | 2 | + | 168 | hypothetical protein | - none - | D23_1c0356 |
| fig\|6666666.609 66.peg.351 | CDS | 325139 | 325255 | 2 | + | 117 | hypothetical protein | - none - | D23_1c0358 |
| fig\|6666666.609 66.peg.351 | CDS | 342384 | 342509 | 3 | + | 126 | hypothetical protein | - none - | D23_1c0376 |

FIG.7C

| | | | | | | | |
|---|---|---|---|---|---|---|---|
| fig\|6666666.609.peg.370 | | | | | | | |
| fig\|6666666.609.peg.401 | CDS | 374277 | 374140 | -3 | - | 138 | hypothetical protein | - none - | D23_1c0406 |
| fig\|6666666.609.peg.425 | CDS | 394947 | 394834 | -3 | - | 114 | hypothetical protein | - none - | D23_1c0431 |
| fig\|6666666.609.peg.435 | CDS | 399146 | 398973 | -2 | - | 174 | hypothetical protein | - none - | D23_1c0438 |
| fig\|6666666.609.peg.436 | CDS | 399498 | 399373 | -3 | - | 126 | hypothetical protein | - none - | D23_1c0439 |
| fig\|6666666.609.peg.450 | CDS | 418345 | 418193 | -1 | - | 153 | hypothetical protein | - none - | D23_1c0453 |
| fig\|6666666.609.peg.462 | CDS | 428472 | 428329 | -3 | - | 144 | hypothetical protein | - none - | D23_1c0465 |
| fig\|6666666.609.peg.469 | CDS | 437662 | 437775 | 1 | + | 114 | hypothetical protein | - none - | D23_1c0473 |
| fig\|6666666.609.peg.476 | CDS | 444457 | 444311 | -1 | - | 147 | hypothetical protein | - none - | D23_1c0480 |
| fig\|6666666.609.peg.488 | CDS | 455538 | 455371 | -3 | - | 168 | hypothetical protein | - none - | D23_1c0492 |
| fig\|6666666.609.peg.494 | CDS | 462416 | 462285 | -2 | - | 132 | hypothetical protein | - none - | D23_1c0498 |
| fig\|6666666.609.peg.495 | CDS | 463405 | 462413 | -1 | - | 993 | hypothetical protein | - none - | D23_1c0499 |
| fig\|6666666.609.peg.499 | CDS | 468057 | 467896 | -3 | - | 162 | hypothetical protein | - none - | D23_1c0503 |
| fig\|6666666.609.peg.502 | CDS | 469703 | 469870 | 2 | + | 168 | hypothetical protein | - none - | D23_1c0506 |
| fig\|6666666.609.peg.567 | CDS | 527054 | 527206 | 2 | + | 153 | hypothetical protein | - none - | D23_1c0567 |
| fig\|6666666.609.peg.570 | CDS | 530171 | 530284 | 2 | + | 114 | hypothetical protein | - none - | D23_1c0571 |

FIG. 7D

| | | | | | | | |
|---|---|---|---|---|---|---|---|
| fig\|6666666.609 66.peg.571 | CDS | 530407 | 530535 | 1 | + | 129 | hypothetical protein | - none - | D23_1c0572 |
| fig\|6666666.609 66.peg.584 | CDS | 541934 | 541812 | -2 | - | 123 | hypothetical protein | - none - | D23_1c0586 |
| fig\|6666666.609 66.peg.591 | CDS | 544721 | 544834 | 2 | + | 114 | hypothetical protein | - none - | D23_1c0591 |
| fig\|6666666.609 66.peg.600 | CDS | 551404 | 551517 | 1 | + | 114 | hypothetical protein | - none - | D23_1c0600 |
| fig\|6666666.609 66.peg.630 | CDS | 576475 | 576609 | 1 | + | 135 | hypothetical protein | - none - | D23_1c0633 |
| fig\|6666666.609 66.peg.667 | CDS | 615143 | 615012 | -2 | - | 132 | hypothetical protein | - none - | D23_1c0670 |
| fig\|6666666.609 66.peg.674 | CDS | 623711 | 623827 | 2 | + | 117 | hypothetical protein | - none - | D23_1c0678 |
| fig\|6666666.609 66.peg.686 | CDS | 637484 | 637326 | -2 | - | 159 | hypothetical protein | - none - | D23_1c0693 |
| fig\|6666666.609 66.peg.695 | CDS | 647548 | 647402 | -1 | - | 147 | hypothetical protein | - none - | D23_1c0702 |
| fig\|6666666.609 66.peg.702 | CDS | 652766 | 652948 | 2 | + | 183 | hypothetical protein | - none - | D23_1c0709 |
| fig\|6666666.609 66.peg.727 | CDS | 674585 | 674716 | 2 | + | 132 | hypothetical protein | - none - | D23_1c0734 |
| fig\|6666666.609 66.peg.729 | CDS | 675190 | 674996 | -1 | - | 195 | hypothetical protein | - none - | D23_1c0736 |
| fig\|6666666.609 66.peg.778 | CDS | 718480 | 718674 | 1 | + | 195 | hypothetical protein | - none - | D23_1c0783 |
| fig\|6666666.609 66.peg.784 | CDS | 723900 | 724055 | 3 | + | 156 | hypothetical protein | - none - | D23_1c0790 |
| fig\|6666666.609 66.peg.800 | CDS | 734018 | 734161 | 2 | + | 144 | hypothetical protein | - none - | D23_1c0807 |
| fig\|6666666.609 66.peg.809 | CDS | 739386 | 739240 | -3 | - | 147 | hypothetical protein | - none - | D23_1c0813 |

FIG. 7E

| | | | | | | | | |
|---|---|---|---|---|---|---|---|---|
| fig\|6666666.609.peg.806 | CDS | 744823 | 744647 | -1 | - | 177 | hypothetical protein | - none - | D23_1c0817 |
| fig\|6666666.609.peg.811 | CDS | 773025 | 773147 | 3 | + | 123 | hypothetical protein | - none - | D23_1c0847 |
| fig\|6666666.609.peg.841 | CDS | 779394 | 779245 | -3 | - | 150 | hypothetical protein | - none - | D23_1c0853 |
| fig\|6666666.609.peg.847 | CDS | 783597 | 783757 | 3 | + | 171 | hypothetical protein | - none - | D23_1c0859 |
| fig\|6666666.609.peg.853 | CDS | 794389 | 794558 | 1 | + | 180 | hypothetical protein | - none - | D23_1c0872 |
| fig\|6666666.609.peg.867 | CDS | 861629 | 861754 | 2 | + | 126 | hypothetical protein | - none - | D23_1c0934 |
| fig\|6666666.609.peg.929 | CDS | 861857 | 861720 | -2 | - | 138 | hypothetical protein | - none - | D23_1c0935 |
| fig\|6666666.609.peg.930 | CDS | 873991 | 874104 | 1 | + | 114 | hypothetical protein | - none - | D23_1c0951 |
| fig\|6666666.609.peg.946 | CDS | 890193 | 890345 | 3 | + | 153 | hypothetical protein | - none - | D23_1c0970 |
| fig\|6666666.609.peg.964 | CDS | 890326 | 890442 | 1 | + | 117 | hypothetical protein | - none - | D23_1c0971 |
| fig\|6666666.609.peg.965 | CDS | 900234 | 900398 | 3 | + | 165 | hypothetical protein | - none - | D23_1c0982 |
| fig\|6666666.609.peg.974 | CDS | 915551 | 915688 | 2 | + | 138 | hypothetical protein | - none - | D23_1c0993 |
| fig\|6666666.609.peg.983 | CDS | 918535 | 918419 | -1 | - | 117 | hypothetical protein | - none - | D23_1c0997 |
| fig\|6666666.609.peg.987 | CDS | 928500 | 928315 | -3 | - | 186 | hypothetical protein | - none - | D23_1c1010 |
| fig\|6666666.609.peg.1000 | CDS | 942037 | 942186 | 1 | + | 150 | hypothetical protein | - none - | D23_1c1024 |

FIG. 7F

| | | | | | | | |
|---|---|---|---|---|---|---|---|
| fig\|6666666.609 66.peg.1027 | CDS | 952378 | 952208 | -1 | - | 171 | hypothetical protein | - none - | D23_1c1036 |
| fig\|6666666.609 66.peg.1040 | CDS | 965355 | 965495 | 3 | + | 141 | hypothetical protein | - none - | D23_1c1051 |
| fig\|6666666.609 66.peg.1051 | CDS | 973589 | 973461 | -2 | - | 129 | hypothetical protein | - none - | D23_1c1064 |
| fig\|6666666.609 66.peg.1069 | CDS | 992670 | 992536 | -3 | - | 135 | hypothetical protein | - none - | D23_1c1083 |
| fig\|6666666.609 66.peg.1091 | CDS | 1020710 | 1020862 | 2 | + | 153 | hypothetical protein | - none - | D23_1c1103 |
| fig\|6666666.609 66.peg.1112 | CDS | 1043119 | 1043253 | 1 | + | 135 | hypothetical protein | - none - | D23_1c1121 |
| fig\|6666666.609 66.peg.1113 | CDS | 1043368 | 1043511 | 1 | + | 144 | hypothetical protein | - none - | D23_1c1122 |
| fig\|6666666.609 66.peg.1115 | CDS | 1043900 | 1043736 | -2 | - | 165 | hypothetical protein | - none - | D23_1c1123 |
| fig\|6666666.609 66.peg.1139 | CDS | 1065051 | 1064932 | -3 | - | 120 | hypothetical protein | - none - | D23_1c1149 |
| fig\|6666666.609 66.peg.1168 | CDS | 1092982 | 1092851 | -1 | - | 132 | hypothetical protein | - none - | D23_1c1175 |
| fig\|6666666.609 66.peg.1198 | CDS | 1121909 | 1121763 | -2 | - | 147 | hypothetical protein | - none - | D23_1c1204 |
| fig\|6666666.609 66.peg.1205 | CDS | 1128452 | 1128580 | 2 | + | 129 | hypothetical protein | - none - | D23_1c1211 |
| fig\|6666666.609 66.peg.1232 | CDS | 1150415 | 1150546 | 2 | + | 132 | hypothetical protein | - none - | D23_1c1237 |
| fig\|6666666.609 66.peg.1235 | CDS | 1150882 | 1151043 | 1 | + | 162 | hypothetical protein | - none - | D23_1c1240 |
| fig\|6666666.609 66.peg.1250 | CDS | 1161926 | 1161813 | -2 | - | 114 | hypothetical protein | - none - | D23_1c1257 |
| fig\|6666666.609 66.peg.1250 | CDS | 1162096 | 1162263 | 1 | + | 168 | hypothetical protein | - none - | D23_1c1258 |

FIG. 7G

| | | | | | | | |
|---|---|---|---|---|---|---|---|
| fig\|6666666.609.peg.1251 | CDS | 1162260 | 1162415 | 3 | + | 156 | hypothetical protein | - none - | D23_1c1259 |
| fig\|6666666.609.peg.1252 | CDS | 1181609 | 1181776 | 2 | + | 168 | hypothetical protein | - none - | D23_1c1280 |
| fig\|6666666.609.peg.1273 | CDS | 1182136 | 1181990 | -1 | - | 147 | hypothetical protein | - none - | D23_1c1282 |
| fig\|6666666.609.peg.1275 | CDS | 1189440 | 1189327 | -3 | - | 114 | hypothetical protein | - none - | D23_1c1290 |
| fig\|6666666.609.peg.1285 | CDS | 1200901 | 1200761 | -1 | - | 141 | hypothetical protein | - none - | D23_1c1301 |
| fig\|6666666.609.peg.1292 | CDS | 1206663 | 1206902 | 3 | + | 240 | hypothetical protein | - none - | D23_1c1308 |
| fig\|6666666.609.peg.1300 | CDS | 1268913 | 1268800 | -3 | - | 114 | hypothetical protein | - none - | D23_1c1366 |
| fig\|6666666.609.peg.1359 | CDS | 1298101 | 1297967 | -1 | - | 135 | hypothetical protein | - none - | D23_1c1393 |
| fig\|6666666.609.peg.1387 | CDS | 1303729 | 1303556 | -1 | - | 174 | hypothetical protein | - none - | D23_1c1402 |
| fig\|6666666.609.peg.1395 | CDS | 1324808 | 1324990 | 2 | + | 183 | hypothetical protein | - none - | D23_1c1419 |
| fig\|6666666.609.peg.1412 | CDS | 1349336 | 1349214 | -2 | - | 123 | hypothetical protein | - none - | D23_1c1444 |
| fig\|6666666.609.peg.1438 | CDS | 1374021 | 1374137 | 3 | + | 117 | hypothetical protein | - none - | D23_1c1469 |
| fig\|6666666.609.peg.1462 | CDS | 1380471 | 1380340 | -3 | - | 132 | hypothetical protein | - none - | D23_1c1473 |
| fig\|6666666.609.peg.1466 | CDS | 1388559 | 1388395 | -3 | - | 165 | hypothetical protein | - none - | D23_1c1481 |
| fig\|6666666.609.peg.1475 | CDS | 1394795 | 1394911 | 2 | + | 117 | hypothetical protein | - none - | D23_1c1486 |
| fig\|6666666.609.peg.1480 | | | | | | | | | |

FIG. 7H

| | | | | | | |
|---|---|---|---|---|---|---|
| fig\|666666.609 66.peg.1488 | CDS | 1402082 | 1401924 | -2 | - | 159 | hypothetical protein | - none - | D23_1c1494 |
| fig\|666666.609 66.peg.1503 | CDS | 1415346 | 1415224 | -3 | - | 123 | hypothetical protein | - none - | D23_1c1510 |
| fig\|666666.609 66.peg.1520 | CDS | 1430834 | 1430670 | -2 | - | 165 | hypothetical protein | - none - | D23_1c1526 |
| fig\|666666.609 66.peg.1550 | CDS | 1453430 | 1453269 | -2 | - | 162 | hypothetical protein | - none - | D23_1c1557 |
| fig\|666666.609 66.peg.1551 | CDS | 1453630 | 1453451 | -1 | - | 180 | hypothetical protein | - none - | D23_1c1558 |
| fig\|666666.609 66.peg.1561 | CDS | 1459812 | 1459672 | -3 | - | 141 | hypothetical protein | - none - | D23_1c1567 |
| fig\|666666.609 66.peg.1567 | CDS | 1462722 | 1462844 | 3 | + | 123 | hypothetical protein | - none - | D23_1c1571 |
| fig\|666666.609 66.peg.1573 | CDS | 1466953 | 1467108 | 1 | + | 156 | hypothetical protein | - none - | D23_1c1575 |
| fig\|666666.609 66.peg.1603 | CDS | 1491738 | 1491519 | -3 | - | 120 | hypothetical protein | - none - | D23_1c1604 |
| fig\|666666.609 66.peg.1619 | CDS | 1502854 | 1502738 | -1 | - | 117 | hypothetical protein | - none - | D23_1c1617 |
| fig\|666666.609 66.peg.1623 | CDS | 1505626 | 1505739 | 1 | + | 114 | hypothetical protein | - none - | D23_1c1621 |
| fig\|666666.609 66.peg.1649 | CDS | 1533038 | 1532850 | -2 | - | 189 | hypothetical protein | - none - | D23_1c1647 |
| fig\|666666.609 66.peg.1652 | CDS | 1535502 | 1535386 | -3 | - | 117 | hypothetical protein | - none - | D23_1c1650 |
| fig\|666666.609 66.peg.1666 | CDS | 1550134 | 1550247 | 1 | + | 114 | hypothetical protein | - none - | D23_1c1664 |
| fig\|666666.609 66.peg.1670 | CDS | 1553775 | 1553559 | -3 | - | 117 | hypothetical protein | - none - | D23_1c1668 |
| fig\|666666.609 66.peg.1686 | CDS | 1573150 | 1573001 | -1 | - | 150 | hypothetical protein | - none - | D23_1c1686 |

FIG. 71

| | | | | | | |
|---|---|---|---|---|---|---|
| fig\|666666.609.peg.1688 | CDS | 1575055 | 1574942 | -1 | - | 114 | hypothetical protein | - none - | D23_1c1692 |
| fig\|666666.609.peg.1693 | CDS | 1599507 | 1599391 | -3 | - | 117 | hypothetical protein | - none - | D23_1c1716 |
| fig\|666666.609.peg.1718 | CDS | 1611922 | 1612056 | 1 | + | 135 | hypothetical protein | - none - | D23_1c1727 |
| fig\|666666.609.peg.1729 | CDS | 1614522 | 1614355 | -3 | - | 168 | hypothetical protein | - none - | D23_1c1731 |
| fig\|666666.609.peg.1734 | CDS | 1614827 | 1614599 | -2 | - | 129 | hypothetical protein | - none - | D23_1c1732 |
| fig\|666666.609.peg.1735 | CDS | 1618427 | 1618293 | -2 | - | 135 | hypothetical protein | - none - | D23_1c1738 |
| fig\|666666.609.peg.1740 | CDS | 1642217 | 1642050 | -2 | - | 168 | hypothetical protein | - none - | D23_1c1761 |
| fig\|666666.609.peg.1767 | CDS | 1651568 | 1651446 | -2 | - | 123 | hypothetical protein | - none - | D23_1c1772 |
| fig\|666666.609.peg.1777 | CDS | 1662168 | 1662344 | 3 | + | 177 | hypothetical protein | - none - | D23_1c1776 |
| fig\|666666.609.peg.1781 | CDS | 1663286 | 1663158 | -2 | - | 129 | hypothetical protein | - none - | D23_1c1778 |
| fig\|666666.609.peg.1783 | CDS | 1668254 | 1668093 | -2 | - | 162 | hypothetical protein | - none - | D23_1c1785 |
| fig\|666666.609.peg.1790 | CDS | 1672280 | 1672017 | -2 | - | 264 | SSU ribosomal protein S20p | - none - | D23_1c1789 |
| fig\|666666.609.peg.1794 | CDS | 1672473 | 1672634 | 3 | + | 162 | hypothetical protein | - none - | D23_1c1790 |
| fig\|666666.609.peg.1795 | CDS | 1685374 | 1685249 | -1 | - | 126 | hypothetical protein | - none - | D23_1c1808 |
| fig\|666666.609.peg.1810 | CDS | 1727480 | 1727641 | 2 | + | 162 | hypothetical protein | - none - | D23_1c1855 |
| fig\|666666.609.peg.1852 | | | | | | | | | |

FIG. 7J

| | | | | | | |
|---|---|---|---|---|---|---|
| fig\|6666666.609 66.peg.1853 | CDS | 1727757 | 1727873 | 3 | + | 117 | hypothetical protein | - none - | D23_1c1856 |
| fig\|6666666.609 66.peg.1883 | CDS | 1757073 | 1757201 | 3 | + | 129 | hypothetical protein | - none - | D23_1c1885 |
| fig\|6666666.609 66.peg.1908 | CDS | 1784806 | 1784651 | -1 | - | 156 | hypothetical protein | - none - | D23_1c1913 |
| fig\|6666666.609 66.peg.1952 | CDS | 1824892 | 1824704 | -1 | - | 189 | hypothetical protein | - none - | D23_1c1959 |
| fig\|6666666.609 66.peg.1961 | CDS | 1830108 | 1830230 | 3 | + | 123 | hypothetical protein | - none - | D23_1c1968 |
| fig\|6666666.609 66.peg.1964 | CDS | 1831759 | 1831616 | -1 | - | 144 | hypothetical protein | - none - | D23_1c1971 |
| fig\|6666666.609 66.peg.1969 | CDS | 1836022 | 1836150 | 1 | + | 129 | hypothetical protein | - none - | D23_1c1975 |
| fig\|6666666.609 66.peg.1978 | CDS | 1845616 | 1845783 | 1 | + | 168 | hypothetical protein | - none - | D23_1c1984 |
| fig\|6666666.609 66.peg.1981 | CDS | 1848084 | 1848206 | 3 | + | 123 | hypothetical protein | - none - | D23_1c1987 |
| fig\|6666666.609 66.peg.1990 | CDS | 1855948 | 1855835 | -1 | - | 114 | hypothetical protein | - none - | D23_1c1994 |
| fig\|6666666.609 66.peg.1992 | CDS | 1856572 | 1856703 | 1 | + | 132 | hypothetical protein | - none - | D23_1c1996 |
| fig\|6666666.609 66.peg.1995 | CDS | 1860536 | 1860567 | 2 | + | 132 | hypothetical protein | - none - | D23_1c1999 |
| fig\|6666666.609 66.peg.2006 | CDS | 1870373 | 1870546 | 2 | + | 174 | hypothetical protein | - none - | D23_1c2008 |
| fig\|6666666.609 66.peg.2013 | CDS | 1877265 | 1877122 | -3 | - | 144 | hypothetical protein | - none - | D23_1c2015 |
| fig\|6666666.609 66.peg.2016 | CDS | 1881044 | 1880847 | -2 | - | 198 | hypothetical protein | - none - | D23_1c2018 |
| fig\|6666666.609 66.peg.2026 | CDS | 1888279 | 1888148 | -1 | - | 132 | hypothetical protein | - none - | D23_1c2028 |

FIG. 7K

| | | | | | | | |
|---|---|---|---|---|---|---|---|
| fig\|666666.609.peg.2024 | CDS | 1898327 | 1898494 | 2 | + | 168 | hypothetical protein | - none - | D23_1c2039 |
| fig\|666666.609.peg.2034 | CDS | 1922713 | 1922826 | 1 | + | 114 | hypothetical protein | - none - | D23_1c2069 |
| fig\|666666.609.peg.2065 | CDS | 1926506 | 1926390 | -2 | - | 117 | hypothetical protein | - none - | D23_1c2072 |
| fig\|666666.609.peg.2069 | CDS | 1942209 | 1942087 | -3 | - | 123 | hypothetical protein | - none - | D23_1c2092 |
| fig\|666666.609.peg.2090 | CDS | 1957270 | 1957133 | -1 | - | 138 | hypothetical protein | - none - | D23_1c2108 |
| fig\|666666.609.peg.2106 | CDS | 1962848 | 1962729 | -2 | - | 120 | hypothetical protein | - none - | D23_1c2115 |
| fig\|666666.609.peg.2113 | CDS | 1995705 | 1995851 | 3 | + | 147 | hypothetical protein | - none - | D23_1c2148 |
| fig\|666666.609.peg.2150 | CDS | 1999186 | 1999344 | 1 | + | 159 | hypothetical protein | - none - | D23_1c2157 |
| fig\|666666.609.peg.2159 | CDS | 2000147 | 2000022 | -2 | - | 126 | hypothetical protein | - none - | D23_1c2160 |
| fig\|666666.609.peg.2162 | CDS | 2029053 | 2029166 | 3 | + | 114 | hypothetical protein | - none - | D23_1c2180 |
| fig\|666666.609.peg.2182 | CDS | 2029212 | 2029352 | 3 | + | 141 | hypothetical protein | - none - | D23_1c2181 |
| fig\|666666.609.peg.2183 | CDS | 2040442 | 2040612 | 1 | + | 171 | hypothetical protein | - none - | D23_1c2192 |
| fig\|666666.609.peg.2193 | CDS | 2040690 | 2040875 | 3 | + | 186 | hypothetical protein | - none - | D23_1c2193 |
| fig\|666666.609.peg.2195 | CDS | 2061489 | 2061361 | -3 | - | 129 | hypothetical protein | - none - | D23_1c2216 |
| fig\|666666.609.peg.2218 | CDS | 2069466 | 2069332 | -3 | - | 135 | hypothetical protein | - none - | D23_1c2225 |
| fig\|666666.609.peg.2231 | | | | | | | | | |

FIG. 7L

| | | | | | | | |
|---|---|---|---|---|---|---|---|
| fig\|666666666.609 66.peg.2240 | CDS | 2076577 | 2076407 | -1 | - | 171 | hypothetical protein | - none - | D23_1c2234 |
| fig\|666666666.609 66.peg.2247 | CDS | 2083232 | 2083038 | -2 | - | 195 | hypothetical protein | - none - | D23_1c2241 |
| fig\|666666666.609 66.peg.2251 | CDS | 2086807 | 2086661 | -1 | - | 147 | hypothetical protein | - none - | D23_1c2244 |
| fig\|666666666.609 66.peg.2262 | CDS | 2096035 | 2096187 | 1 | + | 153 | hypothetical protein | - none - | D23_1c2255 |
| fig\|666666666.609 66.peg.2282 | CDS | 2116748 | 2116897 | 2 | + | 150 | hypothetical protein | - none - | D23_1c2276 |
| fig\|666666666.609 66.peg.2291 | CDS | 2126813 | 2126977 | 2 | + | 165 | hypothetical protein | - none - | D23_1c2287 |
| fig\|666666666.609 66.peg.2293 | CDS | 2128367 | 2128218 | -2 | - | 150 | hypothetical protein | - none - | D23_1c2289 |
| fig\|666666666.609 66.peg.2316 | CDS | 2149225 | 2149353 | 1 | + | 129 | hypothetical protein | - none - | D23_1c2312 |
| fig\|666666666.609 66.peg.2332 | CDS | 2168192 | 2168052 | -2 | - | 141 | hypothetical protein | - none - | D23_1c2326 |
| fig\|666666666.609 66.peg.2333 | CDS | 2168473 | 2168640 | 1 | + | 168 | hypothetical protein | - none - | D23_1c2327 |
| fig\|666666666.609 66.peg.2339 | CDS | 2172852 | 2172977 | 3 | + | 126 | hypothetical protein | - none - | D23_1c2334 |
| fig\|666666666.609 66.peg.2351 | CDS | 2184641 | 2184453 | -2 | - | 189 | hypothetical protein | - none - | D23_1c2346 |
| fig\|666666666.609 66.peg.2369 | CDS | 2201167 | 2201039 | -1 | - | 129 | hypothetical protein | - none - | D23_1c2365 |
| fig\|666666666.609 66.peg.2397 | CDS | 2225287 | 2225162 | -1 | - | 126 | hypothetical protein | - none - | D23_1c2390 |
| fig\|666666666.609 66.peg.2401 | CDS | 2229650 | 2229480 | -2 | - | 171 | hypothetical protein | - none - | D23_1c2393 |
| fig\|666666666.609 66.peg.2401 | CDS | 2233192 | 2233344 | 1 | + | 153 | hypothetical protein | - none - | D23_1c2397 |

FIG. 7M

| | | | | | | | |
|---|---|---|---|---|---|---|---|
| fig\|666666.609.peg.2405 | CDS | 2254408 | 2254247 | -1 | - | 162 | hypothetical protein | - none - | D23_1c2426 |
| fig\|666666.609.peg.2434 | CDS | 2259106 | 2259264 | 1 | + | 159 | hypothetical protein | - none - | D23_1c2432 |
| fig\|666666.609.peg.2440 | CDS | 2277800 | 2277958 | 2 | + | 159 | hypothetical protein | - none - | D23_1c2452 |
| fig\|666666.609.peg.2461 | CDS | 2285448 | 2285573 | 3 | + | 126 | hypothetical protein | - none - | D23_1c2461 |
| fig\|666666.609.peg.2471 | CDS | 2321107 | 2321223 | 1 | + | 117 | hypothetical protein | - none - | D23_1c2498 |
| fig\|666666.609.peg.2509 | CDS | 2362071 | 2362247 | 3 | + | 177 | hypothetical protein | - none - | D23_1c2545 |
| fig\|666666.609.peg.2555 | CDS | 2417726 | 2417860 | 2 | + | 135 | hypothetical protein | - none - | D23_1c2607 |
| fig\|666666.609.peg.2619 | CDS | 2427773 | 2427892 | 2 | + | 120 | hypothetical protein | - none - | D23_1c2517 |
| fig\|666666.609.peg.2630 | CDS | 2428128 | 2428319 | 3 | + | 192 | hypothetical protein | - none - | D23_1c2518 |
| fig\|666666.609.peg.2631 | CDS | 2428646 | 2428518 | -2 | - | 129 | hypothetical protein | - none - | D23_1c2520 |
| fig\|666666.609.peg.2632 | CDS | 2441648 | 2441788 | 2 | + | 141 | hypothetical protein | - none - | D23_1c2626 |
| fig\|666666.609.peg.2638 | CDS | 2441958 | 2441845 | -3 | - | 114 | hypothetical protein | - none - | D23_1c2627 |
| fig\|666666.609.peg.2639 | CDS | 2490598 | 2490741 | 1 | + | 144 | hypothetical protein | - none - | D23_1c2567 |
| fig\|666666.609.peg.2678 | CDS | 2502217 | 2502050 | -1 | - | 168 | hypothetical protein | - none - | D23_1c2681 |
| fig\|666666.609.peg.2689 | CDS | 2513079 | 2512963 | -3 | - | 117 | hypothetical protein | - none - | D23_1c2698 |
| fig\|666666.609.peg.2705 | | | | | | | | | |

FIG. 8A

Unique D23 genes with no assigned ORF number: 219 (of which 180 are below 200 bp)

| Feature.ID | Type | Start | Stop | Frame | Strand | Length (bp) | Function | Subsystem | D23Gbkid |
|---|---|---|---|---|---|---|---|---|---|
| fig\|666666.609 66.peg.111 | CDS | 108515 | 108628 | 2 | + | 114 | hypothetical protein | - none - | NA |
| fig\|666666.609 66.peg.353 | CDS | 326760 | 326647 | -3 | - | 114 | hypothetical protein | - none - | NA |
| fig\|666666.609 66.peg.404 | CDS | 375917 | 375804 | -2 | - | 114 | hypothetical protein | - none - | NA |
| fig\|666666.609 66.peg.432 | CDS | 397539 | 397426 | -3 | - | 114 | hypothetical protein | - none - | NA |
| fig\|666666.609 66.peg.509 | CDS | 474482 | 474369 | -2 | - | 114 | hypothetical protein | - none - | NA |
| fig\|666666.609 66.peg.589 | CDS | 543008 | 543121 | 2 | + | 114 | hypothetical protein | - none - | NA |
| fig\|666666.609 66.peg.838 | CDS | 770105 | 770218 | 2 | + | 114 | hypothetical protein | - none - | NA |
| fig\|666666.609 66.peg.923 | CDS | 855159 | 855046 | -3 | - | 114 | hypothetical protein | - none - | NA |
| fig\|666666.609 66.peg.943 | CDS | 873193 | 873306 | 1 | + | 114 | hypothetical protein | - none - | NA |
| fig\|666666.609 66.peg.1081 | CDS | 1010260 | 1010373 | 1 | + | 114 | hypothetical protein | - none - | NA |
| fig\|666666.609 66.peg.1333 | CDS | 1235666 | 1235779 | 2 | + | 114 | hypothetical protein | - none - | NA |

FIG. 8B

| | | | | | | | |
|---|---|---|---|---|---|---|---|
| fig\|6666666.609 66.peg.1414 | CDS | 1326350 | 1326463 | 2 | + | 114 | hypothetical protein | - none - | NA |
| fig\|6666666.609 66.peg.1695 | CDS | 1575540 | 1575553 | 3 | + | 114 | hypothetical protein | - none - | NA |
| fig\|6666666.609 66.peg.1875 | CDS | 1749599 | 1749486 | -2 | - | 114 | Mobile element protein | - none - | NA |
| fig\|6666666.609 66.peg.2082 | CDS | 1936491 | 1936378 | -3 | - | 114 | hypothetical protein | - none - | NA |
| fig\|6666666.609 66.peg.2205 | CDS | 2047715 | 2047828 | 2 | + | 114 | hypothetical protein | - none - | NA |
| fig\|6666666.609 66.peg.2370 | CDS | 2201390 | 2201277 | -2 | - | 114 | hypothetical protein | - none - | NA |
| fig\|6666666.609 66.peg.2413 | CDS | 2236764 | 2236651 | -3 | - | 114 | hypothetical protein | - none - | NA |
| fig\|6666666.609 66.peg.2577 | CDS | 2379043 | 2378930 | -1 | - | 114 | hypothetical protein | - none - | NA |
| fig\|6666666.609 66.peg.421 | CDS | 392634 | 392518 | -3 | - | 117 | hypothetical protein | - none - | NA |
| fig\|6666666.609 66.peg.431 | CDS | 397234 | 397350 | 1 | + | 117 | hypothetical protein | - none - | NA |
| fig\|6666666.609 66.peg.1104 | CDS | 1033773 | 1033889 | 3 | + | 117 | hypothetical protein | - none - | NA |
| fig\|6666666.609 66.peg.1856 | CDS | 1730271 | 1730155 | -3 | - | 117 | hypothetical protein | - none - | NA |
| fig\|6666666.609 66.peg.2044 | CDS | 1907891 | 1907775 | -2 | - | 117 | hypothetical protein | - none - | NA |
| fig\|6666666.609 66.peg.2046 | CDS | 1908400 | 1908516 | 1 | + | 117 | hypothetical protein | - none - | NA |
| fig\|6666666.609 66.peg.2250 | CDS | 2086632 | 2086516 | -3 | - | 117 | hypothetical protein | - none - | NA |
| fig\|6666666.609 66.peg.2413 | CDS | 2209362 | 2209246 | -3 | - | 117 | hypothetical protein | - none - | NA |

FIG. 8C

| | | | | | | | |
|---|---|---|---|---|---|---|---|
| fig\|6666666.609<br>66.peg.2378 | CDS | 31960 | 31841 | -1 | - | 120 | hypothetical protein | - none - | NA |
| fig\|6666666.609<br>66.peg.28 | CDS | 496598 | 496717 | 2 | + | 120 | hypothetical protein | - none - | NA |
| fig\|6666666.609<br>66.peg.536 | CDS | 794273 | 794392 | 2 | + | 120 | hypothetical protein | - none - | NA |
| fig\|6666666.609<br>66.peg.866 | CDS | 956342 | 956223 | -2 | - | 120 | hypothetical protein | - none - | NA |
| fig\|6666666.609<br>66.peg.1031 | CDS | 1152349 | 1152230 | -1 | - | 120 | hypothetical protein | - none - | NA |
| fig\|6666666.609<br>66.peg.1238 | CDS | 1184453 | 1184572 | 2 | + | 120 | hypothetical protein | - none - | NA |
| fig\|6666666.609<br>66.peg.1279 | CDS | 1462529 | 1462410 | -2 | - | 120 | hypothetical protein | - none - | NA |
| fig\|6666666.609<br>66.peg.1566 | CDS | 1492079 | 1491960 | -2 | - | 120 | hypothetical protein | - none - | NA |
| fig\|6666666.609<br>66.peg.1604 | CDS | 1495100 | 1495219 | 2 | + | 120 | hypothetical protein | - none - | NA |
| fig\|6666666.609<br>66.peg.1610 | CDS | 1820165 | 1820046 | -2 | - | 120 | hypothetical protein | - none - | NA |
| fig\|6666666.609<br>66.peg.1938 | CDS | 1820392 | 1820511 | 1 | + | 120 | hypothetical protein | - none - | NA |
| fig\|6666666.609<br>66.peg.1940 | CDS | 2040715 | 2040596 | -1 | - | 120 | hypothetical protein | - none - | NA |
| fig\|6666666.609<br>66.peg.2194 | CDS | 2069192 | 2069073 | -2 | - | 120 | hypothetical protein | - none - | NA |
| fig\|6666666.609<br>66.peg.2229 | CDS | 2355482 | 2355601 | 2 | + | 120 | hypothetical protein | - none - | NA |
| fig\|6666666.609<br>66.peg.2542 | CDS | 444630 | 444508 | -3 | - | 123 | hypothetical protein | - none - | NA |
| fig\|6666666.609<br>66.peg.477 | | | | | | | | | |

FIG. 8D

| | | | | | | | | |
|---|---|---|---|---|---|---|---|---|
| fig\|6666666.609 66.peg.634 | CDS | 579242 | 579364 | 2 | + | 123 | hypothetical protein | - none - | NA |
| fig\|6666666.609 66.peg.927 | CDS | 859107 | 859229 | 3 | + | 123 | hypothetical protein | - none - | NA |
| fig\|6666666.609 66.peg.1015 | CDS | 941818 | 941940 | 1 | + | 123 | hypothetical protein | - none - | NA |
| fig\|6666666.609 66.peg.1388 | CDS | 1298114 | 1298236 | 2 | + | 123 | hypothetical protein | - none - | NA |
| fig\|6666666.609 66.peg.1755 | CDS | 1633195 | 1633073 | -1 | - | 123 | hypothetical protein | - none - | NA |
| fig\|6666666.609 66.peg.2224 | CDS | 2067753 | 2067631 | -3 | - | 123 | hypothetical protein | - none - | NA |
| fig\|6666666.609 66.peg.2271 | CDS | 2103666 | 2103788 | 3 | + | 123 | hypothetical protein | - none - | NA |
| fig\|6666666.609 66.peg.2336 | CDS | 2170340 | 2170462 | 2 | + | 123 | hypothetical protein | - none - | NA |
| fig\|6666666.609 66.peg.2415 | CDS | 2237130 | 2237008 | -3 | - | 123 | Hydroxyacylglutathione hydrolase (EC 3.1.2.6) | CBSS-228410.1.pe g.134; CBSS-342610.3.pe g.1536; Glutathione : Non-redox reactions; Methylglyox al Metabolism | NA |
| fig\|6666666.609 66.peg.82 | CDS | 79801 | 79676 | -1 | - | 126 | hypothetical protein | - none - | NA |
| fig\|6666666.609 66.peg.542 | CDS | 541998 | 542123 | 3 | + | 126 | hypothetical protein | - none - | NA |

FIG. 8E

| | | | | | | | |
|---|---|---|---|---|---|---|---|
| fig\|6666666.609 66.peg.585 | CDS | 1176741 | 1176866 | 3 | + | 126 | hypothetical protein | - none - | NA |
| fig\|6666666.609 66.peg.1268 | CDS | 1385674 | 1385799 | 1 | + | 126 | hypothetical protein | - none - | NA |
| fig\|6666666.609 66.peg.1473 | CDS | 1423155 | 1423030 | -3 | - | 126 | hypothetical protein | - none - | NA |
| fig\|6666666.609 66.peg.1510 | CDS | 1573599 | 1573474 | -3 | - | 126 | hypothetical protein | - none - | NA |
| fig\|6666666.609 66.peg.1690 | CDS | 1635456 | 1635331 | -3 | - | 126 | hypothetical protein | - none - | NA |
| fig\|6666666.609 66.peg.1758 | CDS | 1816227 | 1816352 | 3 | + | 126 | hypothetical protein | - none - | NA |
| fig\|6666666.609 66.peg.1935 | CDS | 1832788 | 1832913 | 1 | + | 126 | hypothetical protein | - none - | NA |
| fig\|6666666.609 66.peg.1966 | CDS | 2119314 | 2119439 | 3 | + | 126 | hypothetical protein | - none - | NA |
| fig\|6666666.609 66.peg.2285 | CDS | 28650 | 28522 | -3 | - | 129 | hypothetical protein | - none - | NA |
| fig\|6666666.609 66.peg.21 | CDS | 31632 | 31760 | 3 | + | 129 | hypothetical protein | - none - | NA |
| fig\|6666666.609 66.peg.27 | CDS | 231537 | 231665 | 3 | + | 129 | hypothetical protein | - none - | NA |
| fig\|6666666.609 66.peg.247 | CDS | 272364 | 272492 | 3 | + | 129 | hypothetical protein | - none - | NA |
| fig\|6666666.609 66.peg.300 | CDS | 792354 | 792226 | -3 | - | 129 | hypothetical protein | - none - | NA |
| fig\|6666666.609 66.peg.864 | CDS | 1092637 | 1092509 | -1 | - | 129 | hypothetical protein | - none - | NA |
| fig\|6666666.609 66.peg.1166 | CDS | 1216530 | 1216658 | 3 | + | 129 | hypothetical protein | - none - | NA |
| fig\|6666666.609 66.peg.1314 | | | | | | | | | |

FIG. 8F

| | | | | | | |
|---|---|---|---|---|---|---|
| fig\|6666666.609 66.peg.1730 | CDS | 1612183 | 1612311 | 1 | + | 129 | hypothetical protein | - none - | NA |
| fig\|6666666.609 66.peg.2328 | CDS | 2162434 | 2162306 | -1 | - | 129 | hypothetical protein | - none - | NA |
| fig\|6666666.609 66.peg.122 | CDS | 124194 | 124063 | -3 | - | 132 | hypothetical protein | - none - | NA |
| fig\|6666666.609 66.peg.154 | CDS | 155514 | 155645 | 3 | + | 132 | hypothetical protein | - none - | NA |
| fig\|6666666.609 66.peg.874 | CDS | 801546 | 801677 | 3 | + | 132 | hypothetical protein | - none - | NA |
| fig\|6666666.609 66.peg.894 | CDS | 823808 | 823939 | 2 | + | 132 | hypothetical protein | - none - | NA |
| fig\|6666666.609 66.peg.960 | CDS | 886681 | 886550 | -1 | - | 132 | hypothetical protein | - none - | NA |
| fig\|6666666.609 66.peg.1188 | CDS | 1108861 | 1108730 | -1 | - | 132 | hypothetical protein | - none - | NA |
| fig\|6666666.609 66.peg.1578 | CDS | 1468706 | 1468837 | 2 | + | 132 | hypothetical protein | - none - | NA |
| fig\|6666666.609 66.peg.1950 | CDS | 1824304 | 1824435 | 1 | + | 132 | hypothetical protein | - none - | NA |
| fig\|6666666.609 66.peg.1983 | CDS | 1850338 | 1850469 | 1 | + | 132 | hypothetical protein | - none - | NA |
| fig\|6666666.609 66.peg.2066 | CDS | 1923319 | 1923450 | 1 | + | 132 | hypothetical protein | - none - | NA |
| fig\|6666666.609 66.peg.2445 | CDS | 2263603 | 2263472 | -1 | - | 132 | hypothetical protein | - none - | NA |
| fig\|6666666.609 66.peg.2570 | CDS | 2376200 | 2376331 | 2 | + | 132 | hypothetical protein | - none - | NA |
| fig\|6666666.609 66.peg.296 | CDS | 267656 | 267790 | 2 | + | 135 | hypothetical protein | - none - | NA |
| fig\|6666666.609 66.peg.1080 | CDS | 1016149 | 1016015 | -1 | - | 135 | hypothetical protein | - none - | NA |

FIG. 8G

| | | | | | | |
|---|---|---|---|---|---|---|
| fig\|6666666.609<br>66.peg.1086 | CDS | 1092703 | 1092837 | 1 | + | 135 | hypothetical protein | - none - | NA |
| fig\|6666666.609<br>66.peg.1167 | CDS | 1459112 | 1459246 | 2 | + | 135 | hypothetical protein | - none - | NA |
| fig\|6666666.609<br>66.peg.1560 | CDS | 1486647 | 1486513 | -3 | - | 135 | hypothetical protein | - none - | NA |
| fig\|6666666.609<br>66.peg.1597 | CDS | 1824258 | 1824124 | -3 | - | 135 | hypothetical protein | - none - | NA |
| fig\|6666666.609<br>66.peg.1949 | CDS | 1916861 | 1916995 | 2 | + | 135 | hypothetical protein | - none - | NA |
| fig\|6666666.609<br>66.peg.2059 | CDS | 1995848 | 1995982 | 2 | + | 135 | FIG00858674: hypothetical protein | - none - | NA |
| fig\|6666666.609<br>66.peg.2151 | CDS | 2069201 | 2069335 | 2 | + | 135 | hypothetical protein | - none - | NA |
| fig\|6666666.609<br>66.peg.2230 | CDS | 2194044 | 2194178 | 3 | + | 135 | LSU ribosomal protein L34p | Cell Division Subsystem including YidCD; RNA modificatio n cluster | NA |
| fig\|6666666.609<br>66.peg.2363 | CDS | 2338623 | 2338489 | -3 | - | 135 | hypothetical protein | - none - | NA |
| fig\|6666666.609<br>66.peg.2527 | CDS | 1182314 | 1182177 | -2 | - | 138 | hypothetical protein | - none - | NA |
| fig\|6666666.609<br>66.peg.1276 | CDS | 1218021 | 1218158 | 3 | + | 138 | hypothetical protein | - none - | NA |
| fig\|6666666.609<br>66.peg.1317 | CDS | 1493209 | 1493072 | -1 | - | 138 | hypothetical protein | - none - | NA |
| fig\|6666666.609<br>66.peg.1606 | | | | | | | | | |

FIG. 8H

| | | | | | | |
|---|---|---|---|---|---|---|
| fig\|6666666.609 66.peg.1867 | CDS | 1739233 | 1739370 | 1 | + | Error-prone, lesion bypass DNA polymerase V (UmuC) | - none - | NA |
| fig\|6666666.609 66.peg.2117 | CDS | 1966387 | 1966250 | -1 | - | hypothetical protein | - none - | NA |
| fig\|6666666.609 66.peg.2227 | CDS | 2068598 | 2068735 | 2 | + | hypothetical protein | - none - | NA |
| fig\|6666666.609 66.peg.163 | CDS | 160970 | 160830 | -2 | - | hypothetical protein | - none - | NA |
| fig\|6666666.609 66.peg.173 | CDS | 168825 | 168965 | 3 | + | hypothetical protein | - none - | NA |
| fig\|6666666.609 66.peg.1286 | CDS | 1189481 | 1189521 | 2 | + | hypothetical protein | - none - | NA |
| fig\|6666666.609 66.peg.1416 | CDS | 1328534 | 1328674 | 2 | + | hypothetical protein | - none - | NA |
| fig\|6666666.609 66.peg.1422 | CDS | 1330733 | 1330873 | 2 | + | hypothetical protein | - none - | NA |
| fig\|6666666.609 66.peg.1759 | CDS | 1635699 | 1635839 | 3 | + | hypothetical protein | - none - | NA |
| fig\|6666666.609 66.peg.1775 | CDS | 1649712 | 1649572 | -3 | - | Mobile element protein | - none - | NA |
| fig\|6666666.609 66.peg.1984 | CDS | 1850712 | 1850572 | -3 | - | hypothetical protein | - none - | NA |
| fig\|6666666.609 66.peg.2003 | CDS | 1866906 | 1867046 | 3 | + | hypothetical protein | - none - | NA |
| fig\|6666666.609 66.peg.2080 | CDS | 1935668 | 1935808 | 2 | + | hypothetical protein | - none - | NA |
| fig\|6666666.609 66.peg.2487 | CDS | 2301272 | 2301132 | -2 | - | hypothetical protein | - none - | NA |
| fig\|6666666.609 66.peg.369 | CDS | 342367 | 342224 | -1 | - | hypothetical protein | - none - | NA |
| fig\|6666666.609 66.peg.609 | CDS | 579509 | 579652 | 2 | + | hypothetical protein | - none - | NA |

FIG. 8I

| | | | | | | | |
|---|---|---|---|---|---|---|---|
| fig\|6666666.609.peg.635 | CDS | 928837 | 928980 | 1 | + | 144 | hypothetical protein | - none - | NA |
| fig\|6666666.609.peg.1001 | CDS | 1524746 | 1524503 | -2 | - | 144 | hypothetical protein | - none - | NA |
| fig\|6666666.609.peg.1642 | CDS | 1962886 | 1963029 | 1 | + | 144 | hypothetical protein | - none - | NA |
| fig\|6666666.609.peg.2114 | CDS | 2391861 | 2392004 | 3 | + | 144 | hypothetical protein | - none - | NA |
| fig\|6666666.609.peg.2593 | CDS | 197036 | 196890 | -2 | - | 147 | Integrase | - none - | NA |
| fig\|6666666.609.peg.205 | CDS | 260995 | 261141 | 1 | + | 147 | hypothetical protein | - none - | NA |
| fig\|6666666.609.peg.284 | CDS | 1759287 | 1759141 | -3 | - | 147 | hypothetical protein | - none - | NA |
| fig\|6666666.609.peg.1885 | CDS | 2272001 | 2271855 | -2 | - | 147 | hypothetical protein | - none - | NA |
| fig\|6666666.609.peg.2453 | CDS | 2417974 | 2417828 | -1 | - | 147 | hypothetical protein | - none - | NA |
| fig\|6666666.609.peg.2620 | CDS | 2420545 | 2420399 | -1 | - | 150 | hypothetical protein | - none - | NA |
| fig\|6666666.609.peg.2623 | CDS | 106117 | 106266 | 1 | + | 150 | hypothetical protein | - none - | NA |
| fig\|6666666.609.peg.108 | CDS | 746234 | 746085 | -2 | - | 150 | hypothetical protein | - none - | NA |
| fig\|6666666.609.peg.813 | CDS | 1205130 | 1205279 | 3 | + | 150 | hypothetical protein | - none - | NA |
| fig\|6666666.609.peg.1296 | CDS | 1235992 | 1235843 | -1 | - | 150 | hypothetical protein | - none - | NA |
| fig\|6666666.609.peg.1334 | CDS | 2134634 | 2134485 | -2 | - | 150 | hypothetical protein | - none - | NA |
| fig\|6666666.609.peg.2300 | | | | | | | | | |

FIG. 8J

| | | | | | | | |
|---|---|---|---|---|---|---|---|
| fig\|6666666.609<br>66.peg.35 | CDS | 36062 | 35910 | -2 | - | 153 | hypothetical protein | - none - | NA |
| fig\|6666666.609<br>66.peg.1312 | CDS | 1215961 | 1216113 | 1 | + | 153 | hypothetical protein | - none - | NA |
| fig\|6666666.609<br>65.peg.2143 | CDS | 1990257 | 1990105 | -3 | - | 153 | hypothetical protein | - none - | NA |
| fig\|6666666.609<br>66.peg.359 | CDS | 335237 | 335392 | 2 | + | 156 | hypothetical protein | - none - | NA |
| fig\|6666666.609<br>66.peg.546 | CDS | 506105 | 505950 | -2 | - | 156 | FIG00858972: hypothetical protein | - none - | NA |
| fig\|6666666.609<br>66.peg.1174 | CDS | 1095978 | 1095823 | -3 | - | 156 | Mobile element protein | - none - | NA |
| fig\|6666666.609<br>66.peg.1384 | CDS | 1296435 | 1296280 | -3 | - | 156 | hypothetical protein | - none - | NA |
| fig\|6666666.609<br>65.peg.2575 | CDS | 2378324 | 2378169 | -2 | - | 156 | hypothetical protein | - none - | NA |
| fig\|6666666.609<br>66.peg.89 | CDS | 85217 | 85059 | -2 | - | 159 | hypothetical protein | - none - | NA |
| fig\|6666666.609<br>65.peg.556 | CDS | 516983 | 516825 | -2 | - | 159 | hypothetical protein | - none - | NA |
| fig\|6666666.609<br>66.peg.562 | CDS | 523304 | 523452 | 2 | + | 159 | hypothetical protein | - none - | NA |
| fig\|6666666.609<br>66.peg.1099 | CDS | 1029431 | 1029589 | 2 | + | 159 | hypothetical protein | - none - | NA |
| fig\|6666666.609<br>65.peg.1571 | CDS | 1466563 | 1466405 | -1 | - | 159 | hypothetical protein | - none - | NA |
| fig\|6666666.609<br>66.peg.613 | CDS | 562226 | 562055 | -2 | - | 162 | hypothetical protein | - none - | NA |
| fig\|6666666.609<br>66.peg.886 | CDS | 814562 | 814401 | -2 | - | 162 | hypothetical protein | - none - | NA |
| fig\|6666666.609<br>66.peg.1043 | CDS | 1043720 | 1043559 | -2 | - | 162 | hypothetical protein | - none - | NA |

FIG. 8K

| | | | | | | | |
|---|---|---|---|---|---|---|---|
| fig\|6666666.609 66.peg.1114 | CDS | | | | | - none - | NA |
| fig\|6666666.609 66.peg.291 | CDS | 265661 | 265825 | 2 | + | FIG00856904: hypothetical protein | NA |
| fig\|6666666.609 66.peg.2077 | CDS | 1934012 | 1933848 | -2 | - | hypothetical protein | NA |
| fig\|6666666.609 66.peg.620 | CDS | 568234 | 568401 | 1 | + | Methyltransferase (EC 2.1.1.-) | NA |
| fig\|6666666.609 66.peg.2317 | CDS | 2149354 | 2149521 | 1 | + | Mobile element protein | NA |
| fig\|6666666.609 66.peg.2420 | CDS | 2241817 | 2241550 | -1 | - | hypothetical protein | NA |
| fig\|6666666.609 66.peg.856 | CDS | 785317 | 785147 | -1 | - | hypothetical protein | NA |
| fig\|6666666.609 66.peg.1487 | CDS | 1401876 | 1401706 | -3 | - | FIG00858878: hypothetical protein | NA |
| fig\|6666666.609 66.peg.2286 | CDS | 2119703 | 2119873 | 2 | + | hypothetical protein | NA |
| fig\|6666666.609 66.peg.2707 | CDS | 2514260 | 2514090 | -2 | - | hypothetical protein | NA |
| fig\|6666666.609 66.peg.862 | CDS | 790885 | 790712 | -1 | - | hypothetical protein | NA |
| fig\|6666666.609 66.peg.1450 | CDS | 1360555 | 1360382 | -1 | - | Mobile element protein | NA |
| fig\|6666666.609 66.peg.1572 | CDS | 1466783 | 1466956 | 2 | + | hypothetical protein | NA |
| fig\|6666666.609 66.peg.1608 | CDS | 1494659 | 1494835 | 2 | + | hypothetical protein | NA |
| fig\|6666666.609 66.peg.2416 | CDS | 2237303 | 2237127 | -2 | - | hypothetical protein | NA |
| fig\|6666666.609 66.peg.2668 | CDS | 2479940 | 2479764 | -2 | - | hypothetical protein | NA |

FIG. 8L

| | | | | | | | |
|---|---|---|---|---|---|---|---|
| fig\|6666666.609 66.peg.748 | CDS | 694556 | 694377 | -2 | - | 180 | hypothetical protein | - none - | NA |
| fig\|6666666.609 66.peg.1667 | CDS | 1550475 | 1550296 | -3 | - | 180 | hypothetical protein | - none - | NA |
| fig\|6666666.609 66.peg.2116 | CDS | 1965779 | 1965600 | -2 | - | 180 | hypothetical protein | - none - | NA |
| fig\|6666666.609 66.peg.2144 | CDS | 1990362 | 1990541 | 3 | + | 180 | Mobile element protein | - none - | NA |
| fig\|6666666.609 66.peg.2400 | CDS | 2229074 | 2228895 | -2 | - | 180 | hypothetical protein | - none - | NA |
| fig\|6666666.609 66.peg.287 | CDS | 262264 | 262446 | 1 | + | 183 | hypothetical protein | - none - | NA |
| fig\|6666666.609 66.peg.422 | CDS | 392649 | 392831 | 3 | + | 183 | hypothetical protein | - none - | NA |
| fig\|6666666.609 66.peg.1567 | CDS | 1459862 | 1460044 | 2 | + | 183 | hypothetical protein | - none - | NA |
| fig\|6666666.609 66.peg.2388 | CDS | 2218996 | 2219178 | 1 | + | 183 | hypothetical protein | - none - | NA |
| fig\|6666666.609 66.peg.338 | CDS | 308508 | 308323 | -3 | - | 186 | hypothetical protein | - none - | NA |
| fig\|6666666.609 66.peg.1842 | CDS | 1720173 | 1719988 | -3 | - | 186 | hypothetical protein | - none - | NA |
| fig\|6666666.609 66.peg.286 | CDS | 262147 | 261959 | -1 | - | 189 | hypothetical protein | - none - | NA |
| fig\|6666666.609 66.peg.1202 | CDS | 1125016 | 1124828 | -1 | - | 189 | hypothetical protein | - none - | NA |
| fig\|6666666.609 66.peg.1304 | CDS | 1209919 | 1209731 | -1 | - | 189 | FIG00858878: hypothetical protein | - none - | NA |
| fig\|6666666.609 66.peg.2395 | CDS | 2224520 | 2224332 | -2 | - | 189 | hypothetical protein | - none - | NA |
| fig\|6666666.609 66.peg.338 | CDS | 233011 | 233202 | 1 | + | 192 | hypothetical protein | - none - | NA |

FIG. 8M

| | | | | | | |
|---|---|---|---|---|---|---|
| fig\|6666666.609.peg.250 | CDS | 729662 | 729471 | -2 | - | 192 | hypothetical protein | - none - | NA |
| fig\|6666666.609.peg.794 | CDS | 1639415 | 1639606 | 2 | + | 192 | hypothetical protein | - none - | NA |
| fig\|6666666.609.peg.1764 | CDS | 741018 | 740824 | -3 | - | 195 | hypothetical protein | - none - | NA |
| fig\|6666666.609.peg.808 | CDS | 255673 | 255870 | 1 | + | 198 | Mobile element protein | - none - | NA |
| fig\|6666666.609.peg.276 | CDS | 694591 | 694788 | 1 | + | 198 | hypothetical protein | - none - | NA |
| fig\|6666666.609.peg.749 | CDS | 2523733 | 2523536 | -1 | - | 198 | Mobile element protein | - none - | NA |
| fig\|6666666.609.peg.2718 | CDS | 203959 | 204159 | 1 | + | 201 | FIG00959622: hypothetical protein | - none - | NA |
| fig\|6666666.609.peg.217 | CDS | 631759 | 631959 | 1 | + | 201 | Cold shock protein CspA | Cold shock, CspA family of proteins | NA |
| fig\|6666666.609.peg.682 | CDS | 199189 | 199392 | 1 | + | 204 | SSU ribosomal protein S16p | - none - | NA |
| fig\|6666666.609.peg.208 | CDS | 348880 | 348677 | -1 | - | 204 | dTDP-4-dehydrorhamnose reductase (EC 1.1.1.133) | Rhamnose containing glycans; dTDP-rhamnose synthesis | NA |
| fig\|6666666.609.peg.380 | CDS | 1995706 | 1995503 | -1 | - | 204 | hypothetical protein | - none - | NA |
| fig\|6666666.609.peg.2149 | CDS | 1073050 | 1073259 | 1 | + | 210 | hypothetical protein | - none - | NA |
| fig\|6666666.609.peg.1148 | CDS | 2281343 | 2281134 | -2 | - | 210 | hypothetical protein | - none - | NA |

FIG. 8N

| | | | | | | |
|---|---|---|---|---|---|---|
| fig\|666666.609.peg.2454 | CDS | | | | | |
| fig\|666666.609.peg.522 | CDS | 484104 | 484316 | 3 | + | LSU ribosomal protein L29p (L35e) | - none - | NA |
| fig\|666666.609.peg.1481 | CDS | 1395113 | 1394901 | -2 | - | hypothetical protein | - none - | NA |
| fig\|666666.609.peg.292 | CDS | 265809 | 266024 | 3 | + | hypothetical protein | - none - | NA |
| fig\|666666.609.peg.511 | CDS | 475254 | 475459 | 3 | + | SSU ribosomal protein S12p (S23e) | Mycobacterium virulence operon involved in protein synthesis (SSU ribosomal proteins); Ribosomal protein S12p Asp methylthiotransferase | NA |
| fig\|666666.609.peg.529 | CDS | 490129 | 490347 | 1 | + | Translation initiation factor 1 | Translation initiation factors bacterial | NA |
| fig\|666666.609.peg.2374 | CDS | 2207422 | 2207640 | 1 | + | hypothetical protein | - none - | NA |
| fig\|666666.609.peg.2105 | CDS | 1956719 | 1956940 | 2 | + | hypothetical protein | - none - | NA |
| fig\|666666.609.peg.2502317 | CDS | 2502317 | 2502538 | 2 | + | hypothetical protein | - none - | NA |

FIG. 80

| | | | | | | |
|---|---|---|---|---|---|---|
| fig\|666655.609.peg.2690 | CDS | | | | | NA |
| fig\|666655.609.peg.2153 | CDS | 1996354 | 1996578 | 1 | + | 225 | hypothetical protein | - none - | NA |
| fig\|666666.609.peg.2138 | CDS | 1985283 | 1985510 | 3 | + | 228 | hypothetical protein | - none - | NA |
| fig\|666666.609.peg.442 | CDS | 405529 | 405239 | -1 | - | 231 | hypothetical protein | - none - | NA |
| fig\|666666.609.peg.1716 | CDS | 1598000 | 1597770 | -2 | - | 231 | hypothetical protein | - none - | NA |
| fig\|666666.609.peg.2439 | CDS | 2259000 | 2258770 | -3 | - | 231 | hypothetical protein | - none - | NA |
| fig\|666666.609.peg.1111 | CDS | 1042874 | 1043110 | 2 | + | 237 | Mobile element protein | - none - | NA |
| fig\|666666.609.peg.1999 | CDS | 1865704 | 1865468 | -1 | - | 237 | hypothetical protein | - none - | NA |
| fig\|666666.609.peg.1214 | CDS | 1136308 | 1136069 | -1 | - | 240 | hypothetical protein | - none - | NA |
| fig\|666666.609.peg.1733 | CDS | 1614273 | 1614031 | -3 | - | 243 | hypothetical protein | - none - | NA |
| fig\|666666.609.peg.48 | CDS | 47253 | 47498 | 3 | + | 246 | Alpha-L-Rha alpha-1,3-L-rhamnosyltransferase (EC 2.4.1.-) | Rhamnose containing glycans | NA |
| fig\|666666.609.peg.423 | CDS | 393586 | 393338 | -1 | - | 249 | Mobile element protein | - none - | NA |
| fig\|666666.609.peg.429 | CDS | 396754 | 396506 | -1 | - | 249 | Transglycosylase-associated protein | - none - | NA |
| fig\|666666.609.peg.1147 | CDS | 1072594 | 1072842 | 1 | + | 249 | hypothetical protein | - none - | NA |
| fig\|666666.609.peg.1951 | CDS | 1824656 | 1824408 | -2 | - | 249 | Plasmid stabilization system protein | - none - | NA |

FIG. 8P

| | | | | | | |
|---|---|---|---|---|---|---|
| fig\|6666666.609 66.peg.2579 | CDS | 2380195 | 2380446 | 1 | + | 252 | Mobile element protein | - none - | NA |
| fig\|6666666.609 66.peg.523 | CDS | 484294 | 484548 | 1 | + | 255 | SSU ribosomal protein S17p (S11e) | - none - | NA |
| fig\|6666666.609 66.peg.1022 | CDS | 948522 | 948782 | 3 | + | 261 | Stringent starvation protein B | Carbon Starvation | NA |
| fig\|6666666.609 66.peg.1957 | CDS | 1826664 | 1826936 | 3 | + | 273 | hypothetical protein | - none - | NA |
| fig\|6666666.609 66.peg.2273 | CDS | 2108052 | 2108336 | 3 | + | 285 | putative DNA transport competence protein | - none - | NA |
| fig\|6666666.609 66.peg.46 | CDS | 46807 | 46481 | -1 | - | 327 | Conserved domain protein | - none - | NA |
| fig\|6666666.609 66.peg.2109 | CDS | 1959886 | 1960239 | 1 | + | 354 | hypothetical protein | - none - | NA |
| fig\|6666666.609 66.peg.2429 | CDS | 2248841 | 2248488 | -2 | - | 354 | hypothetical protein | - none - | NA |
| fig\|6666666.609 66.peg.1579 | CDS | 1468834 | 1469334 | 1 | + | 501 | hypothetical protein | - none - | NA |
| fig\|6666666.609 66.peg.293 | CDS | 266114 | 266689 | 2 | + | 576 | hypothetical protein | - none - | NA |

FIG. 9

Neut_0005, Neut_0007, Neut_0008, Neut_0009, Neut_0019, Neut_0020, Neut_0023, Neut_0028, Neut_0031, Neut_0032, Neut_0033,
Neut_0034, Neut_0035, Neut_0036, Neut_0039, Neut_0042, Neut_0044, Neut_0046, Neut_0048, Neut_0052, Neut_0053, Neut_0069,
Neut_0070, Neut_0071, Neut_0072, Neut_0073, Neut_0074, Neut_0075, Neut_0076, Neut_0077, Neut_0080, Neut_0082, Neut_0083,
Neut_0085, Neut_0086, Neut_0087, Neut_0088, Neut_0089, Neut_0090, Neut_0091, Neut_0093, Neut_0094, Neut_0096, Neut_0097,
Neut_0098, Neut_0099, Neut_0100, Neut_0101, Neut_0102, Neut_0103, Neut_0104, Neut_0106, Neut_0107, Neut_0109, Neut_0110,
Neut_0111, Neut_0112, Neut_0113, Neut_0114, Neut_0115, Neut_0118, Neut_0119, Neut_0120, Neut_0121, Neut_0125, Neut_0126,
Neut_0154, Neut_0155, Neut_0157, Neut_0158, Neut_0161, Neut_0354, Neut_0358, Neut_0359, Neut_0365, Neut_0366, Neut_0368,
Neut_0538, Neut_0539, Neut_0577, Neut_0581, Neut_0585, Neut_0617, Neut_0627, Neut_0632, Neut_0633, Neut_0636, Neut_0665,
Neut_0666, Neut_0667, Neut_0668, Neut_0669, Neut_0670, Neut_0671, Neut_0672, Neut_0673, Neut_0674, Neut_0675, Neut_0676,
Neut_0677, Neut_0678, Neut_0679, Neut_0680, Neut_0693, Neut_0737, Neut_0738, Neut_0880, Neut_0885, Neut_0904, Neut_0984,
Neut_1012, Neut_1013, Neut_1014, Neut_1015, Neut_1016, Neut_1057, Neut_1058, Neut_1060, Neut_1062, Neut_1065, Neut_1066,
Neut_1068, Neut_1073, Neut_1075, Neut_1084, Neut_1115, Neut_1120, Neut_1121, Neut_1122, Neut_1123, Neut_1124, Neut_1125,
Neut_1305, Neut_1306, Neut_1307, Neut_1308, Neut_1310, Neut_1311, Neut_1312, Neut_1314, Neut_1319, Neut_1320, Neut_1322,
Neut_1324, Neut_1327, Neut_1334, Neut_1335, Neut_1367, Neut_1369, Neut_1370, Neut_1372, Neut_1399, Neut_1414, Neut_1476,
Neut_1482, Neut_1484, Neut_1485, Neut_1487, Neut_1490, Neut_1597, Neut_1674, Neut_1725, Neut_1728, Neut_1731, Neut_1733,
Neut_1755, Neut_1758, Neut_1759, Neut_1818, Neut_1820, Neut_1846, Neut_1919, Neut_1948, Neut_1980, Neut_2111, Neut_2114,
Neut_2150, Neut_2153, Neut_2200, Neut_2201, Neut_2212, Neut_2215, Neut_2216, Neut_2217, Neut_2218, Neut_2219, Neut_2220,
Neut_2221, Neut_2222, Neut_2223, Neut_2224, Neut_2225, Neut_2226, Neut_2227, Neut_2228, Neut_2229, Neut_2230, Neut_2231,
Neut_2252, Neut_2253, Neut_2254, Neut_2255, Neut_2256, Neut_2257, Neut_2258, Neut_2259, Neut_2260, Neut_2261, Neut_2262,
Neut_2263, Neut_2264, Neut_2265, Neut_2266, Neut_2352, Neut_2353, Neut_2354, Neut_2356, Neut_2411, Neut_2412, Neut_2416,
Neut_2504, Neut_2505, Neut_2533, Neut_2533a, Neut_2534, Neut_2535, Neut_2536, Neut_2540, Neut_2541, Neut_2543, Neut_2547,
Neut_2549, Neut_2551, Neut_2554, Neut_2558, Neut_2559, Neut_2560, Neut_2561, Neut_2562, Neut_2564, Neut_2565, Neut_2566,
Neut_2568, Neut_2569, Neut_2570, Neut_2571, Neut_2572, Neut_2573, Neut_2574, Neut_2576, Neut_2578, Neut_2579, Neut_2582,
Neut_2583, Neut_2585, Neut_2588, Neut_2589, Neut_2590, Neut_2593, Neut_2595, Neut_2596, Neut_2597, Neut_2598, Neut_2599,
Neut_2602, Neut_2603, Neut_2607, Neut_2609, Neut_2612, Neut_2613, Neut_2614, Neut_2617, Neut_2618, Neut_2619, Neut_2620,
Neut_2621, Neut_2623, Neut_2625, Neut_2626, Neut_2627, Neut_2628, Neut_2629, Neut_2630, Neut_2631, Neut_2632, Neut_2633,
Neut_2634, Neut_2635, Neut_2638, Neut_2639, Neut_2641, rplN, rplQ, rplR, rplV, rpmD, rpmI, rpsH, rpsM, rpsN.

FIG. 10

CLUSTAL 2.1 multiple sequence alignment

```
D23-amoA1      VSIFRTEEILKAAKMPPEAVHMSRLIDAVYFPILVVTLIVGTYHMHFMLLAGDWDFWMDWK  60
D23-amoA2      VSIFRTEEILKAAKMPPEAVHMSRLIDAVYFPILVVTLIVGTYHMHFMLLAGDWDFWMDWK  60
C91-amoA1      MSIFRTEEILKAAKMPPEAVHMSRLIDAVYFPILVVTLIVGTYHMHFMLLAGDWDFWMDWK  60
C91-amoA2      MSIFRTEEILKAAKMPPEAVHMSRLIDAVYFPILVVTLIVGTYHMHFMLLAGDWDFWMDWK  60
               :***********************************************************

D23-amoA1      DRQWWPVVTPIVGITYCSAIMYYLWVNYRQPFGATLCVVCLLIGEWLTRYWGFYWWSHYP  120
D23-amoA2      DRQWWPVVTPIVGITYCSAIMYYLWVNYRQPFGATLCVVCLLIGEWLTRYWGFYWWSHYP  120
C91-amoA1      DRQWWPYVTPIVGITYCSAIMYYLWVNYRQPFGATLCVVCLLIGEWLTRYWGFYWWSHYP  120
C91-amoA2      DRQWWPYVTPIVGITYCSAIMYYLWVNYRQPFGATLCVVCLLIGEWLTRYWGFYWWSHYP  120
               *****:******************************************************

D23-amoA1      LNFVTPGIMLPGALMLDFTMYLTRNWLVTALVGGGFFGLLFYPGNWAIFGPTHLPIVVEG  180
D23-amoA2      LNFVTPGIMLPGALMLDFTMYLTRNWLVTALVGGGFFGLLFYPGNWAIFGPTHLPIVVEG  180
C91-amoA1      LNFVTPGIMLPGALMLDFTMYLTRNWLVTALVGGGFFGLMFYPGNWPIFGPTHLPIVVEG  180
C91-amoA2      LNFVTPGIMLPGALMLDFTMYLTRNWLVTALVGGGFFGLMFYPGNWPIFGPTHLPIVVEG  180
               ***************************************:*****.*************

D23-amoA1      TLLSMADYMGHLYVRTGTPEYVRHIEQGSLRTFGGHTTVIAAFFAAFVSMLMPAVWWYLG  240
D23-amoA2      TLLSMADYMGHLYVRTGTPEYVRHIEQGSLRTFGGHTTVIAAFFAAFVSMLMPAVWWYLG  240
C91-amoA1      TLLSMADYMGHLYVRTGTPEYVRHIEQGSLRTFGGHTTVIAAFFAAFVSMLMPAVWWYLG  240
C91-amoA2      TLLSMADYMGHLYVRTGTPEYVRHIEQGSLRTFGGHTTVIAAFFAAFVSMLMPAVWWYLG  240
               ************************************************************

D23-amoA1      KVYCTAFFYVKGKRGRIVQRNDVTAFGEEGFPEGIK  276
D23-amoA2      KVYCTAFFYVKGKRGRIVQRNDVTAFGEEGFPEGIK  276
C91-amoA1      KVYCTAFFYVKGKRGRIVQRNDVTAFGEEGFPEGIK  276
C91-amoA2      KVYCTAFFYVKGKRGRIVQRNDVTAFGEEGFPEGIK  276
               ************************************
```

```
C91-amoC3  MATNILKDKAAQQVADEPTYDSEWFDAKYYKFGLLPILAVAVMWVYFQRTYAYSHGMDS 60
D23-amoC3  MATNILKDKAAQQVADEPTYDKSEWFDAKYYKFGLLPILAVAVMWVYFQRTYAYSHGMDS 60
           *********************:**************************************

C91-amoC3  MEPEFDRIWMGLNRVQMAVLPLIALFTWGWLYKTRWTAEQLANLTPKQEIKRYFYFLMWL 120
D23-amoC3  MEPEFDRIWMGLNRVQMAALPLIALFTWGWLYKTRNTAEQLANLTPKQEIKRYFYFLMWL 120
           ******************:****************: ************************

C91-amoC3  GVYIFAVYWGSSFFTEQDASWHQVIIRDTSFTPSHIPLFYGSFPVYIIMGVSMIIYANTR 180
D23-amoC3  GVYIFAVYWGSSFFTEQDASWHQVIIRDTSFTPSHIPLFYGSFPVYIIMGVSMIIYANTR 180
           ************************************************************

C91-amoC3  LPLYNKGWSFPLIMTVAGPLMSLPNVGLNEWGHAFWFMEELFSAPLHWGFVILAWAALFQ 240
D23-amoC3  LPLYNKGWSFPLIMTVAGPLMSLPNVGLNEWGHAFWFMEELFSAPLHWGFVILAWAALFQ 240
           ************************************************************

C91-amoC3  GGLAVQIIARFSNLLDVEWNKQDRAILDDVITAP 274
D23-amoC3  GGLAVQIIARFSNLLDVEWNKQDRAILDDVVTAP 274
           *****************************:****
```

FIG. 14A

```
D23-hao2    MRIGEYLKGMILCAGLLLIGPVQADISTVFDETYEALKLQRSKATPKETYDALVKRYKDP   60
D23-hao3    MRIGEYLKGMILCAGLLLIGPVQADISTVFDETYEALKLQRSKATPKETYDALVKRYKDP   60
D23-hao1    MRIGEYLKGMILCAGLLLIGPVQADISTVFDETYEALKLQRSKATPKETYDALVKRYKDP   60
C91-hao2    MRIGEYLKGMILCAGLLLIGPVQADISTVFDETYEALKLQRSKATPKETYDALVKRYKDP   60
C91-hao3    MRIGEYLKGMILCAGLLLIGPVQADISTVFDETYEALKLQRSKATPKETYDALVKRYKDP   60
C91-hao1    MRIGEYLKGMILCAGLLLIGPVQADISTVFDETYEALKLQRSKATPKETYDALVKRYKDP   60
            ************************************************************

D23-hao2    AHGAGKGTMGDYWEPIALSIYMDPSHFYKPPVSPKEIAERKDCVECHSDETPVWVRAWKR  120
D23-hao3    AHGAGKGTMGDYWEPIALSIYMDPSTFYKPPVSPKEIAERKDCVECHSDETPVWVRAWKR  120
D23-hao1    AHGAGKGTMGDYWEPIALSIYMDPSTFYKPPVSPKEIAERKDCVECHSDETPVWVRAWKR  120
C91-hao2    AHGAGKGTMGDYWEPIALSIYMDPNTFYKPPVSPKEIAERKDCVECHSDETPVWVRAWKR  120
C91-hao3    AHGAGKGTMGDYWEPIALSIYMDPNTTYKPPVSPKEIAERKDCVECHSDETPVWVRAWKR  120
C91-hao1    AHGAGKGTMGDYWEPIALSIYMDPNTTYKPPVSPKEIAERKDCVECHSDETPVWVRAWKR  120
            ************************:.*****************************:****

D23-hao2    STHANLDKIRNLKPEDPLFYKKGKLEEVENMLRSMGKLGEKEALKEVGCIDCHVDINAKK  180
D23-hao3    STHANLDKIRNLKPEDPLFYKKGKLEEVENMLRSMGKLGEKEALKEVGCIDCHVDINAKK  180
D23-hao1    STHANLDKIRNLKPEDPLFYKKGKLEEVENMLRSMGKLGEKEALKEVGCIDCHVDINAKK  180
C91-hao2    STHANLDKIRNLKPEDPLFYKKGKLEEVENMLRSMGKLGEKEALKEVGCIDCHVDINAKK  180
C91-hao3    STHANLDKIRNLKPEDPLFYKKGKLEEVENMLRSMGKLGEKEVLKEVGCIDCHVDINAKK  180
C91-hao1    STHANLDKIRNLKPEDPLFYKKGKLEEVENMLRSMGKLGEKEVLKEVGCIDCHVDINAKK  180
            ******************************************:***************

D23-hao2    KADHTKDVRMPTADVCGTCHLREFAERESERDTMIWPNGQWPDGRPSHALDYTANIETTV  240
D23-hao3    KADHTKDVRMPTADVCGTCHLREFAERESERDTMIWPNGQWPDGRPSHALDYTANIETTV  240
D23-hao1    KADHTKDVRMPTADVCGTCHLREFAERESERDTMIWPNGQWPDGRPSHALDYTANIETTV  240
C91-hao2    KADHTKDVRMFTADVCGTCHLREFAERESERDTMIWPNGQWPDGRPSHALDYTANIETTV  240
C91-hao3    KADHTKDVRMFTADVCGTCHLREFAERESERDTMIWPNGQWPDGRPSHALDYTANIETTV  240
C91-hao1    KADHTKDVRMFTADVCGTCHLREFAERESERDTMIWPNGQWPDGRPSHALDYTANIETTV  240
            **********:*************************************************

D23-hao2    WAAMPQREVAEGCTMCHTNQMKCDNCHTRHEFSAAESRKFEACATCHSGVDHMNYEAYIM  300
D23-hao3    WAAMPQREVAEGCTMCHTNQMKCDNCHTRHEFSAAESRKFEACATCHSGVDHMNYEAYIM  300
D23-hao1    WAAMPQREVAEGCTMCHTNQMKCDNCHTRHEFSAAESRKFEACATCHSGVDHMNYEAYIM  300
C91-hao2    WAAMPQREVAEGCTMCHTNQMKCDNCHTRHEFSAAESRKFEACATCHSGVDHMNYEAYIM  300
C91-hao3    WAAMPQREVAEGCTMCHTNQMKCDNCHTRHEFSAAESRKFEACATCHSGVDHMNYEAYIM  300
C91-hao1    WAAMPQREVAEGCTMCHTNQMKCDNCHTRHEFSAAESRKFEACATCHSGVDHMNYEAYIM  300
            ************************************************************
```

```
D23-cycB1  MTRLQKGSIGTLLTGALLGIALVAVFGGEAALSTREFCTSCHSMSYPQSELKESTHYGA  60
D23-cycB2  MTRLQKGSIGTLLTGALLGIALVAVFGGEAALSTREFCTSCHSMSYPQSELKESTHYGA  60
C91-cycB1  MTRLQKGSIGTLLTGALLGIALVAVFGGEAALSTREFCTSCHSMSYPQSELKESTHYGA  60
C91-cycB2  MTRLQKGSIGTLLTGALLGIALVAVFGGEAALSTREFCTSCHSMSYPQSELKESTHYGA  60
           ************************************************************

D23-cycB1  LGVNPTCKDCHIPQGIENFHLAVATHVVDGARELWLEMVNDYSTLEKFNERRLEMAHDAR  120
D23-cycB2  LGVNPTCKDCHIPQGIENFHLAVATHVVDGARELWLEMVNDYSTLEKFNERRLEMAHDAR  120
C91-cycB1  LGINPTCKDCHIPQGIENFHLAVATHVVDGARELWLEMVNDYSTLEKFNERRLEMAHDAR  120
C91-cycB2  LGINPTCKDCHIPQGIENFHLAVATHVVDGARELWLEMVNDYSTLEKFNERRLEMAHDAR  120
           ** *********************************************************

D23-cycB1  MNLKKWDSITCRTCHVKPAPPGESAQAEHKKMETEGATCIDCHQNLVHEEAPMTDLNASL  180
D23-cycB2  MNLKKWDSITCRTCHVKPAPPGESAQAEHKKMETEGATCIDCHQNLVHEEAPMTDLNASL  180
C91-cycB1  MNLKKWDSITCRTCHVKPAPPGESAQAEHKKMETEGATCIDCHQNLVHEEAPMTDLNASL  180
C91-cycB2  MNLKKWDSITCRTCHVKPAPPGESAQAEHKKMETEGATCIDCHQNLVHEEAPMTDLNASL  180
           ************************************************************

D23-cycB1  AAGKLVLKPEEGDGDDDDDDDDVDDEEEDEEVEVEVEETETADDSDSASSNHDDDSDDE  239
D23-cycB2  AAGKLVLKPEEGDDDDDDDDDVDDEEEDEEVEVEVEETETADDSDSASSNHDDDSDDE  239
C91-cycB1  AAGKLVLKSEEGDD---DVDDVDDE--DEEVEVEVEETETADDSDSASSNHDDDSDDE  234
C91-cycB2  AAGKLVLKSEEGDDDDDVDDVDDE---DEEVEVEVEETETADDSDSASSNHDDDSDDE  237
           ******** ****         *  .  ** ***************************
```

AMMONIA-OXIDIZING *NITROSOMONAS EUTROPHA* STRAIN D23

CROSS-REFERENCE TO RELATED APPLICATIONS

This application is a Continuation of U.S. patent application Ser. No. 16/856,789 titled AMMONIA-OXIDIZING *NITROSOMONAS EUTROPHA* STRAIN D23 filed on Apr. 23, 2020, which is a Continuation of U.S. patent application Ser. No. 16/596,694 titled AMMONIA-OXIDIZING *NITROSOMONAS EUTROPHA* STRAIN D23 filed on Oct. 8, 2019, which is a Continuation of U.S. patent application Ser. No. 15/304,151 titled AMMONIA-OXIDIZING *NITROSOMONAS EUTROPHA* STRAIN D23 filed on Oct. 14, 2016, which is a U.S. national phase application under 35 U.S.C. § 371 of International (PCT) Patent Application Serial No. PCT/US2015/025909 titled AMMONIA-OXIDIZING *NITROSOMONAS EUTROPHA* STRAIN D23 filed on Apr. 15, 2015, which in turn claims priority to Greek Patent Application Number 20140100217, filed Apr. 15, 2014, U.S. Provisional Application No. 62/002,084, filed May 22, 2014, U.S. Provisional Application No. 62/012,811, filed Jun. 16, 2014, U.S. Provisional Application No. 62/053,588, filed Sep. 22, 2014, and Greek Patent Application Number 20150100115, filed Mar. 13, 2015, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Apr. 13, 2015, is named N2060-7001WO.txt and is 3,590,980 bytes in size.

BACKGROUND

Beneficial bacteria can be used to suppress the growth of pathogenic bacteria. Bacteria and other microorganisms are ubiquitous in the environment. The discovery of pathogenic bacteria and the germ theory of disease have had a tremendous effect on health and disease states. Bacteria are a normal part of the environment of all living things. In the gut, these bacteria are not pathogenic under normal conditions, and in fact improve health by rendering the normal intestinal contents less hospitable for disease causing organisms. Disease prevention is accomplished in a number of ways: nutrients are consumed, leaving less for pathogens; conditions are produced, such as pH and oxygen tension, which are not hospitable for pathogens; compounds are produced that are toxic to pathogens; pathogens are consumed as food by these microorganisms; less physical space remains available for pathogens; and specific binding sites are occupied leaving fewer binding sites available for pathogens. The presence of these desirable bacteria is seen as useful in preventing disease states.

There is a need in the art for improved beneficial bacteria that can suppress the growth of pathogenic bacteria.

SUMMARY

This disclosure provides, inter alia, an optimized strain of *Nitrosomonas eutropha* (*N. eutropha*) designated D23, D23-100 or AOB D23-100, the terms which may be used interchangeably throughout the disclosure.

Ammonia oxidizing bacterial of the genus *Nitrosomonas* are ubiquitous Gram-negative obligate chemolithoautotrophic bacteria with a unique capacity to generate energy exclusively from the conversion of ammonia to nitrite.

*N. eutropha* bacteria disclosed in this application have desirable, e.g. optimized, properties such as the ability to suppress growth of pathogenic bacteria, and an enhanced ability to produce nitric oxide (NO) and nitric oxide ($NO_2^-$) precursors. The *N. eutropha*, e.g., optimized *N. eutropha*, e.g., purified preparations of optimized *N. eutropha* herein may be used, for instance, to treat diseases, e.g., diseases associated with low nitrite levels, skin disorders, and diseases caused by pathogenic bacteria. When referring to *N. eutropha* throughout the disclosure, it may be referring to an optimized strain of *N. eutropha* or a purified preparation of optimized *N. eutropha*.

The present disclosure provides, inter alia, a *Nitrosomonas eutropha* (*N. eutropha*) bacterium, e.g., an optimized *N. eutropha*, e.g., a purified preparation of optimized *N. eutropha*, having at least one property selected from:

an optimized growth rate;
an optimized $NH_4^+$ oxidation rate; and
an optimized resistance to ammonium ion ($NH_4^+$).

The bacterium is optionally axenic.

In embodiments, the optimized growth rate is a rate allowing a continuous culture of *N. eutropha* at an OD600 (optical density at 600 nm) of about 0.15-0.18 to reach an OD600 of about 0.5-0.6 in about 1-2 days. In embodiments, optimized growth rate is a doubling time of about 8 hours when cultured under batch culture conditions. In embodiments, the optimized $NH_4^+$ oxidation rate is a rate of at least about 125 micromoles per minute of oxidizing $NH_4^+$ to $NO_2^+$. In embodiments, the optimized resistance to $NH_4^+$ is an ability to grow in medium comprising about 200 mM $NH_4^+$ for at least about 48 hours.

In some embodiments, the purified preparation of optimized *N. eutropha* bacterium (which is optionally axenic) has at least two properties selected from an optimized growth rate, an optimized $NH_4^+$ oxidation rate, and an optimized resistance to $NH_4^+$. In some embodiments, the purified preparation of optimized *N. eutropha* bacterium (which is optionally axenic) has an optimized growth rate, an optimized $NH_4^-$ oxidation rate, and an optimized resistance to $NH_4^+$. In some embodiments, the purified preparation of optimized *N. eutropha* bacterium (which is optionally axenic) comprises a chromosome that hybridizes under very high stringency to SEQ ID NO: 1.

In some embodiments, the purified preparation of optimized *N. eutropha* bacterium (which is optionally axenic) comprises an AmoA protein having an identity to SEQ ID NO: 6 or 12 selected from at least about 80%, 85%, 90%, 95%, 98%, 99%, 99.5%, and 100% identical, an AmoB protein having an identity to SEQ ID NO: 8 or 14 selected from at least about 80%, 85%, 90%, 95%, 98%, 99%, 99.5%, and 100% identical, an amoC gene having an identity to SEQ ID NO: 4, 10, or 16 selected from at least about 80%, 85%, 90%, 95%, 98%, 99%, 99.5%, and 100% identical, a hydroxylamine oxidoreductase protein having an identity to SEQ ID NO: 18, 20, or 22 selected from at least 80%, 85%, 90%, 95%, 98%, 99%, 99.5%, and 100% identical, a cytochrome c554 protein having an identity to SEQ ID NO: 24, 26, or 28 selected from at least about 80%, 85%, 90%, 95%, 98%, 99%, 99.5%, and 100% identical, or a cytochrome $c_M$552 protein having an identity to SEQ ID NO: 30 or 32 selected from at least about 80%, 85%, 90%, 95%, 98%, 99%, 99.5%, and 100% identical.

In some embodiments, the purified preparation of optimized *N. eutropha* bacterium (which is optionally axenic) comprises 1-5, 5-10, 10-15, 15-20, 20-25, 25-30, or all of the sequence characteristics of Table 2. For instance, in some embodiments, the bacterium or preparation comprises an AmoA1 or AmoA2 protein having (or gene encoding) a mutation relative to *N. eutropha* strain C91 at position 1, e.g., a V at position 1. In some embodiments, the bacterium or preparation comprises an AmoA1 or AmoA2 protein having (or gene encoding) a mutation relative to *N. eutropha* strain C91 at position 160, e.g., an L at position 160. In some embodiments, the bacterium or preparation comprises an AmoA1 or AmoA2 protein having (or gene encoding) a mutation relative to *N. eutropha* strain C91 at position 167, e.g., an A at position 167. In some embodiments, the bacterium or preparation comprises an AmoB1 or AmoB2 protein having (or gene encoding) a mutation relative to *N. eutropha* strain C91 at position 33, e.g., a V at position 33. In some embodiments, the bacterium or preparation comprises an AmoB1 or AmoB2 protein having (or gene encoding) a mutation relative to *N. eutropha* strain C91 at position 165, e.g., an I at position 165. In some embodiments, the bacterium or preparation comprises an AmoC3 protein having (or gene encoding) a mutation relative to *N. eutropha* strain C91 at position 79, e.g., an A at position 79. In some embodiments, the bacterium or preparation comprises an AmoC3 protein having (or gene encoding) a mutation relative to *N. eutropha* strain C91 at position 271, e.g., a V at position 271. In some embodiments, the bacterium or preparation comprises a Hao1, Hao2, or Hao3 protein having (or gene encoding) a mutation relative to *N. eutropha* strain C91 at position 85, e.g., an S at position 85. In some embodiments, the bacterium or preparation comprises a Hao1, Hao2, or Hao3 protein having (or gene encoding) a mutation relative to *N. eutropha* strain C91 at position 312, e.g., an E at position 312. In some embodiments, the bacterium or preparation comprises a Hao1 protein having (or gene encoding) a mutation relative to *N. eutropha* strain C91 at position 163, e.g., an A at position 163. In some embodiments, the bacterium or preparation comprises a c554 CycA1, c554 CycA2, or c554 CycA3 protein having (or gene encoding) a mutation relative to *N. eutropha* strain C91 at position 65, e.g., a T at position 65. In some embodiments, the bacterium or preparation comprises a c554 CycA1 protein having (or gene encoding) a mutation relative to *N. eutropha* strain C91 at position 186, e.g., a T at position 186. In some embodiments, the bacterium or preparation comprises a $c_M552$ CycB1 or $c_M552$ CycB2 protein having (or gene encoding) a mutation relative to *N. eutropha* strain C91 at position 63, e.g., a V at position 63. In some embodiments, the bacterium or preparation comprises a $c_M552$ CycB1 or $c_M552$ CycB2 protein having (or gene encoding) a mutation relative to *N. eutropha* strain C91 at position 189, e.g., a P at position 189. In some embodiments, the bacterium or preparation comprises a $c_M552$ CycB1 or $c_M552$ CycB2 protein having (or gene encoding) a mutation relative to *N. eutropha* strain C91 at position 206, e.g., an insE at position 206. In some embodiments, the bacterium or preparation comprises a $c_M552$ CycB1 or $c_M552$ CycB2 protein having (or gene encoding) a mutation relative to *N. eutropha* strain C91 at position 207, e.g., an insE at position 207. In some embodiments, the bacterium or preparation comprises a $c_M552$ CycB1 protein having (or gene encoding) a mutation relative to *N. eutropha* strain C91 at position 195, e.g., an insD at position 195. In some embodiments, the bacterium or preparation comprises a $c_M552$ CycB1 protein having (or gene encoding) a mutation relative to *N. eutropha* strain C91 at position 196, e.g., an insD at position 196. In some embodiments, the bacterium or preparation comprises a $c_M552$ CycB1 protein having (or gene encoding) a mutation relative to *N. eutropha* strain C91 at position 197, e.g., an insD at position 197.

Combinations of two or more sequence characteristics of Table 2 are also described. The two or more sequence characteristics may be in the same gene or different genes. The two or more sequence characteristics may be in the same protein or different proteins. For instance, in some embodiments, the bacterium or preparation comprises an AmoA1 or AmoA2 protein having (or gene encoding) a mutation relative to *N. eutropha* strain C91 at position 1, e.g., a V at position 1 and a mutation relative to *N. eutropha* strain C91 at position 160, e.g., an L at position 160. In some embodiments, the bacterium or preparation comprises an AmoA1 or AmoA2 protein having (or gene encoding) a mutation relative to *N. eutropha* strain C91 at position 1, e.g., a V at position 1 and a mutation relative to *N. eutropha* strain C91 at position 167, e.g., an A at position 167. In some embodiments, the bacterium or preparation comprises an AmoA1 or AmoA2 protein having (or gene encoding) a mutation relative to *N. eutropha* strain C91 at position 160, e.g., an L at position 160 and a mutation relative to *N. eutropha* strain C91 at position 167, e.g., an A at position 167.

In some embodiments, the bacterium or preparation comprises an AmoB1 or AmoB2 protein having (or gene encoding) a mutation relative to *N. eutropha* strain C91 at position 33, e.g., a V at position 33 and a mutation relative to *N. eutropha* strain C91 at position 165, e.g., an I at position 165.

In some embodiments, the bacterium or preparation comprises an AmoC3 protein having (or gene encoding) a mutation relative to *N. eutropha* strain C91 at position 79, e.g., an A at position 79 and a mutation relative to *N. eutropha* strain C91 at position 271, e.g., a V at position 271.

In some embodiments, the bacterium or preparation comprises a Hao1, Hao2, or Hao3 protein having (or gene encoding) a mutation relative to *N. eutropha* strain C91 at position 85, e.g., an S at position 85 and a mutation relative to *N. eutropha* strain C91 at position 312, e.g., an E at position 312. In some embodiments, the bacterium or preparation comprises a Hao1 protein having (or gene encoding) a mutation relative to *N. eutropha* strain C91 at position 85, e.g., an S at position 85 and a mutation relative to *N. eutropha* strain C91 at position 163, e.g., an A at position 163. In some embodiments, the bacterium or preparation comprises a Hao1 protein having (or gene encoding) a mutation relative to *N. eutropha* strain C91 at position 312, e.g., an E at position 312 and a mutation relative to *N. eutropha* strain C91 at position 163, e.g., an A at position 163.

In some embodiments, the bacterium or preparation comprises a c554 CycA1 protein having (or gene encoding) a mutation relative to *N. eutropha* strain C91 at position 65, e.g., a T at position 65 and a mutation relative to *N. eutropha* strain C91 at position 186, e.g., a T at position 186.

In some embodiments, the bacterium or preparation comprises a $c_M552$ CycB1 protein having (or gene encoding) mutations at any two or more of the following amino acid positions: 63, 189, 194, 195, 196, 197, 206, and 207. For instance, the two or more amino acid positions may comprise: 63 and 189, 63 and 194, 63 and 195, 63 and 196, 63 and 197, 63 and 206, 63 and 207, 189 and 194, 189 and 195, 189 and 196, 189 and 194, 189 and 195, 189 and 196, 189 and 197, 189 and 206, 189 and 207, 194 and 195, 194 and 196, 194 and 197, 194 and 206, 194 and 207, 195 and 196, 195 and 197, 195 and 206, 195 and 207, 196 and 197, 196 and 206, 196 and 207, 197 and 206, 197 and 207, or 206 and 207. In some embodiments, the bacterium or preparation comprises a $c_M$552 CycB1 protein having (or gene encoding) any two or more mutations selected from the group consisting of: I63V, S189P, D194G, 195insD, 196insD, 197insD, 206insE, and 207insE. For instance, the two or more mutations can be selected from the group consisting of: I63V and S189P, I63V and D194G, I63V and 195insD, I63V and 196insD, I63V and 197insD, I63V and 206insE, I63V and 207insE, S189P and D194G, S189P and 195insD, S189P and 196insD, S189P and 197insD, S189P and 206insE, S189P and 207insE, D194G and 195insD, D194G and 196insD, D194G and 197insD, D194G and 206insE, D194G and 207insE, 195insD and 196insD, 195insD and 197insD, 195insD and 206insE, 195insD and 207insE, 196insD and 197insD, 196insD and 206insE, 196insD and 207insE, 197insD and 206insE, 197insD and 207insE, and 206insE and 207insE.

In some embodiments, the bacterium or preparation comprises a $c_M$552 CycB2 protein having (or gene encoding) mutations at any two or more of the following amino acid positions: 63, 189, 206, and 207. For instance, the two or more amino acid positions may comprise: 63 and 189, 63 and 206, 63 and 207, 189 and 206, 189 and 207, or 206 and 207. In some embodiments, the bacterium or preparation comprises a $c_M$552 CycB2 protein having (or gene encoding) any two or more mutations selected from the group consisting of: I63V, S189P, 206insE, and 207insE. For instance, the two or more mutations can be selected from the group consisting of: I63V and S189P, I63V and 206insE, I63V and 207insE, S189P and 206insE, S189P and 207insE, and 206insE and 207insE.

Combinations of three or more sequence characteristics of Table 2 are also described. For instance, in some embodiments, the bacterium or preparation comprises an AmoA1 or AmoA2 protein having (or gene encoding) a mutation relative to N. eutropha strain C91 at position 1, e.g., a V at position 1 and a mutation relative to N. eutropha strain C91 at position 160, e.g., an L at position 160, and a mutation relative to N. eutropha strain C91 at position 167, e.g., an A at position 167.

In some embodiments, the bacterium or preparation comprises a Hao1 protein having (or gene encoding) a mutation relative to N. eutropha strain C91 at position 85, e.g., an S at position 85 and a mutation relative to N. eutropha strain C91 at position 312, e.g., an E at position 312, and a mutation relative to N. eutropha strain C91 at position 163, e.g., an A at position 163.

In some embodiments, the bacterium or preparation comprises a $c_M$552 CycB1 protein having (or gene encoding) mutations at any three or more (e.g., 4, 5, 6, 7, or all) of the following amino acid positions: 63, 189, 194, 195, 196, 197, 206, and 207. For instance, the three mutations may be at positions 195, 196, and 197. In some embodiments, the bacterium or preparation comprises a $c_M$552 CycB1 protein having (or gene encoding) any three or more (e.g., 4, 5, 6, 7, or all) mutations selected from the group consisting of: I63V, S189P, D194G, 195insD, 196insD, 197insD, 206insE, and 207insE. For instance, the three mutations may be 195insD, 196insD, and 197insD.

In some embodiments, the bacterium or preparation comprises a $c_M$552 CycB2 protein having (or gene encoding) mutations at any three or more (e.g., all) of the following amino acid positions: 63, 189, 206, and 207. In some embodiments, the bacterium or preparation comprises a $c_M$552 CycB2 protein having (or gene encoding) any three or more (e.g., all) mutations selected from the group consisting of: I63V, S189P, 206insE, and 207insE.

In some embodiments, the bacterium or preparation comprises mutations relative to N. eutropha strain C91 in at least two genes, e.g., at least two genes listed in Table 2. The two genes may be, for instance, AmoA1 and AmoA2, AmoA1 and AmoB1, AmoA1 and AmoB2, AmoA1 and AmoC1, AmoA1 and AmoC2, AmoA1 and AmoC3, AmoA1 and Hao1, AmoA1 and Hao2, AmoA1 and Hao3, AmoA1 and c554 CycA1, AmoA1 and c554 CycA2, AmoA1 and c554 CycA3, AmoA1 and cM552 CycB1, AmoA1 and cM552 CycB2, AmoA2 and AmoB1, AmoA2 and AmoB2, AmoA2 and AmoC1, AmoA2 and AmoC2, AmoA2 and AmoC3, AmoA2 and Hao1, AmoA2 and Hao2, AmoA2 and Hao3, AmoA2 and c554 CycA1, AmoA2 and c554 CycA2, AmoA2 and c554 CycA3, AmoA2 and cM552 CycB1, AmoA2 and cM552 CycB2, AmoB1 and AmoB2, AmoB1 and AmoC1, AmoB1 and AmoC2, AmoB1 and AmoC3, AmoB1 and Hao1, AmoB1 and Hao2, AmoB1 and Hao3, AmoB1 and c554 CycA1, AmoB1 and c554 CycA2, AmoB1 and c554 CycA3, AmoB1 and cM552 CycB1, AmoB1 and cM552 CycB2, AmoB2 and AmoC1, AmoB2 and AmoC2, AmoB2 and AmoC3, AmoB2 and Hao1, AmoB2 and Hao2, AmoB2 and Hao3, AmoB2 and c554 CycA1, AmoB2 and c554 CycA2, AmoB2 and c554 CycA3, AmoB2 and cM552 CycB1, AmoB2 and cM552 CycB2, AmoC1 and AmoC2, AmoC1 and AmoC3, AmoC1 and Hao1, AmoC1 and Hao2, AmoC1 and Hao3, AmoC1 and c554 CycA1, AmoC1 and c554 CycA2, AmoC1 and c554 CycA3, AmoC1 and cM552 CycB1, AmoC1 and cM552 CycB2, AmoC2 and AmoC3, AmoC2 and Hao1, AmoC2 and Hao2, AmoC2 and Hao3, AmoC2 and c554 CycA1, AmoC2 and c554 CycA2, AmoC2 and c554 CycA3, AmoC2 and cM552 CycB1, AmoC2 and cM552 CycB2, AmoC3 and Hao1, AmoC3 and Hao2, AmoC3 and Hao3, AmoC3 and c554 CycA1, AmoC3 and c554 CycA2, AmoC3 and c554 CycA3, AmoC3 and cM552 CycB1, AmoC3 and cM552 CycB2, Hao1 and Hao2, Hao1 and Hao3, Hao1 and c554 CycA1, Hao1 and c554 CycA2, Hao1 and c554 CycA3, Hao1 and cM552 CycB1, Hao1 and cM552 CycB2, Hao2 and Hao3, Hao2 and c554 CycA1, Hao2 and c554 CycA2, Hao2 and c554 CycA3, Hao2 and cM552 CycB1, Hao2 and cM552 CycB2, Hao3 and c554 CycA1, Hao3 and c554 CycA2, Hao3 and c554 CycA3, Hao3 and cM552 CycB1, Hao3 and cM552 CycB2, c554 CycA1 and c554 CycA2, c554 CycA1 and c554 CycA3, c554 CycA1 and cM552 CycB1, c554 CycA1 and cM552 CycB2, c554 CycA2 and c554 CycA3, c554 CycA2 and cM552 CycB1, c554 CycA2 and cM552 CycB2, c554 CycA3 and cM552 CycB1, c554 CycA3 and cM552 CycB2, or cM552 CycB1 and cM552 CycB2.

In some embodiments, the bacterium or preparation comprises mutations relative to N. eutropha strain C91 in at least three genes, e.g., at least three (e.g., 4, 5, 6, 7, 8, 9, 10, 11, 12, 13, 14, or all) genes listed in Table 2. The three genes may be, for instance AmoA1 and AmoA2 and AmoA3; AmoC1 and AmoC2 and AmoC3; or Hao1 and Hao2 and Hao3.

In some embodiments, the bacterium or preparation comprises at least one structural difference, e.g., at least one mutation, relative to a wild-type bacterium such as N. eutropha strain C91. In some embodiments, the bacterium or preparation comprises a nucleic acid that can be amplified using a pair of primers described herein, e.g., a primer comprising a sequence of SEQ ID NO: 64 and a primer comprising a sequence of SEQ ID NO: 65. In some embodiments, the bacterium or preparation comprises a nucleic acid or protein at least 80%, 85%, 90%, 95%, 98%, 99%, 99.5%, or 100% identical to a gene of FIG. 6, 7, or 8, or a protein encoded by a gene of FIG. 6, 7, or 8. In some embodiments, the bacterium or preparation comprises a nucleic acid or protein at least 80%, 85%, 90%, 95%, 98%, 99%, 99.5%, or 100% identical to a sequence of any of SEQ ID NOS: 64-66 or a protein encoded by a sequence of any of SEQ ID NOS: 64-66.

In some aspects, the present disclosure provides, inter alia, an *N. eutropha* bacterium, or a purified preparation thereof, comprising a mutation in an ammonia monooxygenase gene, a hydroxylamine oxidoreductase gene, a cytochrome c554 gene, or a cytochrome $c_m 552$ gene. The mutation may be relative to a wild-type bacterium such as *N. eutropha* strain C91. The mutation may be in one or more of the amoA1 gene, the amoA2 gene, amoB1 gene, the amoB2 gene, and the amoC3 gene. The *N. eutropha* bacterium, or a purified preparation thereof may have a mutation at a position described herein, e.g., in Table 2. The *N. eutropha* bacterium, or a purified preparation thereof may have a mutation wherein said mutation is a mutation described herein, e.g., in Table 2.

In some embodiments, the mutation may be in one or more of the hao1 gene, the hao2 gene, or the hao3 gene. The *N. eutropha* bacterium, or a purified preparation thereof may have a mutation at a position described herein, e.g., in Table 2. The *N. eutropha* bacterium, or a purified preparation thereof may have a mutation wherein said mutation is a mutation described herein, e.g., in Table 2.

In some embodiments, the mutation may be in one or more of the c554 cycA1 gene, the c554 cycA2 gene, and the c554 cycA3 gene. The *N. eutropha* bacterium, or a purified preparation thereof may have a mutation at a position described herein, e.g., in Table 2. The *N. eutropha* bacterium, or a purified preparation thereof may have a mutation wherein said mutation is a mutation described herein, e.g., in Table 2.

In some embodiments, the mutation may be in one or more of the $c_M 552$ cycB1 gene and the $c_M 552$ cycB2 gene. The *N. eutropha* bacterium, or a purified preparation thereof may have a mutation at a position described herein, e.g., in Table 2. The *N. eutropha* bacterium, or a purified preparation thereof may have a mutation wherein said mutation is a mutation described herein, e.g., in Table 2.

In certain aspects the *N. eutropha* bacterium, or a purified preparation thereof, described in the preceding four paragraphs may be based on a *N. eutropha* bacterium, e.g., an optimized *N. eutropha*, e.g., a purified preparation of optimized *N. eutropha*, having at least one property selected from:

an optimized growth rate;
an optimized $NH_4^+$ oxidation rate; and
an optimized resistance to ammonium ion ($NH_4^+$).

In certain aspects, the *N. eutropha* bacterium, or a purified preparation thereof, described in the preceding five paragraphs may have a mutation in at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 positions of one or more of amoA1 gene, amoA2 gene, amoB1 gene, amoB2 gene, amoC3 gene, hao1 gene, hao2 gene, hao3 gene, c554 cycA1 gene, c554 cycA2 gene, c554 cycA3 gene, $c_M 552$ cycB1 gene, and c554 cycB2 gene.

In some embodiments, the *N. eutropha* bacterium has an optimized growth rate, e.g., an optimized growth rate described herein, and a structural difference such as a mutation (e.g., relative to a wild-type strain such as *N. eutropha* strain C91), e.g., a mutation described herein, e.g., a mutation of Table 2. In some embodiments, the *N. eutropha* bacterium has an optimized $NH_4^+$ oxidation rate, e.g., an optimized $NH_4^+$ oxidation rate described herein, and a structural difference such as a mutation (e.g., relative to a wild-type strain such as *N. eutropha* strain C91), e.g., a mutation described herein, e.g., a mutation of Table 2. In some embodiments, the *N. eutropha* bacterium has an optimized resistance to $NH_4^+$, e.g., an optimized resistance to $NH_4^+$ described herein, and a structural difference such as a mutation (e.g., relative to a wild-type strain such as *N. eutropha* strain C91), e.g., a mutation described herein, e.g., a mutation of Table 2.

In some embodiments, the *N. eutropha* bacterium comprises a nucleic acid that can be amplified using a pair of primers described herein, e.g., a primer comprising a sequence of SEQ ID NO: 64 and a primer comprising a sequence of SEQ ID NO: 65.

In certain aspects, this disclosure provides an *N. eutropha* bacterium (which is optionally axenic) comprising a chromosome that hybridizes at high stringency to SEQ ID NO: 1.

In embodiments, the chromosome hybridizes at very high stringency to SEQ ID NO: 1. In embodiments, the *N. eutropha* bacterium (which is optionally axenic) comprises a gene that is at least about 80%, 85%, 90%, 95%, 97%, 98%, 99%, or 100% identical to one or more genes of FIGS. 6-8 (e.g., 10, 20, 30, 40, 50, 100, or all genes of any one or more of FIGS. 6, 7, and 8).

In embodiments, the *N. eutropha* bacterium (which is optionally axenic) lacks any plasmid that is at least about 80%, 85%, 90%, 95%, 97%, 98%, 99%, or 100% identical to SEQ ID NO: 2 (pNeut1) or SEQ ID NO: 3 (pNeut2), as described by Stein et al. Whole-genome analysis of the ammonia-oxidizing bacterium, *Nitrosomonas eutropha* C91: implications for niche adaptation. Environmental Microbiology (2007) 9(12), 2993-3007. In embodiments, the *N. eutropha* (which is optionally axenic) lacks one or more genes present on the plasmids of SEQ ID NO: 2 or SEQ ID NO: 3. For instance, the *N. eutropha* (which is optionally axenic) may lack at least 2, 3, 4, 5, 10, 15, or 20 genes present on one or both of pNeut1 and pNeut2. pNeut1 contains 55 protein-coding sequences while pNeutP2 contains 52 protein-coding sequences. In embodiments, the *N. eutropha* bacterium (which is optionally axenic) lacks any plasmid.

In certain aspects, this disclosure provides an *N. eutropha* bacterium (which is optionally axenic) comprising one or more of an amoA1 gene at least about 98.9% identical to SEQ ID NO: 7 and an amoA2 gene at least about 98.8% identical to SEQ ID NO: 13.

In certain aspects, this disclosure provides an *N. eutropha* bacterium (which is optionally axenic) comprising one or more of an AmoA1 protein at least about 99.0% identical to SEQ ID NO: 6 and an AmoA2 protein at least about 99.0% identical to SEQ ID NO: 12.

In certain aspects, this disclosure provides an *N. eutropha* bacterium (which is optionally axenic) comprising one or more of an amoB1 gene at least about 99.2% identical to SEQ ID NO: 9 and an amoB2 gene at least about 99.2% identical to SEQ ID NO: 15.

In embodiments, the *N. eutropha* bacterium (which is optionally axenic) further comprises one or more of an amoA1 or amoA2 gene at least about 98.9% identical to SEQ ID NO: 7 or 13.

In certain aspects, this disclosure provides an *N. eutropha* bacterium (which is optionally axenic) comprising one or more of an AmoB1 protein at least about 99.6% identical to SEQ ID NO: 8 and an AmoB1 protein at least about 99.6% identical to SEQ ID NO: 14.

In embodiments, the *N. eutropha* bacterium (which is optionally axenic) further comprises one or more of an AmoA1 protein at least about 99.0% identical to SEQ ID NO: 6 and an AmoA2 protein at least about 99.0% identical to SEQ ID NO: 12.

In certain aspects, this disclosure provides an *N. eutropha* bacterium (which is optionally axenic) comprising one or more of an amoC1 gene at least about 99.9% identical to SEQ ID NO: 5, an amoC2 gene at least about 99.9% identical to SEQ ID NO: 11, and an amoC3 gene at least about 99.0% identical to SEQ ID NO: 17.

In embodiments, the *N. eutropha* bacterium (which is optionally axenic) further comprises one or more of an amoA1 gene at least about 98.9% identical to SEQ ID NO: 7, an amo2 gene at least about 98.9% identical to SEQ ID NO: 13, an amoB1 gene at least about 99.2% identical to SEQ ID NO: 9, and an amoB2 gene at least about 99.2% identical to SEQ ID NO: 15.

In certain aspects, this disclosure provides an *N. eutropha* bacterium (which is optionally axenic) comprising an AmoC3 protein at least about 99.4% identical to SEQ ID NO: 16.

In embodiments, the *N. eutropha* bacterium (which is optionally axenic) further comprises one or more of an AmoA1 protein at least about 99.0% identical to SEQ ID NO: 6, an AmoA2 protein at least about 99.0% identical to SEQ ID NO: 12, an AmoB1 protein at least about 99.6% identical to SEQ ID NO: 8, and an AmoB1 protein at least about 99.6% identical to SEQ ID NO: 14.

In certain aspects, this disclosure provides an *N. eutropha* bacterium (which is optionally axenic) comprising one or more of a hao1 gene at least about 99.1% identical to SEQ ID NO: 19, a hao2 gene at least about 99.5% identical to SEQ ID NO: 21, and a hao3 gene at least about 99.3% identical to SEQ ID NO: 23.

In embodiments, the *N. eutropha* bacterium (which is optionally axenic) further comprises one or more of an amoA1 gene at least about 98.9% identical to SEQ ID NO: 7, an amo2 gene at least about 98.9% identical to SEQ ID NO: 13, an amoB1 gene at least about 99.2% identical to SEQ ID NO: 9, an amoB2 gene at least about 99.2% identical to SEQ ID NO: 15, an amoC1 gene at least about 99.9% identical to SEQ ID NO: 5, an amoC2 gene at least about 99.9% identical to SEQ ID NO: 11, and an amoC3 gene at least about 99.0% identical to SEQ ID NO: 17.

In certain aspects, this disclosure provides an *N. eutropha* bacterium (which is optionally axenic) comprising one or more of a Hao1 protein at least about 99.6% identical to SEQ ID NO: 18, a Hao2 protein at least about 99.7% identical to SEQ ID NO: 20, and a Hao3 protein at least about 99.7% identical to SEQ ID NO: 22.

In embodiments, the *N. eutropha* bacterium (which is optionally axenic) further comprises an AmoA1 protein at least about 99.0% identical to SEQ ID NO: 6, an AmoA2 protein at least about 99.0% identical to SEQ ID NO: 12, an AmoB1 protein at least about 99.6% identical to SEQ ID NO: 8, an AmoB1 protein at least about 99.6% identical to SEQ ID NO: 14, or an AmoC3 protein at least about 99.4% identical to SEQ ID NO: 16.

In certain aspects, this disclosure provides an *N. eutropha* bacterium (which is optionally axenic) comprising one or more of a cycA1 gene at least about 98.1% identical to SEQ ID NO: 25, a cycA2 gene at least about 98.8% identical to SEQ ID NO: 27, and a cycA3 gene at least about 99.4% identical to SEQ ID NO: 28.

In embodiments, the *N. eutropha* bacterium (which is optionally axenic) further comprises one or more of an amoA1 gene at least about 98.9% identical to SEQ ID NO: 7, an amo2 gene at least about 98.9% identical to SEQ ID NO: 13, an amoB1 gene at least about 99.2% identical to SEQ ID NO: 9, an amoB2 gene at least about 99.2% identical to SEQ ID NO: 15, an amoC1 gene at least about 99.9% identical to SEQ ID NO: 5, an amoC2 gene at least about 99.9% identical to SEQ ID NO: 11, an amoC3 gene at least about 99.0% identical to SEQ ID NO: 17, a hao1 gene at least about 99.1% identical to SEQ ID NO: 19, a hao2 gene at least about 99.5% identical to SEQ ID NO: 21, and a hao3 gene at least about 99.3% identical to SEQ ID NO: 23.

In certain aspects, this disclosure provides an *N. eutropha* bacterium (which is optionally axenic) comprising one or more of a CycA1 protein at least about 99.2% identical to SEQ ID NO: 24, a CycA2 protein at least about 99.7% identical to SEQ ID NO: 26, and a CycA3 protein at least about 99.7% identical to SEQ ID NO: 28.

In embodiments, the *N. eutropha* bacterium (which is optionally axenic) further comprises one or more of an AmoA1 protein at least about 99.0% identical to SEQ ID NO: 6, an AmoA2 protein at least about 99.0% identical to SEQ ID NO: 12, an AmoB1 protein at least about 99.6% identical to SEQ ID NO: 8, an AmoB1 protein at least about 99.6% identical to SEQ ID NO: 14, an AmoC3 protein at least about 99.4% identical to SEQ ID NO: 16, a Hao1 protein at least about 99.6% identical to SEQ ID NO: 18, a Hao2 protein at least about 99.7% identical to SEQ ID NO: 20, and a Hao3 protein at least about 99.7% identical to SEQ ID NO: 22.

In certain aspects, this disclosure provides an *N. eutropha* bacterium (which is optionally axenic) comprising one or more of a cycB1 gene at least about 96.8% identical to SEQ ID NO: 31 and a cycB2 gene at least about 97.2% identical to SEQ ID NO: 33.

In embodiments, the *N. eutropha* bacterium (which is optionally axenic) further comprises one or more of an amoA1 gene at least about 98.9% identical to SEQ ID NO: 7, an amo2 gene at least about 98.9% identical to SEQ ID NO: 13, an amoB1 gene at least about 99.2% identical to SEQ ID NO: 9, an amoB2 gene at least about 99.2% identical to SEQ ID NO: 15, an amoC1 gene at least about 99.9% identical to SEQ ID NO: 5, an amoC2 gene at least about 99.9% identical to SEQ ID NO: 11, an amoC3 gene at least about 99.0% identical to SEQ ID NO: 17, a hao1 gene at least about 99.1% identical to SEQ ID NO: 19, a hao2 gene at least about 99.5% identical to SEQ ID NO: 21, a hao3 gene at least about 99.3% identical to SEQ ID NO: 23, a cycA1 gene at least about 98.1% identical to SEQ ID NO: 25, a cycA2 gene at least about 98.8% identical to SEQ ID NO: 27, and a cycA3 gene at least about 99.4% identical to SEQ ID NO: 28.

In certain aspects, this disclosure provides an *N. eutropha* bacterium (which is optionally axenic) comprising one or more of a CycB1 protein at least about 97.2% identical to SEQ ID NO: 30 or a CycB2 protein at least about 98.8% identical to SEQ ID NO: 32.

In embodiments, the *N. eutropha* bacterium (which is optionally axenic) further comprises one or more of an AmoA1 protein at least about 99.0% identical to SEQ ID NO: 6, an AmoA2 protein at least about 99.0% identical to SEQ ID NO: 12, an AmoB1 protein at least about 99.6% identical to SEQ ID NO: 8, an AmoB1 protein at least about 99.6% identical to SEQ ID NO: 14, an AmoC3 protein at least about 99.4% identical to SEQ ID NO: 16, a Hao1 protein at least about 99.6% identical to SEQ ID NO: 18, a Hao2 protein at least about 99.7% identical to SEQ ID NO: 20, a Hao3 protein at least about 99.7% identical to SEQ ID NO: 22, a CycA1 protein at least about 99.2% identical to SEQ ID NO: 24, a CycA2 protein at least about 99.7% identical to SEQ ID NO: 26, and a CycA3 protein at least about 99.7% identical to SEQ ID NO: 28.

In certain aspects, this disclosure provides an *N. eutropha* bacterium (which is optionally axenic) comprising one or more genes according to SEQ ID NOS: 5, 7, 9, 11, 13, 15, 17, 19, 21, 23, 25, 27, 29, 31, and 33.

In certain aspects, this disclosure provides an *N. eutropha* bacterium (which is optionally axenic) comprising one or more proteins according to SEQ ID NOS: 4, 6, 8, 10, 12, 14, 16, 18, 20, 22, 24, 26, 28, 30, and 32.

In certain aspects, this disclosure provides an *N. eutropha* bacterium (which is optionally axenic) comprising a protein that is mutant relative to *N. eutropha* strain C91 at least 1, 2, 3, 4, 5, 10, 15, 20, 25, 30, or all of the amino acid positions listed in Table 2.

In certain aspects, this disclosure provides an *N. eutropha* bacterium (which is optionally axenic) comprising proteins that are mutant relative to *N. eutropha* strain C91 at all of the amino acid positions listed in Table 2.

In certain aspects, this disclosure provides an *N. eutropha* bacterium (which is optionally axenic) of strain D23, 25 vials of said bacterium, designated AOB D23-100, having been deposited with the ATCC® American Type Culture Collection biological material depository, patent depository on Apr. 8, 2014 under accession number PTA-121157.

In embodiments, the *N. eutropha* bacterium (which is optionally axenic) is transgenic.

In embodiments, the *N. eutropha* bacterium (which is optionally axenic) has at least one property selected from an optimized growth rate, an optimized $NH_4^+$ oxidation rate, and an optimized resistance to $NH_4^+$.

In embodiments, the *N. eutropha* bacterium (which is optionally axenic) has at least two properties selected from an optimized growth rate, an optimized $NH_4^+$ oxidation rate, and an optimized resistance to $NH_4^+$.

In embodiments, the *N. eutropha* bacterium (which is optionally axenic) has an optimized growth rate, an optimized $NH_4^+$ oxidation rate, and an optimized resistance to $NH_4^+$.

In embodiments, the *N. eutropha* bacterium as described herein (e.g., strain D23) is substantially free of bacteria, other ammonia oxidizing bacteria, fungi, viruses, or pathogens (e.g., animal pathogens, e.g., human pathogens), or any combination thereof.

In certain aspects, this disclosure provides a composition comprising the *N. eutropha* bacterium as described herein (e.g., strain D23), wherein the composition is substantially free of other organisms.

In certain aspects, this disclosure provides a composition comprising the *N. eutropha* bacterium as described herein (e.g., strain D23) and further comprising a second organism (e.g., a second strain or species), wherein the composition is substantially free of other organisms (e.g., strains or species). In embodiments, the second organism is an ammonia oxidizing bacterium.

In embodiments, the second organism is selected from the group consisting of *Nitrosomonas, Nitrosococcus, Nitrosospria, Nitrosocystis, Nitrosolobus, Nitrosovibrio, Lactobacillus, Streptococcus,* and *Bifidobacter*, and combinations thereof.

This disclosure also provides a composition comprising the *N. eutropha* bacterium as described herein (e.g., strain D23) and further comprising a second and a third organism (e.g., of other strains or species), wherein the composition is substantially free of other organisms (e.g., strains or species). This disclosure also provides a composition comprising the *N. eutropha* bacterium as described herein (e.g., strain D23) and further comprising 2, 3, 4, 5, 6, 7, 8, 9, or 10 other organisms (e.g., of other strains or species), wherein the composition is substantially free of other organisms (e.g., strains or species).

In some aspects, this disclosure provides a composition comprising a cell suspension of an actively dividing culture of *N. eutropha* bacteria having an OD600 of at least about 0.1, 0.15, 0.2, 0.25, 0.3, 0.35, 0.4, 0.45, 0.5, 0.6, 0.7, or 0.8, wherein the composition is substantially free of other organisms.

In some aspects, this disclosure provides a composition for topical administration, comprising the *N. eutropha* bacterium as described herein (e.g., strain D23) and a pharmaceutically or cosmetically acceptable excipient suitable for topical administration. In embodiments, the composition is substantially free of other organisms. In embodiments, the composition further comprises a second organism (e.g., of another strain or specie). In embodiments, the composition further comprises 2, 3, 4, 5, 6, 7, 8, 9, or 10 other organisms (e.g., of other strains or species). The second organism may be, for example, an ammonia oxidizing bacterium. In embodiments, the second organism is selected from the group consisting of *Nitrosomonas, Nitrosococcus, Nitrosospria, Nitrosocystis, Nitrosolobus, Nitrosovibrio, Lactobacillus, Streptococcus,* and *Bifidobacter*, and combinations thereof.

In embodiments, the composition is a powder, cosmetic, cream, stick, aerosol, salve, wipe, or bandage. In embodiments, the composition further comprises a moisturizing agent, deodorizing agent, scent, colorant, insect repellant, cleansing agent, or UV-blocking agent. In embodiments, the excipient is an anti-adherent, binder, coat, disintegrant, filler, flavor, color, lubricant, glidant, sorbent, preservative, or sweetener. In embodiments, the concentration of *N. eutropha* in the composition is about $10^{11}$-$10^{13}$ CFU/L. In embodiments, the concentration of *N. eutropha* in the composition is about $10^9$ CFU/ml. In embodiments, the mass ratio of *N. eutropha* to pharmaceutical excipient may be about 0.1 gram per liter to about 100 grams per liter. In some embodiments, the mass ratio of *N. eutropha* to pharmaceutical excipient is 1 gram per liter.

In some aspects the composition and/or excipient may be in the form of one or more of a liquid, a solid, or a gel. For example, liquid suspensions may include, but are not limited to, water, saline, phosphate-buffered saline, or an ammonia oxidizing storage buffer. Gel formulations may include, but are not limited to agar, silica, polyacrylic acid (for example Carbopol®), carboxymethyl cellulose, starch, guar gum, alginate or chitosan. In some embodiments, the formulation may be supplemented with an ammonia source including, but not limited to ammonium chloride or ammonium sulfate.

In some aspects, this disclosure provides a composition comprising at least about 10, 20, 50, 100, 200, 500, 1,000, 2,000, or 10,000 L, e.g., at about $10^{11}$ CFU/L, $10^{12}$ CFU/L, $10^{13}$ CFU/L of the *N. eutropha* bacterium as described herein (e.g., strain D23). In some embodiments, the composition is at a concentration of at least about $10^9$ CFU/L, $10^{10}$ CFU/L, $10^{11}$ CFU/L, or $10^{12}$ CFU/L. In some aspects, this disclosure provides a composition comprising at least about 1, 2, 5, 10, 20, 50, 100, 200, or 500 g of the *N. eutropha* bacterium described herein, e.g., as a dry formulation such as a powder.

In some aspects, this disclosure provides an article of clothing comprising the *N. eutropha* as described herein (e.g., strain D23). In embodiments, the article of clothing is packaged. In embodiments, the article of clothing is packaged in a material that is resistant to gaseous exchange or resistant to water. The article of clothing may be provided, e.g., at a concentration that provides one or more of a treatment or prevention of a skin disorder, a treatment or prevention of a disease or condition associated with low nitrite levels, a treatment or prevention of body odor, a treatment to supply nitric oxide to a subject, or a treatment to inhibit microbial growth.

In some aspects, this disclosure provides a cloth comprising the *N. eutropha* as described herein (e.g., strain D23).

In some aspects, this disclosure provides a yarn comprising the *N. eutropha* as described herein (e.g., strain D23).

In some aspects, this disclosure provides a thread comprising the *N. eutropha* as described herein (e.g., strain D23).

In some aspects, this disclosure provides a method of obtaining, e.g., manufacturing, an (optionally axenic) *N. eutropha* bacterium having an optimized growth rate, an optimized $NH_4^+$ oxidation rate, or an optimized resistance to $NH_4^+$, comprising:
 (a) culturing the bacterium under conditions that select for one or more of an optimized growth rate, an optimized $NH_4^+$ oxidation rate, or an optimized resistance to $NH_4^+$, thereby producing a culture;
 (b) testing a sample from the culture for an optimized growth rate, an optimized $NH_4^+$ oxidation rate, or an optimized resistance to $NH_4^+$; and
 (c) repeating the culturing and testing steps until a bacterium having an optimized growth rate, an optimized $NH_4^+$ oxidation rate, or an optimized resistance to $NH_4^+$ is obtained.

In embodiments, the method comprises a step of obtaining an *N. eutropha* bacterium from a source, such as soil or the skin of an individual. In embodiments, culturing the bacterium under conditions that select for one or more (e.g., 2 or 3) of an optimized growth rate, an optimized $NH_4^+$ oxidation rate, or an optimized resistance to $NH_4^+$ comprises culturing the bacterium in *N. europaea* medium that comprises about 200 mM $NH_4^+$. In embodiments, the method comprises a step of creating an axenic culture. In embodiments, the method comprises a step of co-culturing the *N. eutropha* together with at least one other type of ammonia oxidizing bacteria. In embodiments, the *N. eutropha* of step (a) lack an optimized growth rate, an optimized $NH_4^+$ oxidation rate, and an optimized resistance to $NH_4^+$. In embodiments, step (c) comprises repeating the culturing and testing steps until a bacterium having at least two of an optimized growth rate, an optimized $NH_4^+$ oxidation rate, and an optimized resistance to $NH_4^+$ is obtained.

In some aspects, this disclosure provides an *N. eutropha* bacterium as described herein (e.g., strain D23), produced by the methods described above.

In some aspects, this disclosure provides a method of testing a preparation of (optionally axenic) *N. eutropha*, comprising:
 assaying the *N. eutropha* for one or more of an optimized growth rate, an optimized $NH_4^+$ oxidation rate, or an optimized resistance to $NH_4^+$; and
 if the *N. eutropha* has one or more of an optimized growth rate, an optimized $NH_4^+$ oxidation rate, or an optimized resistance to $NH_4^+$, classifying the *N. eutropha* as accepted.

In embodiments, the method further comprises a step of testing the preparation for contaminating organisms. In embodiments, the method further comprises a step of removing a sample from the preparation and conducting testing on the sample. In embodiments, the method further comprises testing medium in which the *N. eutropha* is cultured. In embodiments, the method further comprises packaging *N. eutropha* from the preparation into a package. In embodiments, the method further comprises placing *N. eutropha* from the preparation into commerce.

In some aspects, this disclosure provides a method of producing, e.g., manufacturing *N. eutropha*, comprising contacting *N. eutropha* with culture medium and culturing the *N. eutropha* until an OD600 of at least about 0.3, 0.4, 0.5, 0.6, 0.7, or 0.8 is reached. In some embodiments, the method comprises culturing the *N. eutropha* until an OD600 of at about 0.3-0.4, 0.4-0.5, 0.5-0.6, 0.6-0.7, or 0.7-0.8 is reached.

In embodiments, the method further comprises assaying the *N. eutropha* and culture medium for contaminating organisms. In embodiments, the method further comprises assaying the *N. eutropha* for one or more (e.g., 2 or 3) of an optimized growth rate, an optimized $NH_4^+$ oxidation rate, or an optimized resistance to $NH_4$. In embodiments, the method comprises producing at least at least about 10, 20, 50, 100, 200, 500, 1,000, 2,000, 5,000, or 10,000 L per day of *N. eutropha*, e.g., at about $10^{12}$ CFUs/L. In some embodiments, the *N. eutropha* is at a concentration of about $10^9$, $10^{10}$, $10^{11}$, $10^{12}$, $10^{13}$, or $10^{14}$ CFUs/L. In some embodiments, the *N. eutropha* is at a concentration of least about $10^9$, $10^{10}$, $10^{11}$, $10^{12}$, $10^{13}$, or $10^{14}$ CFUs/L.

In some aspects, this disclosure provides a method of producing, e.g., manufacturing, *N. eutropha*, comprising contacting *N. eutropha* with culture medium and culturing the *N. eutropha* until about at least about 1,000 L at about $10^{12}$ CFU/L *N. eutropha* are produced.

In embodiments, the method further comprises a step of assaying the *N. eutropha* for one or more (e.g., 2 or 3) of an optimized growth rate, an optimized $NH_4^+$ oxidation rate, or an optimized resistance to $NH_4^+$.

In embodiments, the method further comprises a step of testing the *N. eutropha* or culture medium for contaminating organisms. In embodiments, the *N. eutropha* brought into contact with the culture medium is an *N. eutropha* having one or more (e.g., 2 or 3) of an optimized growth rate, an optimized $NH_4^+$ oxidation rate, or an optimized resistance to $NH_4^+$.

In some aspects, this disclosure provides a method of producing, e.g., manufacturing *N. eutropha*, comprising:
 (a) contacting *N. eutropha* with a culture medium; and
 (b) culturing the *N. eutropha* for 1-2 days, thereby creating a culture, until the culture reaches an OD600 of about 0.5-0.6.

In embodiments, the method further comprises a step of assaying the *N. eutropha* for one or more of an optimized growth rate, an optimized $NH_4^+$ oxidation rate, or an optimized resistance to $NH_4^+$. In embodiments, the method further comprises a step of testing the culture for contaminating organisms, e.g., bacteria, viruses, fungi, or pathogens, or a combination thereof. In embodiments, the *N. eutropha* of step (a) is an *N. eutropha* having one or more (e.g., 2 or 3) of an optimized growth rate, an optimized $NH_4^+$ oxidation rate, or an optimized resistance to $NH_4^-$. In embodiments, the method comprises producing at least at least about 1,000 L per day at about $10^{12}$ CFUs/L of N. eutropha.

In some aspects, this disclosure provides a N. eutropha bacterium produced by the methods described above.

In embodiments, a preparation of N. eutropha made by the methods described above. In some aspects, the preparation may comprise about 0.1 milligrams to about 100 milligrams (mg) of N. eutropha.

In some aspects, a reaction mixture may be provided comprising N. eutropha at an optical density of about 0.5 to about 0.6. In some aspects, this disclosure provides a method of producing N. eutropha-bearing clothing, comprising contacting an article of clothing with of the N. eutropha as described herein (e.g., strain D23).

In embodiments, the method comprises producing at least 10, 100, or 1000 articles of clothing. In embodiments, the method comprises contacting the article of clothing with at least $10^{10}$ CFUs of N. eutropha. In embodiments, the method further comprises packaging the clothing.

In certain aspects, the present disclosure provides a method of obtaining a formulation of N. eutropha, combining contacting N. eutropha described herein (e.g., strain D23) with a pharmaceutically or cosmetically acceptable excipient.

In embodiments, the method further comprises mixing the N. eutropha and the excipient. In embodiments, the method is performed under conditions that are substantially free of contaminating organisms, e.g., bacteria, viruses, fungi, or pathogens.

In certain aspects, the present disclosure provides a method of packaging N. eutropha, comprising assembling N. eutropha described herein (e.g., strain D23) into a package.

In embodiments, the package is resistant to gaseous exchange or resistant to water. In embodiments, the package is permeable to gaseous exchange, $NH_3$, $NH_4^+$, or $NO_2^-$.

In certain aspects, the present disclosure provides a method of inhibiting microbial growth on a subject's skin, comprising topically administering to a subject in need thereof an effective dose of the N. eutropha bacteria described herein (e.g., strain D23).

In embodiments, the effective dose is approximately $1\times10^9$ CFU, $2\times10^9$ CFU, $5\times10^9$ CFU, $1\times10^{10}$ CFU, $1.5\times10^{10}$ CFU, $2\times10^{10}$ CFU, $5\times10^{10}$ CFU, or $1\times10^{11}$ CFU. In embodiments, the effective dose is at least about $1\times10^9$ CFU, $2\times10^9$ CFU, $5\times10^9$ CFU, $1\times10^{10}$ CFU, $1.5\times10^{10}$ CFU, $2\times10^{10}$ CFU, $5\times10^{10}$ CFU, or $1\times10^{11}$ CFU. In embodiments, the effective dose is approximately $1\times10^9$ CFU-$2\times10^9$ CFU, $2\times10^9$ CFU-$5\times10^9$ CFU, $5\times10^9$ CFU-$1\times10^{10}$ CFU, $1\times10^{10}$ CFU-$1.5\times10^{10}$ CFU, $1\times10^{10}$ CFU-$2\times10^{10}$ CFU, $1.5\times10^{10}$ CFU-$2\times10^{10}$ CFU, $2\times10^{10}$ CFU-$5\times10^{10}$ CFU, or $5\times10^{10}$ CFU-$1\times10^{11}$ CFU. In embodiments, the bacterium is administered at a concentration of about $1\times10^8$, $2\times10^8$, $5\times10^8$, $1\times10^9$, $2\times10^9$, $5\times10^9$, or $1\times10^{10}$ CFU/ml. In embodiments, the bacterium is administered at a concentration of at least about $1\times10^8$, $2\times10^8$, $5\times10^8$, $1\times10^9$, $2\times10^9$, $5\times10^9$, or $1\times10^{10}$ CFU/ml. In embodiments, the bacterium is administered at a concentration of about $1\times10^8$-$2\times10^8$, $2\times10^8$-$5\times10^8$, $5\times1$-$1\times10^9$, $10^9$-$2\times10^9$, $2\times10^9$-$5\times10^9$, or $5\times10^9$-$1\times10^{10}$ CFU/ml. In embodiments, the administration is performed twice per day. In embodiments, the subject is a human. In embodiments, the microbial growth to be inhibited is growth of Pseudomonas aeruginosa or Staphylococcus aureus (S. aureus or SA), Streptococcus pyogenes (S. pyogenes or SP), or Acinetobacter baumannii (A. baumannii or AB).

In certain aspects, the present disclosure provides a method of supplying nitric oxide to a subject, comprising positioning an effective dose of the N. eutropha bacteria described herein (e.g., strain D23) in close proximity to the subject.

In certain aspects, the present disclosure provides a method of reducing body odor, comprising topically administering to a subject in need thereof an effective dose of the N. eutropha bacteria described herein (e.g., strain D23).

In certain aspects, the present disclosure provides a method of treating a disease associated with low nitrite levels, comprising topically administering to a subject in need thereof a therapeutically effective dose of the N. eutropha bacteria described herein (e.g., strain D23).

In embodiments, the disease is HIV dermatitis, infection in a diabetic foot ulcer, atopic dermatitis, acne, e.g., acne vulgaris, eczema, contact dermatitis, allergic reaction, psoriasis, skin infections, vascular disease, vaginal yeast infection, a sexually transmitted disease, heart disease, atherosclerosis, baldness, leg ulcers secondary to diabetes or confinement to bed, angina, particularly chronic, stable angina pectoris, ischemic diseases, congestive heart failure, myocardial infarction, ischemia reperfusion injury, laminitis, hypertension, hypertrophic organ degeneration, Raynaud's phenomenon, fibrosis, fibrotic organ degeneration, allergies, autoimmune sensitization, end stage renal disease, obesity, impotence, or cancer.

In certain aspects, the present disclosure provides a method of treating a skin disorder, comprising topically administering to a subject in need thereof a therapeutically effective dose of the N. eutropha bacteria as described herein (e.g., strain D23). In related aspects, the disclosure provides an N. eutropha bacteria as described herein (e.g., strain D23) for treating a disorder such as a skin disorder. In related aspects, the disclosure provides an N. eutropha bacteria as described herein (e.g., strain D23) for the manufacture of a medicament, e.g., a medicament for treating a skin disorder.

In embodiments, the skin disorder is acne, e.g., acne vulgaris, rosacea, eczema, or psoriasis. In some embodiments, the skin disorder is an ulcer, e.g., venous ulcer, e.g., leg ulcer, e.g., venous leg ulcer, e.g., infection in a diabetic foot ulcer. In some embodiments, topically administering comprises pre-treating the subject with N. eutropha, e.g., an N. eutropha described herein. In some embodiments, topically administering comprises topically administering prior to occurrence of the skin disorder. In some embodiments, topically administering comprises topically administering subsequent to occurrence of the skin disorder.

In certain aspects, the present disclosure provides a method of promoting wound healing or closure, comprising administering to a wound an effective dose of the N. eutropha bacteria as described herein (e.g., strain D23). In related aspects, the disclosure provides an N. eutropha bacteria as described herein (e.g., strain D23) for promoting wound healing. In related aspects, the disclosure provides an N. eutropha bacteria as described herein (e.g., strain D23) for the manufacture of a medicament, e.g., a medicament for promoting wound healing.

In embodiments, the wound comprises one or more undesirable bacteria, e.g., pathogenic bacteria. In embodiments, the wound comprises S. aureus, P. aeruginosa, P. aeruginosa, or A. baumannii.

In embodiments, the N. eutropha is administered to the subject prior to occurrence of the wound. In embodiments, administering to the wound comprises administering to the subject prior to occurrence of the wound. In embodiments, the method further comprises administering N. eutropha (e.g., an N. eutropha described herein, e.g., strain D23) to the wound subsequent to occurrence of the wound. In some aspects, the disclosure provides a method of killing or inhibiting growth of pathogenic bacteria comprising contacting, e.g., applying, N. eutropha bacteria (e.g., N. eutropha described herein, e.g., strain D23) to the skin.

In embodiments, the pathogenic bacteria contribute to one or more of the following conditions: HIV dermatitis, an ulcer, e.g., venous ulcer, e.g., leg ulcer, e.g., venous leg ulcer, e.g., infection in a diabetic foot ulcer, atopic dermatitis, acne, e.g., acne vulgaris, eczema, contact dermatitis, allergic reaction, psoriasis, uticaria, rosacea, skin infections, vascular disease, vaginal yeast infection, a sexually transmitted disease, heart disease, atherosclerosis, baldness, leg ulcers secondary to diabetes or confinement to bed, angina, particularly chronic, stable angina pectoris, ischemic diseases, congestive heart failure, myocardial infarction, ischemia reperfusion injury, laminitis, hypertension, hypertrophic organ degeneration, Raynaud's phenomenon, fibrosis, fibrotic organ degeneration, allergies, autoimmune sensitization, end stage renal disease, obesity, impotence, pneumonia, primary immunodeficiency, epidermal lysis bulosa, or cancer.

In embodiments, the condition is an ulcer, e.g., venous ulcer, e.g., leg ulcer, e.g., venous leg ulcer, e.g., infection in a diabetic foot ulcer. In embodiments, the condition is a venous leg ulcer. In embodiments, the condition is acne, e.g., acne vulgaris. In embodiments, the condition is acne vulgaris. In embodiments, the pathogenic bacteria is one or more of *Propionibacterium acnes, Pseudomonas aeruginosa, Staphylococcus aureus, Streptococcus pyogenes*, or *Acinetobacter baumannii*. In embodiments, the method further comprises determining whether the subject is in need of killing or inhibiting growth of pathogenic bacteria, e.g., determining that the subject is in need of killing or inhibiting growth of pathogenic bacteria. In embodiments, the method further comprises selecting the subject in need of killing or inhibiting growth of pathogenic bacteria.

In some embodiments, the N. eutropha catalyze the following reactions.

At a neutral pH, ammonia generated from ammonium around neutral pH conditions is the substrate of the initial reaction. The conversion of ammonia to nitrite takes place in two steps catalyzed respectively by ammonia monooxygenase (Amo) and hydroxylamine oxidoreductase (Hao), as follows:

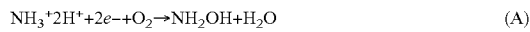
$$NH_3^+ 2H^+ + 2e^- + O_2 \rightarrow NH_2OH + H_2O \quad (A)$$

$$NH_2OH + H_2O \rightarrow NO_2^- + 4e^- + 5H^+ \quad (B)$$

In some instances, reaction B is reported as follows, to indicate nitrous acid ($HNO_2$) formation at low pH:

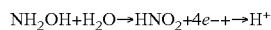
$$NH_2OH + H_2O \rightarrow HNO_2 + 4e^- + H^+$$

In certain embodiments, the N. eutropha has a doubling time of less than 4, 5, 6, 7, 8, 9, or 10 hours, for instance about 8 hours, e.g., 7-9 hours or 6-10 hours, when grown under batch culture conditions. In some embodiments, the doubling time is at least 3, 4, 5, or 6 hours under batch culture conditions. In some embodiments, the N. eutropha has a doubling time of less than 16, 18, 20, 22, 24, or 26 hours, for instance about 20 hours, e.g., 19-21 hours or 18-22 hours, when grown under chemostat (i.e., continuous culture) conditions. In some embodiments, the doubling time is at least 10, 12, 14, 16, or 18 hours under chemostat conditions.

In certain embodiments, a continuous culture of N. eutropha at an OD600 of about 0.15-0.18 is capable of reaching an OD600 of about 0.5-0.6 in about 1-2 days. For instance, in some embodiments, a continuous culture of N. eutropha may grow from an OD600 of about 0.15 to at least 0.3, 0.4, 0.5, 0.6, 0.7, or 0.8 over about 1 day; in embodiments the culture may reach an OD in range of 0.4-0.6 or 0.3-0.7 over about 1 day. In embodiments, the continuous culture of N. eutropha may grow from an OD600 of about 0.15 to at least 0.3, 0.4, 0.5, 0.6, 0.7, or 0.8 over about 2 days; in embodiments the culture may reach an OD in the range of 0.4-0.6 or 0.3-0.7 over about 2 days. In some embodiments, the continuous culture conditions comprise growth in a bioreactor in *N. europaea* medium, optionally comprising about 200 mM $NH_4^+$. In some embodiments, the continuous culture conditions are conditions set out in Example 2.

In certain embodiments, the N. eutropha are capable of converting $NH_4^+$ (e.g., at about 200 mM) to nitrite (e.g., reaching up to about 180 mM) at a rate of at least about 50, 75, 125, or 150 micromoles $NO_2^-$ per minute, e.g., about 100-150, 75-175, 75-125, 100-125, 125-150, or 125-175 micromoles/minute, e.g., about 125 micromoles $NO_2^-$ per minute. In some embodiments, the reaction rates are measured in an about 1 L chemostat culture of about $10^9$ CFU/ml over the course of 24 hours.

In certain embodiments, the N. eutropha are capable of growing in medium comprising at least 50 mM, 75 mM, 100 mM, 125 mM, 150 mM, 175 mM, 200 mM, 225 mM, 250 mM, 275 mM, or 300 mM $NH_4^-$ (or $NH_3$), e.g., about 150-200, 175-225, 200-250, 225-275, 250-300 mM, e.g., about 200 or about 250 mM. In certain embodiments, the N. eutropha is grown in a bioreactor under these concentrations of ammonium. In some embodiments, when the N. eutropha is grown under these concentrations of ammonium, the concentration of nitrate or nitrite is capable of reaching at least 60, 80, 100, 120, 140, 160, or 180 mM, e.g., about 140-180, 160-200, or 140-200 mM, e.g., about 160 or 180 mM.

In certain aspects, the present disclosure provides high density cultures of N. eutropha, e.g., N. eutropha strain D23. For instance, the high density culture composition may comprise a cell suspension of an actively dividing culture of N. eutropha bacteria having an OD600 of at least about 0.1, 0.2, 0.3, 0.4, 0.5, 0.6, or 0.7, e.g., about 0.2-0.6, 0.3-0.6, 0.4-0.6, 0.5-0.6, or 0.4-0.7, wherein the composition is substantially free of other organisms.

In some embodiments, the N. eutropha are stable for at least 2 weeks, 1 month, 2 months, 3 months, 4 months, 5 months, or 6 months when stored at 4° C. In some embodiments, the method of storage comprises resuspending the cells in a buffer comprising one or more of $Na_2HPO_4$ and $MgCl_2$, for instance 50 mM $Na_2HPO_4$ and 2 mM $MgCl_2$, for instance the storage buffer described in Example 2. For example, the storage conditions may be those specified in Example 2. In some embodiments, the N. eutropha are continuously cultured at 200 mM $NH_4^+$ at a pH of 6-8, e.g., 7, before storage at 4°. Stability can include one or more of 1) retaining viability, 2) retaining a relevant property such as the ability to produce a given level of nitrite.

In certain embodiments, $NH_4^+$ and $NH_3$ may be used interchangeably throughout the disclosure.

This disclosure provides, inter alia, a method of changing a composition of a skin microbiome of a subject. The method comprises administering, e.g., applying, a preparation comprising ammonia oxidizing bacteria to a surface of the skin, wherein the amount and frequency of administration, e.g., application, is sufficient to reduce the proportion of pathogenic bacteria on the surface of the skin.

Ammonia oxidizing bacteria are, in some embodiments, ubiquitous Gram-negative obligate chemolithoautotrophic bacteria with a unique capacity to generate energy exclusively from the conversion of ammonia to nitrite.

In some embodiments, the method may further comprise, selecting the subject on the basis of the subject being in need of a reduction in the proportion of pathogenic bacteria on the surface of the skin.

In some embodiments, the preparation comprising ammonia oxidizing bacteria comprises at least one of ammonia, ammonium salts, and urea.

In some embodiments, the preparation comprising ammonia oxidizing bacteria comprises a controlled release material, e.g., slow release material.

In some embodiments, the preparation of ammonia oxidizing bacteria, comprises an excipient, e.g., one of a pharmaceutically acceptable excipient or a cosmetically acceptable excipient. The excipient, e.g., one of the pharmaceutically acceptable excipient and the cosmetically acceptable excipient, may be suitable for one of topical, nasal, pulmonary, and gastrointestinal administration. The excipient, e.g., one of the pharmaceutically acceptable excipient and the cosmetically acceptable excipient may be a surfactant. The surfactant may be selected from the group consisting of cocamidopropyl betaine (ColaTeric COAB), polyethylene sorbitol ester (e.g., Tween 80), ethoxylated lauryl alcohol (RhodaSurf 6 NAT), sodium laureth sulfate/lauryl glucoside/cocamidopropyl betaine (Plantapon 611 L UP), sodium laureth sulfate (e.g., RhodaPex ESB 70 NAT), alkyl polyglucoside (e.g., Plantaren 2000 N UP), sodium laureth sulfate (Plantaren 200), Dr. Bronner's Castile soap, lauramine oxide (ColaLux Lo), sodium dodecyl sulfate (SDS), polysulfonate alkyl polyglucoside (PolySufanate 160 P), sodium lauryl sulfate (Stepanol-WA Extra K), and any combination thereof. Dr. Bronner's Castile soap comprises water, organic coconut oil, potassium hydroxide, organic olive oil, organic fair deal hemp oil, organic jojoba oil, citric acid, and tocopherol. In some embodiments, the excipient comprises one or more of, e.g., all of, water, organic coconut oil, potassium hydroxide, organic olive oil, organic fair deal hemp oil, organic jojoba oil, citric acid, and tocopherol.

In some embodiments, the preparation may be substantially free of other organisms.

In some embodiments, the preparation may be disposed in a powder, cosmetic, cream, stick, aerosol, salve, wipe, or bandage. The preparation may be provided as a powder, cosmetic, cream, stick, aerosol, salve, wipe, or bandage.

In some embodiments, the preparation may comprise a moisturizing agent, deodorizing agent, scent, colorant, insect repellant, cleansing agent, or UV-blocking agent.

In some embodiments, the excipient, e.g., the pharmaceutically acceptable excipient or the cosmetically acceptable excipient may comprise an anti-adherent, binder, coat, disintegrant, filler, flavor, color, lubricant, glidant, sorbent, preservative, or sweetener.

In some embodiments, the preparation comprising ammonia oxidizing bacteria may comprise between about $10^8$ and about $10^{14}$ CFU/L. In certain aspects, the preparation may comprise between about $1 \times 10^9$ CFU/L and about $10 \times 10^9$ CFU/L.

In some embodiments, the preparation comprising ammonia oxidizing bacteria may comprise between about 50 milligrams (mg) and about 1000 mg of ammonia oxidizing bacteria.

In some embodiments, the mass ratio of ammonia oxidizing bacteria to the excipient, e.g., the pharmaceutically acceptable excipient or the cosmetically acceptable excipient is in a range of about 0.1 grams per liter to about 1 gram per liter.

In some embodiments, the preparation of ammonia oxidizing bacteria are useful in the treatment or prevention of a disease or condition associated with low nitrite levels, a treatment or prevention of body odor, a treatment to supply nitric oxide to a subject, or a treatment to inhibit microbial growth, e.g., pathogenic bacterial growth.

In some embodiments, the ammonia oxidizing bacteria is selected from the group consisting of *Nitrosomonas*, *Nitrosococcus*, *Nitrosospria*, *Nitrosocystis*, *Nitrosolobus*, *Nitrosovibrio*, and combinations thereof. The preparation may further comprise an organism selected from the group consisting of *Lactobacillus*, *Streptococcus*, *Bifidobacter*, and combinations thereof. In certain aspects, the preparation is substantially free of organisms other than ammonia oxidizing bacteria.

In some embodiments, the preparation comprising ammonia oxidizing bacteria may comprise ammonia oxidizing bacteria in a growth state. In some embodiments, the preparation comprising ammonia oxidizing bacteria may comprise ammonia oxidizing bacteria in a storage state.

In some embodiments, the methods of the present disclosure may be used to deliver a cosmetic product. In some embodiments, the methods of the present disclosure may be used to deliver a therapeutic product. The preparation may be useful for treatment of at least one of HIV dermatitis, infection in a diabetic foot ulcer, atopic dermatitis, acne, e.g., acne vulgaris, eczema, contact dermatitis, allergic reaction, psoriasis, uticaria, rosacea, skin infections, vascular disease, vaginal yeast infection, a sexually transmitted disease, heart disease, atherosclerosis, baldness, leg ulcers secondary to diabetes or confinement to bed, angina, particularly chronic, stable angina pectoris, ischemic diseases, congestive heart failure, myocardial infarction, ischemia reperfusion injury, laminitis, hypertension, hypertrophic organ degeneration, Raynaud's phenomenon, fibrosis, fibrotic organ degeneration, allergies, autoimmune sensitization, end stage renal disease, obesity, impotence, pneumonia, primary immunodeficiency, epidermal lysis bulosa, or cancer.

In certain aspects, the preparation may be useful for treatment of at least one of acne, e.g., acne vulgaris, eczema, psoriasis, uticaria, rosacea, and skin infections.

In some embodiments, the preparation may be provided in a container, the preparation and the container having a weight of less than about 50, 100, 200, 300, 400, 500, 600, 700, 800, 900, 1000, 1500, or 2000 grams.

In some embodiments, the preparation has less than about 0.1% to about 10% of surfactant. In certain aspects, the preparation may be substantially free of surfactant.

In some embodiments, the preparation may comprise a chelator. In some embodiments, the preparation may be substantially free of a chelator.

In some embodiments, the method may comprise applying the preparation about 1, 2, 3, 4, 5, 6, 7, 8, 9, 10, 11, 12, 13, 14, 15, 16, 17, 18, 19, 20, 21, 22, 23, or 24 times per day. In certain aspects, the preparation may be applied one time per day. In certain other aspects, the preparation may be applied two times per day.

In some embodiments, the preparation may be applied for about 1-3, 3-5, 5-7, 7-9, 5-10, 10-14, 12-18, 12-21, 21-28, 28-35, 35-42, 42-49, 49-56, 46-63, 63-70, 70-77, 77-84, or 84-91 days. In certain aspects, the preparation may be applied for about 16 days.

In some embodiments, the method may further comprise obtaining a sample from the surface of the skin. In certain aspects, the method may further comprise isolating DNA of bacteria in the sample. In certain aspects, the method may further comprise sequencing DNA of bacteria in the sample.

In some embodiments, administering the ammonia oxidizing bacteria provides for an increase in the proportion of non-pathogenic bacteria on the surface. In certain aspects, the non-pathogenic bacteria may be commensal non-pathogenic bacteria. In certain aspects, the non-pathogenic bacteria is commensal non-pathogenic bacteria of a genus of *Staphylococcus*. In certain aspects, the non-pathogenic bacteria may be commensal non-pathogenic bacteria *Staphylococcus epidermidis*.

In some embodiments, the proportion of non-pathogenic bacteria *Staphylococcus* is, or is identified as being, increased after about 1, 2, 3, 4, 5, 6, 7, 8, 9, or 10 weeks. In certain aspects, the proportion of non-pathogenic bacteria *Staphylococcus epidermidis Staphylococcus* is, or is identified as being, increased after about 1, 2, 3, 4, 5, 6, 7, 8, 9, or 10 weeks.

In some embodiments, potentially pathogenic or disease associated *Propionibacteria* is, or is identified as being, reduced after about 1, 2, 3, 4, 5, 6, 7, 8, 9, or 10 weeks.

In some embodiments, potentially pathogenic or disease associated *Stenotrophomonas* is, or is identified as being, reduced after about 1, 2, 3, 4, 5, 6, 7, 8, 9, or 10 weeks.

In some embodiments, the surface of the skin comprises a wound.

In some embodiments, a method of treating acne e.g., acne vulgaris, may be provided by one or more methods of the present disclosure. In some embodiments, a method of treating eczema may be provided by one or more methods of the present disclosure. In some embodiments, a method of treating psoriasis may be provided by one or more methods of the present disclosure. In some embodiments, a method of treating uticaria may be provided by one or more methods of the present disclosure. In some embodiments, a method of treating rosacea may be provided by one or more methods of the present disclosure. In some embodiments, a method of treating skin infection may be provided by one or more methods of the present disclosure. In some embodiments, a method of reducing an amount of undesirable bacteria on a surface of a subject is provided.

In some embodiments, the method herein (e.g., a method of administering a *N. eutropha* bacterium, e.g., a bacterium of strain D23 to a subject in need thereof), further comprise treating the subject with an antibiotic. In embodiments, the antibiotic is Tetracycline, a Lincosamide such as Clindamycin, a Macrolide such as Erythromycin, an Aminoglycoside such as Gentamicin, a β-lactam such as Piperacillin, a β-lactamase inhibitor such as Tazobactam, or any combination thereof (such as a combination of a β-lactam such as Piperacillin and a β-lactamase inhibitor such as Tazobactam). In some embodiments, the antibiotic is an antibiotic to which the bacterium is sensitive. In embodiments, the antibiotic is administered after the bacterium has achieved the desired therapeutic effect. In embodiments, the antibiotic is an antibiotic to which the bacterium is resistant. In embodiments, the antibiotic is administered before or during the period in which the bacterium is producing its therapeutic effect.

It is understood that compositions and methods herein involving a bacterium can also involve a plurality of bacteria. For instance, a method of administering a *N. eutropha* bacterium can also involve administering a plurality of *N. eutropha* bacteria.

The present disclosure also provides, in certain aspects, a nucleic acid comprising a sequence of consecutive nucleotides (e.g., 15-100 nucleotides) from within the D23 genome, e.g., a sequence of a gene provided herein, e.g., a gene described in Table 1, FIGS. 6A-6P, FIGS. 7A-7M, FIGS. 8A-8P (sometimes referred to collectively as FIG. 6, FIG. 7, or FIG. 8, respectively), or Supplementary Table 1, or SEQ ID NO: 66, or a reverse complement of any of the foregoing. In a related aspect, the present disclosure provides a nucleic acid comprising a sequence of consecutive nucleotides (e.g., 15-100 nucleotides) from within SEQ ID NO: 1 or a reverse complement thereof. In a related aspect, the present disclosure provides a nucleic acid comprising a sequence of consecutive nucleotides (e.g., 15-100 nucleotides) from within a gene of Table 1 (e.g., a sequence of SEQ ID NO: 5, 7, 9, 11, 13, 15, 17, 19, 21, 23, 25, 27, 29, 31, or 33) or a reverse complement thereof.

In some embodiments, the nucleic acid has a non-naturally occurring sequence or another modification such as a label, or both. In some embodiments, the sequence of consecutive nucleotides is not a sequence found in *N. eutropha* strain C91. In some embodiments, the nucleic acid comprises a heterologous sequence 5' to the sequence of 15-100 consecutive nucleotides, or a heterologous sequence 3' to the sequence of 15-100 consecutive nucleotides, or both. In some embodiments, the nucleic acid has a length of 10-15, 15-20, 20-25, 25-30, 30-24, 35-40 nucleotides. In some embodiments, the nucleic acid is bound, e.g., covalently bound, to a detectable label, e.g., a fluorescent label. In some embodiments, the nucleic acid comprises 10-15, 15-20, 20-25, 25-30, 30-24, 35-40, 40-50, 50-60, 60-70, 70-80, 80-90, or 90-100 consecutive nucleotides from within the D23 genome. In some embodiments, the nucleic acid comprises at least about 10, 15, 20, 25, 30, 35, 40, 50, 60, 70, 80, 90, 100, 150, 200, 250, 300, 350, 400, 450, 500, 600, 700, 800, 900, or 1000 consecutive nucleotides from within the D23 genome. In some embodiments, the nucleic acid is DNA.

In some aspects, the disclosure provides a composition or a kit comprising a first nucleic acid and a second nucleic acid. In some embodiments, the first nucleic acid comprises consecutive nucleotides (e.g., 15-100) from within SEQ ID NO: 1, SEQ ID NO: 66, a gene of FIGS. 6-8, or a gene of Table 1, or a reverse complement thereof. In some embodiments, the second nucleic acid comprises consecutive nucleotides (e.g., 15-100) from within SEQ ID NO: 1, SEQ ID NO: 66, a gene of FIGS. 6-8, or a gene of Table 1, or a reverse complement thereof. In some embodiments, the nucleic acid has a non-naturally occurring sequence, e.g., a sequence not found in *N. eutropha* strain C91. In some embodiments, the first nucleic acid and the second nucleic acid define an amplicon in a gene of Table 1, e.g., a sequence of SEQ ID NO: 5, 7, 9, 11, 13, 15, 17, 19, 21, 23, 25, 27, 29, 31, or 33) or a reverse complement thereof.

In some embodiments, the first nucleic acid has a sequence that corresponds to a first region of SEQ ID NO: 1, and the reverse complement of the second nucleic acid has a sequence that corresponds to a second region of SEQ ID NO: 1, and the first and second regions are separated by a distance suitable for PCR. In some embodiments, the reverse complement of the first nucleic acid has a sequence that corresponds to a first region of SEQ ID NO: 1, and the second nucleic acid has a sequence that corresponds to a second region of SEQ ID NO: 1, and the first and second regions are separated by a distance suitable for PCR. In an embodiment, the distance suitable for PCR is no more than 50, 100, 150, 200, 250, 300, 350, 400, 450, 500, 600, 700, 800, 900, or 1000 nucleotides of SEQ ID NO: 1. In some embodiments, the first nucleic acid and second nucleic acid delineate an amplicon in SEQ ID NO: 1. In some embodiments, the first nucleic acid and second nucleic acid each has a melting temperature (Tm) suitable for PCR, e.g., about 55-65° or about 60-65° C. In some embodiments, the Tm of the first nucleic acid is within 10, 9, 8, 7, 6, 5, 4, 3, 2, or 1° C. of the Tm of the second nucleic acid.

In some embodiments, the first nucleic acid, the second nucleic acid, or each of the first nucleic acid and second nucleic acid further comprises a heterologous sequence 5' to the sequence of consecutive nucleotides. Alternatively or in combination, in some embodiments, the first nucleic acid, the second nucleic acid, or each of the first nucleic acid and second nucleic acid further comprises a heterologous sequence 3' to the sequence of consecutive nucleotides from within SEQ ID NO: 1 or SEQ ID NO: 66. In some embodiments, the first nucleic acid, the second nucleic acid, or each of the first nucleic acid and second nucleic acid has a length of 15-20, 20-25, 25-30, 30-24, or 35-40 nucleotides. In some embodiments, the first nucleic acid, the second nucleic acid, or each of the first nucleic acid and second nucleic acid is bound, e.g., covalently bound, to a detectable label, e.g., a fluorescent label. In some embodiments, the first nucleic acid comprises, or consists of, a sequence of SEQ ID NO: 64. In some embodiments, the second nucleic acid comprises, or consists of, a sequence of SEQ ID NO: 65. In some embodiments, the first nucleic acid, the second nucleic acid, or both, are DNA.

In some embodiments, the composition or kit comprises at least two (e.g., 3, 4, 5, 6, 7, 8, 9, or 10) pairs of primers, each pair recognizing an amplicon in a gene of Table 1 (e.g., a sequence of SEQ ID NO: 5, 7, 9, 11, 13, 15, 17, 19, 21, 23, 25, 27, 29, 31, or 33) or a reverse complement thereof. In some embodiments, a first pair of primers recognizes an amplicon in an Amo gene (e.g., AmoA1, AmoA2, AmoB1, AmoB2, AmoC1, AmoC2, or AmoC3) and the second pair of primers recognizes an amplicon in an Amo gene (e.g., AmoA1, AmoA2, AmoB1, AmoB2, AmoC1, AmoC2, or AmoC3). In some embodiments, a first pair of primers recognizes an amplicon in an AmoA gene (e.g., AmoA1 or AmoA2). In some embodiments, a second pair of primers recognizes an amplicon in an AmoB gene (e.g., AmoB1 or AmoB2). In some embodiments, a third pair of primers recognizes an amplicon in an AmoC gene (e.g., AmoC1, AmoC2, or AmoC3).

In some embodiments, the kit comprises a first container in which the first nucleic acid is disposed and a second container in which the second nucleic acid is disposed. The kit may comprise additional containers, e.g., for a third, fourth, fifth, or sixth nucleic acid. In some embodiments, a pair of primers recognizing an amplicon is stored in a single container.

The present disclosure also provides, in some aspects, a nucleic acid comprising, or consisting of, the sequence of SEQ ID NO: 64. The present disclosure also provides, in some aspects, a nucleic acid comprising, or consisting of, the sequence of SEQ ID NO: 65. The present disclosure also provides, in some aspects, the present disclosure provides a molecule comprising a nucleic acid described herein and a detectable label, e.g., a fluorescent label. The nucleic acid may consist of a sequence of SEQ ID NO: 64 or SEQ ID NO: 65, for example.

The present disclosure provides, in some aspects, a composition comprising a first molecule and a second molecule. In some embodiments, the first molecule comprises a nucleic acid described herein, e.g., a nucleic acid consisting of the sequence of SEQ ID NO: 64, and optionally comprises a detectable label, e.g., a fluorescent label. In some embodiments, the second molecule comprises a nucleic acid described herein, e.g., a nucleic acid consisting of the sequence of SEQ ID NO: 65, and optionally comprises a detectable label, e.g., a fluorescent label.

In some embodiments, the kit comprises a first container in which the first molecule is disposed and a second container in which the second molecule is disposed.

In some embodiments, a kit described herein further comprises one or more of a buffer, an enzyme (e.g., a polymerase such as a thermostable polymerase such as Taq), nucleotides (e.g., dNTPs), and chain-terminating nucleotides (e.g., dideoxy nucleotides) which are optionally dye-labeled; these components may be provided separately or as part of a single composition.

In certain aspects, this disclosure provides a method of detecting whether a D23 *N. eutropha* nucleic acid is present in a sample, comprising: performing a polymerase chain reaction (PCR) on the sample using primers specific to D23 *N. eutropha*, and determining whether a PCR product is produced, wherein the presence of a PCR product indicates that the D23 *N. eutropha* nucleic acid was present in the sample. In embodiments, at least two PCR reactions are performed, e.g., 3, 4, 5, 6, 7, 8, 9 or 10 PCR reactions. In embodiments, the PCR reactions are performed in separate reaction volumes. In embodiments, two or more PCR reactions are performed in multiplex.

In some embodiments, the primers specific to D23 *N. eutropha* are a first nucleic acid and second nucleic acid described herein, e.g., a first and second nucleic acid from a composition or kit described herein. In some embodiments, the first primer comprises or consists of a sequence of SEQ ID NO: 65, and the second primer comprises or consists of a sequence of SEQ ID NO: 66.

In some embodiments, the PCR reaction is a quantitative or real-time PCR reaction. In some embodiments, the PCR reaction comprises a TaqMan reaction. In some embodiments, the PCR reaction comprises cycling the temperature of a reaction mixture between a denaturing temperature (e.g., about 95° C.), an annealing temperature (e.g., 45-68, 55-65, or 60-65° C.), and an elongation temperature (e.g., about 68° C.) for a number of cycles sufficient to produce a detectable PCR product, e.g., about 10, 15, 20, 25, or 30 cycles. In some embodiments, detecting the PCR product comprises detecting fluorescence from the PCR product. In some embodiments, a positive control is performed, e.g., using a known D23 *N. eutropha* nucleic acid as a template. In some embodiments, a negative control is used, e.g., using no template or using another bacterial nucleic acid as a template.

In certain aspects, the disclosure provides a method of detecting whether a D23 *N. eutropha* nucleic acid is present in a sample, comprising detecting binding of a nucleic acid described herein to a sample, wherein the presence of binding indicates that the D23 *N. eutropha* nucleic acid was present in the sample. In some embodiments, binding is detected by primer extension or RNase protection.

In some embodiments of the methods herein, the sample comprises at least 2, 3, 4, 5, 6, 7, 8, 9, or 10 strains of bacteria. In some embodiments, the sample is from the skin of a subject, e.g., a human subject. In some embodiments, the methods herein comprise detecting one or more additional types of bacterium in the sample, e.g., *Pseudomonas aeruginosa, Staphylococcus aureus, Streptococcus pyogenes*, or *Acinetobacter baumannii*.

The disclosure contemplates all combinations of any one or more of the foregoing aspects and/or embodiments, as well as combinations with any one or more of the embodiments set forth in the detailed description and examples.

BRIEF DESCRIPTION OF THE DRAWINGS

FIG. 5I shows body weight of test subjects over the course of testing.

Figure 1:
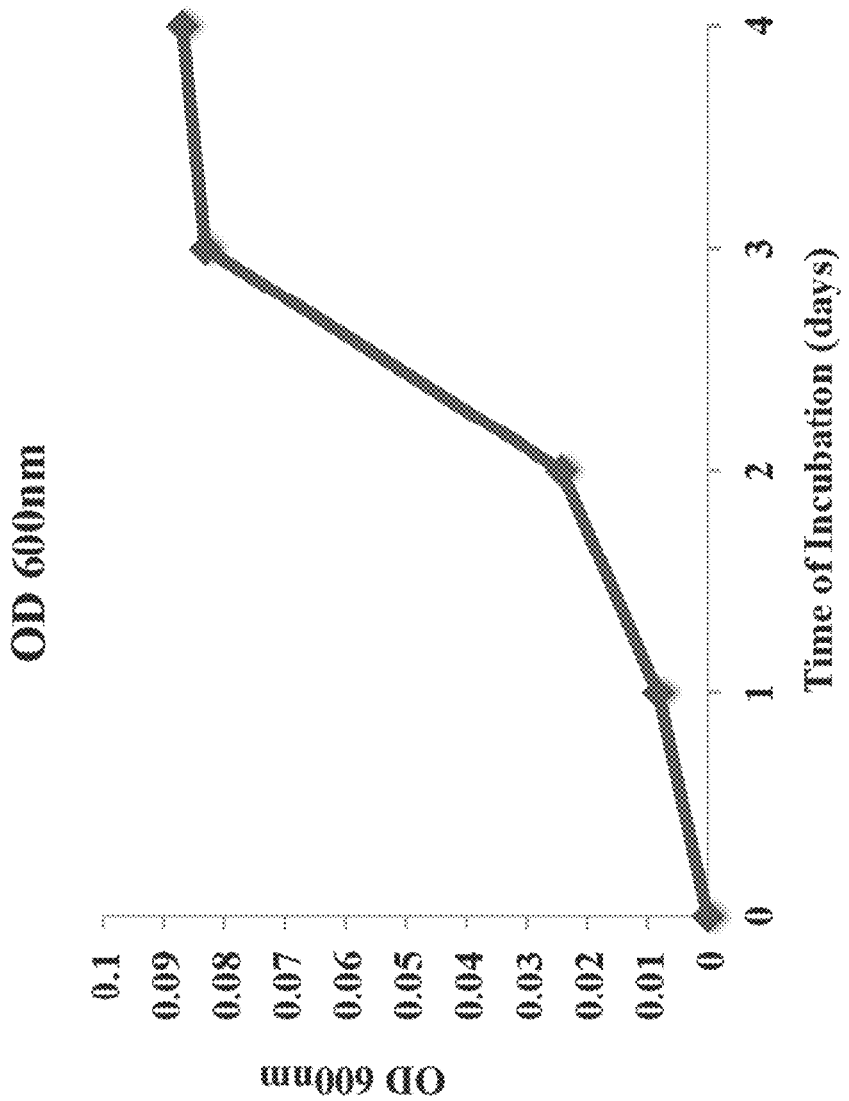
FIG. 1 shows the growth of a mixed culture of bacteria comprising *N. eutropha* strain D23. The optical density at a 600 nm wavelength is plotted relative to time.

Changed patterns in abundance of species were detected by 16S rDNA sequencing in Day 0 versus Day 8 samples collected from AOB users.

FIG. 5O shows user evaluation of AOB-001. Assessment of AOB-001 cosmetic effects as provided by 23 volunteers upon completion of the one week application to their scalp and face. Subjects were plotted in order of increasing composite PCT scores. (2=agree strongly; 0=no change; −2=disagree strongly).

FIG. 6A is a table displaying unique D23 genes that have either an assigned open reading frame (ORF) number and a function based on sequence analysis, or a hypothetical gene above 200 base pairs in length. The column headers signify as follows: Feature.ID=a unique identifier for the gene; Type=type of gene, where CDS indicates a protein-coding DNA sequence; Start=starting position of gene in the genome sequence of SEQ ID NO: 1; Stop=end of gene in the genome sequence of SEQ ID NO: 1; Frame=reading frame; Length=length of gene in base pairs; Function=gene or protein function based on sequence analysis; Subsystem=category of gene function; D23GbkId=a gene identifier.

FIGS. 6B-6P are a continuation of the table of FIG. 6A.

FIG. 7A is a table displaying unique D23 genes below 200 base pairs that have an assigned ORF number. Column headers are as described in FIGS. 6A-6P.

FIGS. 7B-7M are a continuation of the table of FIG. 7A.

FIG. 8A is a table displaying unique D23 genes with no assigned ORF number. Column headers are as described in FIGS. 6A-6P.

FIG. 8B-8P are a continuation of the table of FIG. 8A.

FIG. 9 lists unique C91 genes that do not have a homolog in D23.

FIG. 10 is a sequence alignment between the AmoA1 and AmoA2 proteins in *N. eutropha* strains D23 and C91. The SEQ ID of each protein is listed in Table 1. FIG. 10 discloses SEQ ID NOS 6, 12, 36 and 42, respectively, in order of appearance.

Figure 11:
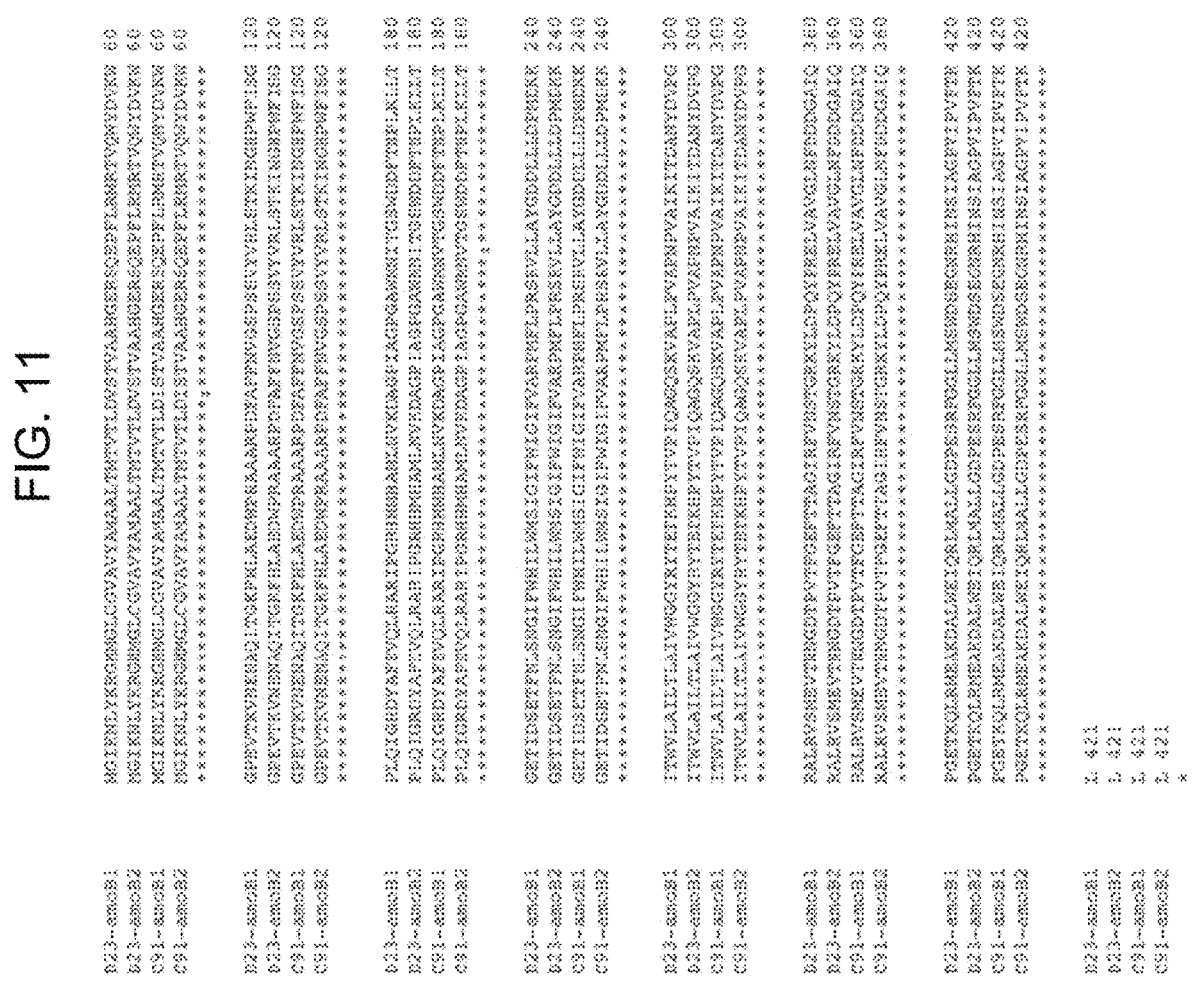

FIG. 11 is a sequence alignment between the AmoB1 and AmoB2 proteins in *N. eutropha* strains D23 and C91. The SEQ ID of each protein is listed in Table 1. FIG. 11 discloses SEQ ID NOS 8, 14, 38 and 44, respectively, in order of appearance.

Figure 12:
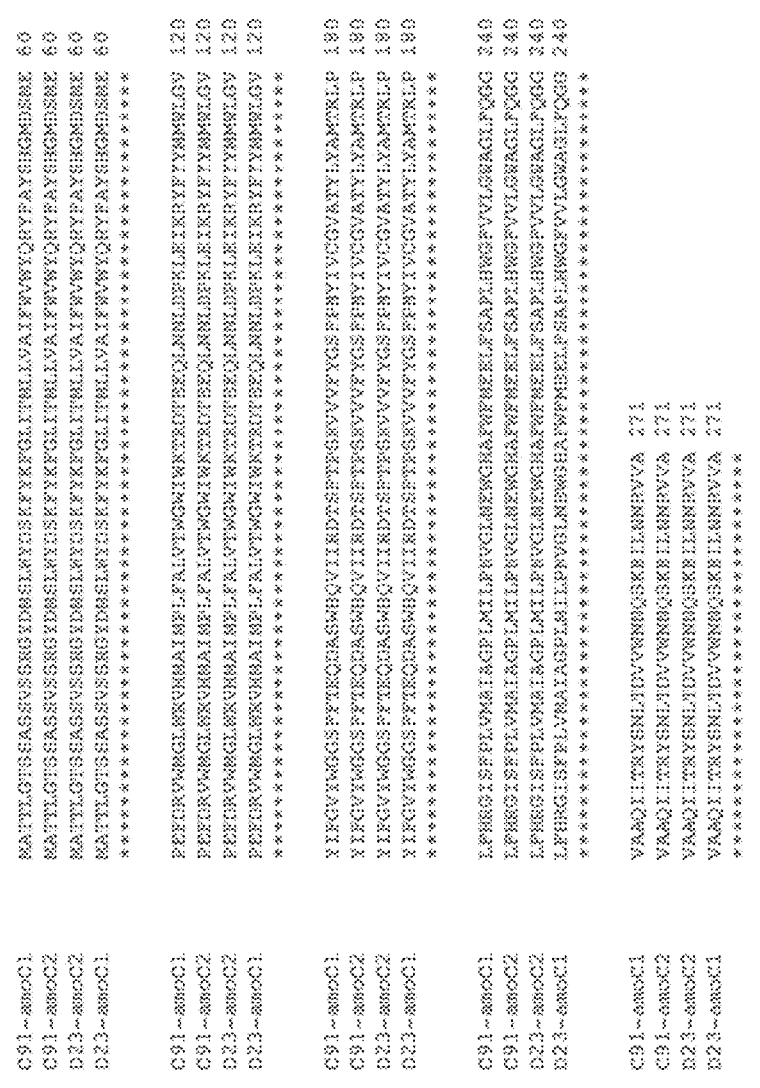

FIG. 12 is a sequence alignment between the AmoC1 and AmoC2 proteins in *N. eutropha* strains D23 and C91. The SEQ ID of each protein is listed in Table 1. FIG. 12 discloses SEQ ID NOS 34, 40, 10 and 4, respectively, in order of appearance.

FIG. 13 is a sequence alignment between the AmoC3 proteins in *N. eutropha* strains D23 and C91. The SEQ ID of each protein is listed in Table 1. FIG. 13 discloses SEQ ID NOS 46 and 16, respectively, in order of appearance.

FIG. 14A shows a sequence alignment between the Hao1, Hao2, and Hao3 proteins in *N. eutropha* strains D23 and C91. The SEQ ID of each protein is listed in Table 1.

FIG. 14B is a continuation of FIG. 14A. FIGS. 14A-14B disclose SEQ ID NOS 20, 22, 18, 50, 52 and 48, respectively, in order of appearance.

FIG. 15 is a sequence alignment between the cycA1, cycA2, and cycA3 genes in *N. eutropha* strains D23 and C91. The SEQ ID of each protein is listed in Table 1. FIG. 15 discloses SEQ ID NOS 26, 28, 24, 58, 56 and 54, respectively, in order of appearance.

FIG. 16 is a sequence alignment between the cycB1 and cycB2 genes in *N. eutropha* strains D23 and C91. The SEQ ID of each protein is listed in Table 1. FIG. 16 discloses SEQ ID NOS 30, 32, 60 and 62, respectively, in order of appearance.

Figure 17:
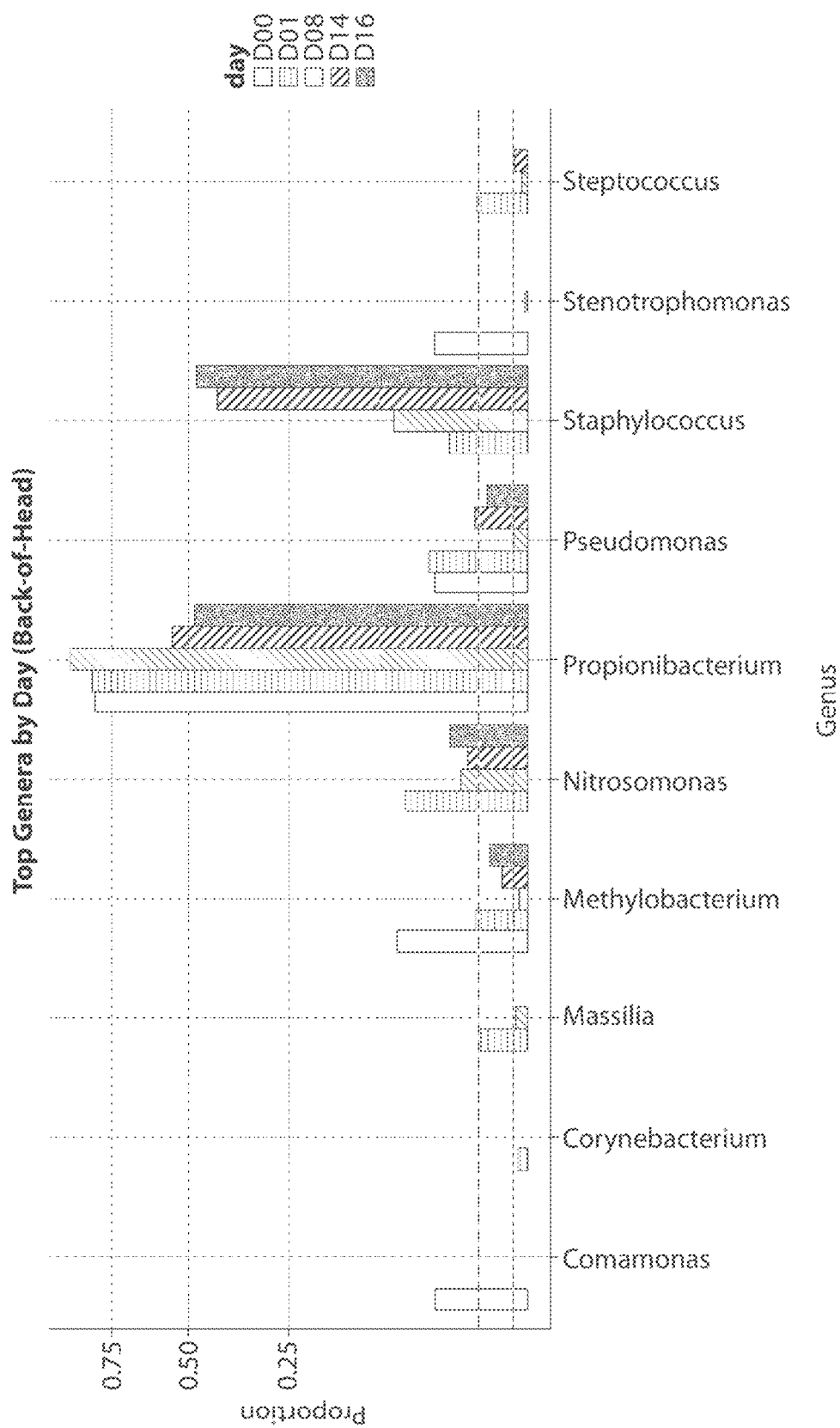

FIG. 17 shows a bar graph of proportion of bacteria, by genus versus day.

Figure 18:
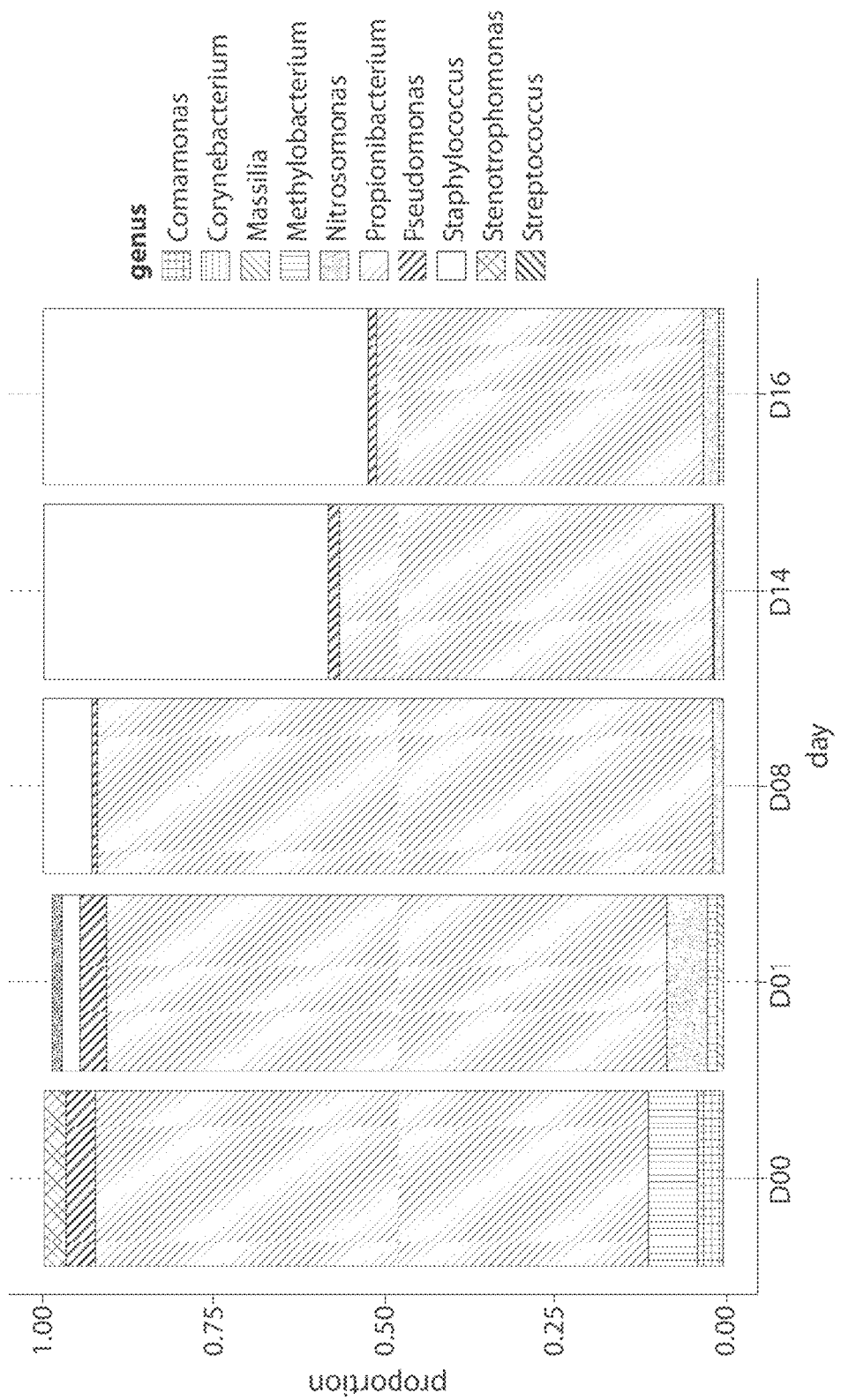

FIG. 18 shows a bar graph of proportion of bacteria, by genus versus bacteria genus, for day 0, day 1, day 8, day 14, and day 16.

Supplementary Table 1 displays the genome annotation of 2,777 genes identified in strain D23 using sequence analysis. Column headers are as described in FIG. 6. "C91 Alias" refers to a homolog in strain C91. Supplementary Table 1 is appended to the end of the Detailed Description and Examples.

Supplementary Table 2 displays the sequences of selected proteins genes identified in strain D23.

Supplementary Table 2 is appended to the end of the Detailed Description and Examples.

DETAILED DESCRIPTION

Ammonia-oxidizing bacteria (AOB) of the genus *Nitrosomonas* are Gram-negative obligate autotrophic bacteria with a unique capacity to generate nitrite and nitric oxide exclusively from ammonia as an energy source. They are widely present both in soil and water environments and are essential components of environmental nitrification processes. Due to the roles of nitrite and nitric oxide on human skin as important components of several physiological functions, such as vasodilation, skin inflammation and wound healing, these bacteria may have beneficial properties for both healthy and immunopathological skin conditions. These bacteria may be safe for use in humans because they are slow-growing, cannot grow on organic carbon sources, may be sensitive to soaps and antibiotics, and have never been associated with any disease or infection in animals or humans.

1. Definitions

An ammonia oxidizing bacterium refers to a bacterium capable of oxidizing ammonia or ammonium to nitrite at a rate, e.g., a substantial rate, e.g., a pre-determined rate, e.g., at least the rate depicted in any one of FIG. 2A, 2B, 2C, 4A, 4B, or 5 or at least 90%, 80%, 70%, 60%, 50%, 40%, 30%, 20%, or 10% of that rate. In some embodiments, the substantial rate refers to the conversion of ammonium ions ($NH_4^+$)(e.g., at about 200 mM) to nitrite ($NO_2^-$) at a rate of at least 50, 75, 125, or 150 micromoles $NO_2$ per minute, e.g., about 100-150, 75-175, 75-125, 100-125, 125-150, or 125-175 micromoles/minute, e.g., about 125 micromoles $NO_2$ per minute. Examples of ammonia oxidizing bacteria include *N. eutropha* strains D23 and C91, and other bacteria in the genera *Nitrosomonas, Nitrosococcus*, Nitrosospira, *Nitrosocystis, Nitrosolobus*, and *Nitrosovibrio*. D23 *Nitrosomonas eutropha* strain refers to the strain, designated AOB D23-100, deposited with the American Type Culture Collection (ATCC® biological material depository with the address 10801 University Blvd, Manassas, Virginia 20110) on Apr. 8, 2014 having accession number PTA-121157. The D23 *Nitrosomonas eutropha* of accession number PTA-121157 has a genome sequence as set out in SEQ ID NO: 1 herein. The nucleic acid sequence(s), e.g., genome sequence, of accession number PTA-121157 are hereby incorporated by reference in their entireties.

Optimized *Nitrosomonas eutropha* (*N. eutropha*), as that term is used herein, refers to an *N. eutropha* having an optimized growth rate; an optimized $NH_4^+$ oxidation rate; or optimized resistance to $NH_4^+$. In an embodiment it differs from naturally occurring *N. eutropha* by at least one nucleotide, e.g., a nucleotide in a gene selected from ammonia monooxygenase, hydroxylamine oxidoreductase, cytochrome c554, and cytochrome $c_M$552. The difference can arise, e.g., through selection of spontaneously arising mutation, induced mutation, or directed genetic engineering, of the *N. eutropha*. In an embodiment it differs from a naturally occurring *N. eutropha* in that it has a constellation of alleles, not present together in nature. These differences may provide for one or more of a treatment or prevention of a skin disorder, a treatment or prevention of a disease or condition associated with low nitrite levels, a treatment or prevention of body odor, a treatment to supply nitric oxide to a subject, and a treatment to inhibit microbial growth.

As used herein, "axenic" refers to a composition comprising an organism that is substantially free of other organisms. For example, an axenic culture of ammonia oxidizing bacteria is a culture that is substantially free of organisms other than ammonia oxidizing bacteria. For example, an axenic culture of *N. eutropha* is a culture that is substantially free of organisms other than *N. eutropha*. In some embodiments, "substantially free" denotes undetectable by a method used to detect other organisms, e.g., plating the culture and examining colony morphology, or PCR for a conserved gene such as 16S RNA. An axenic composition may comprise elements that are not organisms, e.g., it may comprise nutrients or excipients. Any embodiment, preparation, composition, or formulation of ammonia oxidizing bacteria discussed herein may comprise, consist essentially of, or consist of optionally axenic ammonia oxidizing bacteria.

Throughout this disclosure, formulation may refer to a composition or preparation.

As used herein, an "autotroph", e.g., an autotrophic bacterium, is any organism capable of self-nourishment by using inorganic materials as a source of nutrients and using photosynthesis or chemosynthesis as a source of energy. Autotrophic bacteria may synthesize organic compounds from carbon dioxide and ATP derived from other sources, oxidation of ammonia to nitrite, oxidation of hydrogen sulfide, and oxidation of $Fe^{2+}$ to $Fe^{3+}$ Autotrophic bacteria of the present disclosure are incapable of causing infection.

Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concomitant" or "concurrent delivery". In other embodiments, the delivery of one treatment ends before the delivery of the other treatment begins. This is sometimes referred to herein as "successive" or "sequential delivery." In embodiments of either case, the treatment is more effective because of combined administration. For example, the second treatment is a more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive (i.e., synergistic). The delivery can be such that an effect of the first treatment delivered is still detectable when the second is delivered.

Complete *N. europaea* medium refers to the *N. europaea* growth medium described in Ensign et al., "In vitro activation of ammonia monooxygenase from *Nitrosomonas europaea* by copper." J Bacteriol. 1993 April; 175(7):1971-80.

To "culture" refers to a process of placing an amount of a desired bacterium under conditions that promote its growth, i.e., promoting cell division. The conditions can involve a specified culture medium, a set temperature range, and/or an agitation rate. Bacteria can be cultured in a liquid culture or on plates, e.g., agar plates.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

The terms "nucleic acid," "nucleic acid sequence," "nucleotide sequence," or "polynucleotide sequence," and "polynucleotide" are used interchangeably. They refer to a polymeric form of nucleotides of any length, e.g., deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a nonnatural arrangement.

As used herein, the term "optimized growth rate" refers to one or more of: a doubling time of less than about 4, 5, 6, 7, 8, 9, or 10 hours when cultured under batch conditions as described herein in Example 2; a doubling time of less than about 16, 18, 20, 22, 24, or 26 hours, when grown under chemostat conditions as described herein in Example 2; or growing from an OD600 of about 0.15 to at least about 0.3, 0.4, 0.5, 0.6, 0.7, or 0.8 over about 1 or 2 days. In an embodiment, optimized growth rate is one having a doubling time that it is at least 10, 20, 30, 40, or 50% shorter than that of a naturally occurring *N. eutropha*.

As used herein, "optimized $NH_4^+$ oxidation rate" refers to a rate of at least about 50, 75, 125, or 150 micromoles per minute of converting $NH_3$ or $NH_4^+$ into $NO_2^-$. For instance, the rate may be at least about 50, 75, 125, or 150 micromoles per minute of converting $NH_4^+$ (e.g., at about 200 mM) to $NO_2^-$. In an embodiment, an optimized $NH_4^+$ oxidation rate is one in which $NH_3$ or $NH_4^+$ is converted into $NO_2^-$ at least 10, 20, 30, 40, or 50% more rapidly than is seen with a naturally occurring *N. eutropha*.

Percent (%) amino acid sequence identity, with respect to the amino acid sequences here (e.g., proteins expressed by *N. eutropha* D23) is defined as the percentage of amino acid residues in a candidate sequence that are identical with the amino acid residues in the reference sequence, which may be a naturally-occurring *N. eutropha* sequence or an *N. eutropha* D23 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the means of those skilled in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. For instance, the WU-BLAST-2 software may be used to determine amino acid sequence identity (Altschul et al, Methods in Enzymology 266, 460-480 (1996). WU-BLAST-2 uses several search parameters, most of which are set to the default values. The adjustable parameters are set with the following values: overlap span=1, overlap fraction=0.125, world threshold (T)=I 1. HSP score (S) and HSP S2 parameters are dynamic values and are established by the program itself, depending upon the composition of the particular sequence, however, the minimum values may be adjusted as appropriate.

Amino acid substitutions can be the result of replacing one amino acid with another amino acid having similar structural and/or chemical properties, such as the replacement of a leucine with a serine, i.e., conservative amino acid replacements. Typical but not limiting conservative substitutions are the replacements, for one another, among the aliphatic amino acids Ala, Val, Leu and Ile; interchange of Ser and Thr containing hydroxy residues, interchange of the acidic residues Asp and Glu, interchange between the amide-containing residues Asn and Gln, interchange of the basic residues Lys and Arg, interchange of the aromatic residues Phe and Tyr, and interchange of the small-sized amino acids Ala, Ser, Thr, Met and Gly. Additional conservative substitutions include the replacement of an amino acid by another of similar spatial or steric configuration, for example the interchange of Asn for Asp, or Gln for Glu.

Amino acid substitutions can also be the result of replacing one amino acid with another amino acid having dis-similar structural and/or chemical properties, i.e., non-conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vivo or in vitro assays for, e.g., metabolizing urea or ammonia.

Percent (%) sequence identity with respect to the nucleic acid sequences here (e.g., the *N. eutropha* D23 genome and portions thereof) is defined as the percentage of nucleotides in a candidate sequence that are identical with the nucleotides in the reference sequence, which may be a naturally-occurring *N. eutropha* sequence or an *N. eutropha* D23 sequence, after aligning the sequences and introducing gaps, if necessary, to achieve the maximum percent sequence identity. Alignment for purposes of determining percent nucleotide sequence identity can be achieved in various ways that are within the means of those skilled in the art, for instance, using publicly available computer software such as BLAST. Those skilled in the art can determine appropriate parameters for measuring alignment, including any algorithms needed to achieve maximal alignment over the full length of the sequences being compared.

The terms "polypeptide", "peptide" and "protein" (if single chain) are used interchangeably herein to refer to amino acid polymers. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

As used herein, "optimized resistance to $NH_4^+$" refers to an ability to grow in conditions of greater than 50, 75, 100, 125, 150, 175, 200, 225, 250, 275, or 300 mM $NH_3$ or $NH_4^+$ for at least about 24 or 48 hours. In an embodiment, an optimized resistance to $NH_4^+$ refers to the ability to grow at least 10, 20, 30, 40, or 50% more rapidly, or at least 10, 20, 30, 40, or 50% longer, in the presence of a selected concentration of $NH_3$ or $NH_4^+$ than can a naturally occurring *N. eutropha*.

As used herein with respect to a comparison between nucleic acid or protein sequences, "similar" means having homology. A similar gene or protein may comprise, e.g., substitutions (such as conservative or non-conservative substitutions), insertions (e.g., of at least 1, 2, 3, 4, 5, 10, 15, 20, 25, 30 amino acids, and for example up to 2, 3, 4, 5, 10, 15, 20, 25, 30, or 50 amino acids, or any positive combination thereof, or the number of nucleotides necessary to encode said amino acids), or deletions (e.g., of at least 1, 2, 3, 4, 5, 10, 15, 20, 25, 30 amino acids, and for example up to 2, 3, 4, 5, 10, 15, 20, 25, 30, or 50 amino acids, or any positive combination thereof, or the number of nucleotides necessary to encode said amino acids), or any combination thereof. Each of substitutions, insertions, and deletions may be positioned at the N-terminus, C-terminus, or a central region of the protein or gene. In embodiments, a conservative substitution is one that does not alter the charge and/or polarity and/or approximate size and/or geometry at the substituted position.

As used herein, "transgenic" means comprising one or more exogenous portions of DNA. The exogenous DNA is derived from another organism, e.g., another bacterium, a bacteriophage, an animal, or a plant.

As used herein, treatment of a disease or condition refers to reducing the severity or frequency of at least one symptom of that disease or condition, compared to a similar but untreated patient. Treatment can also refer to halting, slowing, or reversing the progression of a disease or condition, compared to a similar but untreated patient. Treatment may comprise addressing the root cause of the disease and/or one or more symptoms.

As used herein a therapeutically effective amount refers to a dose sufficient to prevent advancement, or to cause regression of a disease or condition, or which is capable of relieving a symptom of a disease or condition, or which is capable of achieving a desired result. A therapeutically effective dose can be measured, for example, as a number of bacteria or number of viable bacteria (e.g., in CFUs) or a mass of bacteria (e.g., in milligrams, grams, or kilograms), or a volume of bacteria (e.g., in $mm^3$).

As used herein, the term "viability" refers to the autotrophic bacteria's, e.g., ammonia oxidizing bacteria's, ability to oxidize ammonia, ammonium, or urea to nitrite at a pre-determined rate. In some embodiments, the rate refers to the conversion of ammonium ions ($NH_4^+$) (e.g., at about 200 mM) to nitrite ($NO_2^-$) at a rate of at least 50, 75, 125, or 150 micromoles $NO_2^-$ per minute, e.g., about 100-150, 75-175, 75-125, 100-125, 125-150, or 125-175 micromoles/minute, e.g., about 125 micromoles $NO_2^-$ per minute.

"Growth media" or "AOB media," as referred to herein comprises the following components of Table 3 or Table 4 herein.

In some embodiments, the states most relevant to the present disclosure are the state of growth, e.g., maximal growth, characterized by a pH of at least about 7.6, ammonia, trace minerals, oxygen and carbon dioxide. Another state may be characterized by a pH of about 7.4 or less and characterized by an absence of carbon dioxide. Under low carbon dioxide conditions, ammonia oxidizing bacteria, e.g., *Nitrosomonas*, continues to oxidize ammonia into nitrite and generates ATP, but lacking carbon dioxide, e.g., lacking sufficient carbon dioxide, to fix and generate protein, it instead generates polyphosphate, which it uses as an energy storage medium. This may allow the ammonia oxidizing bacteria to remain in a "storage state" for a period of time, e.g., a pre-determined period of time, for example, at least 1, 2, 3, 4, 5, 6, 7, days, 1, 2, 3, 4 weeks, 1, 2, 3, 4, 5, 6, 7, 8, 9, 10, 11, 12 months, 1, 2, 3, 4, or 5 years. In some embodiments, the ammonia oxidizing bacteria may remain in a storage state for at least about 6 months to about 1 year.

As used herein, "growth state" refers to autotrophic bacteria, e.g., ammonia oxidizing bacteria, in a state or in an environment, e.g., a media, e.g., a culture media, e.g., a growth media, that may have a pH of at least about 7.6. Levels of at least one of ammonia, ammonium ions, and urea may be between about 1 micromolar and 1000 millimolar. Levels of trace materials are between about 0.01 micromolar iron and 200 micromolar iron. Levels of oxygen are between about 5% and 100% oxygen saturation (e.g., of media). Levels of carbon dioxide are between about 20 ppm and 10% saturation (e.g., of media). In certain aspects, levels of at least one of ammonia, ammonium ions, and urea may be between about 10 micromolar and 100 millimolar. Levels of trace materials are between about 0.1 micromolar iron and 20 micromolar iron. Levels of oxygen are between about 5% and 100% oxygen saturation. Levels of carbon dioxide are between about 200 ppm and 5% saturation (e.g., of media).

As used herein, "polyphosphate loading state" refers to autotrophic bacteria, e.g., ammonia oxidizing bacteria, in a state or in an environment, e.g., a media, e.g., a culture media, e.g., a growth media, that may have a pH of about 7.4, or less. Levels of at least one of ammonia, ammonium ions, and urea are between about 1 micromolar and 2000 millimolar. Levels of trace materials are between 0.01 micromolar iron and 200 micromolar iron. Levels of oxygen are between about 0% and 100% O2 saturation (e.g., of media). Levels of carbon dioxide are between/less than about zero and 400 ppm, and phosphate levels greater than about 1 micromolar. In certain aspects, levels of at least one of ammonia, ammonium ions, and urea are between about 10 micromolar and 200 millimolar. Levels of trace materials are between 0.1 micromolar iron and 20 micromolar iron. Levels of oxygen are between about 5% and 100% O2 saturation. Levels of carbon dioxide are between/less than about zero and 200 ppm, and phosphate levels greater than about 10 micromolar.

The polyphosphate loading state may be induced for a period of time, e.g., a pre-determined period of time. The pre-determined period of time may the time period that allows sufficient polyphosphate accumulation in the ammonia oxidizing bacteria. This pre-determined period of time is the period of time suitable to provide for sufficient polyphosphate loading to allow for the ammonia oxidizing bacteria to be stored for an extended period of time. The pre-determined period of time may be at least partially based on a period of time of about 0.2-10 times, 0.3-5 times, 0.5-3 times, 0.5-1.5 times, or 0.5 to 1 times the doubling time for the ammonia oxidizing bacteria. The pre-determined period of time may be at least partially based on a period of time of about one doubling time for the ammonia oxidizing bacteria. In some embodiments, the pre-determined period of time is between about 8 hours and 12 hours. In some embodiments, the pre-determined period of time is about 10 hours. In some embodiments, the pre-determined period of time is about 24 hours.

A purpose of the polyphosphate loading state may be to provide AOB with sufficient ammonia, ammonium ions, and/or urea, and $O_2$ such that ATP can be produced, but to deny them $CO_2$ and carbonate such that they are unable to use that ATP to fix $CO_2$ and instead use that ATP to generate polyphosphate which may be stored by the bacteria.

As used herein, the term "storage state" refers to autotrophic bacteria, e.g., ammonia oxidizing bacteria, in a state or in an environment, e.g., a media, e.g., a culture media, e.g., a growth media, having a pH of about 7.4 or less (in some embodiments, the pH may be 7.6 or less). Levels of at least one of ammonia, ammonium ions, and urea are between about 1 and 1000 micromolar. Levels of trace materials are between about 0.1 and 100 micromolar. Levels of oxygen are between about 0 and 100% saturation (e.g., of media). Levels of carbon dioxide are between about 0 and 800 ppm. In certain aspects, levels of at least one of ammonia, ammonium ions, and urea are between about 10 and 100 micromolar. Levels of trace materials are between about 1 and 10 micromolar. Levels of oxygen are between about 0 and 100% saturation (e.g., of media). Levels of carbon dioxide are between about 0 and 400 ppm.

AOB are produced according to some embodiments of the present disclosure by generating AOB biomass during a growth state, then exposing the AOB to a polyphosphate loading state and then removing the media and resuspending the AOB in a buffer, e.g., a storage buffer (i.e., the storage state).

The ammonia oxidizing bacteria may remain in a "storage state" for a period of time, e.g., a pre-determined period of time, for example, at least 1, 2, 3, 4, 5, 6, 7, days, 1, 2, 3, 4 weeks, 1, 2, 3, 4, 5, 6, 7, 8, 9, 10, 11, 12 months, 1, 2, 3, 4, or 5 years. In some embodiments, the ammonia oxidizing bacteria may remain in a storage state for at least about 6 months to about 1 year. Upon revival, the viability of the ammonia oxidizing bacteria is at least about 50%, 60%, 70%, 80%, 90%, or 100% of the viability as of the ammonia oxidizing bacteria prior to storage e.g., in a growth state). In some embodiments, the preparation of ammonia oxidizing bacteria may be prepared, such that no more than 10%, 20%, 30%, 40%, 50%, 60%, or 70% of the ability to oxidize $NH_4^+$ is lost upon storage at selected conditions.

The time that it takes to revive the ammonia oxidizing bacteria from a storage state (or a polyphosphate loading state) may be a pre-determined period of time. For example, the pre-determined period of time may be less than about 75 hours, or less than about 72 hours. The pre-determined period of time may at least partially based on a period time of about 0.2-10 times, 0.3-5 times, 0.5-3 times, 0.5-1.5 times, or 0.5 to 1 times the doubling time for the ammonia oxidizing bacteria. The pre-determined period of time may be at least partially based on a period of time of about one doubling time for the ammonia oxidizing bacteria. The pre-determined period of time may be between about 8 hours and 12 hours. The pre-determined period of time may be about 10 hours. The pre-determined time may be less than about 75 hours, 72 hours, 70 hours, 68 hours, 65 hours, 60 hours, 55 hours, 50 hours, 45 hours, 40 hours, 35 hours, 30 hours, 25 hours, 20 hours, 15 hours, 10 hours, 5 hours, 4 hours, 3, hours, 2 hours, or 1 hour. The pre-determined period of time may be between about 5 minutes and 5 hours. The pre-determined period of time may be about 5-10 minutes, 10-15 minutes, 15-20 minutes, 20-25 minutes, 25-30 minutes, 30-45 minutes, 45-60 minutes, 60 minutes-1.5 hours, 1.5 hours-2 hours, 2 hours-2.5 hours, 2.5 hours-3 hours, 3 hours-3.5 hours, 3.5 hours-4 hours, 4 hours-4.5 hours, 4.5 hours-5 hours. In some embodiments, the pre-determined period of time may be about 2 hours. The pre-determined period of time, e.g., may be the time it may take to achieve revival of the ammonia oxidizing bacteria, e.g., achieve viability of the ammonia oxidizing bacteria as compared to the viability of the bacteria prior to storage (e.g., in a growth state), e.g., at least about 10%, 20%, 30%, 40%, 50%, 60%, 70%, 80%, 90%, 95%, 97%, 98%, 99%, or 100% viability.

2. Ammonia Oxidizing Bacteria (AOBs), *N. eutropha* Strain D23 and Similar Bacteria Autotrophic ammonia oxidizing bacteria, which may be referred to herein as AOBs or AOB, are obligate autotrophic bacteria as noted by Alan B. Hooper and A. Krummel at al. Alan B. Hooper, Biochemical Basis of Obligate Autotrophy in *Nitrosomonas europaea*, Journal of Bacteriology, February 1969, p. 776-779. Antje Krummel et al., Effect of Organic Matter on Growth and Cell Yield of Ammonia-Oxidizing Bacteria, Arch Microbiol (1982) 133: 50-54. These bacteria derive all metabolic energy only from the oxidation of ammonia to nitrite with nitric oxide (NO) as an intermediate product in their respiration chain and derive virtually all carbon by fixing carbon dioxide. They are incapable of utilizing carbon sources other than a few simple molecules.

Ammonia oxidizing bacteria (AOB) are widely found in the environment, and in the presence of ammonia, oxygen and trace metals will fix carbon dioxide and proliferate. AOB may be slow growing and toxic levels of ammonia may kill fish and other organisms before AOB can proliferate and reduce ammonia to non-toxic levels. Slow growth of AOB also may delay the health benefits of the NO and nitrite the AOB produce when applied to the skin.

Supplementing the aquarium, skin, or process with sufficient viable AOB grown and stored for that purpose is desired. AOB do not form spores, so storage in the dry state with high viability is difficult, and storage in the wet state leaves them metabolically active.

Decay of nitrifying capacity during storage of AOB for wastewater treatment has been studied, as for example (Munz G, Lubello C, Oleszkiewicz J A. Modeling the decay of ammonium oxidizing bacteria. Water Res. 2011 January; 45(2): 557-64. Oi: 10.1016/j.watres.2010.09.022.)

Growth, prolonged storage, and restoration of activity of *Nitrosomonas* is discussed by Cassidy et al. (U.S. Pat. No. 5,314,542) where they disclose growing *Nitrosomonas*, removing toxic waste products, storing in sterile water of appropriate salinity for periods of time up to one year, and then reviving by adding buffer ($CaCO_3$) and 200 ppm, of ammonium, which reviving takes 72 hours.

As obligate autotrophs, AOB synthesize protein via the fixing of $CO_2$ using the energy and reducing equivalents generated by the oxidation of ammonia to nitrite. Growth requires ammonia, oxygen, minerals and carbon dioxide.

*Nitrosomonas* may exist in several metabolic states, according to "Polyphosphate and Orthophosphate Content of *Nitrosomonas europaea* as a Function of Growth" by K. R. Terry and A. B. Hooper, Journal of Bacteriology, July 1970, p. 199-206, Vol. 103, No. I.

In certain embodiments of the disclosure, the ammonia oxidizing bacteria may be axenic. The preparation (formulation or composition) of ammonia oxidizing bacteria may comprise, consist essentially of, or consist of axenic ammonia oxidizing bacteria. The ammonia oxidizing bacteria may be from a genus selected from the group consisting of *Nitrosomonas, Nitrosococcus, Nitrosospria, Nitrosocystis, Nitrosolobus, Nitrosovibrio*, and combinations thereof.

This disclosure provides, inter alia, *N. eutropha* strain D23, a unique, e.g., optimized strain of ammonia oxidizing bacteria that can increase production of nitric oxide and nitric oxide precursors on the surface of a subject, e.g., a human subject. This disclosure also provides methods of using the bacteria and articles comprising the bacteria.

In embodiments, the *N. eutropha* is non-naturally occurring. For instance, it may have accumulated desirable mutations during a period of selection. In other embodiments, desirable mutations may be introduced by an experimenter. In some embodiments, the *N. eutropha* may be a purified preparation, and may be an optimized *N. eutropha*.

In preferred embodiments, the *N. eutropha* strain is autotrophic and so incapable of causing infection. A preferred strain utilizes urea as well as ammonia, so that hydrolysis of the urea in sweat would not be necessary prior to absorption and utilization by the bacteria. Also, in order to grow at low pH, the bacteria may either absorb $NH_4^+$ ions or urea. The selected strain should also be capable of living on the external skin of a subject, e.g., a human, and be tolerant of conditions there.

Although this disclosure refers to *N. eutropha* strain D23 in detail, the preparations, methods, compositions, treatments, wearable articles, and articles of clothing may be used with one or more of: one or more other strains of *N. eutropha*, one or more other species of *Nitrosomonas*, and one or more other ammonia oxidizing bacteria. Autotrophic AOBs are obligate autotrophic bacteria as noted by Alan B. Hooper and A. Krummel at al. Alan B. Hooper, Biochemical Basis of Obligate Autotrophy in *Nitrosomonas europaea*, Journal of Bacteriology, February 1969, p. 776-779. Antje Krummel et al., Effect of Organic Matter on Growth and Cell Yield of Ammonia-Oxidizing Bacteria, Arch Microbiol (1982) 133: 50-54. These bacteria derive all metabolic energy only from the oxidation of ammonia to nitrite with nitric oxide (NO) as an intermediate product in their respiration chain and derive virtually all carbon by fixing carbon dioxide. They are incapable of utilizing carbon sources other than a few simple molecules.

In certain embodiments, the *N. eutropha* is the strain deposited with the American Type Culture Collection (ATCC® biological material depository) on Apr. 8, 2014, designated AOB D23-100 (25 vials) under accession number PTA-121157.

In certain embodiments, the *N. eutropha* comprises a chromosome having a sequence at least 70%, 80%, 85%, 90%, 95%, 96%, 97%, 98%, 99%, or 99.5% identical to SEQ ID NO: 1 (the strain D23 whole-genome sequence).

In certain embodiments, a bacterium with the above-mentioned sequence characteristics has one or more of (1) an optimized growth rate as measured by doubling time, (2) an optimized growth rate as measured by OD600, (3) an optimized $NH_4^+$ oxidation rate, (4) an optimized resistance to $NH_4^+$, and (4) an optimized resistance to $NO_2^-$. Particular sub-combinations of these properties are specified in the following paragraph.

In some embodiments, the *N. eutropha* described herein has one or more of: (1) an optimized growth rate as measured by doubling time, (2) an optimized growth rate as measured by OD600, (3) an optimized $NH_4^+$ oxidation rate, (4) an optimized resistance to, $NH_4^+$, and (4) an optimized resistance to, $NO_2$. For instance, the bacterium may have properties (1) and (2); (2) and (3); (3) and (4); or (4) and (5) from the list at the beginning of this paragraph. As another example, the bacterium may have properties (1), (2), and (3); (1), (2), and (4); (1), (2), and (5); (1), (3), and (4); (1), (3), and (5); (1), (4), and (5); (2), (3), and (4); (2), (3), and (5), or (3), (4), and (5) from the list at the beginning of this paragraph. As a further example, the bacterium may have properties (1), (2), (3), and (4); (1), (2), (3), and (5); (1), (2), (4), and (5); (1), (3), (4), and (5); or (2), (3), (4), and (5) from the list at the beginning of this paragraph. In some embodiments, the bacterium has properties (1), (2), (3), (4), and (5) from the list at the beginning of this paragraph.

This disclosure also provides an axenic composition of *N. eutropha* having one or more of: (1) an optimized growth rate as measured by doubling time, (2) an optimized growth rate as measured by OD600, (3) an optimized $NH_4^+$ oxidation rate, (4) an optimized resistance to, $NH_4^+$, and (4) an optimized resistance to, $NO_2^-$. For instance, the axenic *N. eutropha* composition may have properties (1) and (2); (2) and (3); (3) and (4); or (4) and (5) from the list at the beginning of this paragraph. As another example, the axenic *N. eutropha* composition may have properties (1), (2), and (3); (1), (2), and (4); (1), (2), and (5); (1), (3), and (4); (1), (3), and (5); (1), (4), and (5); (2), (3), and (4); (2), (3), and (5), or (3), (4), and (5) from the list at the beginning of this paragraph. As a further example, the axenic *N. eutropha* composition may have properties (1), (2), (3), and (4); (1), (2), (3), and (5); (1), (2), (4), and (5); (1), (3), (4), and (5); or (2), (3), (4), and (5) from the list at the beginning of this paragraph. In some embodiments, the axenic *N. eutropha* composition has properties (1), (2), (3), (4), and (5) from the list at the beginning of this paragraph.

*N. eutropha* strain D23, as deposited in the form of 25 vials on Apr. 8, 2014, in the ATCC® American Type Culture Collection biological material depository, patent depository, designated AOB D23-100, under accession number PTA-121157, comprises a circular genome having SEQ ID NO: 1 or its complement. Accordingly, in some embodiments, an *N. eutropha* strain described herein comprises a nucleic acid sequence, e.g., a genome, that is similar to SEQ ID NO: 1 or its complement.

For instance, the *N. eutropha* may comprise a nucleic acid sequence having a 1,000 base pair portion having at least about 80%, 85%, 90%, 95%, 97%, 98%, 99%, or 99.5% identity to a 1,000 base pair portion of SEQ ID NO: 1 or its complement. The 1,000 base pair portion may span, e.g., nucleotides (n*1,000)+1 to (n+1)*1,000, where n=0, 1, 2, 3 . . . 2538, e.g., nucleotides 1-1,000, 1,001-2,000, and so on through the end of SEQ ID NO: 1.

In embodiments, the *N. eutropha* comprises a nucleic acid sequence having a 2,000 base pair portion having at least about 80%, 85%, 90%, 95%, 97%, 98%, 99%, or 99.5% identity to a 2,000 base pair portion of SEQ ID NO: 1 or its complement. The 2,000 base pair portion may span, e.g., nucleotides (n*2,000)+1 to (n+1)*2,000, where n=0, 1, 2, 3 . . . 1269, e.g., nucleotides 1-2,000, 2,001-4,000, and so on through the end of SEQ ID NO: 1.

In embodiments, the *N. eutropha* comprises a nucleic acid sequence having a 5,000 base pair portion having at least about 80%, 85%, 90%, 95%, 97%, 98%, 99%, or 99.5% identity to a 5,000 base pair portion of SEQ ID NO: 1 or its complement. The 5,000 base pair portion may span, e.g., nucleotides (n*5,000)+1 to (n+1)*5,000, where n=0, 1, 2, 3 . . . 508, e.g., nucleotides 1-5,000, 5,001-10,000, and so on through the end of SEQ ID NO: 1.

In embodiments, the *N. eutropha* comprises a nucleic acid sequence having a 10,000 base pair portion having at least about 80%, 85%, 90%, 95%, 97%, 98%, 99%, or 99.5% identity to a 10,000 base pair portion of SEQ ID NO: 1 or its complement. The 10,000 base pair portion may span, e.g., nucleotides (n*10,000)+1 to (n+1)*10,000, where n=0, 1, 2, 3 . . . 254, e.g., nucleotides 1-10,000, 10,001-20,000, and so on through the end of SEQ ID NO: 1.

In embodiments, the *N. eutropha* comprises a nucleic acid sequence having a 20,000 base pair portion having at least about 80%, 85%, 90%, 95%, 97%, 98%, 99%, or 99.5% identity to a 20,000 base pair portion of SEQ ID NO: 1 or its complement. The 20,000 base pair portion may span, e.g., nucleotides (n*20,000)+1 to (n+1)*20,000, where n=0, 1, 2, 3 . . . 127, e.g., nucleotides 1-20,000, 20,001-40,000, and so on through the end of SEQ ID NO: 1.

In embodiments, the *N. eutropha* comprises a nucleic acid sequence having a 50,000 base pair portion having at least about 80%, 85%, 90%, 95%, 97%, 98%, 99%, or 99.5% identity to a 50,000 base pair portion of SEQ ID NO: 1 or its complement. The 50,000 base pair portion may span, e.g., nucleotides (n*50,000)+1 to (n+1)*50,000, where n=0, 1, 2, 3 . . . 51, e.g., nucleotides 1-50,000, 50,001-100,000, and so on through the end of SEQ ID NO: 1.

In embodiments, the *N. eutropha* comprises a nucleic acid sequence having a 100,000 base pair portion having at least about 80%, 85%, 90%, 95%, 97%, 98%, 99%, or 99.5% identity to a 100,000 base pair portion of SEQ ID NO: 1 or its complement. The 100,000 base pair portion may span, e.g., nucleotides (n*100,000)+1 to (n+1)*100,000, where n=0, 1, 2, 3 . . . 26, e.g., nucleotides 1-100,000, 100,001-20,000, and so on through the end of SEQ ID NO: 1.

In some aspects, the present disclosure provides a composition of *N. eutropha* comprising a chromosome at least about 70%, 80%, 85%, 90%, 95%, 96%, 97%, 98%, 99%, or 99.5% identical to SEQ ID NO: 1. In some aspects, the present disclosure provides an axenic composition of *N. eutropha* comprising a chromosome at least about 70%, 80%, 85%, 90%, 95%, 96%, 97%, 98%, 99%, or 99.5% identical to SEQ ID NO: 1.

In certain embodiments, the *N. eutropha* strain comprises a nucleic acid sequence, e.g., a genome, that hybridizes to SEQ ID NO: 1, or to the genome of the D23 strain deposited in the form of 25 vials with the ATCC® American Type Culture Collection biological material depository, patent depository on Apr. 8, 2014, designated AOB D23-100, under accession number PTA-121157, or their complements, under low stringency, medium stringency, high stringency, or very high stringency, or other hybridization condition described herein. As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; 4) very high stringency hybridization conditions are 0.5M sodium phosphate, 7% SDS at 65° C., followed by one or more washes at 0.2×SSC, 1% SDS at 65° C. Very high stringency conditions (4) are suitable conditions and the ones that should be used unless otherwise specified.

The genome of strain D23 (SEQ ID NO: 1) was compared with the genome of *N. eutropha* C91. An annotation of the D23 genome is shown in Supplementary Table 1, which lists the positions of 2,777 genes in SEQ ID NO: 1 as identified by sequence analysis. In certain embodiments, the *N. eutropha* described herein comprises one or more genes or proteins listed in Supplementary Table 1, or a gene or protein similar to one of said genes or proteins.

Accordingly, in some embodiments, the *N. eutropha* comprises a gene of Supplementary Table 1, or a protein encoded by said gene. In certain embodiments, the *N. eutropha* comprises a gene that is similar (e.g., at least 70%, 80%, 85%, 90%, 95%, 97%, 98%, 99%, or 99.5% identical) to a gene of Supplementary Table 1, or a protein encoded by said gene. In embodiments, the *N. eutropha* comprises genes or proteins that are identical or similar to at least 2, 3, 4, 5, 10, 20, 30, 40, 50, 100, 150, 200, 250, 300, 350, 400, 450, 500, 1000, 1500, 2000, 2500, or all the genes of Supplementary Table 1, or a protein encoded by said genes.

In some embodiments, the *N. eutropha* described herein (e.g., strain D23) comprises one or more genes or proteins that are absent from strain C91, or a gene or protein similar to one of said genes or proteins. Examples of these genes are set out in FIGS. 6-8 and are described in more detail in Example 4 herein.

Accordingly, with respect to FIG. 6, in some embodiments, the *N. eutropha* comprises genes that are identical or similar (e.g., at least 70%, 80%, 85%, 90%, 95%, 97%, 98%, 99%, or 99.5% identical) to 1, 2, 3, 4, 5, 10, 15, 20, 30, 40, 50, 60, 70, 80, 90, 100, 110, 120, 130, 140, 150, 160, or all of the genes in FIG. 6. In some embodiments, the *N. eutropha* comprises proteins that are identical or similar (e.g., at least 70%, 80%, 85%, 90%, 95%, 97%, 98%, 99%, or 99.5% identical) to 1, 2, 3, 4, 5, 10, 15, 20, 30, 40, 50, 60, 70, 80, 90, 100, 110, 120, 130, 140, 150, 160, or all of the proteins encoded by the genes listed in FIG. 6.

With respect to FIG. 7, in some embodiments, the *N. eutropha* comprises genes that are identical or similar (e.g., at least 70%, 80%, 85%, 90%, 95%, 97%, 98%, 99%, or 99.5% identical) to 1, 2, 3, 4, 5, 10, 15, 20, 30, 40, 50, 60, 70, 80, 90, 100, 110, 120, 130, 140, 150, 160, or all of the genes in FIG. 7. In some embodiments, the *N. eutropha* comprises proteins that are identical or similar (e.g., at least 70%, 80%, 85%, 90%, 95%, 97%, 98%, 99%, or 99.5% identical) to 1, 2, 3, 4, 5, 10, 15, 20, 30, 40, 50, 60, 70, 80, 90, 100, 110, 120, 130, 140, 150, 160, or all of the proteins encoded by the genes listed in FIG. 7.

With respect to FIG. 8, in some embodiments, the *N. eutropha* comprises genes that are identical or similar (e.g., at least 70%, 80%, 85%, 90%, 95%, 97%, 98%, 99%, or 99.5% identical) to 1, 2, 3, 4, 5, 10, 15, 20, 30, 40, 50, 60, 70, 80, 90, 100, 110, 120, 130, 140, 150, 200, or all of the genes in FIG. 8. In some embodiments, the *N. eutropha* comprises proteins that are identical or similar (e.g., at least 70%, 80%, 85%, 90%, 95%, 97%, 98%, 99%, or 99.5% identical) to 1, 2, 3, 4, 5, 10, 15, 20, 30, 40, 50, 60, 70, 80, 90, 100, 110, 120, 130, 140, 150, 200, or all of the proteins encoded by the genes listed in FIG. 8.

With respect to FIGS. 6-8 collectively, in some embodiments, the *N. eutropha* comprises genes that are identical or similar (e.g., at least 70%, 80%, 85%, 90%, 95%, 97%, 98%, 99%, or 99.5% identical) to 1, 2, 3, 4, 5, 10, 20, 40, 60, 80, 100, 150, 200, 250, 300, 350, 400, 450, 500, or all of the genes in FIGS. 6-8. In some embodiments, the *N. eutropha* comprises proteins that are identical or similar (e.g., at least 70%, 80%, 85%, 90%, 95%, 97%, 98%, 99%, or 99.5% identical) to 1, 2, 3, 4, 5, 10, 20, 40, 60, 80, 100, 150, 200, 250, 300, 350, 400, 450, 500, or all of the proteins encoded by genes listed in FIGS. 6-8.

In some embodiments, the *N. eutropha* described herein (e.g., strain D23) lacks one or more genes or proteins that are unique to strain C91, or a gene or protein similar to one of said genes or proteins. Examples of these genes are set out in FIG. 9 and are described in more detail in Example 4 herein. Accordingly, in some embodiments, the *N. eutropha* described herein lacks at least 1, 2, 3, 4, 5, 10, 20, 50, 100, 150, 200, 250, or all of the genes of FIG. 9. In some embodiments, the *N. eutropha* described herein lacks up to 2, 3, 4, 5, 10, 20, 50, 100, 150, 200, 250, or all of the genes of FIG. 9. In embodiments, the *N. eutropha* described herein lacks about 1-5, 5-10, 10-20, 20-50, 50-100, 100-150, 150-200, 200-250, or 250-all of the genes of FIG. 9.

Sequencing of the D23 genome revealed several genes of potential interest, including genes involved in ammonia metabolism (e.g., ammonia monooxygenase, hydroxylamine oxidoreductase, cytochrome c554, and cytochrome $c_M552$). All of these genes are present in multiple copies, and in general the copies are not identical to each other. One set of genes of interest is the ammonia monooxygenase synthesis operon amoCAB, which is present in two copies, along with a third copy of amoC. The operons have homologs in C91, i.e., Neut_2078/7/6 and Neut_2319/8/7. Another set of genes of interest is hydroxylamine oxidoreductase (hao), which is present in three copies. The hao homologs in C91 are designated Neut_1672, 1793, and 2335. A third set of genes of interest is the cytochrome c554 gene encoded by cycA, which is present in three copies. The corresponding C91 genes are designated Neut_1670, 1791, and 2333. A fourth set of genes of interest is the cytochrome $c_M552$ genes encoded by cycB, which are present in two copies. The homologous C91 genes are designated Neut_1790 and 2332. Each group of genes is summarized in Table 1 and is discussed in more detail below.

TABLE 1

Sequences of ammonia metabolism genes in *N. eutropha* strain D23.

| SEQ ID in strain D23 | SEQ ID in strain C91 | Type | Gene name |
|---|---|---|---|
| 1. ammonia monooxygenase | | | |
| 4 | 34 | Protein | amoC1 |
| 5 | 35 | DNA | amoC1 |
| 6 | 36 | Protein | amoA1 |
| 7 | 37 | DNA | amoA1 |
| 8 | 38 | Protein | amoB1 |
| 9 | 39 | DNA | amoB1 |
| 10 | 40 | Protein | amoC2 |
| 11 | 41 | DNA | amoC2 |
| 12 | 42 | Protein | amoA2 |
| 13 | 43 | DNA | amoA2 |
| 14 | 44 | Protein | amoB2 |
| 15 | 45 | DNA | amoB2 |
| 16 | 46 | Protein | amoC3 |
| 17 | 47 | DNA | amoC3 |
| 2. hydroxylamine oxidoreductase | | | |
| 18 | 48 | Protein | hao1 |
| 19 | 49 | DNA | hao1 |
| 20 | 50 | Protein | hao2 |
| 21 | 51 | DNA | hao2 |
| 22 | 52 | Protein | hao3 |
| 23 | 53 | DNA | hao3 |
| 3. cytochrome c554 | | | |
| 24 | 54 | Protein | c554 cycA1 |
| 25 | 55 | DNA | c554 cycA1 |
| 26 | 56 | Protein | c554 cycA2 |
| 27 | 57 | DNA | c554 cycA2 |
| 28 | 58 | Protein | c554 cycA3 |
| 29 | 59 | DNA | c554 cycA3 |
| 4. cytochrome $c_M552$ | | | |
| 30 | 60 | Protein | $c_M552$ cycB1 |
| 31 | 61 | DNA | $c_M552$ cycB1 |
| 32 | 62 | Protein | $c_M552$ cycB2 |
| 33 | 63 | DNA | $c_M552$ cycB2 |

In some aspects, the *N. eutropha* described herein comprises genes identical to or similar to the genes and proteins of Table 1.

More particularly, in certain aspects, this disclosure provides a composition of *N. eutropha*, e.g., a purified preparation of *N. eutropha* comprising a nucleic acid sequence at least about 70%, 80%, 85%, 90%, 95%, 96%, 97%, 98%, 99%, or 99.5% identical to an ammonia monooxygenase sequence of Table 1. In certain aspects, this disclosure provides a composition of *N. eutropha* comprising a nucleic acid sequence at least about 70%, 80%, 85%, 90%, 95%, 96%, 97%, 98%, 99%, or 99.5% identical to a hydroxylamine oxidoreductase sequence of Table 1. In certain aspects, this disclosure provides a composition of *N. eutropha* comprising a nucleic acid sequence at least about 70%, 80%, 85%, 90%, 95%, 96%, 97%, 98%, 99%, or 99.5% identical to a cytochrome c554 sequence of Table 1. In certain aspects, this disclosure provides a composition of *N. eutropha* comprising nucleic acid sequences at least about 70%, 80%, 85%, 90%, 95%, 96%, 97%, 98%, 99%, or 99.5% identical to a cytochrome $c_M552$ sequence of Table 1.

In certain aspects, this disclosure provides a composition of *N. eutropha* comprising an amino acid sequence at least about 70%, 80%, 85%, 90%, 95%, 96%, 97%, 98%, 99%, 99.2%, 99.3%, 99.4%, 99.5%, or 99.6% identical to an ammonia monooxygenase sequence of Table 1. In certain aspects, this disclosure provides a composition of *N. eutropha* comprising an amino acid sequence at least about 70%, 80%, 85%, 90%, 95%, 96%, 97%, 98%, 99%, 99.4%, 99.5%, 99.6%, or 99.7% identical to hydroxylamine oxidoreductase sequence of Table 1. In certain aspects, this disclosure provides a composition of *N. eutropha* comprising an amino acid sequence at least about 70%, 80%, 85%, 90%, 95%, 96%, 97%, 98%, 99%, 99.1%, 99.2%, 99.3%, 99.5%, 99.6%, or 99.7% identical to a cytochrome c554 sequence of Table 1. In certain aspects, this disclosure provides a composition of *N. eutropha* comprising amino acid sequences at least about 70%, 80%, 85%, 90%, 95%, 96%, 97%, 97.1%, 97.2%, 97.5%, 98%, 98.5%, 98.6%, 98.7%, 98.8%, 99%, or 99.5% identical to a cytochrome $c_M552$ sequence of Table 1.

In some embodiments, the *N. eutropha* are present in an axenic composition, and e.g., in the form of a purified preparation of optimized *N. eutropha*.

More particularly, in certain aspects, this disclosure provides an axenic composition of *N. eutropha* comprising a nucleic acid sequence at least about 70%, 80%, 85%, 90%, 95%, 96%, 97%, 98%, 98.5%, 98.8%, 98.9%, 99%, 99.2%, 99.3%, 99.4%, 99.5%, or 99.6% identical to an ammonia monooxygenase sequence of Table 1. In certain aspects, this disclosure provides an axenic composition of *N. eutropha* comprising a nucleic acid sequence at least about 70%, 80%, 85%, 90%, 95%, 96%, 97%, 98%, 99%, or 99.5% identical to a hydroxylamine oxidoreductase sequence of Table 1. In certain aspects, this disclosure provides an axenic composition of *N. eutropha* comprising a nucleic acid sequence at least about 70%, 80%, 85%, 90%, 95%, 96%, 97%, 98%, 99%, or 99.5% identical to a cytochrome c554 sequence of Table 1. In certain aspects, this disclosure provides an axenic composition of *N. eutropha* comprising nucleic acid sequences at least about 70%, 80%, 85%, 90%, 95%, 96%, 97%, 98%, 99%, or 99.5% identical to a cytochrome $c_M552$ sequence of Table 1.

In certain aspects, this disclosure provides an axenic composition of *N. eutropha* comprising an amino acid sequence at least about 70%, 80%, 85%, 90%, 95%, 96%, 97%, 98%, 98.5%, 98.8%, 98.9%, 99%, 99.2%, 99.3%, 99.4%, 99.5%, or 99.6% identical to an ammonia monooxygenase sequence of Table 1. In certain aspects, this disclosure provides an axenic composition of *N. eutropha* comprising an amino acid sequence at least about 70%, 80%, 85%, 90%, 95%, 96%, 97%, 98%, 99%, 99.4%, 99.5%, 99.6%, or 99.7% identical to hydroxylamine oxidoreductase sequence of Table 1. In certain aspects, this disclosure provides an axenic composition of *N. eutropha* comprising an amino acid sequence at least about 70%, 80%, 85%, 90%, 95%, 96%, 97%, 98%, 99%, 99.1%, 99.2%, 99.3%, 99.5%, 99.6%, or 99.7% identical to a cytochrome c554 sequence of Table 1. In certain aspects, this disclosure provides an axenic composition of *N. eutropha* comprising amino acid sequences at least about 70%, 80%, 85%, 90%, 95%, 96%, 97%, 97.1%, 97.2%, 97.5%, 98%, 98.5%, 98.6%, 98.7%, 98.8%, 99%, or 99.5% identical to a cytochrome $c_M552$ sequence of Table 1.

In some embodiments, the *N. eutropha* comprises a gene or protein comprising a sequence at least about 70%, 80%, 85%, 90%, 95%, 96%, 97%, 98%, 99%, or 99.5% identical to a strain D23 sequence of Table 1, e.g., any of SEQ IDs 4-33. Substitutions may be conservative or non-conservative; also, insertions and deletions are contemplated. In some embodiments, the *N. eutropha* comprises a gene or protein comprising a sequence of Table 1, e.g., any of SEQ IDs 4-33. In some embodiments, the protein has an N-terminal and/or C-terminal extension or deletion of up to about 1, 2, 3, 4, 5, 6, 8, 10, 15, 20, 25, 50, or 100 amino acids.

Alignment of the nucleic acid sequences of Table 1 shows the percent identity between homologs in C91 and D23. The following paragraphs discuss this percent identity and describe various genes having homology to the D23 genes of Table 1.

More specifically, the amoA1 genes are about 98.8% identical (i.e., at 821/831 positions). Accordingly, in some embodiments, the *N. eutropha* described herein comprise D23 nucleotides at at least 1, 2, 3, 4, 5, 6, 7, 8, 9, 10, or all of the positions that differ in this gene between strains C91 and D23. In embodiments, the *N. eutropha* described herein comprise D23 nucleotides at at most 1, 2, 3, 4, 5, 6, 7, 8, 9, 10, or all of the positions that differ in this gene between strains C91 and D23. In embodiments, the *N. eutropha* described herein comprise a gene at least about 98.8%, 98.9%, 99.0%, 99.2%, 99.4%, 99.6%, 99.8%, or 100% identical to the D23 amoA1 gene.

The amoA2 genes are about 98.8% identical (i.e., at 821/831 positions). Accordingly, in some embodiments, the *N. eutropha* described herein comprise D23 nucleotides at at least 1, 2, 3, 4, 5, 6, 7, 8, 9, 10, or all of the positions that differ in this gene between strains C91 and D23. In embodiments, the *N. eutropha* described herein comprise D23 nucleotides at at most 1, 2, 3, 4, 5, 6, 7, 8, 9, 10, or all of the positions that differ in this gene between strains C91 and D23. In embodiments, the *N. eutropha* described herein comprise a gene at least about 98.8%, 98.9%, 99.0%, 99.2%, 99.4%, 99.6%, 99.8%, or 100% identical to the D23 amoA2 gene.

The amoB1 genes are about 99.1% identical (i.e., at 1255/1266 positions). Accordingly, in some embodiments, the *N. eutropha* described herein comprise D23 nucleotides at at least 1, 2, 3, 4, 5, 6, 7, 8, 9, 10, 11, or all of the positions that differ in this gene between strains C91 and D23. In embodiments, the *N. eutropha* described herein comprise D23 nucleotides at at most 1, 2, 3, 4, 5, 6, 7, 8, 9, 10, 11, or all of the positions that differ in this gene between strains C91 and D23. In embodiments, the *N. eutropha* described herein comprise a gene at least about 99.1%, 99.2%, 99.4%, 99.6%, 99.8%, or 100% identical to the D23 amoB1 gene.

The amoB2 genes are about 99.1% identical (i.e., at 1254/1266 positions). Accordingly, in some embodiments, the *N. eutropha* described herein comprise D23 nucleotides at at least 1, 2, 3, 4, 5, 6, 7, 8, 9, 10, 11, 12 or all of the positions that differ in this gene between strains C91 and D23. In embodiments, the *N. eutropha* described herein comprise D23 nucleotides at at most 1, 2, 3, 4, 5, 6, 7, 8, 9, 10, 11, 12 or all of the positions that differ in this gene between strains C91 and D23. In embodiments, the *N. eutropha* described herein comprise a gene at least about 99.1%, 99.2%, 99.4%, 99.6%, 99.8%, or 100% identical to the D23 amoB2 gene.

The amoC1 genes are about 99.8% identical (i.e., at 814/816 positions). Accordingly, in some embodiments, the *N. eutropha* described herein comprise D23 nucleotides at at least 1, 2, or all of the positions that differ in this gene between strains C91 and D23. In embodiments, the *N. eutropha* described herein comprise D23 nucleotides at at most 1, 2, or all of the positions that differ in this gene between strains C91 and D23. In embodiments, the *N. eutropha* described herein comprise a gene at least about 99.8%, 99.9%, or 100% identical to the D23 amoC1 gene.

The amoC2 genes are about 99.8% identical (i.e., at 814/816 positions). Accordingly, in some embodiments, the *N. eutropha* described herein comprise D23 nucleotides at at least 1, 2, or all of the positions that differ in this gene between strains C91 and D23. In embodiments, the *N. eutropha* described herein comprise D23 nucleotides at at most 1, 2, or all of the positions that differ in this gene between strains C91 and D23. In embodiments, the *N. eutropha* described herein comprise a gene at least about 99.8%, 99.9%, or 100% identical to the D23 amoC2 gene.

The amoC3 genes are about 98.9% identical (i.e., at 816/825 positions). Accordingly, in some embodiments, the *N. eutropha* described herein comprise D23 nucleotides at at least 1, 2, 3, 4, 5, 6, 7, 8, 9, or all of the positions that differ in this gene between strains C91 and D23. In embodiments, the *N. eutropha* described herein comprise D23 nucleotides at at most 1, 2, 3, 4, 5, 6, 7, 8, 9, or all of the positions that differ in this gene between strains C91 and D23. In embodiments, the *N. eutropha* described herein comprise a gene at least about 98.9%, 99.0%, 99.2%, 99.4%, 99.6%, 99.8%, or 100% identical to the D23 amoC3 gene.

The hao1 genes are about 99.0% identical (i.e., at 1696/1713 positions). Accordingly, in some embodiments, the *N. eutropha* described herein comprise D23 nucleotides at at least 1, 2, 3, 4, 5, 6, 7, 8, 9, 10, 11, 12, 13, 14, 15, 16, 17, or all of the positions that differ in this gene between strains C91 and D23. In embodiments, the *N. eutropha* described herein comprise D23 nucleotides at at most 1, 2, 3, 4, 5, 6, 7, 8, 9, 10, 11, 12, 13, 14, 15, 16, 17, or all of the positions that differ in this gene between strains C91 and D23. In embodiments, the *N. eutropha* described herein comprise a gene at least about 99.0%, 99.2%, 99.4%, 99.6%, 99.8%, or 100% identical to the D23 hao1 gene.

The hao2 genes are about 99.4% identical (i.e., at 1702/1713 positions). Accordingly, in some embodiments, the *N. eutropha* described herein comprise D23 nucleotides at at least 1, 2, 3, 4, 5, 6, 7, 8, 9, 10, 11, or all of the positions that differ in this gene between strains C91 and D23. In embodiments, the *N. eutropha* described herein comprise D23 nucleotides at at most 1, 2, 3, 4, 5, 6, 7, 8, 9, 10, 11, or all of the positions that differ in this gene between strains C91 and D23. In embodiments, the *N. eutropha* described herein comprise a gene at least about 99.4%, 99.6%, 99.8%, or 100% identical to the D23 hao2 gene.

The hao3 genes are about 99.2% identical (i.e., at 1700/1713 positions). Accordingly, in some embodiments, the *N. eutropha* described herein comprise D23 nucleotides at at least 1, 2, 3, 4, 5, 6, 7, 8, 9, 10, 11, 12, 13, or all of the positions that differ in this gene between strains C91 and D23. In embodiments, the *N. eutropha* described herein comprise D23 nucleotides at at most 1, 2, 3, 4, 5, 6, 7, 8, 9, 10, 11, 12, 13, or all of the positions that differ in this gene between strains C91 and D23. In embodiments, the *N. eutropha* described herein comprise a gene at least about 99.2%, 99.4%, 99.6%, 99.8%, or 100% identical to the D23 hao3 gene.

The cycA1 genes are about 98.0% identical (i.e., at 694/708 positions). Accordingly, in some embodiments, the *N. eutropha* described herein comprise D23 nucleotides at at least 1, 2, 3, 4, 5, 6, 7, 8, 9, 10, 11, 12, 13, 14, or all of the positions that differ in this gene between strains C91 and D23. In embodiments, the *N. eutropha* described herein comprise D23 nucleotides at at most 1, 2, 3, 4, 5, 6, 7, 8, 9, 10, 11, 12, 13, 14, or all of the positions that differ in this gene between strains C91 and D23. In embodiments, the *N. eutropha* described herein comprise a gene at least about 98.0%, 98.2%, 98.4%, 98.6%, 98.8%, 99.0%, 99.2%, 99.4%, 99.6%, 99.8%, or 100% identical to the D23 cycA1 gene.

The cycA2 genes are about 98.7% identical (i.e., at 699/708 positions). Accordingly, in some embodiments, the *N. eutropha* described herein comprise D23 nucleotides at at least 1, 2, 3, 4, 5, 6, 7, 8, 9, 10, 11, or all of the positions that differ in this gene between strains C91 and D23. In embodiments, the *N. eutropha* described herein comprise D23 nucleotides at at most 1, 2, 3, 4, 5, 6, 7, 8, 9, 10, 11, or all of the positions that differ in this gene between strains C91 and D23. In embodiments, the *N. eutropha* described herein comprise a gene at least about 98.7%, 98.8%, 99.0%, 99.2%, 99.4%, 99.6%, 99.8%, or 100% identical to the D23 cycA2 gene.

The cycA3 genes are about 99.3% identical (i.e., at 703/708 positions). Accordingly, in some embodiments, the *N. eutropha* described herein comprise D23 nucleotides at at least 1, 2, 3, 4, 5, or all of the positions that differ in this gene between strains C91 and D23. In embodiments, the *N. eutropha* described herein comprise D23 nucleotides at at most 1, 2, 3, 4, 5, or all of the positions that differ in this gene between strains C91 and D23. In embodiments, the *N. eutropha* described herein comprise a gene at least about 99.3%, 99.4%, 99.6%, 99.8%, or 100% identical to the D23 cycA3 gene.

The cycB1 genes are about 96.7% identical (i.e., at 696/720 positions). Accordingly, in some embodiments, the *N. eutropha* described herein comprise D23 nucleotides at at least 1, 2, 3, 4, 5, 6, 7, 8, 9, 10, 11, 12, 13, 14, 15, 16, 17, 18, 19, 20, 21, 22, 23, 24, 25, 26, or all of the positions that differ in this gene between strains C91 and D23. In embodiments, the *N. eutropha* described herein comprise D23 nucleotides at at most 1, 2, 3, 4, 5, 6, 7, 8, 9, 10, 11, 12, 13, 14, 15, 16, 17, 18, 19, 20, 21, 22, 23, 24, 25, 26, or all of the positions that differ in this gene between strains C91 and D23. In embodiments, the *N. eutropha* described herein comprise a gene at least about 96.7%, 96.8%, 97.0%, 97.2%, 97.4%, 97.6%, 97.8%, 98.0%, 98.2%, 98.4%, 98.4%, 98.6%, 98.8%, 99.0%, 99.2%, 99.4%, 99.6%, 99.8%, or 100% identical to the D23 cycB1 gene.

The cycB2 genes are about 97.1% identical (i.e., at 702/723 positions). Accordingly, in some embodiments, the *N. eutropha* described herein comprise D23 nucleotides at at least 1, 2, 3, 4, 5, 6, 7, 8, 9, 10, 11, 12, 13, 14, 15, 16, 17, 18, 19, 20, 21, or all of the positions that differ in this gene between strains C91 and D23. In embodiments, the *N. eutropha* described herein comprise D23 nucleotides at at most 1, 2, 3, 4, 5, 6, 7, 8, 9, 10, 11, 12, 13, 14, 15, 16, 17, 18, 19, 20, 21, or all of the positions that differ in this gene between strains C91 and D23. In embodiments, the *N. eutropha* described herein comprise a gene at least about 97.1%, 97.2%, 97.4%, 97.6%, 97.8%, 98.0%, 98.2%, 98.4%, 98.4%, 98.6%, 98.8%, 99.0%, 99.2%, 99.4%, 99.6%, 99.8%, or 100% identical to the D23 cycB2 gene.

The following four paragraphs describe genes and proteins of Table 1 in more detail.

Ammonia monooxygenase is an enzyme involved in ammonia oxidation, that catalyzes the reaction $NH_3+O_2+2e^-+2H^+ \rightleftharpoons NH_2OH+H_2O$ (Ensign et al., 1993). In *N. eutropha* strain D23, the ammonia monooxygenase operon comprises three genes designated amoA, amoB, and amoC. Strain D23 comprises two copies of the entire operon, and a third copy of amoC. These genes and the corresponding proteins are listed in Table 1 above. In certain embodiments, the *N. eutropha* described herein comprise 1 or 2 ammonia monooxygenase subunit A genes and/or protein of Table 1 (e.g., the D23 sequences of Table 1), or genes and/or proteins similar thereto. In some embodiments, the *N. eutropha* described herein comprise 1 or 2 ammonia monooxygenase subunit B genes and/or proteins of Table 1 (e.g., the D23 sequences of Table 1), or genes and/or proteins similar thereto. In certain embodiments, the *N. eutropha* described herein comprise 1, 2, or 3 ammonia monooxygenase subunit C genes and/or proteins of Table 1 (e.g., the D23 sequences of Table 1), or genes and/or proteins similar thereto. In some embodiments, the *N. eutropha* described herein comprise at least one or two each of (a) an ammonia monooxygenase subunit A gene and/or protein of Table 1 (e.g., the D23 sequences of Table 1), (b) an ammonia monooxygenase subunit B gene and/or protein of Table 1 (e.g., the D23 sequences of Table 1), and (c) an ammonia monooxygenase subunit C gene and/or protein of Table 1 (e.g., the D23 sequences of Table 1). For instance, the *N. eutropha* may comprise all of the ammonia monooxygenase genes and/or proteins of Table 1 (e.g., the D23 sequences of Table 1), or genes and/or proteins similar thereto. Even more specifically, in some embodiments, the *N. eutropha* comprises all of the D23 ammonia monooxygenase genes of Table 1. In some embodiments, the *N. eutropha* comprises all of the D23 ammonia monooxygenase proteins of Table 1. Hydroxylamine oxidoreductases catalyze the general reaction $NH_2OH+O_2 \rightleftharpoons NO_2^-\ H_2O$. They typically use heme as a cofactor. *N. eutropha* strain D23 comprises three hydroxylamine oxidoreductases, designated hao1, hao2, and hao3. These genes and the corresponding proteins are listed in Table 1 above. In some embodiments, the *N. eutropha* described herein comprise 1, 2, or 3 hydroxylamine oxidoreductase genes and/or proteins of Table 1 (e.g., the D23 sequences of Table 1), or genes and/or proteins similar thereto. For instance, the *N. eutropha* may comprise all of the hydroxylamine oxidoreductase genes and/or proteins of Table 1 (e.g., the D23 sequences of Table 1), or genes and/or proteins similar thereto. Even more specifically, in some embodiments, the *N. eutropha* comprises all of the D23 hydroxylamine oxidoreductase genes of Table 1. In some embodiments, the *N. eutropha* comprises all of the D23 hydroxylamine oxidoreductase proteins of Table 1.

The capacity of D23 to aerobically catabolize ammonia as the sole source of energy and reductant requires two specialized protein complexes, Amo and Hao as well as the cytochromes c554 and $c_m552$, which relay the electrons to the quinone pool. The NO reductase activity of c554 is important during ammonia oxidation at low oxygen concentrations. *N. eutropha* strain D23 comprises three cytochrome c554 genes, designated cycA1, cycA2, and cycA3. These genes and the corresponding proteins are listed in Table 1 above. In some embodiments, the *N. eutropha* described herein comprise 1, 2, or 3 cytochrome c554 genes and/or proteins of Table 1 (e.g., the D23 sequences of Table 1), or genes and/or proteins similar thereto. For instance, the *N. eutropha* may comprise all of the cytochrome c554 genes and/or proteins of Table 1 (e.g., the D23 sequences of Table 1), or genes and/or proteins similar thereto. Even more specifically, in some embodiments, the *N. eutropha* comprises all of the D23 cytochrome c554 genes of Table 1. In some embodiments, the *N. eutropha* comprises all of the D23 cytochrome c554 proteins of Table 1.

The capacity of D23 to aerobically catabolize ammonia as the sole source of energy and reductant requires two specialized protein complexes, Amo and Hao as well as the Cytochromes c554 and $c_m552$, which relay the electrons to the quinone pool. Cytochrome $c_m552$ reduces quinones, with electrons originating from Hao. *N. eutropha* strain D23 comprises two cytochrome $c_M552$ genes, designated cycB1 and cycB2. These genes and the corresponding proteins are listed in Table 1 above. In some embodiments, the *N. eutropha* described herein comprise 1 or 2 cytochrome $c_M552$ genes and/or proteins of Table 1 (e.g., the D23 sequences of Table 1), or genes and/or proteins similar thereto. For instance, the *N. eutropha* may comprise both of the cytochrome $c_M552$ genes and/or proteins of Table 1 (e.g., the D23 sequences of Table 1), or genes and/or proteins similar thereto. Even more specifically, in some embodiments, the *N. eutropha* comprises both of the D23 cytochrome $c_M552$ genes of Table 1. In some embodiments, the *N. eutropha* comprises both of the D23 Cytochrome $c_M552$ proteins of Table 1.

In some embodiments, the *N. eutropha* described herein comprises a combination of genes and/or proteins selected from Table 1. This combination may comprise, for instance, genes and/or proteins listed in the preceding four paragraphs. For instance, the combination may comprise genes and/or proteins from two classes within Table 1. Accordingly, in some embodiments, the *N. eutropha* comprises one or more ammonia monooxygenase genes and/or proteins and one or more hydroxylamine oxidoreductase genes and/or proteins as described in Table 1, or as described in the preceding four paragraphs. In embodiments, the *N. eutropha* comprises one or more ammonia monooxygenase genes and/or proteins and one or more cytochrome c554 genes and/or proteins as described in Table 1, or as described in the preceding four paragraphs. In embodiments, the *N. eutropha* comprises one or more ammonia monooxygenase genes and/or proteins and one or more cytochrome $c_M552$ genes and/or proteins as described in Table 1, or as described in the preceding four paragraphs. In embodiments, the *N. eutropha* comprises one or more hydroxylamine oxidoreductase genes and/or proteins and one or more cytochrome c554 genes and/or proteins as described in Table 1, or as described in the preceding four paragraphs. In embodiments, the *N. eutropha* comprises one or more hydroxylamine oxidoreductase genes and/or proteins and one or more cytochrome $c_M552$ genes and/or proteins as described in Table 1, or as described in the preceding four paragraphs.

The combination may also comprise genes and/or proteins from three classes within Table 1. Accordingly, in some embodiments, the *N. eutropha* comprises one or more ammonia monooxygenase genes and/or proteins and one or more hydroxylamine oxidoreductase genes and/or proteins and one or more cytochrome c554 genes and/or proteins as described in Table 1, or as described in the aforementioned four paragraphs. In embodiments, the *N. eutropha* comprises one or more ammonia monooxygenase genes and/or proteins and one or more hydroxylamine oxidoreductase genes and/or proteins and one or more cytochrome $c_M552$ genes and/or proteins as described in Table 1, or as described in the aforementioned four paragraphs. In embodiments, the *N. eutropha* comprises one or more one or more ammonia monooxygenase genes and/or proteins and one or more cytochrome c554 genes and/or proteins and/or one or more cytochrome $c_M$552 genes and/or proteins as described in Table 1, or as described in the aforementioned four paragraphs. In embodiments, the *N. eutropha* comprises one or more one or more hydroxylamine oxidoreductase genes and/or proteins and one or more cytochrome c554 genes and/or proteins and/or one or more cytochrome $c_M$552 genes and/or proteins as described in Table 1, or as described in the aforementioned four paragraphs.

The combination may comprise genes and/or proteins from all four classes within Table 1. Accordingly, in some embodiments, the *N. eutropha* comprises one or more ammonia monooxygenase genes and/or proteins and one or more hydroxylamine oxidoreductase genes and/or proteins and one or more cytochrome c554 genes and/or proteins and/or one or more cytochrome $c_M$552 genes as described in Table 1, or as described in the aforementioned four paragraphs.

Table 2 (below) lists sequence differences between the D23 and C91 proteins of Table 1. For example, AmoA1 has M at position 1 in C91 but V at position 1 in D23, and this difference is abbreviated as M1V in Table 2. As another example, the D23 CycB1 has an insertion of DDD between residues 194 and 195 of the C91 protein, so that the added residues are residues number 195, 196, and 197 of the D23 protein and this difference is abbreviated as 195insD, 196insD, and 197insD respectively in Table 2. The sequence alignments that form the basis for Table 2 are shown in FIGS. 10-16.

TABLE 2

Amino acid sequence differences between
*N. eutropha* strains D23 and C91

| Protein | Sequence characteristics of D23 compared to C91 |
|---|---|
| 1. ammonia monooxygenase | |
| AmoA1 | M1V, M160L, P167A |
| AmoA2 | M1V, M160L, P167A |
| AmoB1 | I33V, V165I |
| AmoB2 | I33V, V165I |
| AmoC1 | N/A |
| AmoC2 | N/A |
| AmoC3 | V79A, I271V |
| 2. hydroxylamine oxidoreductase | |
| Hao1 | N85S, V163A, G312E |
| Hao2 | N85S, G312E |
| Hao3 | N85S, G312E |
| 3. cytochrome c554 | |
| c554 CycA1 | A65T, A186T |
| c554 CycA2 | A65T |
| c554 CycA3 | A65T |
| 4. cytochrome $c_M$552 | |
| $c_M$552 CycB1 | I63V, S189P, D194G, 195insD, 196insD, 197insD, 206insE, 207insE |
| $c_M$552 CycB2 | I63V, S189P, 206insE, 207insE |

Accordingly, the *N. eutropha* described herein may comprise one or more of the sequence characteristics listed in Table 2. For instance, the *N. eutropha* may comprise at least 1, 2, 3, 4, 5, 10, 15, 20, 25, 30, or all of the sequence characteristics of Table 2. In some embodiments, the *N. eutropha* comprises no more than 2, 3, 4, 5, 10, 15, 20, 25, 30, or all of the sequence characteristics of Table 2. In embodiments, the *N. eutropha* comprises 1-5, 5-10, 10-15, 15-20, 20-25, 25-30, or all of the sequence characteristics of Table 2. The *N. eutropha* may also comprise fragments of said proteins.

As to individual categories of genes or proteins, in some embodiments, the *N. eutropha* comprises at least 1, 2, 3, 4, 5, 6, 7, 8, 9, 10, or all of the sequence characteristics of Table 2, Section 1 (which describes ammonia monooxygenases). In embodiments, the *N. eutropha* comprises 1-5, 3-7, 4-8, or 5-10 of the sequence characteristics of Table 2, Section 1. For instance, in some embodiments, the *N. eutropha* comprises at least 1, 2, or 3 sequence characteristics of an amoA gene or protein as listed in Table 2, and/or no more than 2 or 3 of these characteristics. The *N. eutropha* may also comprise at least 1 or 2 sequence characteristics of an amoB gene or protein as listed in Table 2. In addition, the *N. eutropha* may comprise at least 1 or 2 sequence characteristics of the amoC3 gene as listed in Table 2. The *N. eutropha* may also comprise fragments of said proteins.

With respect to hao genes and proteins, the *N. eutropha* may comprise at least 1, 2, 3, 4, 5, 6, 7, 8, or all of the sequence characteristics of Table 2, Section 2 (which describes hydroxylamine oxidoreductases). In embodiments, the *N. eutropha* comprises 1-4, 2-5, 3-6, or 4-8 of the sequence characteristics of Table 2, Section 2. The *N. eutropha* may also comprise at least 1, 2 or 3 sequence characteristics of Hao1 as listed in Table 1, and/or no more than 2 or 3 of these characteristics. The *N. eutropha* may also comprise at least 1 or 2 sequence characteristics of Hao2 or Hao3 as listed in Table 2. The *N. eutropha* may also comprise fragments of said proteins.

Turning now to cytochrome c554, the *N. eutropha* may comprise at least 1, 2, 3, 4, or all of the sequence characteristics of Table 2, Section 3 (which describes cytochrome c554). In embodiments, the *N. eutropha* comprises at most 2, 3, 4, or all of the sequence characteristics of Table 2 Section 3. In embodiments, the *N. eutropha* comprises at least 1 or 2 sequence characteristics of cytochrome c554 CycA1 as listed in Table 2. The *N. eutropha* may also comprise at least 1 sequence characteristic of c554 CycA2 or c554 CycA3 as listed in Table 2. The *N. eutropha* may also comprise fragments of said proteins.

With respect to the $c_M$552 genes and proteins, the *N. eutropha* may comprise at least 1, 2, 3, 4, 5, 6, 7, 8, 9, 10, or all of the sequence characteristics of Table 2, Section 4 (which describes cytochrome $c_M$552). In embodiments, the *N. eutropha* comprises at most 2, 3, 4, 5, 6, 7, 8, 9, 10, or all the sequence characteristics of Table 2, Section 4. For instance, in embodiments the *N. eutropha* comprises 1-5, 2-7, 3-8, or 5-10 sequence characteristics of Table 2, Section 4. In embodiments, at least 1, 2, 3, 4, 5, 6, or 7 sequence characteristics of $c_M$552 CycB1 as listed in Table 2, and/or no more than 2, 3, 4, 5, 6, or 7 of these characteristics. The *N. eutropha* may also comprise at least 1, 2, or 3 sequence characteristics of $c_M$552 CycB2 as listed in Table 2, and/or no more than 2 or 3 of these characteristics. The *N. eutropha* may also comprise fragments of said proteins.

It is understood that the paragraphs above, which refer to sequence characteristics of various *N. eutropha* proteins, also describe the sequences of nucleic acids that encode these proteins.

The sequencing analysis described herein revealed that strain D23 lacks plasmids. Consequently, in some embodiments, the *N. eutropha* bacterium lacks plasmids, i.e., all of its DNA is contained in the chromosome. In some embodiments, the *N. eutropha* bacterium lacks endogenous plasmids, but carries one or more transgenic plasmids.

This D23 strain is not believed to be a product of nature, but rather has acquired certain mutations and characteristics during an extended period of culture and selection in the laboratory. For instance, D23 has an ability to grow in conditions of greater than about 200 or 250 mM $NH_4^+$ for more than 24 hours.

In some embodiments, the *N. eutropha* disclosed herein differ from naturally occurring bacteria in the abundance of siderophores. For instance, the *N. eutropha* may have elevated or reduced levels of siderophores compared to *N. eutropha* C91. Generally, siderophores are secreted iron-chelating compounds that help bacteria scavenge iron from their environment. Some siderophores are peptides, and others are small organic molecules.

The AOBs, for example, *N. eutropha* contemplated in this disclosure may comprise mutations relative to wild-type *N. eutropha* and/or the *N. eutropha* sequences disclosed herein. These mutations may, e.g., occur spontaneously, be introduced by random mutagenesis, or be introduced by targeted mutagenesis. For instance, the *N. eutropha* may lack one or more genes or regulatory DNA sequences that wild-type *N. eutropha* typically comprises. The *N. eutropha* may also comprise point mutations, substitutions, insertions, deletions, and/or rearrangements relative to the sequenced strain or a wild-type strain. The *N. eutropha* may be a purified preparation of optimized *N. eutropha*.

In certain embodiments, the *N. eutropha* is transgenic. For instance, it may comprise one or more genes or regulatory DNA sequences that wild-type *N. eutropha* D23 lacks. More particularly, the *N. eutropha* may comprise, for instance, a reporter gene, a selective marker, a gene encoding an enzyme, or a promoter (including an inducible or repressible promoter). In some embodiments the additional gene or regulatory DNA sequence is integrated into the bacterial chromosome; in some embodiments the additional gene or regulatory DNA sequence is situated on a plasmid, for instance a plasmid related to a plasmid found in *N. eutropha* N91.

In some preferred embodiments, the *N. eutropha* differs by at least one nucleotide from naturally occurring bacteria. For instance, the *N. eutropha* may differ from naturally occurring bacteria in a gene or protein that is part of a relevant pathway, e.g., an ammonia metabolism pathway, a urea metabolism pathway, or a pathway for producing nitric oxide or nitric oxide precursors. More particularly, the *N. eutropha* may comprise a mutation that elevates activity of the pathway, e.g., by increasing levels or activity of an element of that pathway.

The above-mentioned mutations can be introduced using any suitable technique. Numerous methods are known for introducing mutations into a given position. For instance, one could use site-directed mutagenesis, oligonucleotide-directed mutagenesis, or site-specific mutagenesis. Non-limiting examples of specific mutagenesis protocols are described in, e.g., Mutagenesis, pp. 13.1-13.105 (Sambrook and Russell, eds., Molecular Cloning A Laboratory Manual, Vol. 3, 3.sup.rd ed. 2001). In addition, non-limiting examples of well-characterized mutagenesis protocols available from commercial vendors include, without limitation, Altered Sites® II in vitro Mutagenesis Systems (Promega Corp., Madison, Wis.); Erase-a-Base® System (Promega, Madison, Wis.); GeneTailor™ Site-Directed Mutagenesis System (Invitrogen, Inc., Carlsbad, Calif.); QuikChange® II Site-Directed Mutagenesis Kits (Stratagene, La Jolla, Calif.); and Transformer™ Site-Directed Mutagenesis Kit (BD-Clontech, Mountain View, Calif.).

In some embodiments, the preparation of ammonia oxidizing bacteria may comprise a concentration or amount of ammonia oxidizing bacteria in order to at least partially treat a condition or disease. The preparation of ammonia oxidizing bacteria may comprise a concentration or amount of ammonia oxidizing bacteria in order to alter, e.g., reduce or increase, an amount, concentration or proportion of a bacterium, or genus of bacteria, on a surface, e.g., a skin surface. The bacteria may be non-pathogenic or pathogenic, or potentially pathogenic.

In some embodiments, the preparation of ammonia oxidizing bacteria may comprise between about $10^8$ to about $10^{14}$ CFU/L. The preparation may comprise at least $10^8$, $10^9$, $10^{10}$, $10^{11}$, $2\times10^{11}$, $5\times10^{11}$, $10^{12}$, $2\times10^{12}$, $5\times10^{12}$, $10^{13}$, $2\times10^{13}$, $5\times10^{13}$, or $10^{14}$; or about $10^8$-$10^9$, $10^9$-$10^{10}$, $10^{10}$-$10^{11}$, $10^{11}$-$10^{12}$, $10^{12}$-$10^{13}$, or $10^{13}$-$10^{14}$ CFU/L. In certain aspects, the preparation may comprise between about $1\times10^9$ CFU/L to about $10\times10^9$ CFU/L. In certain aspects, the preparation may comprise between about $1\times10^9$ CFU to about $10\times10^9$ CFU.

In some embodiments, the preparation of ammonia oxidizing bacteria may comprise between about 0.1 milligrams (mg) and about 1000 mg of ammonia oxidizing bacteria. In certain aspects, the preparation may comprise between about 50 mg and about 1000 mg of ammonia oxidizing bacteria. The preparation may comprise between about 0.1-0.5 mg, 0.2-0.7 mg, 0.5-1.0 mg, 0.5-2 mg, 0.5-5 mg, 2.5-5 mg, 2.5-7.0 mg, 5.0-10 mg, 7.5-15 mg, 10-15 mg, 15-20 mg, 15-25 mg, 20-30 mg, 25-50 mg, 25-75 mg, 50-75 mg, 50-100 mg, 75-100 mg, 100-200 mg, 200-300 mg, 300-400 mg, 400-500 mg, 500-600 mg, 600-700 mg, 700-800 mg, 800-900 mg, 900-1000 mg, 100-250 mg, 250-500 mg, 100-500 mg, 500-750 mg, 750-1000 mg, or 500-1000 mg.

In some embodiments, the preparation of ammonia oxidizing bacteria may comprise a mass ratio of ammonia oxidizing bacteria to an excipient, e.g., a pharmaceutically acceptable excipient or a cosmetically acceptable excipient in a range of about 0.1 grams per liter to about 1 gram per liter. The preparation may comprise a mass ratio of ammonia oxidizing bacteria to an excipient in a range of about 0.1-0.2, 0.2-0.3, 0.1-0.5, 0.2-0.7, 0.5-1.0, or 0.7-1.0 grams per liter.

In some embodiments, the preparation of ammonia oxidizing bacteria may be in a growth state. A growth state may be provided by exposing ammonia oxidizing bacteria to an environment that may promote growth. The growth state may be a state, e.g., ammonia oxidizing bacteria in an environment that allows immediate availability of ammonia oxidizing bacteria to convert ammonium ions ($NH_4^+$) to nitrite ($NO_2^-$). The growth state may comprise providing ammonia oxidizing bacteria in an environment having a pH of greater than about 7.6. The growth state may also comprise providing ammonia oxidizing bacteria in an environment having ammonia, ammonium salts, and/or urea, trace minerals and sufficient oxygen and carbon dioxide, as described above in Section 1.

In some embodiments, the preparation of ammonia oxidizing bacteria may be in a polyphosphate loading state, wherein the state or the environment, e.g., a media, e.g., a culture media, e.g., a growth media, may have a pH of less than about 7.4. Levels of at least one of ammonia, ammonium ions, and urea may be between about 10 micromolar and 200 millimolar. Levels of trace materials may be between 0.1 micromolar iron and 20 micromolar iron. Levels of oxygen may be between about 5% and 100% oxygen saturation. Levels of carbon dioxide may be between/less than about zero and 200 ppm, and phosphate levels greater than about 10 micromolar. The purpose of the polyphosphate loading state is to provide AOB with ammonia and oxygen such that ATP can be produced, but to deny them carbon dioxide and carbonate such that they are unable to use that ATP to fix carbon dioxide and instead use that ATP to generate polyphosphate which may be stored.

In some embodiments, the preparation of ammonia oxidizing bacteria may be in a storage state. A storage state may be defined as ammonia oxidizing bacteria in an environment in which they may be stored to be later revived. The storage state may be a state, e.g., ammonia oxidizing bacteria in an environment that allows availability of ammonia oxidizing bacteria after being revived, e.g., after being place in an environment promoting a growth state for a pre-determined period of time.

The storage state may comprise providing ammonia oxidizing bacteria in an environment having a pH of less than about 7.4. The storage state may also comprise providing ammonia oxidizing bacteria in an environment having ammonia, ammonia salts, and/or urea, trace minerals, oxygen, and low concentrations of carbon dioxide, as described above in Section 1.

Storage may also be accomplished by storing at 4° C. for up to several months. The storage buffer in some embodiments may comprise 50 mM $Na_2HPO_4$-2 mM $MgCl_2$ (pH 7.6).

In some embodiments, ammonia oxidizing bacteria may be cryopreserved. A 1.25 ml of ammonia oxidizing bacteria mid-log culture may be added to a 2 ml cryotube and 0.75 ml of sterile 80% glycerol. Tubes may be shaken gently, and incubate at room temperature for 15 min to enable uptake of the cryoprotective agents by the cells. The tubes may be directly stored in a −80° C. freezer for freezing and storage.

For resuscitation of cultures, frozen stocks may be thawed on ice for 10-20 minutes, and then centrifuged at 8,000×g for 3 minutes at 4° C. The pellet may be washed by suspending it in 2 ml AOB medium followed by another centrifugation at 8,000×g for 3 minutes at 4° C. to reduce potential toxicity of the cryoprotective agents. The pellet may be resuspended in 2 ml of AOB medium, inoculated into 50 ml of AOB medium containing 50 mM $NH_4^+$, and incubated in dark at 30° C. by shaking at 200 rpm.

In some embodiments, the preparation of ammonia oxidizing bacteria may comprise ammonia oxidizing bacteria in a storage state and/or ammonia oxidizing bacteria in a polyphosphate loading state and/or ammonia oxidizing bacteria in a growth state.

Without wishing to be bound by theory, by maintaining ammonia oxidizing bacteria under conditions or in an environment of low carbon dioxide, with sufficient oxygen and ammonia, they may accumulate polyphosphate for a pre-determined period, e.g., for a period of about one doubling time, e.g., for about 8-12 hours, e.g., for about 10 hours. The ammonia oxidizing bacteria may accumulate sufficient polyphosphate to extend their storage viability, storage time, and accelerate their revival. This may occur with or without the addition of buffer and ammonia.

The presence of sufficient stored polyphosphate may allow the ammonia oxidizing bacteria the ATP resources to maintain metabolic activity even in the absence of ammonia and oxygen, and to survive insults that would otherwise be fatal.

The process of oxidation of ammonia to generate ATP has two steps. The first step is the oxidation of ammonia to hydroxylamine by ammonia monoxoygenase (Amo), followed by the conversion of hydroxylamine to nitrite by hydroxylamine oxidoreductase (Hao). Electrons from the second step (conversion of hydroxylamine to nitrite) are used to power the first step (oxidation of ammonia to hydroxylamine).

If an ammonia oxidizing bacteria does not have hydroxylamine to generate electrons for Amo, then hydroxylamine is not available for Hao. For example, acetylene irreversibly inhibits the enzyme crucial for the first step in the oxidation of ammonia to nitrite, the oxidation of ammonia to hydroxylamine. Once AOB are exposed to acetylene, Amo is irreversibly inhibited and new enzyme must be synthesized before hydroxylamine can be generated. In a normal consortium biofilm habitat, AOB may share and receive hydroxylamine form other AOB (even different strains with different susceptibilities to inhibitors) and so the biofilm tends to be more resistant to inhibitors such as acetylene than an individual organism. AOB can use stored polyphosphate to synthesize new Amo, even in the absence of hydroxylamine.

Any embodiment, preparation, composition, or formulation of ammonia oxidizing bacteria discussed herein may comprise, consist essentially of, or consist of optionally axenic ammonia oxidizing bacteria.

3. Methods of Producing *N. eutropha*

Methods of culturing various *Nitrosomonas* species are known in the art. *N. eutropha* may be cultured, for example, using *N. europaea* medium as described in Example 2 below. Ammonia oxidizing bacteria may be cultured, for example, using the media described in Table 3 or Table 4, above.

*N. eutropha* may be grown, for example, in a liquid culture or on plates. Suitable plates include 1.2% R2A agar, 1.2% agar, 1.2% agarose, and 1.2% agarose with 0.3 g/L pyruvate.

In some embodiments, ammonia oxidizing bacteria, such as *N. eutropha* is cultured in organic free media. One advantage of using organic free media is that it lacks substrate for heterotrophic bacteria to metabolize except for that produced by the autotrophic bacteria. Another advantage of using the as-grown culture is that substantial nitrite accumulates in the culture media, and this nitrite is also inhibitory of heterotrophic bacteria and so acts as a preservative during storage.

In some embodiments, ammonia oxidizing bacteria such as an *N. eutropha* strain with improved, e.g. optimized, properties is produced by an iterative process of propagation and selecting for desired properties. In some embodiments, the selection and propagation are carried out simultaneously. In some embodiments, the selection is carried out in a reaction medium (e.g., complete *N. europaea* medium) comprising 50 mM, 75 mM, 100 mM, 125 mM, 150 mM, 175 mM, 200 mM, 225 mM, 250 mM, 275 mM, or 300 mM $NH_4^+$, e.g., at least 200 mM $NH_4^+$. In some embodiments, the period of propagation and/or selection is at least 1, 2, 3, or 6 months. In embodiments, the period of propagation and/or selection is at least 1, 2, 4, 6, 8, or 10 years.

In some aspects, the ammonia oxidizing bacteria, such as the *N. eutropha* are manufactured on a commercial scale. In some embodiments, commercial scale refers to a liquid culturing method with a culture medium volume of at least 10,000, 20,000, 30,000, 50,000, or 100,000 liters (L). In some embodiments, the bacteria are produced in a bioreactor. The bioreactor may maintain the bacteria at a constant temperature, e.g., about 26-30 degrees Celsius using, for example a thermal jacket for insulation, a temperature sensor, and a heating or cooling element. The bioreactor may have an apparatus for stirring the culture to improve distribution of nutrients like ammonia, urea, oxygen, carbon dioxide, and various minerals. The bioreactor may also have an inlet tube for addition of new medium, and an outlet tube for collection of cells. The bioreactor may also have an aerator for distributing oxygen and/or carbon dioxide to the culture. The bioreactor may be, e.g., a batch reactor, a fed batch reactor, or a continuous reactor. In some embodiments, commercial scale production of N. eutropha yields a batch of 1,000 to 100,000 L per day at about $10^{12}$ CFU/liter and 1,000 to 100,000. The commercial scale production may yield e.g., a batch of 1,000-5,000, 5,000-10,000, 10,000-50,000, or 50,000-100,000 L/day. The commercial scale production may yield e.g., a batch of 1,000-5,000, 5,000-10,000, 10,000-50,000, or 50,000-100,000 L per batch. In some embodiments, the yield is at a concentration of at least $10^{10}$, $10^{11}$, $2\times10^{11}$, $5\times10^{11}$, or $10^{12}$, or about $10^{10}$-$10^{11}$, $10^{11}$-$10^{12}$, $10^{12}$-$10^{13}$, or $10^{13}$-$10^{14}$ CFU/L In some embodiments, typically including commercial scale production, quality control (QC) testing steps are carried out. The general steps of QC typically comprise, 1) culturing N. eutropha, 2) performing a testing step on the culture or an aliquot thereof, and 3) obtaining a value from the testing step, and optionally: 4) comparing the obtained value to a reference value or range of acceptable values, and 5) if the obtained value meets the acceptable reference value or range, then classifying the culture as acceptable, and if the obtained value does not meet the acceptable reference value or range, then classifying the culture as unacceptable. If the culture is classified as acceptable, the culture may, e.g., be allowed to continue growing and/or may be harvested and added to a commercial product. If the culture is classified as unacceptable, the culture may, e.g., be safely disposed of or the defect may be remedied.

The testing step may comprise measuring the optical density (OD) of the culture. OD is measured in a spectrophotometer, and provides information on the amount of light transmitted through the sample as distinguished from light absorbed or scattered. In some embodiments, the OD600 (e.g., optical density of light with a wavelength of 600 nm) may be determined. This measurement typically indicates the concentration of cells in the medium, where a higher optical density corresponds to a higher cell density.

The testing step may comprise measuring the pH of the culture. The pH of an N. eutropha culture indicates the rate of nitrogen oxidation, and can also indicate whether the culture comprises a contaminating organism. pH may be measured using, e.g., a pH-sensing device comprising a electrode (such as a hydrogen electrode, quinhydron-Electrode, antimony electrode, glass electrode), a pH-sensing device comprising a semiconductor, or a color indicator reagent such as pH paper.

In certain embodiments, producing the ammonia oxidizing bacteria such as N. eutropha comprises carrying out various quality control steps. For instance, one may test the medium in which the N. eutropha is grown, e.g., to determine whether it has an appropriate pH, whether it has a sufficiently low level of waste products, and/or whether it has a sufficiently high level or nutrients. One may also test for the presence of contaminating organisms. A contaminating organism is typically an organism other than an ammonia oxidizing bacteria such as N. eutropha, for instance an organism selected Microbacterium sp., Alcaligenaceae bacterium, Caulobacter sp., Burkodelia multivorans, Escherichia coli, Klebsiella pneumoniae, and Staphylococcus aureus. One may test for contaminants by, e.g., extracting DNA, amplifying it, and sequencing a conserved gene such as 16S rRNA. One may also test for contaminants by plating culture on agar plates and observing colony morphology. N. eutropha typically forms red colonies, so non-red colonies are often indicative of contaminating organisms.

4. Compositions Comprising Ammonia Oxidizing Bacteria; Compositions Comprising N. eutropha The present disclosure provides, inter alia, compositions comprising ammonia oxidizing bacteria, e.g., a preparation of ammonia oxidizing bacteria, or a purified preparation of ammonia oxidizing bacteria e.g., a natural product, or a fortified natural product. The compositions comprising ammonia oxidizing bacteria, e.g., a preparation of ammonia oxidizing bacteria, or a purified preparation of ammonia oxidizing bacteria may be provided in a cosmetic product or a therapeutic product. The preparation may comprise, inter alia, at least one of ammonia, ammonium salts, and urea.

The present disclosure provides, inter alia, compositions comprising N. eutropha, e.g., a purified preparation of an optimized N. eutropha. In some embodiments, the N. eutropha in the compositions has at least one property selected from an optimized growth rate, an optimized $NH_4^+$ oxidation rate, and an optimized resistance to $NH_4^+$.

In some aspects, the present disclosure provides compositions with a defined number of species. For instance, this disclosure provides a composition having N. eutropha and one other type of organism, and no other types of organism. In other examples, the composition has N. eutropha and 2, 3, 4, 5, 6, 7, 8, 9, or 10 other types of organism, and no other types of organism. The other type of organism in this composition may be, for instance, a bacterium, such as an ammonia-oxidizing bacterium. Suitable ammonia-oxidizing bacteria for this purpose include those in the genera Nitrosomonas, Nitrosococcus, Nitrosospira, Nitrosocystis, Nitrosolobus, or Nitrosovibrio.

In some embodiments, the composition comprising N. eutropha provides conditions that support N. eutropha viability. For instance, the composition may promote N. eutropha growth and metabolism or may promote a dormant state (e.g., freezing) from which viable N. eutropha can be recovered. When the composition promotes growth or metabolism, it may contain water and/or nutrients that N. eutropha consumes, e.g., as ammonium, ammonia, urea, oxygen, carbon dioxide, or trace minerals. In some embodiments, the composition comprising ammonia oxidizing bacteria provides conditions that support ammonia oxidizing bacteria viability. For instance, the composition may promote ammonia oxidizing bacteria growth and metabolism or may promote a dormant state (e.g., freezing) or storage state as described herein, from which viable ammonia oxidizing bacteria can be recovered. When the composition promotes growth or metabolism, it may contain water and/or nutrients that ammonia oxidizing bacteria consumes, e.g., as ammonium ions, ammonia, urea, oxygen, carbon dioxide, or trace minerals.

In some embodiments, one or more other organisms besides ammonia oxidizing bacteria may be included in the preparation of ammonia oxidizing bacteria. For example, an organism of the genus selected from the group consisting of Lactobacillus, Streptococcus, Bifidobacter, and combinations thereof, may be provided in the preparation of ammonia oxidizing bacteria. In some embodiments, the preparation may be substantially free of other organisms.

Preparations of ammonia oxidizing bacteria may comprise between about between about $10^8$ to about $10^{14}$ CFU/L. The preparation may comprise at least about $10^8$, $10^9$, $10^{10}$, $10^{11}$, $2\times10^{11}$, $5\times10^{11}$, $10^{12}$, $2\times10^{12}$, $5\times10^{12}$, $10^{13}$, $2\times10^{13}$, $5\times10^{13}$, or $10^{14}$; or about $10^8$-$10^9$, $10^9$-$10^{10}$, $10^{10}$-$10^{11}$, $10^{10}$-$10^{12}$, $10^{12}$-$10^{13}$ or $10^{13}$-$10^{14}$ CFU/L.

In some embodiments, the preparation may comprise at least $10^8$, $10^9$, $10^{10}$, $10^{11}$, $2\times10^{11}$, $5\times10^{11}$, $10^{12}$, $2\times10^{12}$, $5 \times 10^{12}$, $10^{13}$, $2 \times 10^{13}$, $5 \times 10^{13}$, or $10^{14}$; or about $10^8$-$10^9$, $10^9$-$10^{10}$, $10^{10}$-$10^{11}$, $10^{11}$-$10^{12}$, $10^{12}$-$10^{13}$, or $10^{13}$-$10^{14}$ CFU/ml.

In some embodiments, the preparation may comprise between about $1 \times 10^9$ to about $10 \times 10^9$ CFU/L. In some embodiments, the preparation may comprise about $3 \times 10^{10}$ CFU, e.g., $3 \times 10^{10}$ CFU per day. In some embodiments, the preparation may comprise about $1 \times 10^9$ to about $10 \times 10^9$ CFU, e.g., about $1 \times 10^9$ to about $10 \times 10^9$ CFU per day.

In some embodiments, the preparation of ammonia oxidizing bacteria may comprise between about 0.1 milligrams (mg) and about 1000 mg of ammonia oxidizing bacteria. In certain aspects, the preparation may comprise between about 50 mg and about 1000 mg of ammonia oxidizing bacteria. The preparation may comprise between about 0.1-0.5 mg, 0.2-0.7 mg, 0.5-1.0 mg, 0.5-2 mg, 0.5-5 mg, 2.5-5 mg, 2.5-7.0 mg, 5.0-10 mg, 7.5-15 mg, 10-15 mg, 15-20 mg, 15-25 mg, 20-30 mg, 25-50 mg, 25-75 mg, 50-75 mg, 50-100 mg, 75-100 mg, 100-200 mg, 200-300 mg, 300-400 mg, 400-500 mg, 500-600 mg, 600-700 mg, 700-800 mg, 800-900 mg, 900-1000 mg, 100-250 mg, 250-500 mg, 100-500 mg, 500-750 mg, 750-1000 mg, or 500-1000 mg.

In some embodiments, the preparation of ammonia oxidizing bacteria my comprise a mass ratio of ammonia oxidizing bacteria to an excipient, e.g., a pharmaceutically acceptable excipient or a cosmetically acceptable excipient in a range of about 0.1 grams per liter to about 1 gram per liter. The preparation may comprise a mass ratio of ammonia oxidizing bacteria to an excipient in a range of about 0.1-0.2, 0.2-0.3, 0.1-0.5, 0.2-0.7, 0.5-1.0, or 0.7-1.0 grams per liter.

Advantageously, a formulation may have a pH that promotes AOB, e.g., N. eutropha viability, e.g., metabolic activity. Urea would hydrolyze to ammonia and would raise the pH to 7 to 8. AOB are very active at this pH range and would lower the pH to about 6 where the $NH_3$ converts to ammonium and is unavailable. Lower pH levels, e.g. about pH 4, are also acceptable. The ammonia oxidizing bacteria, e.g., N. eutropha may be combined with one or more pharmaceutically or cosmetically acceptable excipients. In some embodiments, "pharmaceutically acceptable excipient" refers to a pharmaceutically-acceptable material, composition, or vehicle, such as a liquid or solid filler, diluent, solvent, or encapsulating material. In some embodiments, each excipient is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 21st ed.; Lippincott Williams & Wilkins: Philadelphia, Pa., 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, Fla., 2009.

In some embodiments, a cosmetically acceptable excipient refers to a cosmetically acceptable material, composition, or vehicle, such as a liquid or solid filler, diluent, solvent, or encapsulating material. In some embodiments, each excipient is cosmetically acceptable in the sense of being compatible with the other ingredients of a cosmetic formulation, and suitable for use in contact with the tissue or organ of humans and animals without excessive toxicity, irritation, allergic response, immunogenicity, or other problems or complications, commensurate with a reasonable benefit/risk ratio.

While it is possible for the active ingredient, e.g., ammonia oxidizing bacteria, e.g., N. eutropha, to be administered alone, in many embodiments it present in a pharmaceutical formulation or composition. Accordingly, this disclosure provides a pharmaceutical formulation comprising ammonia oxidizing bacteria, for example, N. eutropha and a pharmaceutically acceptable excipient. Pharmaceutical compositions may take the form of a pharmaceutical formulation as described below.

The pharmaceutical formulations described herein include those suitable for oral, parenteral (including subcutaneous, intradermal, intramuscular, intravenous, and intraarticular), inhalation (including fine particle dusts or mists which may be generated by means of various types of metered doses, pressurized aerosols, nebulizers or insufflators, and including intranasally or via the lungs), rectal and topical (including dermal, transdermal, transmucosal, buccal, sublingual, and intraocular) administration, although the most suitable route may depend upon, for example, the condition and disorder of the recipient.

The formulations may conveniently be presented in unit dosage form and may be prepared by any of the methods known in the art of pharmacy. Typically, methods include the step of bringing the active ingredient (e.g., ammonia oxidizing bacteria, e.g., N. eutropha) into association with a pharmaceutical carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations may be presented as discrete units such as capsules, cachets or tablets, each containing a predetermined amount of, e.g., N. eutropha; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., Remington's Pharmaceutical Sciences by E. W. Martin. See also Wang, Y. J. and Hanson, M. A., Journal of Parenteral Science and Technology, Technical Report No. 10, Supp. 42:2 S, 1988.

The ammonia oxidizing bacteria, e.g., N. eutropha compositions can, for example, be administered in a form suitable for immediate release or extended release. Suitable examples of sustained-release systems include suitable polymeric materials, for example semi-permeable polymer matrices in the form of shaped articles, e.g., films, or microcapsules; suitable hydrophobic materials, for example as an emulsion in an acceptable oil; or ion exchange resins. Sustained-release systems may be administered orally; rectally; parenterally; intracisternally; intravaginally; intraperitoneally; topically, for example as a powder, ointment, gel, drop or transdermal patch; bucally; or as a spray.

Preparations for administration can be suitably formulated to give controlled release of ammonia oxidizing bacteria, e.g., N. eutropha. For example, the pharmaceutical compositions may be in the form of particles comprising one or more of biodegradable polymers, polysaccharide jellifying and/or bioadhesive polymers, or amphiphilic polymers.

These compositions exhibit certain biocompatibility features which allow a controlled release of an active substance. See U.S. Pat. No. 5,700,486.

Exemplary compositions include suspensions which can contain, for example, microcrystalline cellulose for imparting bulk, alginic acid or sodium alginate as a suspending agent, methylcellulose as a viscosity enhancer, dicalcium phosphate, starch, magnesium stearate and/or lactose and/or other excipients, binders, extenders, disintegrants, diluents and lubricants, mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. The surfactant may be a zwitterionic surfactant, a non-ionic surfactant, or an anionic surfactant.

Excipients, such as surfactants that may be used with embodiments of the present disclosure may include one or more of cocamidopropyl betaine (ColaTeric COAB), polyethylene sorbitol ester (e.g., Tween 80), ethoxylated lauryl alcohol (RhodaSurf 6 NAT), sodium laureth sulfate/lauryl glucoside/cocamidopropyl betaine (Plantapon 611 L UP), sodium laureth sulfate (e.g., RhodaPex ESB 70 NAT), alkyl polyglucoside (e.g., Plantaren 2000 N UP), sodium laureth sulfate (Plantaren 200), Dr. Bronner's Castile soap, Dr. Bronner's Castile baby soap, Lauramine oxide (ColaLux Lo), sodium dodecyl sulfate (SDS), polysulfonate alkyl polyglucoside (PolySufanate 160 P), sodium lauryl sulfate (Stepanol-WA Extra K), and combinations thereof. Dr. Bronner's Castile soap and Dr. Bronner's baby soap comprises water, organic coconut oil, potassium hydroxide, organic olive oil, organic fair deal hemp oil, organic jojoba oil, citric acid, and tocopherol.

In some embodiments, surfactants may be used with ammonia oxidizing bacteria in amounts that allow nitrite production to occur. In some embodiments, the preparation may have less than about 0.0001% to about 10% of surfactant. In some embodiments, the preparation may have between about 0.1% and about 10% surfactant. In some embodiments, the concentration of surfactant used may be between about 0.0001% and about 10%. In some embodiments, the preparation may be substantially free of surfactant.

In some embodiments, the formulation, e.g., preparation, may include other components that may enhance effectiveness of ammonia oxidizing bacteria, or enhance a treatment or indication.

In some embodiments, a chelator may be included in the preparation. A chelator may be a compound that may bind with another compound, e.g., a metal. The chelator may provide assistance in removing an unwanted compound from an environment, or may act in a protective manner to reduce or eliminate contact of a particular compound with an environment, e.g., ammonia oxidizing bacteria, e.g. a preparation of ammonia oxidizing bacteria, e.g., an excipient. In some embodiments, the preparation may be substantially free of chelator.

Formulations may also contain anti-oxidants, buffers, bacteriostats that prevent the growth of undesired bacteria, solutes, and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of a sterile liquid carrier, for example saline or water-for-injection, immediately prior to use. Extemporaneous solutions and suspensions may be prepared from powders, granules and tablets of the kind previously described. Exemplary compositions include solutions or suspensions which can contain, for example, suitable non-toxic, pharmaceutically acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. An aqueous carrier may be, for example, an isotonic buffer solution at a pH of from about 3.0 to about 8.0, a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. The composition in some embodiments does not include oxidizing agents.

Excipients that can be included are, for instance, proteins, such as human serum albumin or plasma preparations. If desired, the pharmaceutical composition may also contain minor amounts of non-toxic auxiliary substances, such as wetting or emulsifying agents, preservatives, and pH buffering agents and the like, for example sodium acetate or sorbitan monolaurate. In some embodiments, excipients, e.g., a pharmaceutically acceptable excipient or a cosmetically acceptable excipient, may comprise an anti-adherent, binder, coat, disintegrant, filler, flavor, color, lubricant, glidant, sorbent, preservative, or sweetener. In some embodiments, the preparation may be substantially free of excipients.

In some embodiments, the preparation may be substantially free of one or more of the compounds or substances listed in the disclosure.

Exemplary compositions for aerosol administration include solutions in saline, which can contain, for example, benzyl alcohol or other suitable preservatives, absorption promoters to enhance bioavailability, and/or other solubilizing or dispersing agents. Conveniently in compositions for aerosol administration the ammonia oxidizing bacteria, e.g., *N. eutropha* is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin can be formulated to contain a powder mix of the *N. eutropha* and a suitable powder base, for example lactose or starch. In certain embodiments, *N. eutropha* is administered as an aerosol from a metered dose valve, through an aerosol adapter also known as an actuator. Optionally, a stabilizer is also included, and/or porous particles for deep lung delivery are included (e.g., see U.S. Pat. No. 6,447,743).

Formulations may be presented with carriers such as cocoa butter, synthetic glyceride esters or polyethylene glycol. Such carriers are typically solid at ordinary temperatures, but liquefy and/or dissolve at body temperature to release the ammonia oxidizing bacteria, e.g., *N. eutropha*.

Exemplary compositions for topical administration include a topical carrier such as Plastibase (mineral oil gelled with polyethylene). In some aspects, the composition and/or excipient may be in the form of one or more of a liquid, a solid, or a gel. For example, liquid suspensions may include, but are not limited to, water, saline, phosphate-buffered saline, or an ammonia oxidizing storage buffer. Gel formulations may include, but are not limited to agar, silica, polyacrylic acid (for example Carbopol®), carboxymethyl cellulose, starch, guar gum, alginate or chitosan. In some embodiments, the formulation may be supplemented with an ammonia source including, but not limited to ammonium chloride or ammonium sulfate.

In some embodiments, an ammonia oxidizing bacteria, e.g., *N. eutropha* composition is formulated to improve NO penetration into the skin. A gel-forming material such as KY jelly or various hair gels would present a diffusion barrier to NO loss to ambient air, and so improve the skin's absorption of NO. The NO level in the skin will generally not greatly exceed 20 nM/L because that level activates GC and would cause local vasodilatation and oxidative destruction of excess NO.

It should be understood that in addition to the ingredients particularly mentioned above, the formulations as described herein may include other agents conventional in the art having regard to the type of formulation in question.

The formulation, e.g., preparation, e.g., composition may be provided in a container, delivery system, or delivery device, having a weight, including or not including the contents of the container, that may be less than about 50, 100, 200, 300, 400, 500, 600, 700, 800, 900, 1000, 1500, or 2000 grams.

Suitable unit dosage formulations are those containing an effective dose, as hereinbefore recited, or an appropriate fraction thereof, of ammonia oxidizing bacteria, e.g., *N. eutropha*.

A therapeutically effective amount of ammonia oxidizing bacteria, e.g., *N. eutropha* may be administered as a single pulse dose, as a bolus dose, or as pulse doses administered over time. Thus, in pulse doses, a bolus administration of ammonia oxidizing bacteria, e.g., *N. eutropha* is provided, followed by a time period wherein ammonia oxidizing bacteria, e.g., *N. eutropha* is administered to the subject, followed by a second bolus administration. In specific, non-limiting examples, pulse doses are administered during the course of a day, during the course of a week, or during the course of a month.

In some embodiments, a preparation of ammonia oxidizing bacteria, e.g., a formulation, e.g., a composition, may be applied for a pre-determined number of days. This may be based, for example, at least in part, on the severity of the condition or disease, the response to the treatment, the dosage applied and the frequency of the dose. For example, the preparation may be applied for about 1-3, 3-5, 5-7, 7-9, 5-10, 10-14, 12-18, 12-21, 21-28, 28-35, 35-42, 42-49, 49-56, 46-63, 63-70, 70-77, 77-84, 84-91 days, for about 1 month, for about 2 months, for about 3 months. In some embodiments, the ammonia oxidizing bacteria is administered for an indefinite period of time, e.g., greater than one year, greater than 5 years, greater than 10 years, greater than 15 years, greater than 30 years, greater than 50 years, greater than 75 years. In certain aspects, the preparation may be applied for about 16 days.

In some embodiments, a preparation of ammonia oxidizing bacteria, e.g., a formulation, e.g., a composition, may be applied a pre-determined number of times per day. This may be based, for example, at least in part, on the severity of the condition or disease, the response to the treatment, the dosage applied and the frequency of the dose. For example, the preparation may be applied 1, 2, 3, 4, 5, 6, 7, 8, 9, 10, 11, 12, 13, 14, 15, 16, 17, 18, 19, 20, 21, 22, 23, 24 times per day.

In some embodiments, the preparation may be applied one time per day. In other embodiments, the preparation may be applied two times per day. In some embodiments, the preparation may be applied a first pre-determined amount for a certain number of days, and a second pre-determined amount for a certain subsequent number of days. In some embodiments, the preparation may be applied for about 16 days.

Consumer Products

Ammonia oxidizing bacteria, e.g., *N. eutropha* may be associated with a variety of consumer products, and examples of such products are set out below. In some embodiments, the ammonia oxidizing bacteria, e.g., *N. eutropha* associated with a product is admixed with the product, for example, spread evenly throughout the product, and in some embodiments, ammonia oxidizing bacteria, e.g., the *N. eutropha* associated with a product is layered on the product.

In some embodiments, ammonia oxidizing bacteria, e.g., *N. eutropha* is associated with a powder. Powders are typically small particulate solids that are not attached to each other and that can flow freely when tilted. Exemplary powders for consumer use include talcum powder and some cosmetics (e.g., powder foundation).

In some embodiments, the ammonia oxidizing bacteria is associated with a cosmetic. The cosmetic may be a substance for topical application intended to alter a person's appearance, e.g., a liquid foundation, a powder foundation, blush, or lipstick. The cosmetic may be any substance recited in the Food and Drug Administration regulations, e.g., under 21 C.F.R. § 720.4.

The cosmetic may be at least one of a baby product, e.g., a baby shampoo, a baby lotion, a baby oil, a baby powder, a baby cream; a bath preparation, e.g., a bath oil, a tablet, a salt, a bubble bath, a bath capsule; an eye makeup preparation, e.g., an eyebrow pencil, an eyeliner, an eye shadow, an eye lotion, an eye makeup remover, a mascara; a fragrance preparation, e.g., a colognes, a toilet water, a perfume, a powder (dusting and talcum), a sachet; hair preparations, e.g., hair conditioners, hair sprays, hair straighteners, permanent waves, rinses, shampoos, tonics, dressings, hair grooming aids, wave sets; hair coloring preparations, e.g., hair dyes and colors, hair tints, coloring hair rinses, coloring hair shampoos, hair lighteners with color, hair bleaches; makeup preparations, e.g., face powders, foundations, leg and body paints, lipstick, makeup bases, rouges, makeup fixatives; manicuring preparations, e.g., basecoats and undercoats, cuticle softeners, nail creams and lotions, nail extenders, nail polish and enamel, nail polish and enamel removers; oral hygiene products, e.g., dentifrices, mouthwashes and breath fresheners; bath soaps and detergents, deodorants, douches, feminine hygiene deodorants; shaving preparations, e.g., aftershave lotions, beard softeners, talcum, preshave lotions, shaving cream, shaving soap; skin care preparations, e.g., cleansing, depilatories, face and neck, body and hand, foot powders and sprays, moisturizing, night preparations, paste masks, skin fresheners; and suntan preparations, e.g., gels, creams, and liquids, and indoor tanning preparations.

In some embodiments, the formulations, compositions, or preparations described herein, may comprise, be provided as, or disposed in at least one of a baby product, e.g., a baby shampoo, a baby lotion, a baby oil, a baby powder, a baby cream; a bath preparation, e.g., a bath oil, a tablet, a salt, a bubble bath, a bath capsule; a powder (dusting and talcum), a sachet; hair preparations, e.g., hair conditioners, rinses, shampoos, tonics, face powders, cuticle softeners, nail creams and lotions, oral hygiene products, mouthwashes, bath soaps, douches, feminine hygiene deodorants; shaving preparations, e.g., aftershave lotions, skin care preparations, e.g., cleansing, face and neck, body and hand, foot powders and sprays, moisturizing, night preparations, paste masks, skin fresheners; and suntan preparations, e.g., gels, creams, and liquids.

In some embodiments, ammonia oxidizing bacteria, e.g., N. eutropha is associated with a cosmetic. The cosmetic may be a substance for topical application intended to alter a person's appearance, e.g., a liquid foundation, a powder foundation, blush, or lipstick. Other components may be added to these cosmetic preparations as selected by one skilled in the art of cosmetic formulation such as, for example, water, mineral oil, coloring agent, perfume, aloe, glycerin, sodium chloride, sodium bicarbonate, pH buffers, UV blocking agents, silicone oil, natural oils, vitamin E, herbal concentrates, lactic acid, citric acid, talc, clay, calcium carbonate, magnesium carbonate, zinc oxide, starch, urea, and erythorbic acid, or any other excipient known by one of skill in the art, including those disclosed herein.

In some embodiments, the preparation may be disposed in, or provided as, a powder, cosmetic, cream, stick, aerosol, salve, wipe, or bandage.

In some embodiments, ammonia oxidizing bacteria, e.g., N. eutropha is associated with a cream. The cream may be a fluid comprising a thickening agent, and generally has a consistency that allows it to be spread evenly on the skin. Exemplary creams include moisturizing lotion, face cream, and body lotion.

In some embodiments, ammonia oxidizing bacteria, e.g., the N. eutropha is associated with a stick. A stick is typically a solid that, when placed in contact with a surface, transfers some of the stick contents to the surface. Exemplary sticks include deodorant stick, lipstick, lip balm in stick form, and sunscreen applicator sticks.

In some embodiments, ammonia oxidizing bacteria, e.g., the N. eutropha is associated with an aerosol. An aerosol is typically a colloid of fine solid particles or fine liquid droplets, in a gas such as air. Aerosols may be created by placing the N. eutropha (and optionally carriers) in a vessel under pressure, and then opening a valve to release the contents. The container may be designed to only exert levels of pressure that are compatible with N. eutropha viability. For instance, the high pressure may be exerted for only a short time, and/or the pressure may be low enough not to impair viability. Examples of consumer uses of aerosols include for sunscreen, deodorant, perfume, hairspray, and insect repellant.

In some embodiments, ammonia oxidizing bacteria, e.g., the N. eutropha is associated with a salve. A salve may be a topically applied agent with a liquid or cream-like consistency, intended to protect the skin or promote healing. Examples of salves include burn ointments and skin moisturizers.

In some embodiments, ammonia oxidizing bacteria, e.g., the N. eutropha is associated with a wipe. A wipe may be a flexible material suitable for topically applying a liquid or cream onto skin. The wipe may be, e.g., paper-based or cloth based. Exemplary wipes include tissues and wet wipes.

The compositions comprising ammonia oxidizing bacteria, e.g., N. eutropha may also comprise one or more of a moisturizing agent, deodorizing agent, scent, colorant, insect repellant, cleansing agent, or UV-blocking agent.

For instance, the moisturizing agent may be an agent that reduces or prevents skin dryness. Exemplary moisturizing agents include humectants (e.g., urea, glycerin, alpha hydroxy acids and dimethicone) and emollients (e.g., lanolin, mineral oil and petrolatum). Moisturizing agents may be included, e.g., in ammonia oxidizing bacteria, e.g., N. eutropha-containing creams, balms, lotions, or sunscreen.

A deodorizing agent may be an agent that reduces unwanted odors. A deodorizing agent may work by directly neutralizing odors, preventing perspiration, or preventing the growth of odor-producing bacteria. Exemplary deodorizing agents include aluminum salts (e.g., aluminum chloride or aluminum chlorohydrate), cyclomethicone, talc, baking soda, essential oils, mineral salts, hops, and witch hazel. Deodorizing agents are typically present in spray or stick deodorants, and can also be found in some soaps and clothing.

An insect repellant may be an agent that can be applied to surfaces (e.g., skin) that discourage insects and other arthropods from lighting on the surface. Insect repellants include DEET (N,N-diethyl-m-toluamide), p-menthane-3,8-diol (PMD), icaridin, nepetalactone, citronella oil, neem oil, bog myrtle, dimethyl carbate, Tricyclodecenyl allyl ether, and IR3535 (3-[N-Butyl-N-acetyl]-aminopropionic acid, ethyl ester).

A cleansing agent may be an agent that removes dirt or unwanted bacteria from a surface like skin. Exemplary cleansing agents include bar soaps, liquid soaps, and shampoos.

A UV-blocking agent may be an agent that can be applied to a surface to reduce the amount of ultraviolet light the surface receives. A UV-blocking agent may block UV-A and/or UV-B rays. A UV blocking agent can function by absorbing, reflecting, or scattering UV. Exemplary UV-blocking agents include absorbers, e.g., homosalate, octisalate (also called octyl salicylate), octinoxate (also called octyl methoxycinnamate or OMC), octocrylene, oxybenzone, and avobenzone, and reflectors (e.g., titanium dioxide and zinc oxide). UV-blocking agents are typically present in sunscreens, and can also be found in skin creams and some cosmetics.

In some embodiments, ammonia oxidizing bacteria, e.g., N. eutropha is associated with a conditioner. Conditioner generally refers to a substance with cream-like consistency that can be applied to hair to improve its appearance, strength, or manageability.

In some embodiments, ammonia oxidizing bacteria, e.g., N. eutropha is associated with cloth. Cloth generally refers to a flexible material suitable to be made into clothing, e.g., having enough material strength to withstand everyday motion by a wearer. Cloth can be fibrous, woven, or knit; it can be made of a naturally occurring material or a synthetic material. Exemplary cloth materials include cotton, flax, wool, ramie, silk, denim, leather, nylon, polyester, and spandex, and blends thereof.

In some embodiments, ammonia oxidizing bacteria, e.g., N. eutropha is associated with yarn. Yarn generally refers to a long, thin spun flexible material that is suitable for knitting or weaving. Yarn can be made of, e.g., wool, cotton, polyester, and blends thereof.

In some embodiments, ammonia oxidizing bacteria, e.g., N. eutropha is associated with thread. Thread generally refers to a long, thin spun flexible material that is suitable for sewing. Thread generally has a thinner diameter than yarn. Thread can be made of, e.g., cotton, polyester, nylon, silk, and blends thereof.

Articles of clothing such as, for example, shoes, shoe inserts, pajamas, sneakers, belts, hats, shirts, underwear, athletic garments, helmets, towels, gloves, socks, bandages, and the like, may also be treated with ammonia oxidizing bacteria, e.g., *N. eutropha*. Bedding, including sheets, pillows, pillow cases, and blankets may also be treated with ammonia oxidizing bacteria, e.g., *N. eutropha*. In some embodiments, areas of skin that cannot be washed for a period of time may also be contacted with ammonia oxidizing bacteria, e.g., *N. eutropha*. For example, skin enclosed in orthopedic casts which immobilize injured limbs during the healing process, and areas in proximity to injuries that must be kept dry for proper healing such as stitched wounds may benefit from contact with the ammonia oxidizing bacteria, e.g., *N. eutropha*.

In some aspects, the present disclosure provides a wearable article comprising an *N. eutropha* strain as described herein. A wearable article may be a light article that can be closely associated with a user's body, in a way that does not impede ambulation. Examples of wearable articles include a wristwatch, wristband, headband, hair elastic, hair nets, shower caps, hats, hairpieces, and jewelry. The wearable article comprising an ammonia oxidizing bacteria, e.g., *N. eutropha* strain described herein may provide, e.g., at a concentration that provides one or more of a treatment or prevention of a skin disorder, a treatment or prevention of a disease or condition associated with low nitrite levels, a treatment or prevention of body odor, a treatment to supply nitric oxide to a subject, or a treatment to inhibit microbial growth.

In some embodiments, the ammonia oxidizing bacteria, e.g., *N. eutropha* is associated with a product intended to contact the hair, for example, a brush, comb, shampoo, conditioner, headband, hair elastic, hair nets, shower caps, hats, and hairpieces. Nitric oxide formed on the hair, away from the skin surface, may be captured in a hat, scarf or face mask and directed into inhaled air.

Articles contacting the surface of a human subject, such as a diaper, may be associated with ammonia oxidizing bacteria, e.g., *N. eutropha*. Because diapers are designed to hold and contain urine and feces produced by incontinent individuals, the urea in urine and feces can be hydrolyzed by skin and fecal bacteria to form free ammonia which is irritating and may cause diaper rash. Incorporation of bacteria that metabolize urea into nitrite or nitrate, such as ammonia oxidizing bacteria, e.g., *N. eutropha*, may avoid the release of free ammonia and may release nitrite and ultimately NO which may aid in the maintenance of healthy skin for both children and incontinent adults. The release of nitric oxide in diapers may also have antimicrobial effects on disease causing organisms present in human feces. This effect may continue even after disposable diapers are disposed of as waste and may reduce the incidence of transmission of disease through contact with soiled disposable diapers In some embodiments, the product comprising ammonia oxidizing bacteria, e.g., *N. eutropha* is packaged. The packaging may serve to compact the product or protect it from damage, dirt, or degradation. The packaging may comprise, e.g., plastic, paper, cardboard, or wood. In some embodiments the packaging is impermeable to bacteria. In some embodiments the packaging is permeable to oxygen and/or carbon dioxide.

5. Methods of Treatment with *N. eutropha*

The present disclosure provides various methods of treating diseases and conditions using ammonia oxidizing bacteria, e.g., *N. eutropha*. The ammonia oxidizing bacteria, e.g., *N. eutropha* that may be used to treat diseases and conditions include all the ammonia oxidizing bacteria, e.g., *N. eutropha* compositions described in this application, e.g., a purified preparation of optimized ammonia oxidizing bacteria, e.g., *N. eutropha*, e.g. those in Section 2 above, for instance strain D23.

For instance, the disclosure provides uses, for treating a condition or disease (e.g., inhibiting microbial growth on a subject's skin), an optionally axenic composition of *N. eutropha* comprising a nucleic acid sequence at least about 70%, 80%, 85%, 90%, 95%, 96%, 97%, 98%, 99%, or 99.5% identical to SEQ ID NO: 1; an optionally axenic composition of *N. eutropha* comprising a nucleic acid sequence at least about 70%, 80%, 85%, 90%, 95%, 96%, 97%, 98%, 99%, or 99.5% identical to any one of the strain D23 nucleic acids of Table 1. In embodiments, the *N. eutropha* comprises at least 1, 2, 3, 4, 5, 6, 7, 8, 9, 10, 11, 12, 13, 14, 15, or all of the strain D23 nucleic acids of Table 1. In embodiments, the *N. eutropha* comprises one or more nucleic acids of FIGS. 6-8. As a further example, this disclosure provides uses, for treating a condition or disease, an optionally axenic composition of *N. eutropha* comprising an amino acid sequence at least about 70%, 80%, 85%, 90%, 95%, 96%, 97%, 98%, 99%, or 99.5% identical to any one of the strain D23 protein sequences of Table 1. In embodiments, the *N. eutropha* comprises at least 1, 2, 3, 4, 5, 6, 7, 8, 9, 10, 11, 12, 13, 14, 15, or all of the strain D23 protein sequences of Table 1. In embodiments, the *N. eutropha* comprises one or more proteins encoded by the nucleic acids of FIGS. 6-8. The *N. eutropha* of this paragraph may be used to treat, e.g., diabetic ulcers, e.g., diabetic foot ulcers, chronic wounds, acne, rosacea, eczema, or psoriasis.

In certain embodiments, the disclosure provides uses, for treating a condition or disease (e.g., inhibiting microbial growth on a subject's skin), an optionally axenic composition of *N. eutropha* having one or more of: (1) an optimized growth rate, (2) an optimized $NH_4^+$ oxidation rate, (3) an optimized resistance to $NH_3$, (4) an optimized resistance to, $NH_4^+$, and (5) an optimized resistance to, $NO_2^-$. For instance, the axenic *N. eutropha* composition may have properties (1) and (2); (2) and (3); (3) and (4); or (4) and (5) from the list at the beginning of this paragraph. As another example, the axenic *N. eutropha* composition may have properties (1), (2), and (3); (1), (2), and (4); (1), (2), and (5); (1), (3), and (4); (1), (3), and (5); (1), (4), and (5); (2), (3), and (4); (2), (3), and (5), or (3), (4), and (5) from the list at the beginning of this paragraph. As a further example, the optionally axenic *N. eutropha* composition may have properties (1), (2), (3), and (4); (1), (2), (3), and (5); (1), (2), (4), and (5); (1), (3), (4), and (5); or (2), (3), (4), and (5) from the list at the beginning of this paragraph. In some embodiments, the axenic *N. eutropha* composition has properties (1), (2), (3), (4), and (5) from the list at the beginning of this paragraph. The *N. eutropha* of this paragraph may be used to treat, e.g., diabetic ulcers, e.g., diabetic foot ulcers, chronic wounds, acne, rosacea, eczema, or psoriasis.

In some embodiments, optionally axenic *N. eutropha* (e.g., strain D23) are used to treat a subject. Subjects may include an animal, a mammal, a human, a non-human animal, a livestock animal, or a companion animal.

In some embodiments, optionally axenic *N. eutropha* described herein (e.g., the *N. eutropha* described in this Section and in Section 2 above, e.g., strain D23) are used to inhibit the growth of other organisms. For instance, *N. eutropha* D23 is well-adapted for long-term colonization of human skin, and in some embodiments it out-competes other bacteria that are undesirable on the skin. Undesirable skin bacteria include, e.g., those that can infect wounds, raise the risk or severity of a disease, or produce odors. Certain undesirable skin bacteria include S. aureus, P. aeruginosa, S. pyogenes, and A. baumannii. The N. eutropha described herein may out-compete other organisms by, e.g., consuming scarce nutrients, or generating byproducts that are harmful to other organisms, e.g., changing the pH of the skin to a level that is not conducive to the undesirable organism's growth.

Accordingly, the present disclosure provides, inter alia, a method of inhibiting microbial growth on a subject's skin, comprising topically administering to a human in need thereof an effective dose of optionally axenic N. eutropha bacteria as described herein (e.g., strain D23). Similarly, the present disclosure provides optionally axenic N. eutropha as described herein (e.g., strain D23) for use in inhibiting microbial growth on a subject's skin. Likewise, the present disclosure provides a use of optionally axenic N. eutropha (e.g., strain D23) in the manufacture of a medicament for inhibiting microbial growth on a subject's skin.

The present disclosure also provides a method of supplying nitric oxide to a subject, comprising positioning an effective dose of optionally axenic N. eutropha bacteria described herein (e.g., strain D23) in close proximity to the subject. Similarly, the present disclosure provides optionally axenic N. eutropha (e.g., strain D23) as described herein for use in supplying nitric oxide to a subject. Likewise, the present disclosure provides a use of optionally axenic N. eutropha (e.g., strain D23) in the manufacture of a medicament or composition suitable for position in close proximity to a subject.

The present disclosure also provides a method of reducing body odor, comprising topically administering to a subject in need thereof an effective dose of optionally axenic N. eutropha bacteria described herein (e.g., strain D23). Similarly, the present disclosure provides optionally axenic N. eutropha as described herein (e.g., strain D23) for use in reducing body odor in a subject. Likewise, the present disclosure provides a use of optionally axenic N. eutropha as described herein (e.g., strain D23) in the manufacture of a medicament or composition for reducing body odor.

The present disclosure also provides a method of treating or preventing a disease associated with low nitrite levels, comprising topically administering to a subject in need thereof a therapeutically effective dose of optionally axenic N. eutropha bacteria described herein (e.g., strain D23). Similarly, the present disclosure provides a topical formulation of optionally axenic N. eutropha as described herein (e.g., strain D23) for use in treating a disease associated with low nitrite levels. Likewise, the present disclosure provides a use of optionally axenic N. eutropha as described herein (e.g., strain D23) in the manufacture of a topical medicament for treating a disease associated with low nitrite levels.

The present disclosure also provides a method of treating or preventing a skin disorder or skin infection, comprising topically administering to a subject in need thereof a therapeutically effective dose of optionally axenic N. eutropha bacteria as described herein (e.g., strain D23). Similarly, the present disclosure provides optionally axenic N. eutropha as described herein (e.g., strain D23) for use in treating a skin disorder in a subject. Likewise, the present disclosure provides a use of optionally axenic N. eutropha as described herein (e.g., strain D23) in the manufacture of a medicament for treating skin disorder. In embodiments, the skin disorder is acne, rosacea, eczema, psoriasis, or urticaria; the skin infection is impetigo.

While not wishing to be bound by theory, it is proposed that treatment of acne with a therapeutically effective dose of optionally axenic N. eutropha bacteria as described herein (e.g., strain D23) may involve the downregulation of inflammation due to NO generation; and/or limiting and/or inhibiting the spread and proliferation of Propionibacterium acnes associated with acne vulgaris through acidified nitrite and NO production.

For instance, the disclosure provides uses, for treating a condition or disease (e.g., inhibiting microbial growth on a subject's skin), a composition of ammonia oxidizing bacteria. In embodiments, the ammonia oxidizing bacteria may be used to treat, e.g., chronic wounds, acne, rosacea, eczema, psoriasis, uticaria, skin infections, or diabetic ulcers, e.g., diabetic foot ulcers.

The systems and methods of the present disclosure may provide for, or contain contents, to be useful for treating or preventing a skin disorder, treating or preventing a disease or condition associated with low nitrite levels, a treating or preventing body odor, treating to supply nitric oxide to a subject, or treating to inhibit microbial growth.

The systems and methods of the present disclosure may provide for reducing an amount of undesirable bacteria from an environment, e.g., a surface of a subject.

The systems and methods of the present disclosure may provide for, or contain contents, to be useful in a treatment of at least one of HIV dermatitis, infection in a diabetic foot ulcer, atopic dermatitis, acne, eczema, contact dermatitis, allergic reaction, psoriasis, uticaria, rosacea, skin infections, vascular disease, vaginal yeast infection, a sexually transmitted disease, heart disease, atherosclerosis, baldness, leg ulcers secondary to diabetes or confinement to bed, angina, particularly chronic, stable angina pectoris, ischemic diseases, congestive heart failure, myocardial infarction, ischemia reperfusion injury, laminitis, hypertension, hypertrophic organ degeneration, Raynaud's phenomenon, fibrosis, fibrotic organ degeneration, allergies, autoimmune sensitization, end stage renal disease, obesity, impotence, pneumonia, primary immunodeficiency, epidermal lysis bulosa, or cancer.

The systems and methods of the present disclosure may provide for, or contain contents, to be useful in a treatment of at least one of acne, eczema, psoriasis, uticaria, rosacea, skin infections and wounds, e.g., an infected wound.

In some embodiments, ammonia oxidizing bacteria may be used to treat a subject. Subjects may include an animal, a mammal, a human, a non-human animal, a livestock animal, or a companion animal.

In some embodiments, ammonia oxidizing bacteria described herein are used to inhibit the growth of other organisms. For instance, ammonia oxidizing bacteria may be well-adapted for long-term colonization of human skin, and in some embodiments it out-competes other bacteria that are undesirable on the skin. Undesirable skin bacteria include, e.g., those that can infect wounds, raise the risk or severity of a disease, or produce odors. Undesirable bacteria may be referred to as pathogenic bacteria. Certain undesirable skin bacteria include Staphylococcus aureus (S. aureus), e.g., methicillin resistant Staphylococcus aureus Pseudomonas aeruginosa (P. aeruginosa), Streptococcus pyogenes (S. pyogenes), Acinetobacter baumannii (A. baumannii), Propionibacteria, and Stenotrophomonas. The ammonia oxidizing bacteria described herein may out-compete other organisms by, e.g., consuming scarce nutrients, or generating byproducts that are harmful to other organisms, e.g., changing the pH of the skin to a level that is not conducive to the undesirable organism's growth.

Accordingly, the present disclosure provides, inter alia, a method of inhibiting microbial growth on a subject's skin, comprising topically administering to a human in need thereof an effective dose of ammonia oxidizing bacteria as described herein. Similarly, the present disclosure provides ammonia oxidizing bacteria as described herein for use in inhibiting microbial growth on a subject's skin. Likewise, the present disclosure provides a use of ammonia oxidizing bacteria in the manufacture of a medicament for inhibiting microbial growth on a subject's skin.

The present disclosure provides, inter alia, a method of changing a composition of a skin microbiome, e.g., modulating a composition of a skin microbiome, e.g., modulating or changing the proportions of the skin microbiome, in an environment, e.g., a surface, e.g., a surface of a subject. The method may comprise administering, e.g., applying, a preparation comprising ammonia oxidizing bacteria to an environment, e.g., a surface, e.g., a surface of a subject. In some embodiments, the amount and frequency of administration, e.g., application, may be sufficient to reduce the proportion of pathogenic bacteria on the surface of the skin. In some embodiments, the subject may be selected on the basis of the subject being in need of a reduction in the proportion of pathogenic bacteria on the surface of the skin.

The present disclosure may further provide obtaining a sample from the surface of the skin, and isolating DNA of bacteria in the sample. Sequencing of the DNA of bacteria in the sample may also be performed to determine or monitor the amount or proportion of bacteria in a sample of a subject.

The present disclosure may also provide for increasing the proportion of non-pathogenic bacteria on the surface. In some embodiments, the non-pathogenic bacteria may be commensal non-pathogenic bacteria. In some embodiments, the non-pathogenic bacteria may be of the *Staphylococcus* genus. In some embodiments, the non-pathogenic bacteria may be *Staphylococcus epidermidis*. In some embodiments, the non-pathogenic bacteria that is increased in proportion may be of the *Staphylococcus* genus, comprising at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% *Staphylococcus epidermidis*.

The increase in the proportion of non-pathogenic bacteria may occur with a pre-determined period of time, e.g., in less than 1 day, 2 days, 3 days, 4 days, 5 days, 1 week, 2 weeks, 3 weeks, or 4 weeks, or in less than 1-3, 3-5, 5-7, 7-9, 5-10, 10-14, 12-18, 12-21, 21-28, 28-35, 35-42, 42-49, 49-56, 46-63, 63-70, 70-77, 77-84, 84-91 days.

The increase in the proportion of *Staphylococcus* bacteria, e.g., *Staphylococcus epidermidis*, may be observed in less than about 3 weeks, e.g., about 16 days, e.g., about 2 weeks.

The present disclosure may provide for decreasing the proportion of pathogenic bacteria, e.g., potentially pathogenic bacteria, e.g., disease-associated bacteria on the surface. In some embodiments, the pathogenic bacteria may be *Propionibacteria*. In some embodiments, the pathogenic bacteria may be *Stenotrophomonas*.

The decrease in the proportion of pathogenic bacteria may occur with a pre-determined period of time, e.g., in less than 1 day, 2 days, 3 days, 4 days, 5 days, 1 week, 2 weeks, 3 weeks, or 4 weeks, or in less than 1-3, 3-5, 5-7, 7-9, 5-10, 10-14, 12-18, 12-21, 21-28, 28-35, 35-42, 42-49, 49-56, 46-63, 63-70, 70-77, 77-84, 84-91 days.

The decrease in the proportion of *Propionibacteria* bacteria and/or *Stenotrophomonas* may be observed in less than about 3 weeks, e.g., about 16 days, e.g., about 2 weeks.

The present disclosure also provides a method of supplying nitric oxide to a subject, comprising positioning an effective dose of ammonia oxidizing bacteria described herein in close proximity to the subject. Similarly, the present disclosure provides ammonia oxidizing bacteria as described herein for use in supplying nitric oxide to a subject. Likewise, the present disclosure provides a use of in the manufacture of a medicament or composition suitable for position in close proximity to a subject.

The present disclosure also provides a method of reducing body odor, comprising topically administering to a subject in need thereof an effective dose of ammonia oxidizing bacteria described herein. Similarly, the present disclosure provides ammonia oxidizing bacteria as described herein for use in reducing body odor in a subject. Likewise, the present disclosure provides a use of ammonia oxidizing bacteria as described herein in the manufacture of a medicament or composition for reducing body odor.

The present disclosure also provides a method of treating or preventing a disease associated with low nitrite levels, comprising topically administering to a subject in need thereof a therapeutically effective dose of ammonia oxidizing bacteria described herein. Similarly, the present disclosure provides a topical formulation of ammonia oxidizing bacteria as described herein for use in treating a disease associated with low nitrite levels. Likewise, the present disclosure provides a use of ammonia oxidizing bacteria as described herein in the manufacture of a topical medicament for treating a disease associated with low nitrite levels.

The present disclosure also provides a method of treating or preventing a skin disorder or skin infection, comprising topically administering to a subject in need thereof a therapeutically effective dose of ammonia oxidizing bacteria as described herein. Similarly, the present disclosure provides ammonia oxidizing bacteria as described herein for use in treating a skin disorder in a subject. Likewise, the present disclosure provides a use of ammonia oxidizing bacteria as described herein in the manufacture of a medicament for treating skin disorder. In embodiments, the skin disorder is acne, rosacea, eczema, psoriasis, or urticaria; the skin infection is impetigo.

While not wishing to be bound by theory, it is proposed that treatment of rosacea with a therapeutically effective dose of optionally axenic *N. eutropha* bacteria as described herein (e.g., strain D23) may involve downregulation due to NO generation. This may be due to expression of Kazal-type KLK5/KLK7 inhibitor(s) that may reduce formation of the human cathelicidin peptide LL-37 from its precursor propeptide hCAP18.

While not wishing to be bound by theory, it is proposed that treatment of eczema and/or atopic dermatitis with a therapeutically effective dose of optionally axenic *N. eutropha* bacteria as described herein (e.g., strain D23) may involve downregulation of inflammation due to NO generation; and/or limiting and/or inhibiting the spread and proliferation of *S. aureus* and other skin pathogens often associated with very high colonization rates and skin loads in atopic dermatitis through acidified nitrite and NO production.

While not wishing to be bound by theory, it is proposed that treatment of psoriasis with a therapeutically effective dose of optionally axenic *N. eutropha* bacteria as described herein (e.g., strain D23) may involve downregulation of inflammation due to NO generation and reduction in formation of human cathelicidin peptide LL-37.

While not wishing to be bound by theory, it is proposed that treatment of psoriasis with a therapeutically effective dose of optionally axenic *N. eutropha* bacteria as described herein (e.g., strain D23) may involve downregulation of inflammation due to NO generation.

While not wishing to be bound by theory, it is proposed that treatment of impetigo or other skin and soft tissue infections with a therapeutically effective dose of optionally axenic *N. eutropha* bacteria as described herein (e.g., strain D23) may involve limiting and/or inhibiting the spread and proliferation of *S. aureus* and *S. pyogenes*.

The present disclosure also provides a method of promoting wound healing, comprising administering to a wound an effective dose of optionally axenic *N. eutropha* bacteria as described herein (e.g., strain D23). Similarly, the present disclosure provides optionally axenic *N. eutropha* as described herein (e.g., strain D23) for use in treating a wound. Likewise, the present disclosure provides a use of optionally axenic *N. eutropha* as described herein (e.g., strain D23) in the manufacture of a medicament or a composition for treating a wound.

Optionally axenic *N. eutropha* as described herein (e.g., strain D23) may be used to promote wound healing in a patient that has an impaired healing ability, e.g., a diabetic patient.

In some embodiments, this disclosure provides methods of using optionally axenic *N. eutropha* as described herein (e.g., strain D23) to prevent a disease or disorder, e.g., a skin disorder. Prevention, in certain embodiments, means reducing the risk of a subject developing a disease, compared to a similar untreated subject. The risk need not be reduced to zero.

Individuals having a reduced bathing frequency, such as astronauts, submarine crew members, military personnel during a campaign, civilian workers in remote locations, refugees, bedridden individuals and many others may maintain healthier skin by maintaining *N. eutropha* on the skin. With regard to bedridden individuals, the *N. eutropha* in some embodiments reduces the frequency or severity of bed sores by augmenting inadequate circulation.

It is appreciated that many modern degenerative diseases may be caused by a lack of NO species, and that AOB on the external skin can supply those species by diffusion, and that application of AOB to the skin resolves long standing medical conditions. In certain embodiments, AOB are applied to a subject to offset modern bathing practices, especially with anionic detergents remove AOB from the external skin.

One suitable method of topical application to apply sufficient *N. eutropha* and then wear sufficient clothing so as to induce sweating. However, many people will want to derive the benefits of AOB while maintaining their current bathing habits, in which case, a culture of the bacteria can be applied along with sufficient substrate for them to produce NO. A nutrient solution approximating the inorganic composition of human sweat can be used for this purpose.

Using bacteria adapted to media approximating human sweat minimizes the time for them to adapt when applied. Since sweat evaporates once excreted onto the skin surface, using a culture media that has a higher ionic strength is desirable. A concentration approximately twice that of human sweat is suitable, but other conditions are also contemplated. AOB's nutritional needs are typically met with $NH_3$ or urea, $O_2$, $CO_2$, and minerals. In some embodiments, the substrate comprises trace minerals including iron, copper, zinc, cobalt, molybdenum, manganese, sodium, potassium, calcium, magnesium, chloride, phosphate, sulfate, or any combination thereof.

In some embodiments, the present disclosure provides a method of treating a wound by applying a bandage comprising *N. eutropha* to the wound. Also provided are methods of producing such a bandage. The bandage may comprise, for example, an adhesive portion to affix the bandage to undamaged skin near the wound and a soft, flexible portion to cover or overlay the wound. In some embodiments, the bandage contains no other organisms but *N. eutropha*. The bandage may be made of a permeable material that allows gasses like oxygen and carbon dioxide to reach the *N. eutropha* when the bandage is applied to the wound. In certain embodiments, the bandage comprises nutrients for *N. eutropha* such as ammonium, ammonia, urea, or trace minerals. In certain embodiments, the bandage comprises an antibiotic to which the *N. eutropha* is resistant. The antibiotic resistance may arise from one or more endogenous resistance gene or from one or more transgenic.

In some embodiments, the *N. eutropha* is administered at a dose of about $10^8$-$10^9$ CFU, $10^9$-$10^{10}$ CFU, $10^{10}$-$10^{11}$ CFU, or $10^{11}$-$10^{12}$ CFU per application. In some embodiments, the *N. eutropha* is administered topically at a dose of about $10^{10}$-$10^{11}$ CFU, e.g., about $1\times10^{10}$-$5\times10^{10}$, $1\times10^{10}$-$3\times10^{10}$, or $1\times10^{10}$-$2\times10^{10}$ CFU.

In some embodiments, the *N. eutropha* is administered in a volume of about 1-2, 2-5, 5-10, 10-15, 12-18, 15-20, 20-25, or 25-50 ml per dose. In some embodiments, the solution is at a concentration of about $10^8$-$10^9$, $10^9$-$10^{10}$, or $10^{10}$-$10^{11}$ CFUs/ml. In some embodiments, the *N. eutropha* is administered as two 15 ml doses per day, where each dose is at a concentration of $10^9$ CFU/ml.

In some embodiments, ammonia oxidizing bacteria, e.g., the *N. eutropha* is administered once, twice, three, or four times per day. In some embodiments, ammonia oxidizing bacteria, e.g., the *N. eutropha* is administered once, twice, three, four, five, or six times per week. In some embodiments, ammonia oxidizing bacteria, e.g., the *N. eutropha* is administered shortly after bathing. In some embodiments, ammonia oxidizing bacteria, e.g., the *N. eutropha* is administered shortly before sleep.

In certain aspects, the present disclosure provides combination therapies comprising ammonia oxidizing bacteria, e.g., a *N. eutropha* and a second therapeutic. For instance, the disclosure provides physical admixtures of the two (or more) therapies are physically admixed. In other embodiments, the two (or more) therapies are administered in combination as separate formulation. The second therapy may be, e.g., a pharmaceutical agent, surgery, or any other medical approach that treats the relevant disease or disorder. The following paragraphs describe combination therapies capable of treating diabetic ulcers, chronic wounds, acne, rosacea, eczema, and psoriasis.

For instance, in a combination therapy capable of treating diabetic ulcers, the second therapy may comprise, e.g., a wound dressing (e.g., absorptive fillers, hydrogel dressings, or hydrocolloids), angiotensin, angiotensin analogues, platelet-rich fibrin therapy, hyperbaric oxygen therapy, negative pressure wound therapy, debridement, drainage, arterial revascularization, hyperbaric oxygen therapy, low level laser therapy, and gastrocnemius recession. The combination therapy may comprise one or more of the above-mentioned treatments.

In a combination therapy capable of treating chronic wounds, the second therapy may comprise, e.g., an antibiotic (e.g., topical or systemic, and bacteriocidal or bacteriostatic) such as Penicillins, cephalosporins, polymyxins, rifamycins, lipiarmycins, quinolones, sulfonamides, macrolides, lincosamides, tetracyclines, cyclic lipopeptides, glycylcyclines, oxazolidinones, and lipiarmycins; angiotensin, angiotensin analogues; debridement; drainage; wound irrigation; negative pressure wound therapy; application of heat; arterial revascularization; hyperbaric oxygen therapy; antioxidants such as ascorbic acid, glutathione, lipoic acid, carotenes, α-tocopherol, or ubiquinol; low level laser therapy; gastrocnemius recession; growth factors such as vascular endothelial growth factor, insulin-like growth factor 1-2, platelet derived growth factor, transforming growth factor-β, or epidermal growth factor; application of autologous platelets such as those that secrete one or more growth factors such as vascular endothelial growth factor, insulin-like growth factor 1-2, platelet derived growth factor, transforming growth factor-β, or epidermal growth factor; implantation of cultured keratinocytes; allograft; collagen, for instance a dressing comprising collagen; or protease inhibitors such as SLPI. The combination therapy may comprise one or more of the above-mentioned treatments.

In a combination therapy capable of treating acne, the second therapy may comprise, e.g., a medication (e.g., systemic or topical) such as Benzoyl peroxide, antibiotics (such as erythromycin, clindamycin, or a tetracycline), Salicylic acid, hormones (e.g., comprising a progestin such as desogestrel, norgestimate or drospirenone), retinoids such as tretinoin, adapalene, tazarotene, or isotretinoin. The second therapy may also be a procedure such as comedo extraction, corticosteroid injection, or surgical lancing. The combination therapy may comprise one or more of the above-mentioned treatments.

In a combination therapy capable of treating rosacea, the second therapy may comprise, e.g., an antibiotic, e.g., an oral tetracycline antibiotic such as tetracycline, doxycycline, or minocycline, or a topical antibiotic such as metronidazole; azelaic acid; alpha-hydroxy acid; isotretinoin can be prescribed; sandalwood oil; clonidine; beta-blockers such as nadolol and propranolol; antihistamines (such as loratadine); mirtazapine; methylsulfonylmethane or silymarin, optionally in combination with each other; lasers such as dermatological vascular laser or $CO_2$ laser; or light therapies such as intense pulsed light, low-level light therapy or photorejuvenation. The combination therapy may comprise one or more of the above-mentioned treatments.

In a combination therapy capable of treating eczema, the second therapy may comprise, e.g., a corticosteroid such as hydrocortisone or clobetasol propionate, immunosuppressants (topical or systemic) such as pimecrolimus, tacrolimus, ciclosporin, azathioprine or methotrexate, or light therapy such as with ultraviolet light. The combination therapy may comprise one or more of the above-mentioned treatments.

In a combination therapy capable of treating psoriasis, the second therapy may comprise, e.g., a corticosteroid such as desoximetasone; a retinoid; coal tar; Vitamin D or an analogue thereof such as paricalcitol or calcipotriol; moisturizers and emollients such as mineral oil, vaseline, calcipotriol, decubal, or coconut oil; dithranol; or fluocinonide. The combination therapy may comprise one or more of the above-mentioned treatments.

While not wishing to be bound by theory, it is proposed that treatment of psoriasis with a therapeutically effective dose of ammonia oxidizing bacteria described herein may involve downregulation of inflammation due to NO generation and reduction in formation of human cathelicidin peptide LL-37.

While not wishing to be bound by theory, it is proposed that treatment of psoriasis with a therapeutically effective dose of ammonia oxidizing bacteria as described herein may involve downregulation of inflammation due to NO generation.

While not wishing to be bound by theory, it is proposed that treatment of impetigo or other skin and soft tissue infections with a therapeutically effective dose of ammonia oxidizing bacteria as described herein may involve limiting and/or inhibiting the spread and proliferation of *Staphylococcus aureus* (*S. aureus*), e.g., methicillin resistant *Staphylococcus aureus*, *Pseudomonas aeruginosa* (*P. aeruginosa*), *Streptococcus pyogenes* (*S. pyogenes*), *Acinetobacter baumannii* (*A. baumannii*), *Propionibacteria*, and *Stenotrophomonas*.

The present disclosure also provides a method of promoting wound healing, comprising administering to a wound an effective dose of ammonia oxidizing bacteria as described herein. Similarly, the present disclosure provides ammonia oxidizing bacteria as described herein for use in treating a wound. Likewise, the present disclosure provides a use of ammonia oxidizing bacteria as described herein in the manufacture of a medicament or a composition for treating a wound.

Ammonia oxidizing bacteria as described herein may be used to promote wound healing in a patient that has an impaired healing ability, e.g., a diabetic patient.

In some embodiments, this disclosure provides methods of using ammonia oxidizing bacteria as described herein to prevent a disease or disorder, e.g., a skin disorder. Prevention, in certain embodiments, means reducing the risk of a subject developing a disease, compared to a similar untreated subject. The risk need not be reduced to zero.

Individuals having a reduced bathing frequency, such as astronauts, submarine crew members, military personnel during a campaign, civilian workers in remote locations, refugees, bedridden individuals and many others may maintain healthier skin by maintaining ammonia oxidizing bacteria on the skin. With regard to bedridden individuals, the ammonia oxidizing bacteria in some embodiments reduces the frequency or severity of bed sores by augmenting inadequate circulation.

It is appreciated that many modern degenerative diseases may be caused by a lack of NO species, and that ammonia oxidizing bacteria on the external skin can supply those species by diffusion, and that application of ammonia oxidizing bacteria to the skin resolves long standing medical conditions. In certain embodiments, ammonia oxidizing bacteria are applied to a subject to offset modern bathing practices, especially with anionic detergents remove ammonia oxidizing bacteria from the external skin.

One suitable method of topical application to apply sufficient ammonia oxidizing bacteria and then wear sufficient clothing so as to induce sweating. However, many people will want to derive the benefits of ammonia oxidizing bacteria while maintaining their current bathing habits, in which case, a culture of the bacteria can be applied along with sufficient substrate for them to produce NO. A nutrient solution approximating the inorganic composition of human sweat can be used for this purpose. Using bacteria adapted to media approximating human sweat minimizes the time for them to adapt when applied. Since sweat evaporates once excreted onto the skin surface, using a culture media that has a higher ionic strength is desirable. A concentration approximately twice that of human sweat is suitable, but other conditions are also contemplated. Ammonia oxidizing bacteria's nutritional needs are typically met with $NH_3$ or urea, $O_2$, $CO_2$, and minerals. In some embodiments, the substrate comprises trace minerals including iron, copper, zinc, cobalt, molybdenum, manganese, sodium, potassium, calcium, magnesium, chloride, phosphate, sulfate, or any combination thereof.

In some embodiments, the present disclosure provides a method of treating a wound by applying a bandage comprising ammonia oxidizing bacteria to the wound. Also provided are methods of producing such a bandage. The bandage may comprise, for example, an adhesive portion to affix the bandage to undamaged skin near the wound and a soft, flexible portion to cover or overlay the wound. In some embodiments, the bandage contains no other organisms but ammonia oxidizing bacteria. The bandage may made of a permeable material that allows gasses like oxygen and carbon dioxide to reach the ammonia oxidizing bacteria when the bandage is applied to the wound. In certain embodiments, the bandage comprises nutrients for ammonia oxidizing bacteria such as ammonium, ammonia, urea, or trace minerals. In certain embodiments, the bandage comprises an antibiotic to which the ammonia oxidizing bacteria is resistant. The antibiotic resistance may arise from one or more endogenous resistance gene or from one or more transgenes.

In some embodiments, the ammonia oxidizing bacteria, e.g., a preparation of ammonia oxidizing bacteria, is administered at a dose of about $10^8$-$10^9$ CFU, $10^9$-$10^{10}$ CFU, $10^{10}$-$10^{11}$ CFU, or $10^{11}$-$10^{12}$ CFU per application or per day. In some embodiments, the ammonia oxidizing bacteria is administered topically at a dose of about $10^9$-$10^{10}$ CFU, e.g., about $1\times10^9$-$5\times10^9$, $1\times10^9$-$3\times10^9$, or $1\times10^9$-$10\times10^9$ CFU.

In some embodiments, the ammonia oxidizing bacteria is administered in a volume of about 1-2, 2-5, 5-10, 10-15, 12-18, 15-20, 20-25, or 25-50 ml per dose. In some embodiments, the solution is at a concentration of about $10^8$-$10^9$, $10^9$-$10^{10}$, or $10^{10}$-$10^{11}$ CFU/ml. In some embodiments, the ammonia oxidizing bacteria is administered as two 15 ml doses per day, where each dose is at a concentration of $10^9$ CFU/ml.

In some embodiments, the ammonia oxidizing bacteria is administered once, twice, three, or four times per day. In some embodiments, the ammonia oxidizing bacteria is administered once, twice, three, four, five, or six times per week. In some embodiments, the ammonia oxidizing bacteria is administered shortly after bathing. In some embodiments, the ammonia oxidizing bacteria is administered shortly before sleep.

In some embodiments, the ammonia oxidizing bacteria is administered for about 1-3, 3-5, 5-7, 7-9, 5-10, 10-14, 12-18, 12-21, 21-28, 28-35, 35-42, 42-49, 49-56, 46-63, 63-70, 70-77, 77-84, 84-91 days, e.g., for about 1 month, for about 2 months, for about 3 months. In some embodiments, the ammonia oxidizing bacteria is administered for an indefinite period of time, e.g., greater than one year, greater than 5 years, greater than 10 years, greater than 15 years, greater than 30 years, greater than 50 years, greater than 75 years.

6. Experimental Models for Refining D23 Treatments

Treatments comprising ammonia oxidizing bacteria as described herein (optionally in combination with another therapy) can be refined using a number of model systems. These model systems can be used to determine suitable doses and timing of administration.

For instance, with respect to chronic wounds and diabetic ulcers, one may use the mouse skin puncture model. Other models for these disorders include controlled cutaneous ischemia in a guinea pig model, rabbit ear ulcer model, application of calcium to a wound, or topical application of doxorubicin.

With respect to acne, one may use (for example) the Mexican hairless dog model, the Rhino mouse model, or the rabbit ear assay. With respect to rosacea, one may use (for example) intradermal injection of LL-37 into mouse skin or the Syrian hamster model. With respect to eczema, one may use (for example) application of a crude extract of *Dermatophagoides farina*, application of dinitrochlorobenzene to the ears of sensitized guinea pigs, or NC/Nga mice. With respect to psoriasis, one may use (for example) xenograft models in which involved and uninvolved psoriatic skin are transplanted onto immunodeficient mice, application of an antibody directed against interleukin 15 to the skin of SCID mice, and the Sharpin$^{cpdm}$/Sharpin$^{cpdm}$ mouse model.

Treatments comprising ammonia oxidizing bacteria, e.g., *N. eutropha* as described herein (e.g., strain D23) (optionally in combination with another therapy) can be refined using a number of model systems. These model systems can be used to determine suitable doses and timing of administration.

For instance, with respect to chronic wounds and diabetic ulcers, one may use the mouse skin puncture model described herein in Example 6. Other models for these disorders include controlled cutaneous ischemia in a guinea pig model, rabbit ear ulcer model, application of calcium to a wound, or topical application of doxorubicin.

With respect to acne, one may use (for example) the Mexican Hairless Dog model, the Rhino mouse model, or the rabbit ear assay. With respect to rosacea, one may use (for example) intradermal injection of LL-37 into mouse skin or the Syrian hamster model. With respect to eczema, one may use (for example) application of a crude extract of *Dermatophagoides farina*, application of dinitrochlorobenzene to the ears of sensitized guinea pigs, or NC/Nga mice. With respect to psoriasis, one may use (for example) xenograft models in which involved and uninvolved psoriatic skin are transplanted onto immunodeficient mice, application of an antibody directed against interleukin 15 to the skin of SCID mice, and the Sharpin$^{cpdm}$/Sharpin$^{cpdm}$ mouse model.

7. Mechanism of Therapeutic Benefit

While not wishing to be bound by theory, it is believed that one or more of the following mechanisms contributes to the beneficial effect of ammonia oxidizing bacteria, e.g., *N. eutropha* in treating the diseases and conditions discussed herein. Additional mechanistic details are found in International Application WO/2005/030147, which is herein incorporated by reference in its entirety.

In order to understand the beneficial aspects of these bacteria, it is helpful to understand angiogenesis. All body cells, except those within a few hundred microns of the external air, receive all metabolic oxygen from the blood supply. The oxygen is absorbed by the blood in the lung, is carried by red blood cells as oxygenated hemoglobin to the peripheral tissues, where it is exchanged for carbon dioxide, which is carried back and exhaled from the lung. Oxygen must diffuse from the erythrocyte, through the plasma, through the endothelium and through the various tissues until it reached the mitochondria in the cell which consumes it. The human body contains about 5 liters of blood, so the volume of the circulatory system is small compared to that of the body. Oxygen is not actively transported. It passively diffuses down a concentration gradient from the air to the erythrocyte, from the erythrocyte to the cell, and from the cell to cytochrome oxidase where it is consumed. The concentration of oxygen at the site of consumption is the lowest in the body, and the $O_2$ flux is determined by the diffusion resistance and the concentration gradient. Achieving sufficient oxygen supply to all the peripheral tissues requires exquisite control of capillary size and location. If the spacing between capillaries were increased, achieving the same flux of oxygen would require a larger concentration difference and hence a lower $O_2$ concentration at cytochrome oxidase. With more cells between capillaries, the $O_2$ demand would be greater. If the spacing between capillaries were decreased, there would be less space available for the cells that perform the metabolic function of the organ.

In certain aspects, it is appreciated that NO from ammonia oxidizing bacteria is readily absorbed by the outer skin and converted into S-nitrosothiols since the outer skin is free from hemoglobin. M. Stucker et al. have shown that the external skin receives all of its oxygen from the external air in "The cutaneous uptake of atmospheric oxygen contributes significantly to the oxygen supply of human dermis and epidermis. (Journal of Physiology (2002), 538.3, pp. 985-994.) This is readily apparent, because the external skin can be seen to be essentially erythrocyte free. There is circulation of plasma through these layers because they are living and do require the other nutrients in blood, just not the oxygen. S-nitrosothiols formed are stable, can diffuse throughout the body, and constitute a volume source of authentic NO and a source of NO to transnitrosate protein thiols.

In some aspects, it is appreciated that capillary rarefaction may be one of the first indications of insufficient levels of NO. F. T. Tarek et al. have shown that sparse capillaries, or capillary rarefaction, is commonly seen in people with essential hypertension. (Structural Skin Capillary Rarefaction in Essential Hypertension. Hypertension. 1999; 33:998-1001

A great many conditions are associated with the capillary density becoming sparser. Hypertension is one, and researchers reported that sparse capillaries are also seen in the children of people with essential hypertension, and also in people with diabetes. Significant complications of diabetes are hypertension, diabetic nephropathy, diabetic retinopathy, and diabetic neuropathy. R. Candido et al. have found that the last two conditions are characterized by a reduction in blood flow to the affected areas prior to observed symptoms. (Haemodynamics in microvascular complications in type 1 diabetes. Diabetes Metab Res Rev 2002; 18: 286-304.) Reduced capillary density is associated with obesity, and simple weight loss increases capillary density as shown by A Philip et al. in "Effect of Weight Loss on Muscle Fiber Type, Fiber Size, Capilarity, and Succinate Dehydrogenase Activity in Humans. The Journal of Clinical Endocrinology & Metabolism Vol. 84, No. 11 4185-4190, 1999.

Researchers have shown that in primary Raynaud's phenomena (PRP), the nailfold capillaries are sparser (slightly) than in normal controls, and more abundant than in patients that have progressed to systemic sclerosis (SSc). M. Bukhari, Increased Nailfold Capillary Dimensions In Primary Raynaud's Phenomenon And Systemic Sclerosis. British Journal of Rheumatology, Vol. 24 No 35: 1127-1131, 1996. They found that the capillary density decreased from 35 loops/mm$^2$ (normal controls) to 33 (PRP), to 17 (SSc). The average distance between capillary limbs was 18μ, 18μ, and 30μ for controls, PRP and SSc, respectively.

In certain aspects, it is appreciated that the mechanism that the body normally uses to sense "hypoxia" may affect the body's system that regulates capillary density. According to this aspect of the invention, a significant component of "hypoxia" is sensed, not by a decrease in O2 levels, but rather by an increase in NO levels. Lowering of basal NO levels interferes with this "hypoxia" sensing, and so affects many bodily functions regulated through "hypoxia." For Example, anemia is commonly defined as "not enough hemoglobin," and one consequence of not enough hemoglobin is "hypoxia", which is defined as "not enough oxygen." According to some aspects, these common definitions do not account for the nitric oxide mediated aspects of both conditions.

At rest, acute isovolemic anemia is well tolerated. A ⅔ reduction in hematocrit has minimal effect on venous return PvO2, indicating no reduction in either $O_2$ tension or delivery throughout the entire body. Weiskopf et al. Human cardiovascular and metabolic response to acute, severe isovolemic anemia. JAMA 1998, vol 279, No. 3, 217-221. At 50% reduction (from 140 to 70 g Hb/L), the average PvO2 (over 32 subjects) declined from about 77% to about 74% (of saturation). The reduction in $O_2$ capacity of the blood is compensated for by vasodilatation and tachycardia with the heart rate increasing from 63 to 85 bpm. That the compensation is effective is readily apparent, however, the mechanism is not. A typical explanation is that "hypoxia" sensors detected "hypoxia" and compensated with vasodilatation and tachycardia. However, there was no "hypoxia" to detect. There was a slight decrease in blood lactate (a marker for anaerobic respiration) from 0.77 to 0.62 mM/L indicating less anaerobic respiration and less "hypoxia." The 3% reduction in venous return PvO2 is the same level of "hypoxia" one would get by ascending 300 meters in altitude (which typically does not produce tachycardia). With the $O_2$ concentration in the venous return staying the same, and the $O_2$ consumption staying the same, there is no place in the body where there is a reduction in $O_2$ concentration. Compensation during isovolemic anemia may not occur because of $O_2$ sensing.

Thus the vasodilatation that is observed in acute isovolemic anemia may be due to the increased NO concentration at the vessel wall. NO mediates dilatation of vessels in response to shear stress and other factors. No change in levels of NO metabolites would be observed, because the production rate of NO is unchanged and continues to equal the destruction rate. The observation of no "hypoxic" compensation with metHb substitution can be understood because metHb binds NO just as Hb does, so there is no NO concentration increase with metHb substitution as there is with Hb withdrawal.

Nitric oxide plays a role in many metabolic pathways. It has been suggested that a basal level of NO exerts a tonal inhibitory response, and that reduction of this basal level leads to a dis-inhibition of those pathways. Zanzinger et al. have reported that NO has been shown to inhibit basal sympathetic tone and attenuate excitatory reflexes. (Inhibition of basal and reflex-mediated sympathetic activity in the RVLM by nitric oxide. Am. J. Physiol. 268 (Regulatory Integrative Comp. Physiol. 37): R958-R962, 1995.)

In some aspects, it is appreciated that one component of a volume source of NO is low molecular weight S-nitrosothiols produced in the erythrocyte free skin from NO produced on the external skin by ammonia oxidizing bacteria. These low molecular weight S-nitrosothiols are stable for long periods, and can diffuse and circulate freely in the plasma. Various enzymes can cleave the NO from various S-nitrosothiols liberating NO at the enzyme site. It is the loss of this volume source of NO from AOB on the skin that leads to disruptions in normal physiology. The advantage to the body of using S-nitrosothiols to generate NO far from a capillary is that $O_2$ is not required for NO production from S-nitrosothiols. Production of NO from nitric oxide synthase (NOS) does require $O_2$. With a sufficient background of S-nitrosothiols, NO can be generated even in anoxic regions. Free NO is not needed either since NO only exerts effects when attached to another molecule, such as the thiol of a cysteine residue or the iron in a heme, so the effects of NO can be mediated by transnitrosation reactions even in the absence of free NO provided that S-nitrosothiols and transnitrosation enzymes are present.

Frank et al. have shown that the angiogenesis that accompanies normal wound healing is produced in part by elevated VEGF which is induced by increased nitric oxide. (Nitric oxide triggers enhanced induction of vascular endothelial growth factor expression in cultured keratinocytes (HaCaT) and during cutaneous wound repair. FASEB J. 13, 2002-2014 (1999).)

NO has a role in the development of cancer, indicating that the bacteria described herein may be used in methods of cancer treatment and prevention. According to certain aspects, it is appreciated that the presence of NO during hypoxia may prevent cells from dividing while under hypoxic stress, when cells are at greater risk for errors in copying DNA. One relevant cell function is the regulation of the cell cycle. This is the regulatory program which controls how and when the cell replicates DNA, assembles it into duplicate chromosomes, and divides. The regulation of the cell cycle is extremely complex, and is not fully understood. However, it is known that there are many points along the path of the cell cycle where the cycle can be arrested and division halted until conditions for doing so have improved. The p53 tumor suppressor protein is a key protein in the regulation of the cell cycle, and it serves to initiate both cell arrest and apoptosis from diverse cell stress signals including DNA damage and p53 is mutated in over half of human cancers as reported by Ashcroft et al. in "Stress Signals Utilize Multiple Pathways To Stabilize p53." (Molecular And Cellular Biology, May 2000, p. 3224-3233.) Hypoxia does initiate accumulation of p53, and while hypoxia is important in regulating the cell cycle, hypoxia alone fails to induce the downstream expression of p53 mRNA effector proteins and so fails to cause arrest of the cell cycle. Goda et al. have reported that hypoxic induction of cell arrest requires hypoxia-inducing factor-1 (HIF-1α). (Hypoxia-Inducible Factor 1α Is Essential for Cell Cycle Arrest during Hypoxia. Molecular And Cellular Biology, January 2003, p. 359-369.) Britta et al. have reported that NO is one of the main stimuli for HIF-1α. (Accumulation of HIF-1a under the influence of nitric oxide. Blood, 15 Feb. 2001, Volume 97, Number 4.) In contrast, NO does cause the accumulation of transcriptionally active p53 and does cause arrest of the cell cycle and does cause apoptosis. Wang et al., P53 Activation By Nitric Oxide Involves Down-Regulation Of Mdm2. THE JOURNAL OF BIOLOGICAL CHEMISTRY Vol. 277, No. 18, Issue Of May 3, Pp. 15697-15702, 2002.

In certain aspect of the invention, it is appreciated that preventing the necrotic death of cells by preventing the capillary rarefaction that leads to their hypoxic death may prevent autoimmune disorders. When cells are exposed to chronic hypoxia, the production of reactive oxygen species (ROS) is increased, and there is increased damage to the cells metabolic machinery and ultimately to the cells' DNA. Decreased metabolic capacity will decrease capacity for repair of damage due to ROS and due to exogenous carcinogen exposure. Over time, the damage accumulates and increases the chance of three events: the cell will undergo deletion of cancer-preventing genes and the cell will become cancerous, the cell will die through necrosis, or the cell will die through apoptosis. When cells die, either through necrosis or apoptosis, the cell debris must be cleared from the site. Dead cells are phagocytosed by immune cells, including dendritic cells and macrophages. When these cells phagocytose a body, it is digested by various proteolytic enzymes into antigenic fragments, and then these antigens are attached to the major histocompatibility complex (MHC1, MHC2) and the antigen-MHC complex is moved to the surface of the cell where it can interact with T cells and activate the T cells in various ways. Any cell injury releases adjuvants which stimulate the immune system in various ways. In general, cells that undergo necrosis stimulate a greater immune response than cells that undergo apoptosis. Chronic exposure of immune cells to dead and dying cells is therefore likely to lead to autoimmune disorders.

In certain aspects, it is appreciated that low basal NO leads to fibrotic hypertrophy. Once a dead cell has been cleared, a new cell cannot easily take its place, because there is insufficient $O_2$ to support it. Any such new cell would suffer the same fate. The space can remain empty, in which case the organ shrinks, the capillaries draw closer together, new cells are now deprived of the VEGF formerly produced by the now-missing cell, so capillaries ablate and the hypoxic zone reforms. This could result in a general shrinkage of the affected tissues. In tissues that support fibrosis, relatively inert collagen fibers can fill the space. Since the metabolic requirements of the body for the particular organ in question are not reduced, the organ may attempt to grow larger, but now with a significant fibrous content. This may result in fibrotic hypertrophy, such as of the heart and liver. Some organs, such as the brain, cannot grow larger or smaller because the three-dimensional connectivity of nerves and blood vessels are important, and cannot be continuously and simultaneously mapped onto an asymmetrically shrinking brain. The space must be filled with something, and β-amyloid might be the (not so inert) space filler. The kidney cannot grow larger because of the renal capsule, so the number of living cells becomes smaller and they are replaced with fibrotic tissue. If the dead cells are cleared, the tissue shrinks, and the ratio of $NO/O_2$ goes down again, and the capillaries again become sparser. This may set up the vicious circle of end stage renal disease, congestive heart failure/cardiac hypertrophy, primary biliary cirrhosis, Alzheimer's disease, atherosclerosis, inflammatory bowel disease, hypertrophic scar formation, and the multiple connective tissue diseases starting with Raynaud's phenomena and ending with Systemic Sclerosis and primary Sjogren's syndrome where capillary rarefaction is also observed. Ferrini et al, have shown that a reduction in basal NO levels through chronic inhibition of NOS with L-NAME leads to generalized fibrosis of the heart and kidneys. (Antifibrotic Role of Inducible Nitric Oxide Synthase. Nitric Oxide: Biology and Chemistry Vol. 6, No. 3, pp. 283-294 (2002).) It may be that low basal NO leads to fibrotic hypertrophy.

In certain aspects, it is appreciated that capillary rarefaction affects a subject's ability to control their appetite. Capillary rarefaction is observed in the brains of aged humans and animals. Capillary rarefaction is associated with declines in circulating growth factors including insulin like growth factor-1. Neurogenesis in the adult brain is coordinated with angiogenesis. Since the brain regulates many homeostatic functions, increased diffusion lengths between capillaries to control elements of the brain might be "interpreted" as inadequate blood concentrations of those species. The flux of glucose in the brain is quite close to normal metabolic needs, where glucose flux is only 50 to 75% greater than glucose consumption and the glucose transporters across the blood brain barrier are saturable, stereospecific and independent of energy or ion gradients. A large part of the regulation of appetite is mediated through the brain, and capillary rarefaction may cause an adequate blood concentration of "nutrients" (or marker compounds proportional to "nutrients") to be interpreted as insufficient. This may be one cause of obesity.

According to certain aspects, it is appreciated that capillary rarefaction may be a cause of non-insulin dependent diabetes. Non-insulin dependent diabetes (NIDDM) is also known as the Metabolic Syndrome or Diabetes type 2, and is characterized by insulin resistance. The sensitivity of the body to insulin is reduced, and insulin levels increase People with NIDDM have high blood glucose, high blood triglycerides, are typically obese, hypertensive, and typically have significant visceral fat.

Other symptoms accompany NIDDM, which may point to capillary rarefaction as the cause. In a study of 40 men, with and without NIDDM, obese (BMI 29) and lean (BMI 24) (10 of each), Konrad et al. report that blood lactate levels at rest were 1.78, 2.26, 2.42, and 2.76 (mM/L) for lean men without, obese men without, lean men with NIDDM, obese men with NIDDM respectively. (A-Lipoic acid treatment decreases serum lactate and pyruvate concentrations and improves glucose effectiveness in lean and obese patients with type 2 diabetes. Diabetes Care 22:280-287, 1999.) Lactate is a measure of anaerobic glycolysis. When $O_2$ is insufficient to generate ATP through oxidative phosphorylation, cells can produce ATP through anaerobic glycolysis. One of the products of anaerobic glycolysis is lactate, which must be exported from the cells, otherwise the pH drops and function is compromised. Blood lactate is commonly measured in exercise studies, where an increase indicates the work load at which maximum oxidative work can be done. Higher levels of lactate at rest would indicate increased anaerobic glycolysis at rest, which is consistent with capillary rarefaction.

Primary biliary cirrhosis is associated with Raynaud's phenomena, pruritus, sicca syndrome, osteoporosis, portal hypertension, neuropathy, and pancreatic insufficiency, and liver abnormalities are associated with rheumatic diseases. Elevated liver enzymes are a symptom of liver inflammation, and elevated liver enzymes are observed as an early symptom of "asymptomatic" primary biliary cirrhosis. Accordingly, the bacteria described herein may be used to treat liver inflammation.

Torre et al have reported that Alzheimer's disease (AD) is a microvascular disorder with neurological degeneration secondary to hypoperfusion, resulting in part from insufficient nitric oxide. (Review: Evidence that Alzheimer's disease is a microvascular disorder: the role of constitutive nitric oxide, Brain Research Reviews 34 (2000) 119-136.) Accordingly, the bacteria described herein may be used to treat AD.

Adverse health effects that are associated with hypertension may also be consequences of low basal NO. The decreased response to vasodilatation is also consistent with low basal NO. NO is a diffusible molecule that diffuses from a source to a sensor site where it has the signaling effect. With low NO levels, every NO source must produce more NO to generate an equivalent NO signal of a certain intensity a certain distance away. NO diffuses in three dimensions and the whole volume within that diffusion range must be raised to the level that will give the proper signal at the sensor location. This may result in higher NO levels at the source and between the source and the sensor. Adverse local effects of elevated NO near a source may then arise from too low a NO background. There is some evidence that this scenario actual occurs. In rat pancreatic islets, Henningsson et al have reported that inhibition of NOS with L-NAME increases total NO production through the induction of iNOS. (Chronic blockade of NO synthase paradoxically increases islet NO production and modulates islet hormone release. Am J Physiol Endocrinol Metab 279: E95-E107, 2000.) Increasing NO by increasing NOS activity will only work up to some limit. When NOS is activated but is not supplied with sufficient tetrahydrobiopterin (BH4) or L-arginine, it becomes "uncoupled" and generates superoxide (O2-) instead of NO. This $O_2^-$ may then destroy NO. Attempting to produce NO at a rate that exceeds the supply of BH4 or L-arginine may instead decrease NO levels. This may result in positive feedback where low NO levels are made worse by stimulation of NOS, and uncoupled NOS generates significant $O_2^-$ which causes local reactive oxygen species (ROS) damage such as is observed in atherosclerosis, end stage renal disease, Alzheimer's, and diabetes.

The bacteria described herein may also be used to delay the signs of aging. Caloric restriction extends lifespan, and Holloszy reported that restricting food intake to 70% of ad lib controls, prolongs life in sedentary rats from 858 to 1,051 days, almost 25%. (Mortality rate and longevity of food restricted exercising male rats: a reevaluation. J. Appl. Physiol. 82(2): 399-403, 1997.) The link between calorie restriction and prolonged life is well established, however, the causal mechanism is not. Lopez-Torres et al. reported that the examination of liver mitochondrial enzymes in rats indicates a reduction in $H_2O_2$ production due to reduced complex I activity associated with calorie restriction. (Influence Of Aging And Long-Term Caloric Restriction On Oxygen Radical Generation And Oxidative DNA Damage In Rat Liver Mitochondria. Free Radical Biology & Medicine Vol. 32 No 9 pp 882-8899, 2002.) $H_2O_2$ is produced by dismutation of $O_2^-$, which is a major ROS produced by the mitochondria during respiration. The main source of $O_2^-$ has been suggested by Kushareva et al. and others to be complex I which catalyzes the NAD/NADH redox couple by reverse flow of electrons from complex III, the site of succinate reduction. The free radical theory, proposed by Beckman, of aging postulates, that free radical damage to cellular DNA, antioxidant systems and DNA repair systems accumulates with age and when critical systems are damaged beyond repair, death ensues. (The Free Radical Theory of Aging Matures. Physiol. Rev. 78: 547-581, 1998.)

As an additional mechanism, NO has been demonstrated by Vasa et al. to activate telomerase and to delay senescence of endothelial cells. (Nitric Oxide Activates Telomerase and Delays Endothelial Cell Senescence. Circ Res. 2000; 87:540-542.) Low basal NO will increase basal metabolic rate by disinhibition of cytochrome oxidase. Increased basal metabolism will also increase cell turn-over and growth rate. Capillary rarefaction, by inducing chronic hypoxia may increase free radical damage and may also increase cell turn-over, and so accelerate aging by both mechanisms.

In some aspects, it is appreciated that autotrophic ammonia-oxidizing bacteria may produce protective aspects for allergies and autoimmune disorders. The best known autoimmune disease is perhaps Diabetes Type 1, which results from the destruction of the insulin producing cells in the pancreas by the immune system. Recurrent pregnancy loss is also associated with autoimmune disorders where the number of positive autoimmune antibodies correlated positively with numbers recurrent pregnancy losses. Systemic Sclerosis, Primary Biliary Cirrhosis, autoimmune hepatitis, and the various rheumatic disorders are other examples of autoimmune disorders. Application of AOB was observed to reduce an allergy, hay fever, as described in WO/2005/030147.

One mechanism by which AOB may exert their protective effect on allergies and autoimmune disorders is through the production of nitric oxide, primarily through the regulatory inhibition of NF-KB and the prevention of activation of immune cells and the induction of inflammatory reactions. NF-KB is a transcription factor that up-regulates gene expression and many of these genes are associated with inflammation and the immune response including genes which cause the release of cytokines, chemokines, and various adhesion factors. These various immune factors cause the migration of immune cells to the site of their release resulting in the inflammation response. Constitutive NO production has been shown to inhibit NF-KB by stabilizing IKBα (an inhibitor of NF-KB) by preventing IKBα degradation.

Administration of an NO donor has been shown by Xu et al. to prevent the development of experimental allergic encephalomyelitis in rats. (SIN-1, a Nitric Oxide Donor, Ameliorates Experimental Allergic Encephalomyelitis in Lewis Rats in the Incipient Phase: The Importance of the Time Window. The Journal of Immunology, 2001, 166: 5810-5816.) In this study, it was demonstrated that administering an NO donor, reduced the infiltration of macrophages into the central nervous system, reduced the proliferation of blood mononuclear cells, and increased apoptosis of blood mononuclear cells. All of these results are expected to reduce the extent and severity of the induced autoimmune response.

Low basal NO may lead to autism via the mechanism that new connections in the brain are insufficiently formed as a result of insufficient basal nitric oxide. While not wishing to be bound in theory, in some embodiments, formation of neural connections is modulated by NO. In these cases, any condition that lowers the range of NO diffusion may decrease the volume size of brain elements that can undergo connections. A brain which developed under conditions of low basal NO levels may be arranged in smaller volume elements because the reduced effective range of NO.

Additional symptoms exhibited in autistic individuals may also point to low NO as a cause, including increased pitch discrimination, gut disturbances, immune system dysfunction, reduced cerebral blood flow, increased glucose consumption of the brain, increased plasma lactate, attachment disorders, and humming. Each of these symptoms may be attributed to a low basal NO level.

Takashi Ohnishi et al. have reported that autistic individuals show decreased blood flow. Takashi Ohnishi et al., Abnormal regional cerebral blood flow in childhood autism. Brain (2000), 123, 1838-1844. J. M. Rumsey et al. have reported that autistic individuals have increased glucose consumption. Rumsey J M, Duara R, Grady C, Rapoport J L, Margolin R A, Rapoport S I, Cutler N R. Brain metabolism in autism. Resting cerebral glucose utilization rates as measured with positron emission tomography. Arch Gen Psychiatry, 1985 May; 42(5):448-55 (abstract). D. C. Chugani has reported that autistic individuals have an increased plasma lactate levels. Chugani D C, et al., Evidence of altered energy metabolism in autistic children. Prog Neuropsychopharmacol Biol Psychiatry. 1999 May; 23(4):635-41.

The occurrence of these effects may be a result of capillary rarefaction in the brain, which may reduce blood flow and $O_2$ supply, such that some of the metabolic load of the brain may be produced through glycolysis instead of oxidative phosphorylation.

Nitric oxide has been demonstrated by B. A. Klyachko et al. to increase the excitability of neurons by increasing the after hyperpolarization through cGMP modification of ion channels. Vitaly A. Klyachko et al., cGMP-mediated facilitation in nerve terminals by enhancement of the spike after hyperpolarization. Neuron, Vol. 31, 1015-1025, Sep. 27, 2001. C. Sandie et al. have shown that inhibition of NOS reduces startle. Carmen Sandi et al., Decreased spontaneous motor activity and startle response in nitric oxide synthase inhibitor-treated rats. European journal of pharmacology 277 (1995) 89-97. Attention-Deficit Hyperactivity Disorder (ADHD) has been modeled using the spontaneously hypertensive rat (SHR) and the Naples high-excitability (NHE) rat. Both of these models have been shown by Raffaele Aspide et al, to show increased attention deficits during periods of acute NOS inhibition. Raffaele Aspide et al., Non-selective attention and nitric oxide in putative animal models of attention-deficit hyperactivity disorder. Behavioral Brain Research 95 (1998) 123-133. Accordingly, the bacteria herein may be used in the treatment of ADHD.

Inhibition of NOS has also been shown by M. R. Dzoljic to inhibit sleep. M. R. Dzoljic, R. de Vries, R. van Leeuwen. Sleep and nitric oxide: effects of 7-nitro indazole, inhibitor of brain nitric oxide synthase. Brain Research 718 (1996) 145-150. G. Zoccoli has reported that a number of the physiological effects seen during sleep are altered when NOS is inhibited, including rapid eye movement and sleep-wake differences in cerebral circulation. G. Zoccoli, et al., Nitric oxide inhibition abolishes sleep-wake differences in cerebral circulation. Am. J. Physiol. Heart Circ Physiol 280: H2598-2606, 2001. NO donors have been shown by L. Kapas et al. to promote non-REM sleep, however, these increases persisted much longer than the persistence of the NO donor, suggesting perhaps a rebound effect. Levente Kapas et al., Nitric oxide donors SIN-1 and SNAP promote nonrapid-eye-movement sleep in rats. Brain Research Bullitin, vol 41, No 5, pp. 293-298, 1996. M. Rosaria et al., Central NO facilitates both penile erection and yawning. Maria Rosaria Melis and Antonio Argiolas. Role of central nitric oxide in the control of penile erection and yawning. Prog Neuro-Psychopharmacol & Biol. Phychiat. 1997, vol 21, pp 899-922. P. Tani et al, have reported that insomnia is a frequent finding in adults with Asperger's. Pekka Tani et al., Insomnia is a frequent finding in adults with Asperger's syndrome. BMC Psychiatry 2003, 3:12. Y. Hoshino has also observed sleep disturbances in autistic children. Hoshino Y, Watanabe H, Yashima Y, Kaneko M, Kumashiro H. An investigation on sleep disturbance of autistic children. Folia Psychiatr Neurol Jpn. 1984; 38(1):45-51. (abstract) K. A. Schreck et al. has observed that the severity of sleep disturbances correlates with severity of autistic symptoms. Schreck K A, et al., Sleep problems as possible predictors of intensified symptoms of autism. Res Dev Disabil. 2004 January-February; 25(1):57-66. (abstract). Accordingly, the bacteria herein may be used in the treatment of insomnia.

W. D. Ratnasooriya et al reported that inhibition of NOS in male rats reduces pre-coital activity, reduces libido, and reduces fertility. W. D. Ratnasooriya et al., Reduction in libido and fertility of male rats by administration of the nitric oxide (NO) synthase inhibitor N-nitro-L-arginine methyl ester. International journal of andrology, 23: 187-191 (2000).

It may be that a number of seemingly disparate disorders, characterized by ATP depletion and eventual organ failure are actually "caused" by nitropenia, caused by a global deficiency in basal nitric oxide. When this occurs in the heart, the result is dilative cardiomyopathy. When this occurs in the brain, the result is white matter hyperintensity, Alzheimer's, vascular depression, vascular dementia, Parkinson's, and the Lewy body dementias. When this occurs in the kidney, the result is end stage renal disease, when this occurs in the liver, the result is primary biliary cirrhosis. When this occurs in muscle, the consequence is fibromyalagia, Gulf War Syndrome, or chronic fatigue syndrome. When this occurs in the bowel, the consequence is ischemic bowel disease. When this occurs in the pancreas, the consequence is first type 2 diabetes, followed by chronic inflammation of the pancreas, followed by autoimmune attack of the pancreas (or pancreatic cancer), followed by type 1 diabetes. When this occurs in the connective tissue, the consequence is systemic sclerosis.

In the remnant kidney model of end stage renal disease, part of the kidney is removed, (either surgically or with a toxin) which increases the metabolic load on the remainder. Superoxide is generated to decrease NO and increase $O_2$ diffusion to the kidney mitochondria. Chronic overload results in progressive kidney capillary rarefaction and progressive kidney failure. In acute kidney failure, putting people in dialysis can give the kidney a "rest", and allows it to recover. In acute renal failure induced by rhabdomyolysis (muscle damage which releases myoglobin into the blood stream) kidney damage is characterized by ischemic damage. Myoglobin scavenges NO, just as hemoglobin does, and would cause vasoconstriction in the kidney leading to ischemia. Myoglobin would also induce local nitropenia and the cascade of events leading to further ATP depletion.

In some aspects, low NO levels lead to reduced mitochondrial biogenesis. Producing the same ATP at a reduced mitochondria density will result in an increase in $O_2$ consumption, or an accelerated basal metabolic rate. An accelerated basal metabolic rate is observed in a number of conditions, including: Sickle cell anemia, Congestive heart failure, Diabetes, Liver Cirrhosis, Crohn's disease, Amyotrophic lateral sclerosis, Obesity, End stage renal disease, Alzheimer's, and chronic obstructive pulmonary disease.

While some increased $O_2$ consumption might be productively used, in many of these conditions uncoupling protein is also up-regulated, indicating that at least part of the increased metabolic rate is due to inefficiency. Conditions where uncoupling protein is known to be up-regulated include obesity and diabetes.

With fewer mitochondria consuming $O_2$ to a lower $O_2$ concentration, the $O_2$ gradient driving $O_2$ diffusion is greater, so the $O_2$ diffusion path length can increase resulting in capillary rarefaction, which is observed in dilative cardiomyopathy, hypertension, diabetes type 2, and renal hypertension.

Copper, either as Cu2+ or as ceruloplasmin (CP) (the main Cu containing serum protein which is present at 0.38 g/L in adult sera and which is 0.32% Cu and contains 94% of the serum copper) catalyzes the formation of S—NO-thiols from NO and thiol containing groups (RSH). The Cu content of plasma is variable and is increased under conditions of infection. Berger et al. reported that the Cu and Zn content of burn-wound exudates is considerable with patients with ⅓ of their skin burned, losing 20 to 40% of normal body Cu and 5 to 10% of Zn content in 7 days. (Cutaneous copper and zinc losses in burns. Burns. 1992 October; 18(5):373-80.) If the patients skin were colonized by AOB, wound exudates which contains urea and Fe, Cu, and Zn that AOB need, would be converted into NO and nitrite, greatly supplementing the local production of NO by iNOS, without consuming resources (such as $O_2$ and L-arginine) in the metabolically challenged wound. A high production of NO and nitrite by AOB on the surface of a wound would be expected to inhibit infection, especially by anaerobic bacteria such as the Clostridia which cause tetanus, gas gangrene, and botulism.

The practice of the present invention may employ, unless otherwise indicated, conventional methods of immunology, molecular biology, and recombinant DNA techniques within the skill of the art. Such techniques are explained fully in the literature. See, e.g., Sambrook, et al. Molecular Cloning: A Laboratory Manual (Current Edition); and Current Protocols in Molecular Biology (F. M. Ausubel, et al. eds., current edition).

8. Nucleic Acids and Proteins from *N. eutropha*

This disclosure provides, among other things, proteins and nucleic acids (optionally, isolated proteins and nucleic acids) that are identical to or similar to those found in strain D23. While not wishing to be bound by theory, it is believed that the sequenced strain of D23 has non-naturally occurring protein and nucleic acid sequences due to an extended period of culture and selection in the laboratory.

These nucleic acids and proteins have numerous uses. For instance, the proteins may be used to generate antibodies or other binding molecules that detect strain D23 or related strains. The proteins may also be used to carry out reactions under high-$NH_4^+$ conditions, because D23 is adapted for growth and metabolism under these conditions. As another example, the nucleic acids may be used to produce proteins for generating antibodies or carrying out reactions as described above. The nucleic acids may also be used to detect strain D23 or related strains, e.g., using a microarray or another hybridization-based assay.

The genome of strain D23 is provided as SEQ ID NO: 1. The genome annotation (including the position and orientation of genes within SEQ ID NO: 1) is provided as Supplementary Table 1. Accordingly, this disclosure provides genes and proteins identical or similar to the genes listed in Supplementary Table 1.

Accordingly, this disclosure provides a nucleic acid (e.g., an isolated nucleic acid) comprising a sequence of a gene of Supplementary Table 1, as well as a protein encoded by said gene. In certain embodiments, the nucleic acid comprises a sequence that is similar (e.g., at least 70%, 80%, 85%, 90%, 95%, 97%, 98%, 99%, or 99.5% identical) to a gene of Supplementary Table 1, or a protein encoded by said gene. The disclosure also provides a composition comprising a nucleic acid that is at least 1, 2, 3, 4, 5, 10, 15, 20, 50, 100, 200, 500, 1,000, 1,500, 2,000, 2,500, or all of the sequences of Supplementary Table 1, or a sequence that is similar thereto (e.g., at least 70%, 80%, 85%, 90%, 95%, 97%, 98%, 99%, or 99.5% identical), or one or more proteins encoded by said nucleic acids. Also provided are fragments of said nucleic acids and proteins.

The present disclosure also provides, inter alia, one or more genes or proteins that are present in strain D23 and absent from strain C91, or a gene or protein similar to one of said genes or proteins. Examples of these genes are set out in FIGS. 6-8 and are described in more detail in Example 4 herein. Examples of these genes and proteins, as well as genes and proteins similar thereto, are described below.

Accordingly, with respect to FIG. 6, this application discloses nucleic acids that are identical or similar (e.g., at least 70%, 80%, 85%, 90%, 95%, 97%, 98%, 99%, or 99.5% identical) to 1, 2, 3, 4, 5, 10, 15, 20, 30, 40, 50, 60, 70, 80, 90, 100, 110, 120, 130, 140, 150, 160, or all of the sequences in FIG. 6. This application also discloses proteins that are identical or similar (e.g., at least 70%, 80%, 85%, 90%, 95%, 97%, 98%, 99%, or 99.5% identical) to 1, 2,3,4, 5, 10, 15, 20, 30, 40, 50, 60, 70, 80, 90, 100, 110, 120, 130, 140, 150, 160, or all of the proteins encoded by the genes listed in FIG. 6. Furthermore, the application discloses fragments of these genes and proteins, e.g., fragments of 0-20, 20-50, 50-100, 100-200, 200-500, 500-1000, or greater than 1000 nucleotides or amino acids. In some embodiments, a plurality of the above-mentioned genes or proteins are affixed to a solid support, e.g., to form a microarray.

With respect to FIG. 7, this application discloses nucleic acids that are identical or similar (e.g., at least 70%, 80%, 85%, 90%, 95%, 97%, 98%, 99%, or 99.5% identical) to 1, 2, 3, 4, 5, 10, 15, 20, 30, 40, 50, 60, 70, 80, 90, 100, 110, 120, 130, 140, 150, 160, or all of the sequences in FIG. 7. This application also discloses proteins that are identical or similar (e.g., at least 70%, 80%, 85%, 90%, 95%, 97%, 98%, 99%, or 99.5% identical) to 1, 2, 3, 4, 5, 10, 15, 20, 30, 40, 50, 60, 70, 80, 90, 100, 110, 120, 130, 140, 150, 160, or all of the proteins encoded by the genes listed in FIG. 7. Furthermore, the application discloses fragments of these genes and proteins, e.g., fragments of 0-20, 20-50, 50-100, 100-200, 200-500, 500-1000, or greater than 1000 nucleotides or amino acids. In some embodiments, a plurality of the above-mentioned genes or proteins are affixed to a solid support, e.g., to form a microarray.

With respect to FIG. 8, this application discloses nucleic acids that are identical or similar (e.g., at least 70%, 80%, 85%, 90%, 95%, 97%, 98%, 99%, or 99.5% identical) to 1, 2, 3, 4, 5, 10, 15, 20, 30, 40, 50, 60, 70, 80, 90, 100, 110, 120, 130, 140, 150, 200, or all of the sequences in FIG. 8. This application also discloses proteins that are identical or similar (e.g., at least 70%, 80%, 85%, 90%, 95%, 97%, 98%, 99%, or 99.5% identical) to 1, 2, 3, 4, 5, 10, 15, 20, 30, 40, 50, 60, 70, 80, 90, 100, 110, 120, 130, 140, 150, 200, or all of the proteins encoded by the genes listed in FIG. 8. Furthermore, the application discloses fragments of these genes and proteins, e.g., fragments of 0-20, 20-50, 50-100, 100-200, 200-500, 500-1000, or greater than 1000 nucleotides or amino acids. In some embodiments, a plurality of the above-mentioned genes or proteins are affixed to a solid support, e.g., to form a microarray.

With respect to FIGS. 6-8 collectively, this application discloses nucleic acids that are identical or similar (e.g., at least 70%, 80%, 85%, 90%, 95%, 97%, 98%, 99%, or 99.5% identical) to 1, 2, 3, 4, 5, 10, 20, 40, 60, 80, 100, 150, 200, 250, 300, 350, 400, 450, 500, or all of the sequences in FIGS. 6-8. This application discloses proteins that are identical or similar (e.g., at least 70%, 80%, 85%, 90%, 95%, 97%, 98%, 99%, or 99.5% identical) to 1, 2, 3, 4, 5, 10, 20, 40, 60, 80, 100, 150, 200, 250, 300, 350, 400, 450, 500, or all of the proteins encoded by genes listed in FIGS. 6-8. Furthermore, the application discloses fragments of these genes and proteins, e.g., fragments of 1-20, 20-50, 50-100, 100-200, 200-500, 500-1000, or greater than 1000 nucleotides or amino acids. In some embodiments, a plurality of the above-mentioned genes or proteins are affixed to a solid support, e.g., to form a microarray.

This disclosure also provides nucleic acid sequences that are fragments of SEQ ID NO: 1. The fragments may be, e.g., 1-20, 20-50, 50-100, 100-200, 200-500, 500-1000, 1,000-2, 000, 2,000-5,000, or 10,000 or more nucleotides in length. The fragments may also be at least about 80%, 85%, 90%, 95%, 97%, 98%, 99%, or 99.5% identity to the corresponding portion of SEQ ID NO: 1 or its complement. The fragment may also be a fragment that hybridizes to SEQ ID NO: 1, or to the genome of the D23 strain deposited with the ATCC® American Type Culture Collection biological material depository, patent depository on Apr. 8, 2014, designated AOB D23-100 under accession number PTA-121157, or their complements, under low stringency, medium stringency, high stringency, or very high stringency, or other hybridization condition described herein.

The disclosure also provides nucleic acid sequences set out in Table 1 (which describes genes involved in ammonia metabolism). Accordingly, in some aspects, this application discloses genes that are identical or similar (e.g., at least 70%, 80%, 85%, 90%, 95%, 96%, 97%, 97.5% 98%, 98.2%, 98.4%, 98.6%, 98.8%, 99%, 99.1%, 99.2%, 99.3% 99.4% 99.5% 99.6%, 99.7%, 99.8%, 99.9%, or 100% identical) to 1, 2, 3, 4, 5, 6, 7, 8, 9, 10, 11, 12, 13, 14, 15, or all of the genes in Table 1. In embodiments, this application discloses proteins that are identical or similar (e.g., at least 70%, 80%, 85%, 90%, 95%, 96%, 97%, 97.5% 98%, 98.2%, 98.4%, 98.6%, 98.8%, 99%, 99.1%, 99.2%, 99.3%, 99.4%, 99.5%, 99.6%, 99.7%, 99.8%, 99.9%, or 100% identical) to 1, 2, 3, 4, 5, 6, 7, 8, 9, 10, 11, 12, 13, 14, 15, or all of the proteins in Table 1.

Alignment of the nucleic acid sequences of Table 1 shows the percent identity between homologs in C91 and D23. The following paragraphs discuss this percent identity and describe various nucleic acids having homology to the D23 genes of Table 1.

More specifically, the amoA1 genes are about 98.8% identical (i.e., at 821/831 positions). Accordingly, in some embodiments, the amoA1 nucleic acid comprises D23 nucleotides at at least 1, 2, 3, 4, 5, 6, 7, 8, 9, 10, or all of the positions that differ in this gene between strains C91 and D23. In embodiments, the amoA1 nucleic acid comprise D23 nucleotides at at most 1, 2, 3, 4, 5, 6, 7, 8, 9, 10, or all of the positions that differ in this gene between strains C91 and D23. In embodiments, the amoA1 nucleic acid comprises a sequence at least about 98.8%, 98.9%, 99.0%, 99.2%, 99.4%, 99.6%, 99.8%, or 100% identical to the D23 amoA1 gene.

The amoA2 genes are about 98.8% identical (i.e., at 821/831 positions). Accordingly, in some embodiments, the amoA2 nucleic acid comprises D23 nucleotides at at least 1, 2, 3, 4, 5, 6, 7, 8, 9, 10, or all of the positions that differ in this gene between strains C91 and D23. In embodiments, the amoA2 nucleic acid comprises D23 nucleotides at at most 1, 2, 3, 4, 5, 6, 7, 8, 9, 10, or all of the positions that differ in this gene between strains C91 and D23. In embodiments, the amoA2 nucleic acid comprises a sequence at least about 98.8%, 98.9%, 99.0%, 99.2%, 99.4%, 99.6%, 99.8%, or 100% identical to the D23 amoA2 gene.

The amoB1 genes are about 99.1% identical (i.e., at 1255/1266 positions). Accordingly, in some embodiments, the amoB1 nucleic acid comprises D23 nucleotides at at least 1, 2, 3, 4, 5, 6, 7, 8, 9, 10, 11, or all of the positions that differ in this gene between strains C91 and D23. In embodiments, the amoB1 nucleic acid comprises D23 nucleotides at at most 1, 2, 3, 4, 5, 6, 7, 8, 9, 10, 11, or all of the positions that differ in this gene between strains C91 and D23. In embodiments, the amoB1 nucleic acid comprises a sequence at least about 99.1%, 99.2%, 99.4%, 99.6%, 99.8%, or 100% identical to the D23 amoB1 gene.

The amoB2 genes are about 99.1% identical (i.e., at 1254/1266 positions). Accordingly, in some embodiments, the amoB2 nucleic acid comprises D23 nucleotides at at least 1, 2, 3, 4, 5, 6, 7, 8, 9, 10, 11, 12 or all of the positions that differ in this gene between strains C91 and D23. In embodiments, the amoB2 nucleic acid comprises D23 nucleotides at at most 1, 2, 3, 4, 5, 6, 7, 8, 9, 10, 11, 12 or all of the positions that differ in this gene between strains C91 and D23. In embodiments, the amoB2 nucleic acid comprises a sequence at least about 99.1%, 99.2%, 99.4%, 99.6%, 99.8%, or 100% identical to the D23 amoB2 gene.

The amoC1 genes are about 99.8% identical (i.e., at 814/816 positions). Accordingly, in some embodiments, the amoC1 nucleic acid comprises D23 nucleotides at at least 1, 2, or all of the positions that differ in this gene between strains C91 and D23. In embodiments, the amoC1 nucleic acid comprises D23 nucleotides at at most 1, 2, or all of the positions that differ in this gene between strains C91 and D23. In embodiments, the amoC1 nucleic acid comprises a sequence at least about 99.8%, 99.9%, or 100% identical to the D23 amoC1 gene.

The amoC2 genes are about 99.8% identical (i.e., at 814/816 positions). Accordingly, in some embodiments, the amoC2 nucleic acid comprises D23 nucleotides at at least 1, 2, or all of the positions that differ in this gene between strains C91 and D23. In embodiments, the amoC2 nucleic acid comprises D23 nucleotides at at most 1, 2, or all of the positions that differ in this gene between strains C91 and D23. In embodiments, the amoC2 nucleic acid comprises a sequence at least about 99.8%, 99.9%, or 100% identical to the D23 amoC2 gene.

The amoC3 genes are about 98.9% identical (i.e., at 816/825 positions). Accordingly, in some embodiments, the amoC3 nucleic acid comprises D23 nucleotides at at least 1, 2, 3, 4, 5, 6, 7, 8, 9, or all of the positions that differ in this gene between strains C91 and D23. In embodiments, the amoC3 nucleic acid comprises D23 nucleotides at at most 1, 2, 3, 4, 5, 6, 7, 8, 9, or all of the positions that differ in this gene between strains C91 and D23. In embodiments, the amoC3 nucleic acid comprises a sequence at least about 98.9%, 99.0%, 99.2%, 99.4%, 99.6%, 99.8%, or 100% identical to the D23 amoC3 gene.

The hao1 genes are about 99.0% identical (i.e., at 1696/1713 positions). Accordingly, in some embodiments, the hao1 nucleic acid comprises D23 nucleotides at at least 1, 2, 3, 4, 5, 6, 7, 8, 9, 10, 11, 12, 13, 14, 15, 16, 17, or all of the positions that differ in this gene between strains C91 and D23. In embodiments, the hao1 nucleic acid comprises D23 nucleotides at at most 1, 2, 3, 4, 5, 6, 7, 8, 9, 10, 11, 12, 13, 14, 15, 16, 17, or all of the positions that differ in this gene between strains C91 and D23. In embodiments, the hao1 nucleic acid comprises a sequence at least about 99.0%, 99.2%, 99.4%, 99.6%, 99.8%, or 100% identical to the D23 hao1 gene.

The hao2 genes are about 99.4% identical (i.e., at 1702/1713 positions). Accordingly, in some embodiments, the hao2 nucleic acid comprises D23 nucleotides at at least 1, 2, 3, 4, 5, 6, 7, 8, 9, 10, 11, or all of the positions that differ in this gene between strains C91 and D23. In embodiments, the hao2 nucleic acid comprises D23 nucleotides at at most 1, 2, 3, 4, 5, 6, 7, 8, 9, 10, 11, or all of the positions that differ in this gene between strains C91 and D23. In embodiments, the hao2 nucleic acid comprises a sequence at least about 99.4%, 99.6%, 99.8%, or 100% identical to the D23 hao2 gene.

The hao3 genes are about 99.2% identical (i.e., at 1700/1713 positions). Accordingly, in some embodiments, the hao3 nucleic acid comprises D23 nucleotides at at least 1, 2, 3, 4, 5, 6, 7, 8, 9, 10, 11, 12, 13, or all of the positions that differ in this gene between strains C91 and D23. In embodiments, the hao3 nucleic acid comprises D23 nucleotides at at most 1, 2, 3, 4, 5, 6, 7, 8, 9, 10, 11, 12, 13, or all of the positions that differ in this gene between strains C91 and D23. In embodiments, the hao3 nucleic acid comprises a sequence at least about 99.2%, 99.4%, 99.6%, 99.8%, or 100% identical to the D23 hao3 gene.

The cycA1 genes are about 98.0% identical (i.e., at 694/708 positions). Accordingly, in some embodiments, the cycA1 nucleic acid comprises D23 nucleotides at at least 1, 2, 3, 4, 5, 6, 7, 8, 9, 10, 11, 12, 13, 14, or all of the positions that differ in this gene between strains C91 and D23. In embodiments, the cycA1 nucleic acid comprises D23 nucleotides at at most 1, 2, 3, 4, 5, 6, 7, 8, 9, 10, 11, 12, 13, 14, or all of the positions that differ in this gene between strains C91 and D23. In embodiments, the cycA1 nucleic acid comprises a sequence at least about 98.0%, 98.2%, 98.4%, 98.6%, 98.8%, 99.0%, 99.2%, 99.4%, 99.6%, 99.8%, or 100% identical to the D23 cycA1 gene.

The cycA2 genes are about 98.7% identical (i.e., at 699/708 positions). Accordingly, in some embodiments, the cycA2 nucleic acid comprises D23 nucleotides at at least 1, 2, 3, 4, 5, 6, 7, 8, 9, 10, 11, or all of the positions that differ in this gene between strains C91 and D23. In embodiments, the cycA2 nucleic acid comprises D23 nucleotides at at most 1, 2, 3, 4, 5, 6, 7, 8, 9, 10, 11, or all of the positions that differ in this gene between strains C91 and D23. In embodiments, the cycA2 nucleic acid comprises a sequence at least about 98.7%, 98.8%, 99.0%, 99.2%, 99.4%, 99.6%, 99.8%, or 100% identical to the D23 cycA2 gene.

The cycA3 genes are about 99.3% identical (i.e., at 703/708 positions). Accordingly, in some embodiments, the cycA3 nucleic acid comprises D23 nucleotides at at least 1, 2, 3, 4, 5, or all of the positions that differ in this gene between strains C91 and D23. In embodiments, the cycA3 nucleic acid comprises D23 nucleotides at at most 1, 2, 3, 4, 5, or all of the positions that differ in this gene between strains C91 and D23. In embodiments, the cycA3 nucleic acid comprises a sequence at least about 99.3%, 99.4%, 99.6%, 99.8%, or 100% identical to the D23 cycA3 gene.

The cycB1 genes are about 96.7% identical (i.e., at 696/720 positions). Accordingly, in some embodiments, the cycB1 nucleic acid comprises D23 nucleotides at at least 1, 2, 3, 4, 5, 6, 7, 8, 9, 10, 11, 12, 13, 14, 15, 16, 17, 18, 19, 20, 21, 22, 23, 24, 25, 26, or all of the positions that differ in this gene between strains C91 and D23. In embodiments, the cycB1 nucleic acid comprises D23 nucleotides at at most 1, 2, 3, 4, 5, 6, 7, 8, 9, 10, 11, 12, 13, 14, 15, 16, 17, 18, 19, 20, 21, 22, 23, 24, 25, 26, or all of the positions that differ in this gene between strains C91 and D23. In embodiments, the cycB1 nucleic acid comprises a sequence at least about 96.7%, 96.8%, 97.0%, 97.2%, 97.4%, 97.6%, 97.8%, 98.0%, 98.2%, 98.4%, 98.4%, 98.6%, 98.8%, 99.0%, 99.2%, 99.4%, 99.6%, 99.8%, or 100% identical to the D23 cycB1 gene.

The cycB2 genes are about 97.1% identical (i.e., at 702/723 positions). Accordingly, in some embodiments, the cycB2 nucleic acid comprises D23 nucleotides at at least 1, 2, 3, 4, 5, 6, 7, 8, 9, 10, 11, 12, 13, 14, 15, 16, 17, 18, 19, 20, 21, or all of the positions that differ in this gene between strains C91 and D23. In embodiments, the cycB2 nucleic acid comprises D23 nucleotides at at most 1, 2, 3, 4, 5, 6, 7, 8, 9, 10, 11, 12, 13, 14, 15, 16, 17, 18, 19, 20, 21, or all of the positions that differ in this gene between strains C91 and D23. In embodiments, the cycB2 nucleic acid comprises a sequence at least about 97.1%, 97.2%, 97.4%, 97.6%, 97.8%, 98.0%, 98.2%, 98.4%, 98.4%, 98.6%, 98.8%, 99.0%, 99.2%, 99.4%, 99.6%, 99.8%, or 100% identical to the D23 cycB2 gene.

Further provided herein are vectors comprising nucleotide sequences described herein. In some embodiments, the vectors comprise nucleotides encoding a protein described herein. The vectors include, but are not limited to, a virus, plasmid, cosmid, lambda phage or a yeast artificial chromosome (YAC). Such vectors may include a promoter, an open reading frame with or without introns, and a termination signal.

The present disclosure also provides host cells comprising a nucleic acid as described herein, or a nucleic acid encoding a protein as described herein.

In certain embodiments, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

The cell can be, but is not limited to, a eukaryotic cell, a bacterial cell, an insect cell, or a human cell. If the cell is a bacterial cell, it may be, e.g., *E. coli* or an ammonia-oxidizing bacterium such as *Nitrosomonas* (e.g., *N. eutropha* or *N. europaea*), *Nitrosococcus*, Nitrosospira, *Nitrosocystis*, *Nitrosolobus*, and *Nitrosovibrio*.

9. Adjusting the Skin Microbiome with Ammonia Oxidizing Bacteria

The present disclosure provides for systems and methods for changing the skin microbiome, e.g., the human skin microbiome. The systems and methods may provide treatment of infections or conditions, e.g., related to the skin, e.g., skin infections and/or skin conditions.

Ammonia-oxidizing bacteria (AOB) of the genus *Nitrosomonas* are Gram-negative obligate autotrophic bacteria with a unique capacity to generate nitrite and nitric oxide exclusively from ammonia as an energy source. They are widely present both in soil and water environments and are essential components of environmental nitrification processes. Due to the roles of nitrite and nitric oxide on human skin as important components of several physiological functions, such as vasodilation, skin inflammation and wound healing, these bacteria may have beneficial properties for both healthy and immunopathological skin conditions. These bacteria may be safe for use in humans because they are slow-growing, cannot grow on organic carbon sources, may be sensitive to soaps and antibiotics, and have never been associated with any disease or infection in animals or humans.

Topical application of ammonia oxidizing bacteria to a subject, e.g., a human subject may lead to unexpected changes in the skin microbiome, and more specifically it may lead to increases in the proportion of normal commensal non-pathogenic species and reductions in the proportion of potentially pathogenic, pathogenic, or disease causing organisms.

EXAMPLES

Example 1. Initial Culturing of *N. eutropha*

A soil-derived culture enriched in various ammonia oxidizing bacteria was applied to the skin of an adult male subject as described in WO/2003/057380. The period of growth on the human body selected for a strain with the capacity to colonize human skin for an extended period of time. After several months, the strain was re-isolated from the skin of the individual and cultured in laboratory conditions for a sustained period as described in the subsequent examples. While not wishing to be bound by theory, it is believed that the sustained laboratory culture selected for new mutations improving the strain properties, e.g., improved tolerance for high-ammonia conditions.

Example 2. Growing and Monitoring D23 or Mixtures of Strains that Comprise D23

Culture Conditions

D23 can be grown in batches or by continuous cultivation in a bioreactor. Batch preparation uses the medium of Table 3.

TABLE 3

| Growth Medium for Batch culturing: | | |
|---|---|---|
| | Weight/Volume (in ~1.5 L) | Final Concentration (in ~1.5 L) |
| $(NH_4)_2SO_4$ (MW 132.14) | 4.95 g | 50 mM $NH_4^+$ |
| $KH_2PO_4$ (MW 136.1) | 0.616 g | 3.0 mM |
| 1M $MgSO_4$ | 1.137 ml | 0.76 mM |
| 1M $CaCl_2$ | 0.3 ml | 0.2 mM |
| 30 mM $FeCl_3$/ 50 mM EDTA | 0.5 ml | 10 μM/16.7 μM |
| 50 mM $CuSO_4$ | 30 μl | 1.0 μM |
| Add 1400 ml dd$H_2O$ to flask. Autoclave. Store at room temperature. After autoclaving add: | | |
| Phosphate Buffer | 100 ml | 32 mM $KH_2PO_4$/ 2.7 mM $NaH_2PO_4 \cdot H_2O$ |
| 5% $Na_2CO_3$ | 12 ml | 0.04% |

The medium of Table 3 is inoculated with ~15 ml of a 3 day old culture of D23 (i.e. 1% volume). The cultures are incubated in the dark at 30° C. by shaking at 200 rpm.

Often, a *N. eutropha* D23 mixed culture is grown on complete *N. europaea* media. The culture medium is described below, and additional details on culturing ammonia-oxidizing bacteria are available on the World Wide Web at nitrificationnetwork.org/Nerecipe.php, Ensign et al., 1993, and Stein & Arp, 1998.

Step 1.
Add 900 ml of deionized water to a 2-liter Erlenmeyer flask.
Add in sequence:
3.3 g $(NH_4)_2SO_4$ (50 mM);
0.41 g $KH_2PO_4$
0.75 ml 1 M $MgSO_4$ stock solution
0.2 ml 1 M $CaCl_2$ stock solution
0.33 ml 30 mM $FeSO_4$/50 mM EDTA stock solution
0.01 ml 50 mM $CuSO_4$ stock solution
Sterilize the solution by autoclaving.
Step 2.
Add 400 ml of deionized water to a beaker. Add:
27.22 g $KH_2PO_4$
2.4 g $NaH_2PO_4$ Adjust the pH to 8.0 with 10 N NaOH, and bring the final volume to 500 ml with deionized water.

Sterilize 100 ml fractions of the solution by autoclaving in 250-500 ml Erlenmeyer flasks.

Step 3

Prepare 500 ml of 5% (w/v) $Na_2CO_3$ (anhydrous)

Sterilize the solution by autoclaving.

Step 4

Add 1×100 ml aliquot of solution prepared in Step 2 to the flask prepared in Step 1.

Step 5

Add 8 ml of the solution prepared in Step 3 to the flask prepared in Step 1.

The D23 can also be cultured continuously in a bioreactor. Table 4 describes the appropriate media.

TABLE 4

Growth Medium for continuous culture:

| | Batch medium Weight/ Volume (1 L) (Final concentration) | Feeding solution Weight/ Volume (1 L) (Final concentration) |
|---|---|---|
| $(NH_4)_2SO_4$ (MW 132.14) | 3.3 g (50 mM $NH_4^+$) | 13.2 g (200 mM $NH_4^+$) |
| $KH_2PO_4$ (MW 136.1) | 1.23 g (9.0 mM) | 0.41 g (3.0 mM) |
| 1M $MgSO_4$ | 0.758 ml (0.76 mM) | 0.758 ml (0.76 mM) |
| 1M $CaCl_2$ | 0.2 ml (0.2 mM) | 0.2 ml (0.2 mM) |
| 30 mM $FeCl_3$/50 mM EDTA | 0.333 ml (10 µM/16.7 µM) | 0.333 ml (10 µM/16.7 µM) |
| 50 mM $CuSO_4$ | 20 µl (1.0 µM) | 20 µl (1.0 µM) |
| $ddH_2O$ | 1000 ml | 1000 ml |

Autoclave each solution and store at room temperature.

The batch media, in a bioreactor vessel, is inoculated with ~ 10 ml of a 3 day old *N. eutropha* D23 culture (i.e. 1% volume). The pH is adjusted to 7.6 using 7.5% $Na_2CO_3$. The bioreactor is run in batch mode with below parameters: pH: 7.6 (lower limit: 7.45 & upper limit: 7.8), Temperature: 28° C. (lower limit: 25° C. & upper limit: 32° C.), DO (dissolved oxygen): 45% (lower limit: 10%, upper limit: 100%), Stirrer: 550 rpm.

The OD600 nm of the culture in the bioreactor reaches 0.15 to 0.18 in 3-4 days. At this point, the culture will consume most of the 50 mM $NH_4^+$ present in the AOB growth media, and a user should start feeding the bioreactor with feeding solution at 0.59 ml/min (~10%). The outflow pump should also be turned on at 0.59 ml/min (~10%). The OD600 nm of the bioreactor reaches 0.5-0.6 in 1-2 days of continuous culture. The culture in the bioreactor is tested for heterotrophic contaminants by plating 1 ml of the bioreactor outflow on an LB plate.

Monitoring Growth of N. Eutropha D23

Growth of *N. eutropha* D23 cells is monitored by measuring the OD600 nm of the culture. Typical growth in a batch culture as measured by OD600 nm is between 0.06 to 0.08.

The AOB growth medium contains $NH_4+$ that is stoichiometrically converted to $NO_2-$ by *N. eutropha* D23. Another way to monitor the growth of *N. eutropha* is to follow the release of nitrite ($NO_2-$) in the growth medium. $NO_2-$ concentration is determined with Griess reagents, sulfanilamide and N-naphthylethylenediamine (also called NNEQ). Briefly, sulfanilamide and NNEQ are added to a sample and to known concentrations of sodium nitrite that make up a standard curve. Samples are incubated in the dark for 30 minutes. The absorbance is read at 540 nm.

Another way to follow nitrite production is by using a spectrophotometer by monitoring the optical density (OD) difference between 352 nm and 400 nm. The nitrite concentration is determined using a millimolar extinction coefficient of 0.0225 $mM^{-1}$. This assay can be performed directly by sampling the medium with the cells.

$NO_2$-concentration (mM)=$(OD_{352}-OD_{400})/0.0225$

The growth of a mixed culture comprising D23 was monitored by measuring optical density at 600 nm (OD600 nm) and by measuring Nitrite ($NO_2^-$), and the growth rate is shown in FIGS. 1 and 2. FIG. 1 shows that the optical density at a 600 nm wavelength plateaus slightly below 0.1, after 3 to 4 days. FIG. 2A shows that the amount of nitrite produced plateaus slightly below 25 mM after 3 to 4 days. $NO_2^-$ concentrations in the cultures were determined colorimetrically by the Griess reagent (Hageman & Hucklesby, 1971), and is used as a second indicator for the growth rates and growth phases since the accumulation of $NO_2^-$ is consistently proportional to the increase in cell mass during growth.

Figure 2A:
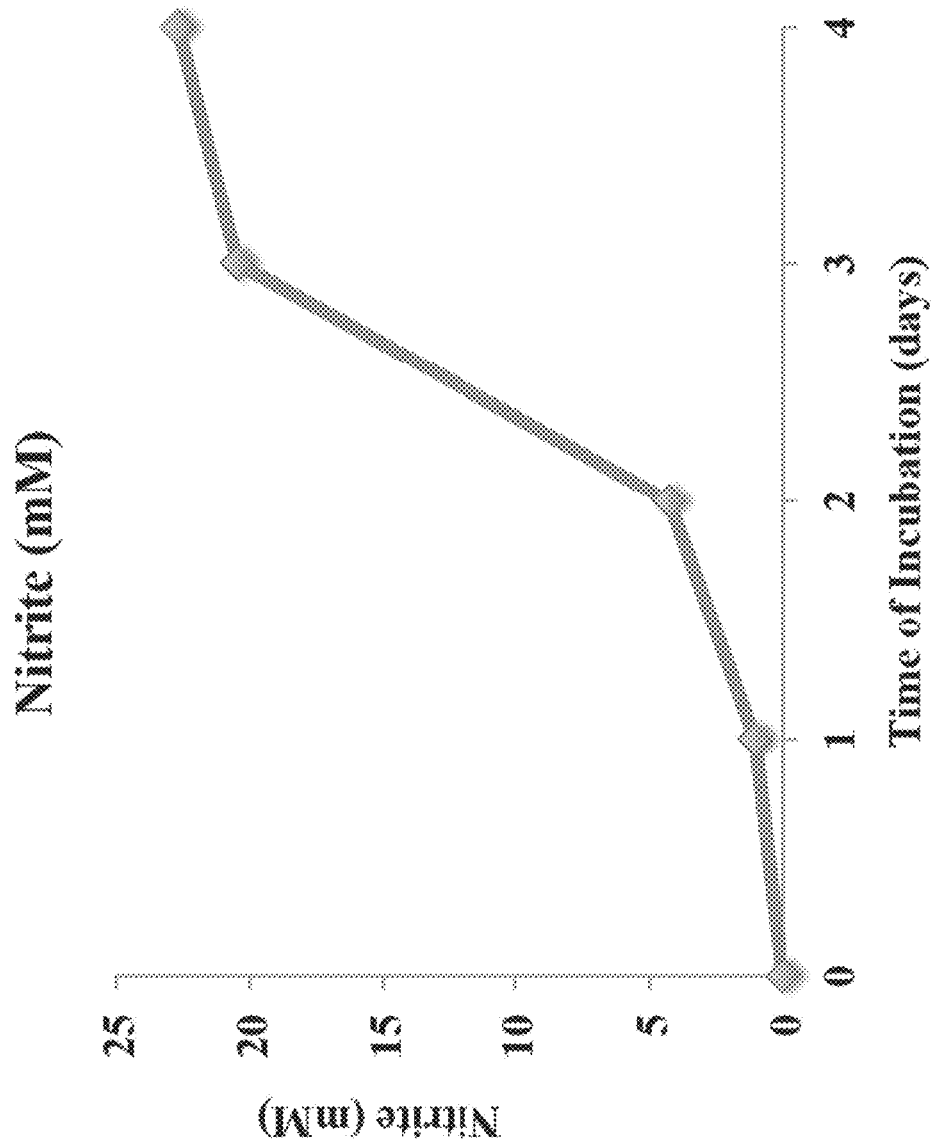
FIG. 2A shows the nitrite production of a mixed culture of bacteria comprising *N. eutropha* strain D23. The nitrite concentration is plotted relative to time.
Figure 2B:
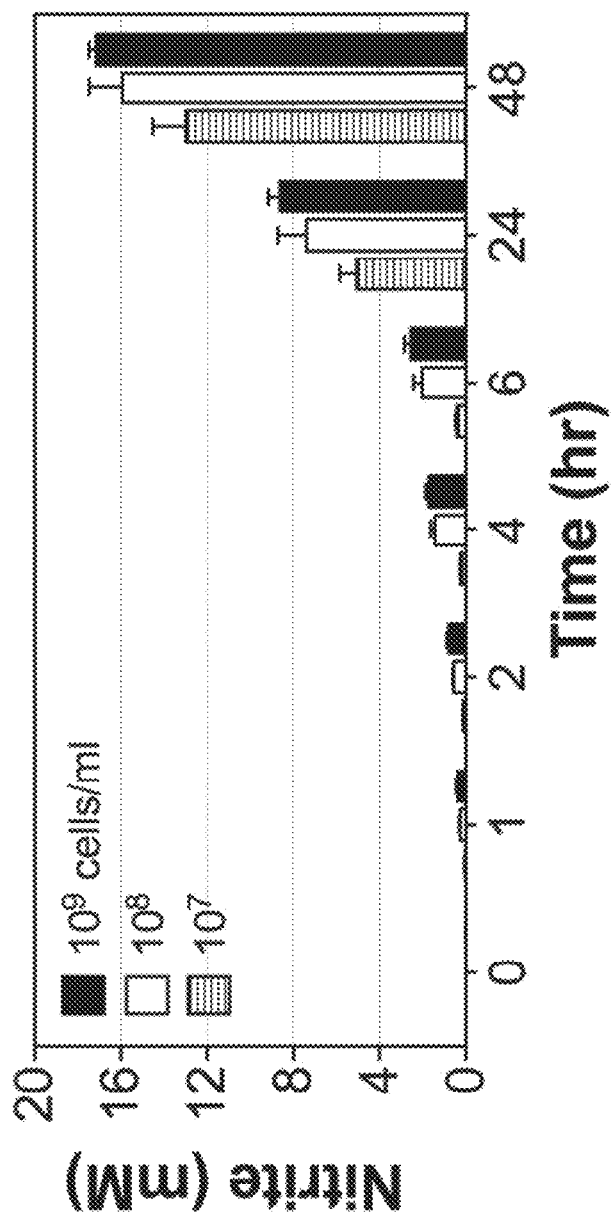
FIG. 2B shows the nitrite production kinetics by *N. eutropha* D23 in batch culture. The nitrite concentration is plotted relative to time.

In FIG. 2B, increasing densities of D23 harvested from continuous culture were suspended in medium supplemented with 50 mM $NH_4^+$ and grown shaking at 30° C. for 48 hours. Nitrite production was measured in supernatant samples using the Griess assay at the time points indicated. Results shown are mean values±SD from three independent experiments.

Figure 2C:
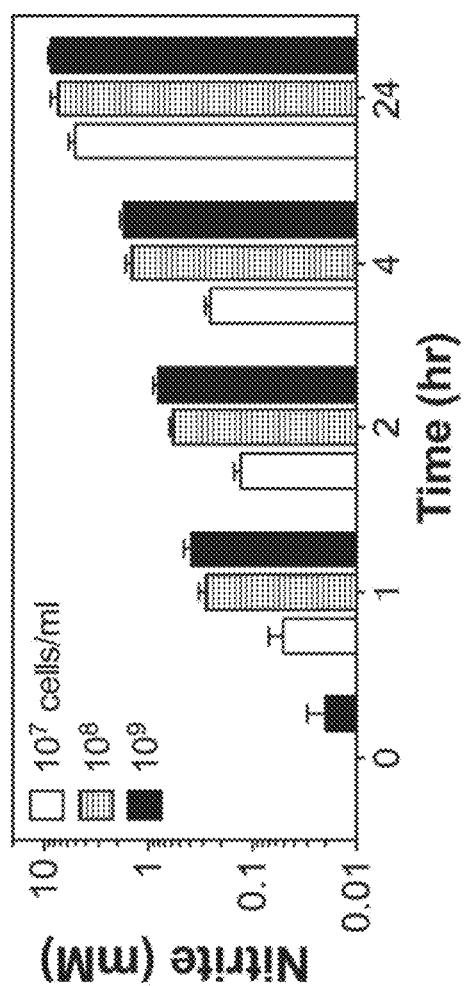
FIG. 2C shows the nitrite production kinetics by *N. eutropha* D23 in vitro. The nitrite concentration is plotted relative to time.

In FIG. 2C, Nitrite production by *N. eutropha* D23 in vitro is shown. Increasing densities of D23 were suspended in mineral salt medium supplemented with 50 mM $NH_4^+$ and grown shaking at 30° C. for 24 hr. Nitrite production was measured in supernatant samples using the Griess assay at the time points indicated.

Storage Conditions

*N. eutropha* suspensions obtained from the continuous culture system showed remarkable stability upon storage at 4° C. for several months, as indicated by the highly consistent nitrite concentrations generated upon subculture under batch growth conditions. Protocols for storing and recovering *N. eutropha* are set out below.

Obtain 500 ml of a *N. eutropha* D23 culture grown to late-exponential phase (OD600=0.5-0.6 in continuous culture). Centrifuge at 10,000×g for 15 min at 20° C. Remove supernatant and resuspend the pellet in 50 ml of AOB storage buffer. Spin as above. Remove supernatant and resuspend thoroughly in a total of 50 ml storage buffer. This would be the 10× AOB stock. Store upright at 4° C. in 50 ml polypropylene tubes.

AOB Storage Buffer (for AOB storage at 4° C.): 50 mM $Na_2HPO_4$-2 mM $MgCl_2$ (pH 7.6) can be made as follows.

In 1 Liter ddH2O: $Na_2HPO_4$—7.098 g $MgCl_2$—0.1904 g

Adjust pH to 7.6. Filter-sterilize.

*N. eutropha* may be cryopreserved as follows. Transfer 1.25 ml of *N. eutropha* D23 mid-log culture to a 2 ml cryotube and 0.75 ml of sterile 80% glycerol. Shake tubes gently, incubate at room temperature for 15 min to enable uptake of the cryoprotective agents by the cells. Then, put tubes directly in a −80° C. freezer for freezing and storage. For resuscitation of cultures, thaw frozen stocks on ice for 10-20 minutes. Centrifuge, at 8,000×g for 3 minutes at 4° C. Discard supernatant and wash the pellet by suspending it in 2 ml AOB medium followed by another centrifugation at 8,000×g for 3 minutes at 4° C. to reduce potential toxicity of the cryoprotective agents in subsequent growth experiments. Discard the supernatant and resuspend the pellet in 2 ml of AOB medium, inoculate into 50 ml of AOB medium containing 50 mM $NH_4^+$, and incubate in dark at 30° C. by shaking at 200 rpm.

Figure 2D:
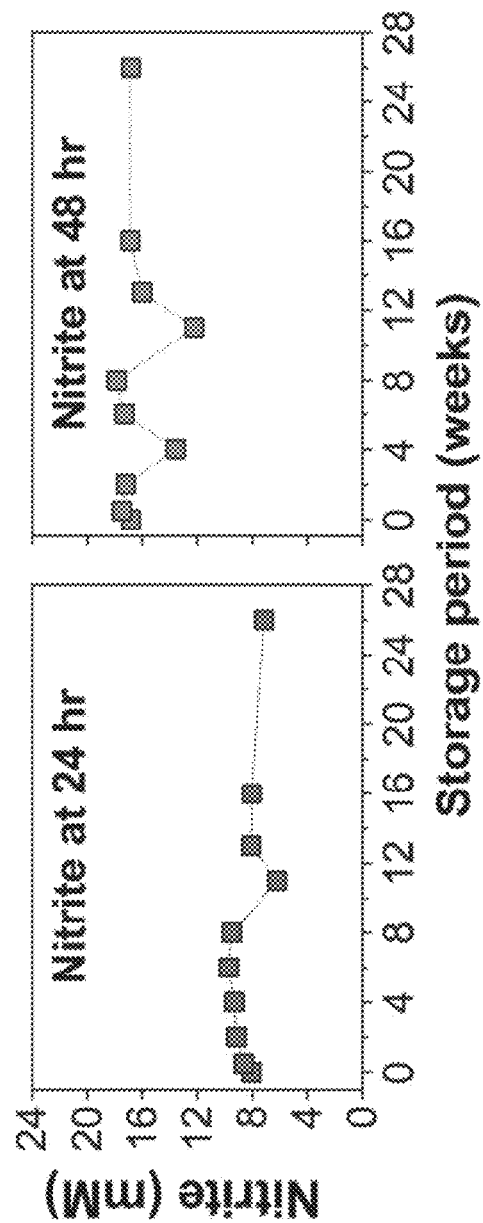
FIG. 2D shows *N. eutropha* D23 stability upon storage at 4° C. The nitrite concentration is plotted relative to time.

In FIG. 2D, stability upon storage at 4° C. was studied. *N. eutropha* D23 previously harvested from continuous culture and stored at 4° C. was inoculated at $10^9$ CFU/ml in mineral salt medium supplemented with 50 mM $NH_4^+$ and grown shaking at 30° C. Nitrite production was determined at 24 and 48 hours post-incubation (left and right panel, respectively). Data shown are representative of a D23 suspension sampled repeatedly over a 6-month period.

Example 3. Creation of an Axenic D23 Culture

To isolate *N. eutropha* D23 in pure culture, four types of media (described below) were made, autoclaved and poured in plates. Sterile nylon membranes were placed on the plates.

*N. europaea* media+1.2% $R_2A$ agar
*N. europaea* media+1.2% agar
*N. europaea* media+1.2% agarose
*N. europaea* media+1.2% agarose+0.3 g/L pyruvate 3 day old *N. eutropha* D23 culture was streaked onto the nylon membranes and the plates were incubated at 30° C. The plates were monitored daily for growth of red colored *N. eutropha* cells. Nylon membranes were transferred to fresh plates once a week.

Reddish colored colonies appeared on plates with $R_2A$ agar or agar by end of 1 week. Single colonies were picked from plates with R2A agar and grown in *N. europaea* media. The cultures grew well in 6 days to 0.08 OD600 nm. Heterotrophic colonies appeared when the culture was plated on LB-Agar plates.

Reddish colored colonies on plates with $R_2A$ agar, agar, agarose, or agarose+pyruvate appeared by end of 2 weeks. Single colonies were picked from plates with agar or agarose and grown in *N. europaea* media. The cultures grew well in 6-8 days to 0.08 OD600 nm. Heterotrophic colonies appeared when the culture was plated on LB-Agar plates.

Bright reddish colonies on plates with $R_2A$ agar, agar, agarose, or agarose+pyruvate appeared by end of 4 weeks. Single colonies were picked from plates with agarose and grown in *N. europaea* media. The cultures grew well in 6-8 days to 0.08 OD600 nm. White colonies appeared when the culture was plated on LB-Agar plates.

Contaminating bacteria (e.g., non-*N. eutropha* bacteria present in the mixed culture) were identified by culturing, amplifying 16S rRNA by PCR, and sequencing of the PCR products. Contaminants were identified as *Microbacterium* sp. and *Alcaligenaceae* bacterium.

To create an axenic culture of D23 (i.e., free of contaminating bacteria) serial dilution was used. Eight single colonies (designated A-H) were picked, and each was placed into a 10 ml culture of *N. europae* medium. For each culture, five sequential 1:10 dilutions were created. For each culture A-H, growth was observed in the two or three most concentrated of the dilutions.

A second serial dilution was carried out. 50 ml of media was inoculated with approximately $2×10^8$ *N. eutropha* cells, and sequential dilutions of 1:50 were made, such that after the fifth dilution, a flask was expected to have approximately one cell. Flasks that exhibited bacterial growth were plated on LB-agar to assay for contaminating bacteria, and no contaminating bacteria were observed. In addition, no contaminating gram positive cells were observed under the microscope.

Accordingly, the serial dilution process yielded an axenic or substantially axenic culture of *N. eutropha*.

Example 4. Sequencing of the D23 Genome

Strain D23 was obtained as described in Example 1, and was made axenic as described in Example 3.

A 10 ml aliquot the bacterial sample was inoculated into approximately 1 L of *N. europaea* growth medium described in Example 2. The culture grew well to optical density of 0.08 at 600 nm in a batch culture in 3 days.

Total DNA of the culture was prepared and sequenced using Illumina® technology and/or SMRT® DNA Sequencing System technology, Pacific Biosciences. The strain was identified as *Nitrosomonas eutropha* and was designated D23.

The genome sequence of D23 was compared to that of *N. eutropha* C91, which is believed to be the only other sequenced strain of *N. eutropha*.

The length of the D23 chromosome is 2,537,572 base pairs, which is shorter than the 2,661,057 base pair chromosome of *N. eutropha* strain C91 chromosome. Based on the 16S-23S operon, strain D23 has 99.46% identity to C91 and 95.38% identity to *N. europaea*. DNA sequencing of *N. eutropha* D23 indicated that this strain lacks plasmids. This contrasts with the sequence of strain C91, which has two plasmids.

Protein-encoding regions and RNA-encoding sequences were identified by sequence analysis. Supplementary Table 1 is a table of annotations that lists the positions of 2,777 genes in the D23 genome (SEQ ID NO: 1).

On the level of individual genes, several genes are present in D23 that are absent in C91. These genes are summarized in FIGS. 6-8. FIG. 6 is a table displaying unique D23 genes with an assigned ORF number and a function based on sequence analysis, or a hypothetical gene above 200 base pairs in length. There are 162 genes in this category. FIG. 7 is a table displaying unique D23 genes below 200 base pairs that have an assigned ORF number. There are 164 of these genes. FIG. 8 is a table displaying unique D23 genes with no assigned ORF number. There are 219 of these genes (of which 180 are below 200 bp in length).

Strain D23 also lacks a number of genes that are present (or lack close homologs) in strain C91. These genes are sometimes referred to as unique C91 genes. These genes include the about 300 genes listed in FIG. 9.

D23 contains several ammonia metabolism genes that differ from their homologs in C91. Certain of these genes are enumerated in Table 1 of the Detailed Description. Sequence alignments were performed between the D23 proteins and their homologs in strain C91. The sequence alignments are shown in FIGS. 10-16 and sequence differences between the two strains are shown in Table 2 of the Detailed Description.

The sequence comparisons revealed the percent sequence identities between the C91 and D23 homologs of each protein. More specifically, FIG. 10 is an alignment between AmoA1 and AmoA2 of strains C91 and D23. Each protein is identical at 273/276 residues, and so each is about 98.9% identical between strains. FIG. 11 is an alignment between AmoB1 and AmoB2 of strains C91 and D23. Both proteins are identical at 419/421 positions, and so are about 99.5% identical between strains. FIG. 12 is an alignment between AmoC1 and AmoC2 of strains C91 and D23. Both proteins are identical throughout. FIG. 13 is an alignment between AmoC3 of strains C91 and D23. This protein is identical at 272/274 positions, and so are about 99.3% identical between strains.

As to the Hao proteins, FIG. 14 (A and B) is an alignment between Hao1, Hao2, and Hao3 of strains C91 and D23. Hao1 is identical at 567/570 positions, and so each is about 99.5% identical between strains. Hao2 and Hao3 are each identical at 568/570 positions, and so are about 99.6% identical between strains.

Turning now to cytochrome c554 proteins, FIG. 15 is an alignment between CycA1, CycA2, and CycA3 of strains C91 and D23. CycA1 is identical at 233/235 positions, and so is about 99.1% identical between strains. CycA2 and CycA3 are each identical at 234/235 positions, and so each is about 99.6% identical between strains.

As to the cytochrome $c_M 552$ proteins, FIG. 16 is an alignment between CycB1 and CycB2 of strains C91 and D23. CycB1 is identical at 232/239 positions, and so is about 97.1% identical between strains. CycB2 is identical at 236/239 positions, and so is about 98.7% identical between strains. Here, the length of the protein is considered 239 amino acids because that is its length in strain D23.

Alignment of the nucleic acid sequences of Table 1 shows the percent identity between homologs in C91 and D23. The amoA1 genes are about 98.8% identical (i.e., at 821/831 positions), the amoA2 genes are about 98.8% identical (i.e., at 821/831 positions), the amoB1 genes are about 99.1% identical (i.e., at 1255/1266 positions), the amoB2 genes are about 99.1% identical (i.e., at 1254/1266 positions), the amoC1 genes are about 99.8% identical (i.e., at 814/816 positions), the amoC2 genes are about 99.8% identical (i.e., at 814/816 positions), and the amoC3 genes are about 98.9% identical (i.e., at 816/825 positions). The hao1 genes are about 99.0% identical (i.e., at 1696/1713 positions), the hao2 genes are about 99.4% identical (i.e., at 1702/1713 positions), and the hao3 genes are about 99.2% identical (i.e., at 1700/1713 positions). Of the cytochrome c554 genes, the cycA1 genes are about 98.0% identical (i.e., at 694/708 positions), the cycA2 genes are about 98.7% identical (i.e., at 699/708 positions), and the cycA3 genes are about 99.3% identical (i.e., at 703/708 positions). Of the cytochrome $c_M 552$ genes, the cycB1 genes are about 96.7% identical (i.e., at 696/720 positions) and the cycB2 genes are about 97.1% identical (i.e., at 702/723 positions).

Example 5. Competitive Growth Studies

A study was designed to determine whether *N. eutropha* strain D23 could inhibit the growth of undesirable bacteria such as *Pseudomonas aeruginosa* (*P. aeruginosa* or PA), *Staphylococcus aureus* (*S. aureus* or SA), *Streptococcus pyogenes* (*S. pyogenes* or SP), *Acinetobacter baumannii* (*A. baumannii* or AB), and *Propionibacterium acnes*, all of which are important pathogenic agents frequently isolated from either one or both of infected skin and wound sites. This protocol may also be used to test other *N. eutropha* strains for the ability to inhibit the growth of undesirable bacteria.

Briefly, a suitable protocol can comprise the following steps. At t=0, a culture is inoculated with *N. eutropha*, and then the *N. eutropha* is incubated for 24 hours. Culture characteristics (e.g., pH and nitrite levels) are assayed. At t=24 hours, the undesirable bacterium is added to the culture. Immediately upon addition, samples are obtained for determining CFU/ml of the undesirable bacteria and optionally CFU/ml of *N. eutropha*, pH, and nitrite levels. Incubation is allowed to proceed for an additional 24 hours. At subsequent timepoints, e.g., t=30 and t=48, one can take the same measurements as at t=24. To determine CFU/ml, one can plate neat/−1/−2/−3/−4/−5 (or higher) to obtain accurate counts.

A more detailed protocol is set out below.

Day 1

1. Mix the 10×AOB stock suspension stored at 4° C. by inverting several times until a homogenous suspension is obtained.
2. Aliquot 10 ml of the suspension in 8×1.5 ml polypropylene tubes.
3. Centrifuge at 17,000×g for 3 min at room temperature.
4. Remove supernatant and any residual buffer from each pellet and resuspend all pellets thoroughly into a total of 10 ml complete AOB medium in a 50 ml polypropylene tube.
5. Pipet 5 ml of 10×AOB suspension in each of two 50 ml polypropylene tubes (Tube 1-2).
6. Prepare five additional tubes (Tube 4-8) containing 10×AOB suspensions in complete AOB medium/0.5× Phosphate Buffer. Aliquot 26 ml of the 10×AOB stock suspension in 16×1.5 ml polypropylene tubes. Obtain pellets as above and resuspend in a total of 26 ml complete AOB medium/0.5× Phosphate Buffer in a 50 ml polypropylene tube.
7. Pipet 5 ml of the 10×AOB suspension in each of five 50 ml polypropylene tubes (Tube 4-8).
8. Also, prepare two tubes with 10× Heat-killed AOB suspensions in either complete AOB medium (Tube 3) or complete AOB medium/0.5×Phosphate Buffer (Tube 9). Aliquot 10 ml of the Heat-killed suspension stored at 4° C. in 8×1.5 ml polypropylene tubes. Centrifuge at 17,000×g for 3 min at room temperature and remove supernatant, as described above for live AOB. Resuspend four pellets in a total of 5 ml complete AOB medium in one 50 ml polypropylene tube (Tube 3) and the remaining four pellets in a total of 5 ml complete AOB medium/0.5×Phosphate Buffer in a second 50 ml polypropylene tube (Tube 9).
9. Add 141 µl of 1 M ammonium sulfate to obtain 25 mM final concentration (Tube 1, 3, 4, 5, 9). Add an equal volume of dH$_2$O to corresponding control tubes (Tube 2, 6, 7).
10. To Tube 8, add 141 µl of fresh 1 M NaNO$_2$.
11. Swirl all tubes gently, but thoroughly, to mix.
12. Immediately after mixing each suspension, remove 0.5 ml from each tube and centrifuge all samples at 17,000×g, 3 min, RT. Transfer supernatants into fresh tubes after completing step 13, and measure both pH and nitrite levels using Griess Reagent to obtain T0 values.
13. Incubate all 50 ml tubes at 30° C. with mixing on an orbital shaker at 150 rpm (upright position) for 24 hr.

TABLE 5

| SAMPLE | Tube | 10x AOB (ml) | 10x Killed AOB (ml) | 1 M $(NH_4)_2SO_4$ (μl) | $H_2O$ (μl) | 1 M $NaNO_2$ | T24 SA/PA in saline (ml) |
|---|---|---|---|---|---|---|---|
| Complete AOB medium | | | | | | | |
| 10x AOB + $NH_4^+$ | 1 | 5 | — | 141 | — | — | 0.5 |
| 10x AOB | 2 | 5 | — | — | 141 | — | 0.5 |
| 10x Killed AOB + $NH_4^+$ | 3 | — | 5 | 141 | — | — | 0.5 |
| Complete AOB medium/0.5x Phosphate Buffer | | | | | | | |
| 10x AOB + $NH_4^+$ | 4 | 5 | — | 141 | — | — | 0.5 |
| 10x AOB + $NH_4^+$ | 5 | 5 | — | 141 | — | — | 0.5 |
| 10x AOB | 6 | 5 | — | — | 141 | — | 0.5 |
| 10x AOB | 7 | 5 | — | — | 141 | — | 0.5 |
| 10x AOB + $NaNO_2$ | 8 | 5 | — | — | — | 141 | 0.5 |
| 10x Killed AOB + $NH_4^+$ | 9 | — | 5 | 141 | — | — | 0.5 |

Day 2

14. At 24 hr, prepare SA, PA, SP or AB inocula to add to the suspensions.
15. From an overnight (20-24 hr) SA or PA culture grown on Tryptic Soy Agar (TSA), or a SP or AB culture prepared on Brain Heart Infusion (BHI) Agar, prepare bacterial suspension in Tryptic Soy Broth (TSB) or BHI broth (BHIB) at ~$2\times10^8$ CFU/ml.
16. Pipet 50 μl of the SA/PA/SP/AB suspension in 9.95 ml saline to obtain ~$10^6$ CFU/ml. Keep on ice, as needed.
17. Vortex SA/PA/SP/AB suspension and add 0.5 ml to Tube 1-9.
18. Swirl all tubes gently, but thoroughly, to mix.
19. Immediately after mixing each suspension, transfer 100 μl from each tube into 0.9 ml TSB or BHIB ($10^{-1}$ dilution) to neutralize samples for CFU determination. In addition, remove 0.5 ml from each tube and centrifuge at 17,000×g, 3 min, RT. Recover supernatants in fresh tubes after completing Step 20 and measure both pH and nitrite levels using Griess Reagent after Step 21 to obtain T24 values.
20. Incubate all 50 ml tubes at 30° C. with mixing on an orbital shaker (150 rpm) for an additional 24 hr.
21. Dilute T24 samples further in TSB or BHIB and plate −2/−3/−4 dilutions on TSA or BHI agar. Incubate plates at 37° C. for 24 hr to obtain SA, PA, SP, or AB viable counts.
22. At 6 and 24 hr post-mixing of SA/PA/SP/AB with AOB, vortex tubes and pipet 100 μl samples into 0.9 ml TSB. Dilute further in TSB or BHIB and plate neat through −5 dilutions on TSA or BHI agar. At each time point, also remove 0.5 ml from each tube and measure both pH and nitrite levels in each supernatant sample, as described above.
23. Incubate TSA or BHI agar plates at 37° C. for 24 hr to obtain T30 (6 hr) and T48 (24 hr) viable counts.
24. Count CFU to determine % killing rates for each time point Griess Reagent Assay for Nitrite Quantification 1. Use the 0.5 ml supernatant samples obtained for pH determination at 0, 2, 6, and 24 hr.
2. Serially dilute 56 μl of the supernatant in 0.5 ml dH2O to obtain 10-100- and 1000-fold dilutions, as needed. For T0 samples, use 1/10 for Tube 1-6, 8, 9, and 1/1000 for Tube 7. For T24/T30/T48 samples, use 1/10, 1/100, 1/1000 for all tubes,
3. To prepare sodium nitrite standards, dilute 10 μl of a fresh 1 M stock in 990 μl complete AOB medium-10% saline to obtain a 10 mM solution.
4. Dilute 10 μl of the 10 mM stock in 990 μl $dH_2O$ to obtain a 100 μM working solution.
5. Prepare standards in $dH_2O$ as shown below. Run standards only with T0 samples.

TABLE 6

| 100 μM sodium nitrite (μl) | $dH_2O$ (μl) | Nitrite conc (μM) | $A_{540\ nm}$ (indicative values) |
|---|---|---|---|
| 0 (blank) | 500 | 0 | 0 |
| 62.5 | 437.5 | 12.5 | 0.307 |
| 125 | 375 | 25 | 0.607 |
| 250 | 250 | 50 | 1.164 |
| 500 | 0 | 100 | 2.35 |

6. To each 0.5 ml sample (or sodium nitrite standard), add 0.25 ml each of Reagent A (58 mM sulfanilamide in 1.5 N HCl) and Reagent B (0.77 mM n-(1-napthyl) ethylene diamine-2HCl in $H_2O$ (light-sensitive; store in dark).
7. Mix and let stand at room temperature for 30 min in the dark (or cover with foil). The color should change to a vivid pink/violet.
8. Read absorbance at 540 nm and determine nitrite concentrations from standard curve.

This protocol was used to test *N. eutropha* D23's ability to inhibit the growth of *P. aeruginosa* (PA), *S. aureus* (SA), *S. pyogenes* (SP), *A. baumannii* (AB), or *P. acnes*. The results of this experiment are shown in FIGS. 3A, 3B, and 3C.

Figure 3A:
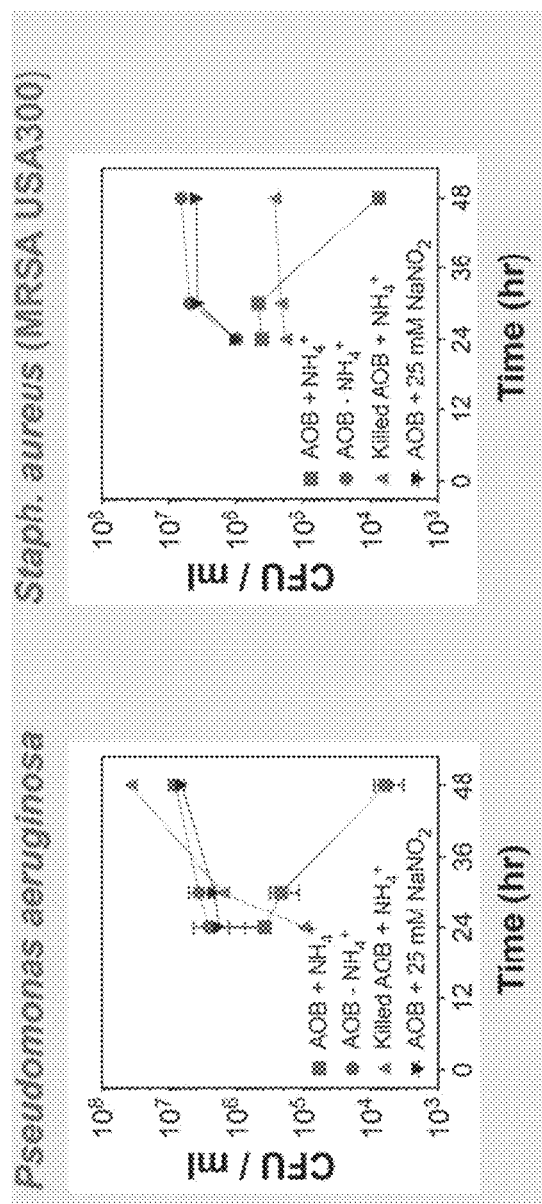
FIG. 3A shows the *N. eutropha* D23's ability to inhibit the growth of *P. aeruginosa* (left panel) and *S. aureus* (right panel) in co-culture experiments. The amount of each type of undesirable bacteria (in CFU/ml) is plotted relative to time. In this figure, "AOB" refers to strain D23.
Figure 3B:
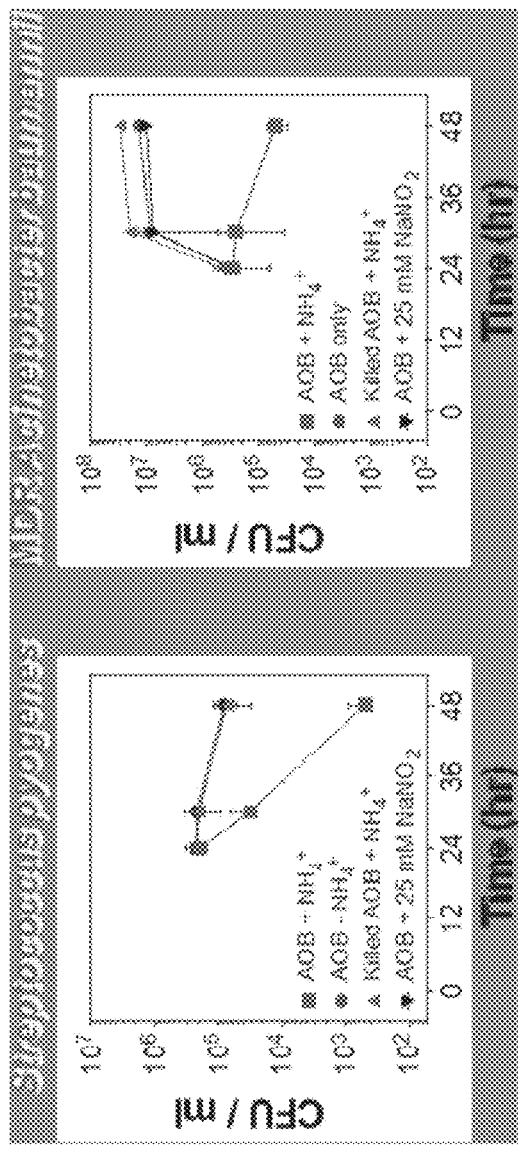
FIG. 3B shows the *N. eutropha* D23's ability to inhibit the growth of *Streptococcus pyogenes* (left panel) and *Acinetobacter baumannii* (right panel) in co-culture experiments. The amount of each type of undesirable bacteria (in CFU/ml) is plotted relative to time. In this figure, "AOB" refers to strain D23.
Figure 3C:
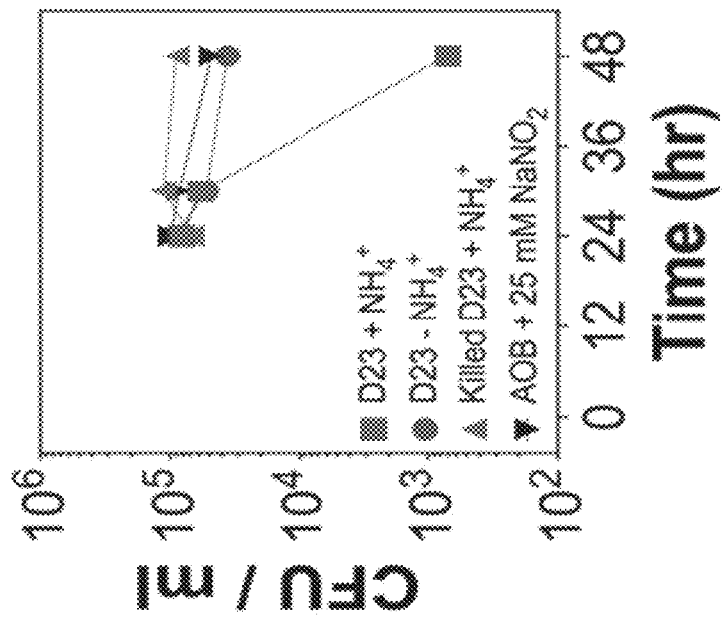
FIG. 3C shows the *N. eutropha* D23's ability to inhibit the growth of *Propionibacterium acnes* in co-culture experiments. The amount of each type of undesirable bacteria (in CFU/ml) is plotted relative to time. In this figure, "AOB" refers to strain D23.

The left panel of FIG. 3A plots CFU/ml of PA versus time, when PA is co-cultured with live *N. eutropha* and ammonium (squares), live *N. eutropha* without ammonium (circles), killed *N. eutropha* and ammonium (triangles), or live *N. eutropha* with $NaNO_2$ (inverted triangles). The right panel of FIG. 3A plots CFU/ml of SA versus time, under the same conditions. The left panel of FIG. 3B plots CFU/ml of SP versus time, under the same conditions. The right panel of FIG. 3B plots CFU/ml AB versus time, under the same conditions. FIG. 3C plots CFU/ml of P. acnes versus time, when P. acnes is co-cultured with live N. eutropha and ammonium (squares), live N. eutropha without ammonium (circles), killed N. eutropha and ammonium (triangles), or live N. eutropha with NaNO₂ (inverted triangles). In all cases, live N. eutropha with ammonium results in declining numbers of PA, SA, SP, AB, or P. acnes whereas the other culture conditions allow the undesirable bacteria to grow. Without being bound by theory, these experiments suggest that nitrite generation from ammonia concurrently with medium acidification by D23 led to strong antibacterial effects, e.g., an approximately 100-fold reduction in viable counts of methicillin-resistant *Staphylococcus aureus, Pseudomonas aeruginosa, Streptococcus pyogenes, Acinetobacter baumannii*, or *P. acnes*. By contrast, control co-cultures of pathogenic bacteria either with heat-killed D23 supplemented with ammonia, or with live D23 without ammonia, did not produce comparable antibacterial effects. The control comprising live N. eutropha culture without ammonium is consistent with the model that N. eutropha's ammonia oxidation activity contributes to its antibacterial effects. The control comprising killed N. eutropha and ammonium indicates that some biological activity of the N. eutropha (e.g., its ammonia oxidation activity) contributes to antibacterial activity. The control comprising live N. eutropha with NaNO₂ indicates that comparable nitrite levels at neutral pH (versus low pH when the bacteria use ammonia) do not have a strong antimicrobial effect, and is consistent with the model that N. eutropha's oxidation of ammonia, rather than nitrite alone, contributes to the antibacterial activity.

Figure 4A:
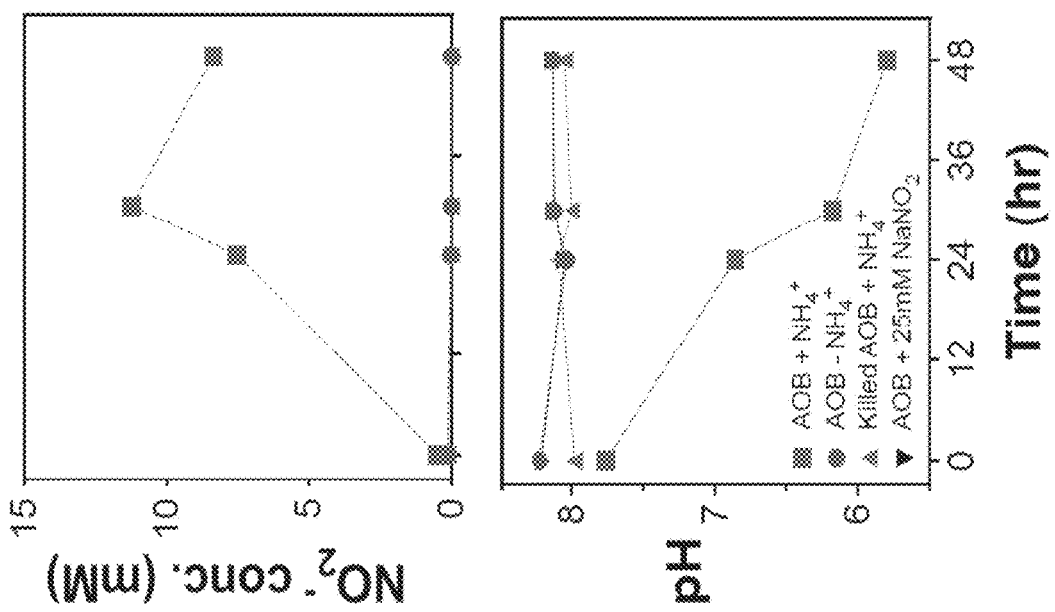
FIG. 4A (top panel) plots the $NO_2^-$ concentration over time in a co-culture experiment. The bottom panel plots pH over time in a co-culture experiment.

The top panel of FIG. 4A plots the $NO_2^-$ concentration over time in the co-cultures described in the paragraph above. $NO_2^-$ concentration is an indication of the rate of $NH_3$ metabolism in the cultures. As above, PA is co-cultured with N. eutropha and ammonium (squares), N. eutropha without ammonium (circles), or killed N. eutropha and ammonium (triangles). Live N. eutropha with ammonium produces dramatically higher $NO_2^-$ levels than the two control cultures, indicating that the live N. eutropha converts ammonium into $NO_2^-$ under the culture conditions. The bottom panel of FIG. 4A plots pH over time in the same co-culturing conditions. pH indicates the metabolic activity of the N. eutropha because the conversion of ammonia to nitrite produces hydrogen ions. PA is co-cultured with N. eutropha and ammonium (squares), N. eutropha without ammonium (circles), killed N. eutropha and ammonium (triangles), or live N. eutropha with NaNO₂ (inverted triangles). Live N. eutropha with ammonium acidifies the medium, in contrast to the three control cultures, indicating that the live N. eutropha metabolizes ammonium under the culture conditions.

Figure 4B:
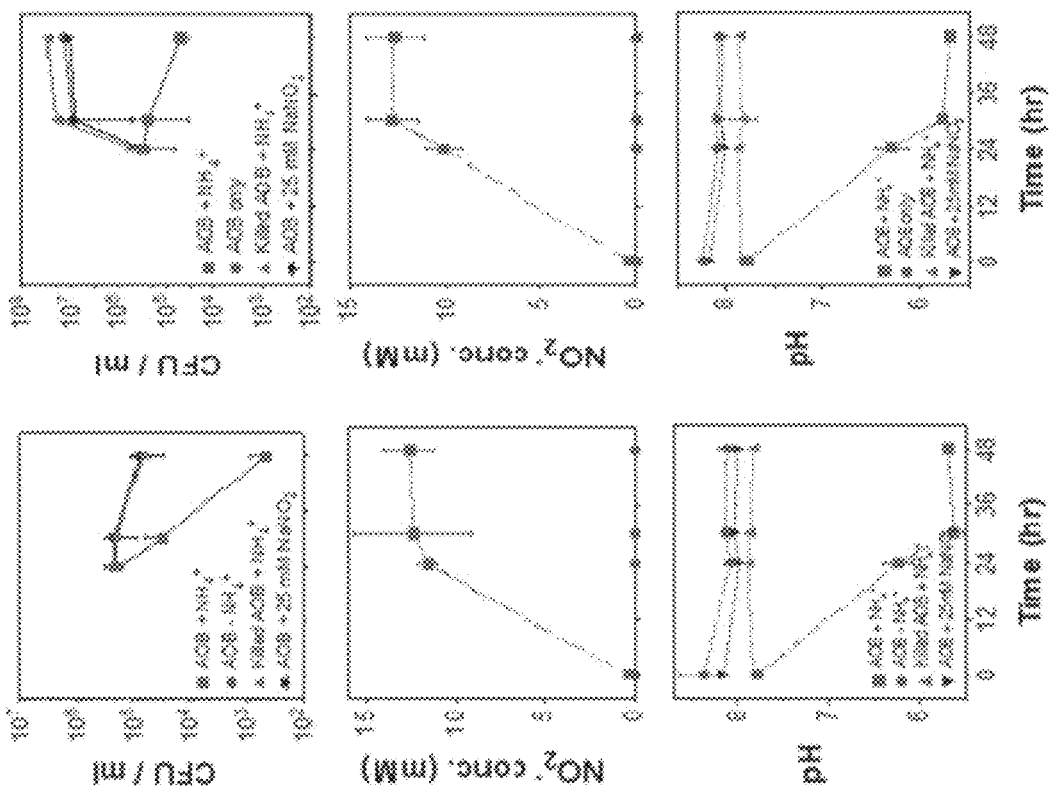
FIG. 4B (top panels) plots the CFU/ml of the indicated bacteria over time in a co-culture experiment. The center panels plot the $NO_2^-$ concentration over time in a co-culture experiment. The bottom panels plot pH over time in a co-culture experiment.
Figure 4C:
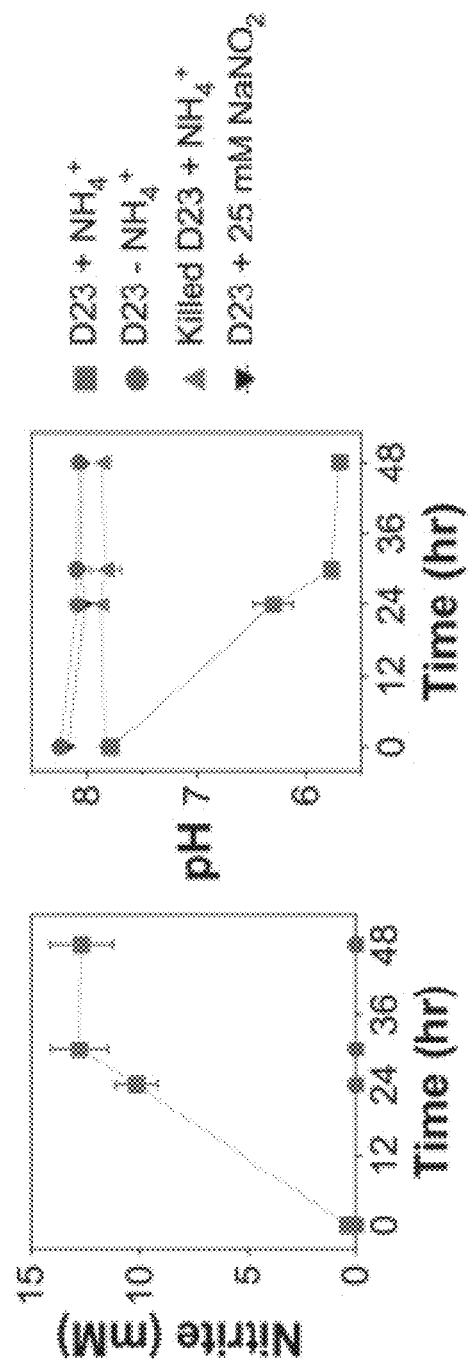
FIG. 4C plots the microbicidal activity of D23 against skin pathogens.

The top panels of FIG. 4B plot the $NO_2^-$ concentration over time in the co-cultures described above. $NO_2^-$ concentration is an indication of the rate of $NH_3$ metabolism in the cultures. As above, S. pyogenes (SP) and A. baumannii (AB) are co-cultured with N. eutropha and ammonium (squares), N. eutropha without ammonium (circles), or killed N. eutropha and ammonium (triangles). Live N. eutropha with ammonium produces dramatically higher $NO_2^-$ levels than the two control cultures, indicating that the live N. eutropha converts ammonium into $NO_2^-$ under the culture conditions.

The bottom panels of FIG. 4B plot pH over time in the same co-culturing conditions. pH indicates the metabolic activity of the N. eutropha because the conversion of ammonia to nitrite produces hydrogen ions. SP and AB are co-cultured with N. eutropha and ammonium (squares), N. eutropha without ammonium (circles), killed N. eutropha and ammonium (triangles), or live N. eutropha with NaNO₂ (inverted triangles). Live N. eutropha with ammonium acidifies the medium, in contrast to the three control cultures, indicating that the live N. eutropha metabolizes ammonium under the culture conditions.

Figure 4D:
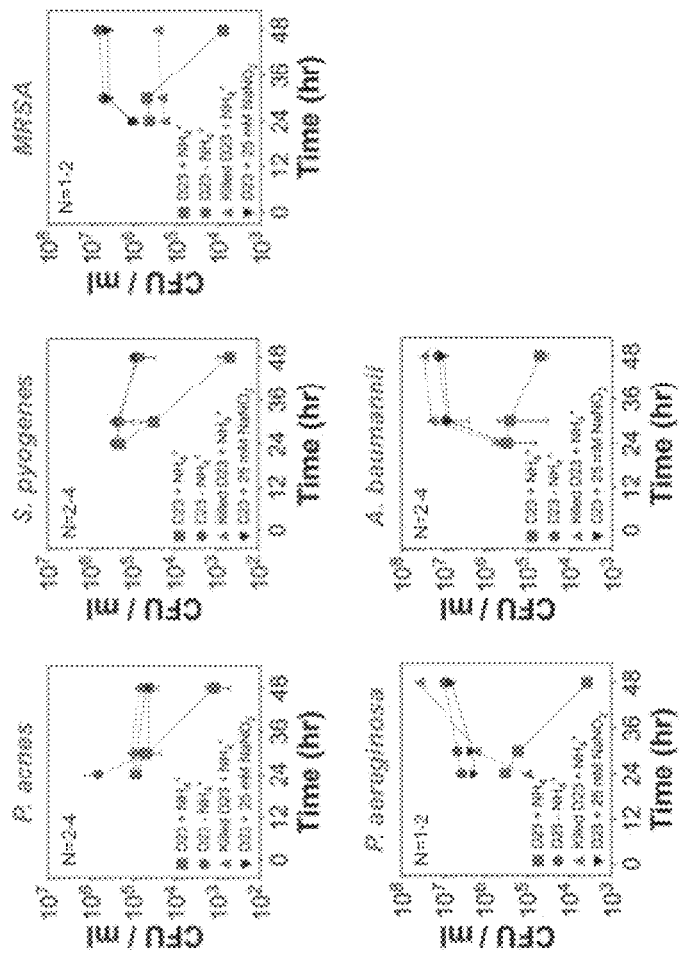
FIG. 4D plots the microbicidal activity of D23 against skin pathogens.
Figure 4E:
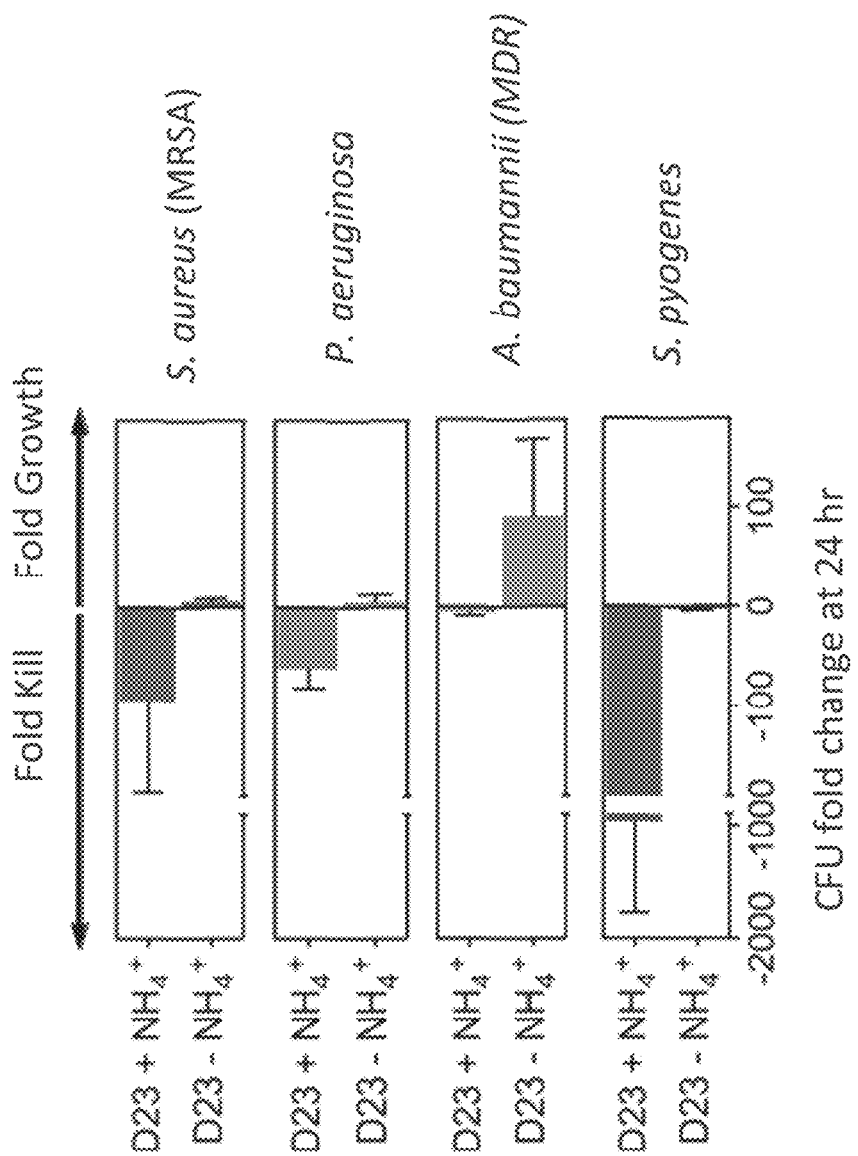
FIG. 4E shows an alternative plot of microbicidal activity of D23 against skin pathogens.

FIG. 4E shows an alternative visualization the data of FIGS. 4A and 4B.

The capacity of *Nitrosomonas eutropha* D23 to inhibit proliferation of pathogenic bacteria due to nitrite production concurrent with acidification (acidified nitrite) was assessed by testing the survival of 5 strains of pathogenic bacteria in co-culture studies with D23 in vitro. The five strains of pathogenic bacteria included *Propionibacterium acnes, Streptococcus pyogenes*, methicillin-resistant *Staphylococcus aureus* (MRSA), *Pseudomonas aeruginosa*, and multi-drug-resistant *Acinetobacter baumannii*. Incubation of N. eutropha D23 ($10^{10}$ cells/ml) in the presence of ammonium led to nitrite concentrations of 10 mM or higher and acidification to pH 6 or lower (FIG. 4B). The combination of increased nitrite concentration and lowering of pH led to bactericidal or bacteriostatic effects and a marked reduction (up to 965-fold) in viable counts of the pathogenic bacterial species tested. The results of these studies are summarized in FIG. 4D and Table 7, below. In contrast to the D23 co-cultures incubated in the presence of ammonium, control co-cultures of the five pathogenic agents with D23 without ammonium, or with heat-killed D23 (B244) supplemented with ammonium, did not lead to any inhibitory or antimicrobial effects.

TABLE 7

Effect of N. eutropha D23 (D23) on relative survival of pathogenic bacteria in vitro

| | Relative Survival (Fold Change) | | |
|---|---|---|---|
| Pathogen Tested | AOB + $NH_3$ | AOB − $NH_3$ | Heat-Killed AOB + $NH_3$ |
| *Priopionibacterium acnes* ATCC 6919 | −114 | −19,067 | −1.05 |
| *Staphylococcus aureus* (MRSA) ATCC BAA-1717 | −117.6 | 8.2 | 2.03 |
| *Pseudomonas aeruginosa* ATCC 15442 | −84.3 | 2.65 | 379 |
| *Streptococcus pyogenes* ATCC 19615 | −965 | −2.88 | −3.81 |
| *Acinetobacter baumannii* (MDR) ATCC BAA-1605 | −5.43 | 92.4 | 89.8 |

Example 6. Wound Healing

The effect of *Nitrosomonas eutropha* D23 (sometimes also called B244) on wound closure in diabetic mice was evaluated in two separate studies. In Study 1, db/db mice (8 mice/group) were pre-treated by body immersion daily for one week with 3 concentrations of D23 ($10^7$, $10^8$ or $10^9$ cells/ml) supplemented with ammonium chloride, or with vehicle control suspension only. Subsequently, full-thickness wounds generated on the back of each animal were treated topically once daily for 14 days with vehicle alone or equal volumes of 3 concentrations of D23 ($10^7$, $10^8$ or $10^9$ cells/ml) in PBS supplemented ammonium chloride. Of the three D23-treated groups, the group receiving the highest dose showed significant improvement in wound closure from day 5 to day 15, with the most pronounced improvement of 83% observed on day 9 post-wounding. The median time to 50% wound closure was significantly reduced ($P<0.05$) for the animals treated with $10^9$ cells/ml of D23, as compared to the animal group receiving vehicle treatment alone.

Initial histopathology analyses of wound tissue samples collected on Day 15 upon study completion did not reveal any gross differences between vehicle- and D23-treated animals. Subsequently, a more in-depth examination of the tissue sections was performed according to the scoring system and parameters adapted and modified form Altavilla, et al (2001). This analysis suggested a trend of increased levels of angiogenesis and maturity of granulation tissue with decreased levels of dermal inflammation in animals treated with $10^9$ cells/ml of D23 versus the vehicle control group, which was consistent with the observed improvement in wound healing rates of the D23-treated animals

*N. eutropha* strain D23 was tested for its ability to accelerate wound healing in a diabetic mouse model, using C57BLKS/J Iar- +Lepr$^{db}$/+Lepr$^{db}$ male mice (non-GLP). A detailed protocol is set out below.

Day −6 to Day 1: Whole-Body Immersion Pre-Treatment of Mice with Test Organism

1. Mix the 10× D23 stock suspension stored at 4° C. by inverting several times until a homogenous suspension is obtained.
2. Pipet 2×29 ml of the 10× stock suspension into two 50 ml polypropylene centrifuge tubes.
3. Centrifuge at 8,000×g for 15 min at 20° C.
4. Remove supernatant and any residual buffer from the pellets and resuspend the two pellets gently but thoroughly into a total of 58 ml room-temperature Phosphate Buffered Saline, pH 7.4 (PBS). This is the 10× D23 (Test Organism) suspension to use for the following steps.
5. Prepare 500 ml baths containing the Test Organism at 1×, 0.1× and 0.01× strength in pre-warmed PBS at 30° C. supplemented with 2 mM NH$_4$Cl, or a Vehicle control bath, as shown below. Prepare and use one bath at a time from the 10× D23 suspension kept at room temperature before continuing with the next bath. This will prevent keeping the Test Substance at 30° C. for long time periods without ammonium. To prevent contamination of the Vehicle control group with the Test Substance, begin with the Vehicle control group before proceeding with the D23 baths.
6. Immerse each group of mice in corresponding baths for 60 sec daily for seven days.
7. Use a fresh 500 ml baths for each daily immersion into the Test Organism or Vehicle control.

TABLE 8

| GROUP | BATH | | | |
|---|---|---|---|---|
| | 10x D23 (room temp.) (ml) | PBS pH 7.4 (ml) | 1M NH$_4$Cl (ml) | CFU/ml |
| Vehicle (control) | — | 500 | 1.0 | 0 |
| 1x D23 | 50 | 450 | 1.0 | $10^9$ |
| 0.1x D23 | 5 | 495 | 1.0 | $10^8$ |
| 0.01x D23 | 0.5 | 499 | 1.0 | $10^7$ |

Day 1: Wounding of Mice by Skin Puncture

1. Generate skin wounds on the back of each mouse by skin puncture after shaving of the back and shoulders.
2. House each mouse separately for the remainder of the study.

Day 1 to Day 15: Topical Treatment of Skin Wounds with Test Organism

1. Mix the 10× D23 stock suspension stored at 4° C. by inverting several times until a homogenous suspension is obtained.
2. Pipet 1 ml of the 10× stock suspension into a 1.5 ml polypropylene tube.
3. Centrifuge at 17,000×g for 3 min at room temperature.
4. Remove supernatant and any residual buffer from the pellet and resuspend pellet gently but thoroughly into a total of 10 ml pre-warmed Phosphate Buffered Saline, pH 7.4 (PBS) at 30° C. This is the 1× D23 (Test Organism) suspension to use for the following steps.
5. Prepare 1×, 0.1× and 0.01× suspensions of the Test Organism in pre-warmed PBS supplemented with 2 mM NH$_4$Cl, or a Vehicle control solution, in 50 ml polypropylene tubes as shown below.
6. Draw 2.0 ml of each suspension using a repetitive pipet.
7. Drip slowly 0.2 ml of the Test Organism (1×, 0.1×, 0.01× groups), or an equal volume of Vehicle control, onto each wound and surrounding shaved skin area. Gently spread applied suspension onto the wound and the entire shaved skin area using a pipet tip.
8. Repeat application of Test Organism or Vehicle control daily for a total of 14 days.
9. Measure wound size by wound planimetry and obtain photo images of each wound on Day 1, 3, 5, 7, 9, 11, 13 and 15 using Image Analyzer (Image-pro plus version 4.5, Media Cybernetics Inc).
10. Calculate % wound closure and wound half-closure time ($CT_{50}$) for each group.

TABLE 9

| GROUP | 1x D23 (ml) | PBS pH 7.4 (ml) | 1M NH$_4$Cl (μl) | CFU/ml | CFU/wound |
|---|---|---|---|---|---|
| Vehicle (control) | — | 5.0 | 10 | 0 | 0 |
| 1x D23 | 5.0 | 0 | 10 | $10^9$ | $2 \times 10^8$ |
| 0.1x D23 | 0.5 | 4.5 | 10 | $10^8$ | $2 \times 10^7$ |
| 0.01x D23 | 0.05 | 4.95 | 10 | $10^7$ | $2 \times 10^6$ |

Day 15 (Upon Study Completion): Collection of Wound Tissues Samples and Histopathology Analyses 1. Obtain half-wound tissue samples from four mice per group using aseptic technique to avoid cross-contamination of tissues.
2. Proceed with histopathology analyses.
3. Store temporarily at −70° C. the remainder half-wound samples and the additional four full-size wound tissues from each group for further evaluation.

Figure 5A:
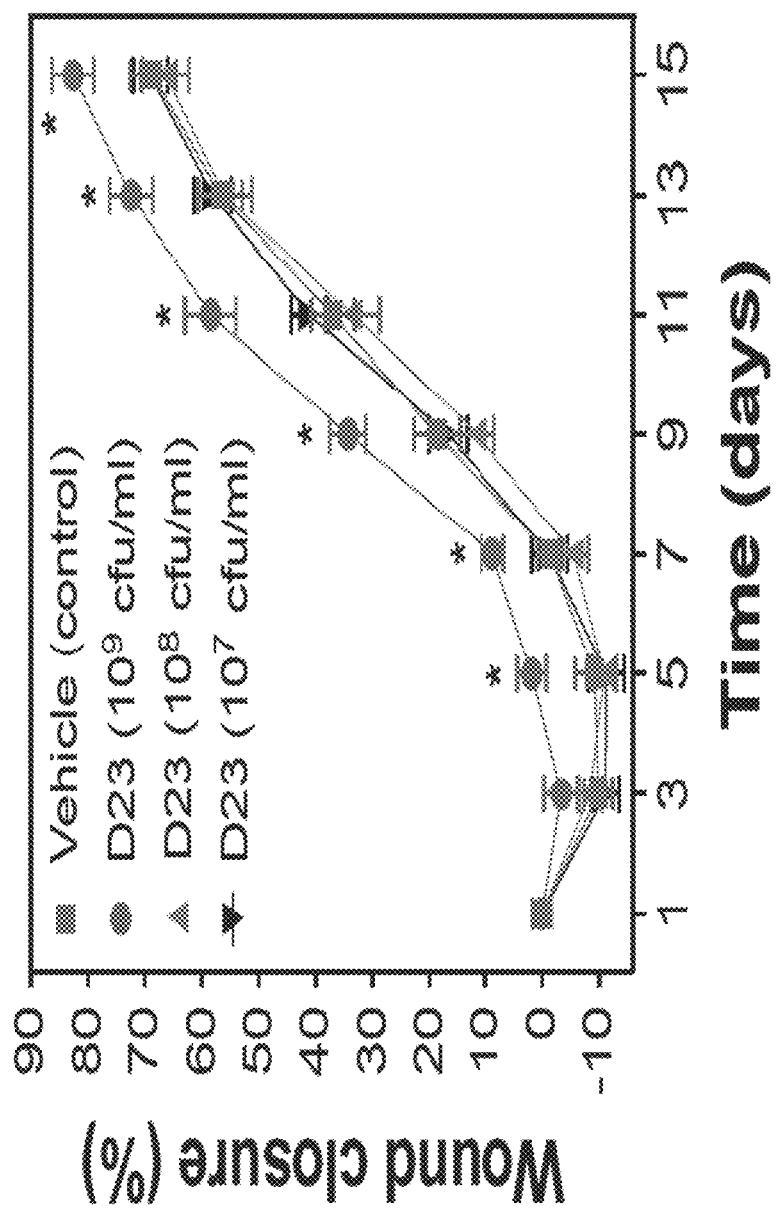
FIG. 5A plots the percent wound closure over time in an experiment testing D23's ability to improve wound healing.

As shown in FIG. 5A, topical application of $10^9$ CFU/ml of strain D23 significantly (*p<0.05) accelerated wound healing. The sample size was N=8 animals/gp. The group receiving the highest doses showed significant improvement in would closure from day 5 to day 15, with the most pronounced improvement of 83% observed on day 9, post-wounding. This study demonstrates the potential therapeutic benefit of ammonia oxidizing bacteria, e.g., D23, to diabetic foot ulcers, chronic wounds, and other related indications.

Figure 5B:
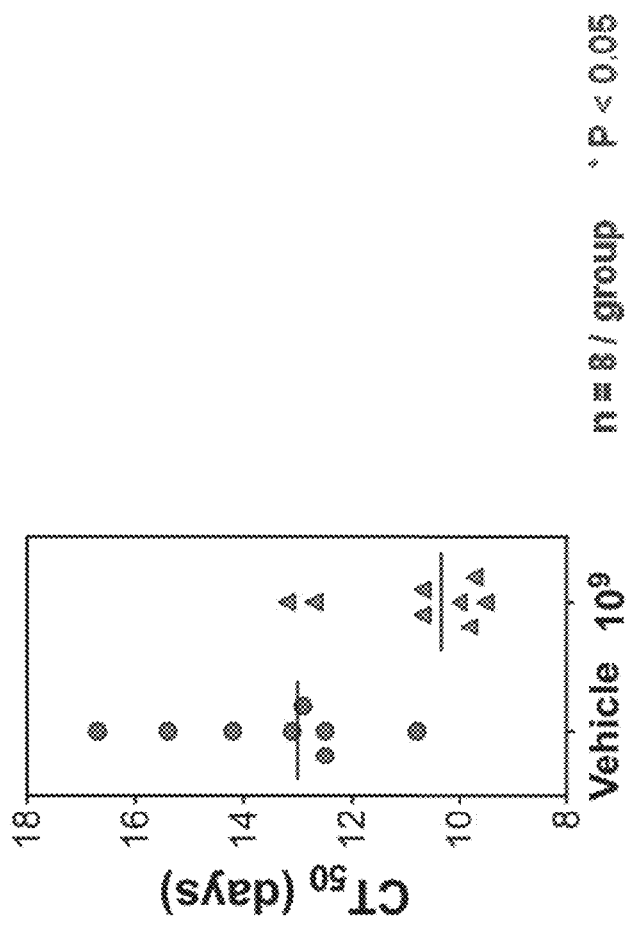
FIG. 5B plots $CT_{50}$ for various D23 treatments.

FIG. 5B is a plot showing $CT_{50}$ versus control (vehicle) and $10^9$ CFU/ml D23. CT50 is the time required to achieve a 50% wound closure. As shown in the plot, those wounds having application of D23 provided for lower $CT_{50}$ values.

Figures 5C, 5D:
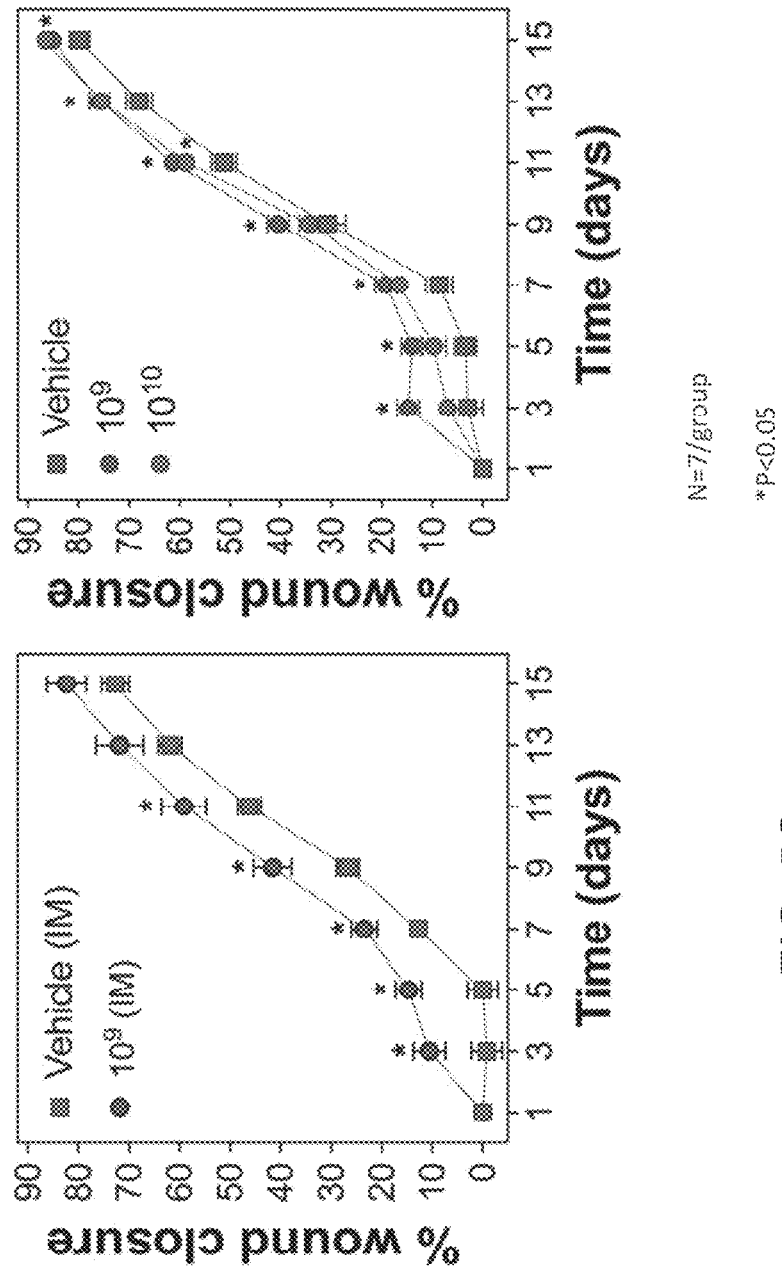
FIG. 5C plots the percent wound closure over time in an experiment testing D23's ability to improve wound healing.
FIG. 5D plots the percent wound closure over time in an experiment testing D23's ability to improve wound healing.

FIG. 5C is a plot of another experiment in which the protocol above was carried out to obtain wound closure measurements versus time. Control (vehicle) wounds were tested and compared to D23 at $10^9$ CFU/ml wounds. This plot shows the effects of D23 when immersion pre-treatment and topical application was carried out.

FIG. 5D is a plot of another experiment in which the protocol above was carried out, without immersion pre-treatment, to obtain wound closure measurements versus time. Control (vehicle) wounds were tested and compared to applications of D23 at $10^9$ CFU/ml and $10^{10}$ CFU/ml to wounds. This plot shows the effects of D23 when topical application was carried out.

Figure 5E:
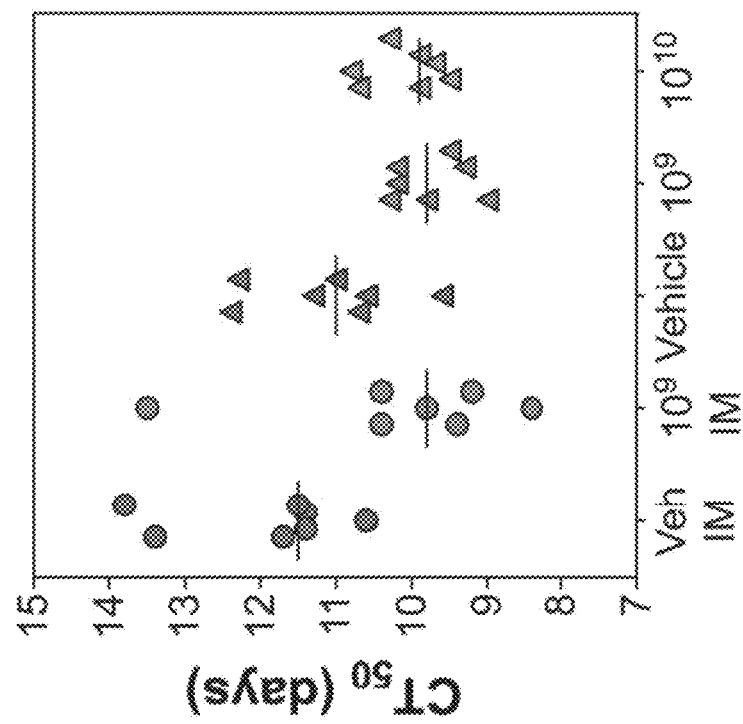
FIG. 5E plots $CT_{50}$ for various D23 treatments.

FIG. 5E is a plot showing $CT_{50}$ versus control (vehicle) and $10^9$ CFU/ml D23, with and without immersion pre-treatment, and $10^9$ CFU/ml D23 without pre-treatment. As shown in the plot, those wounds having application of D23 provided for lower CT50 values.

Figure 5F:
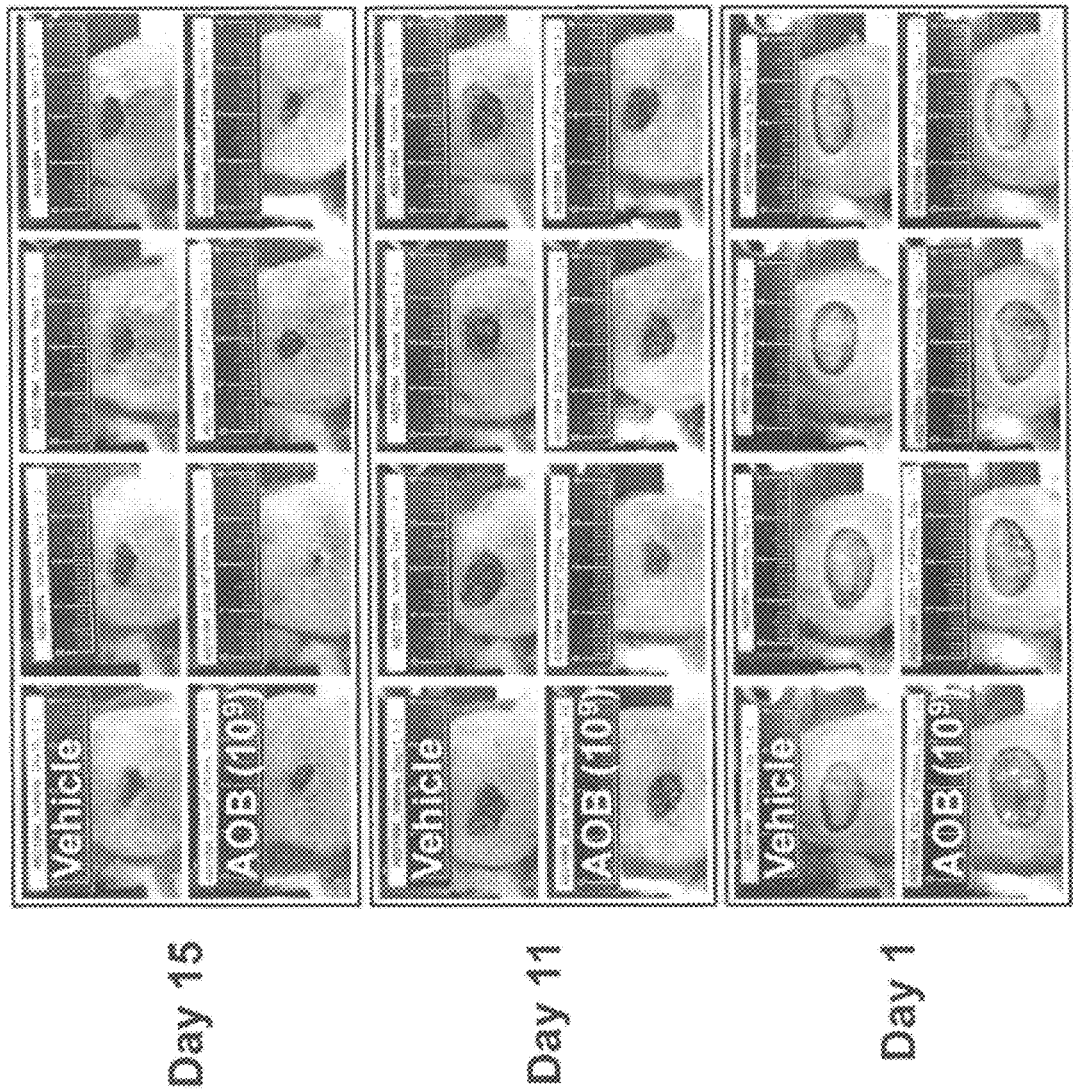
FIG. 5F shows images of D23 enhanced wound healing in diabetic mice at Day 1, Day 11, and Day 15.

FIG. 5F are images of the wound healing experiments, at Day 1, Day 11, and Day 15. AOB represents D23.

Possible modulation of inflammatory responses coupled with ant-infective action of D23 could prove an effective topical treatment against diabetic and other chronic wounds.

Figure 5G:
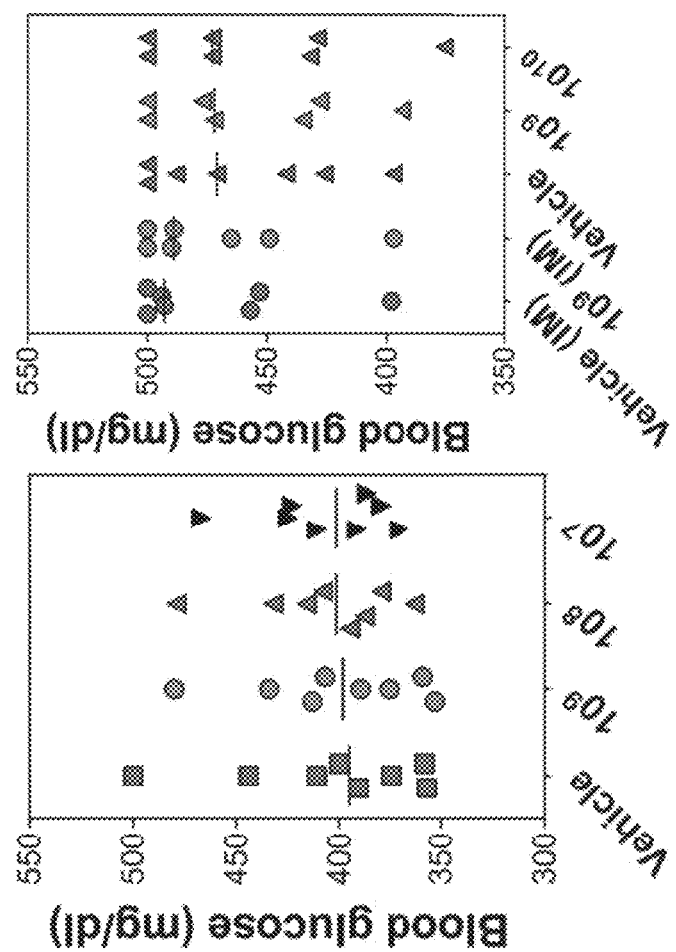
FIG. 5G shows blood glucose measurements for various concentrations of D23.
Figure 5H:
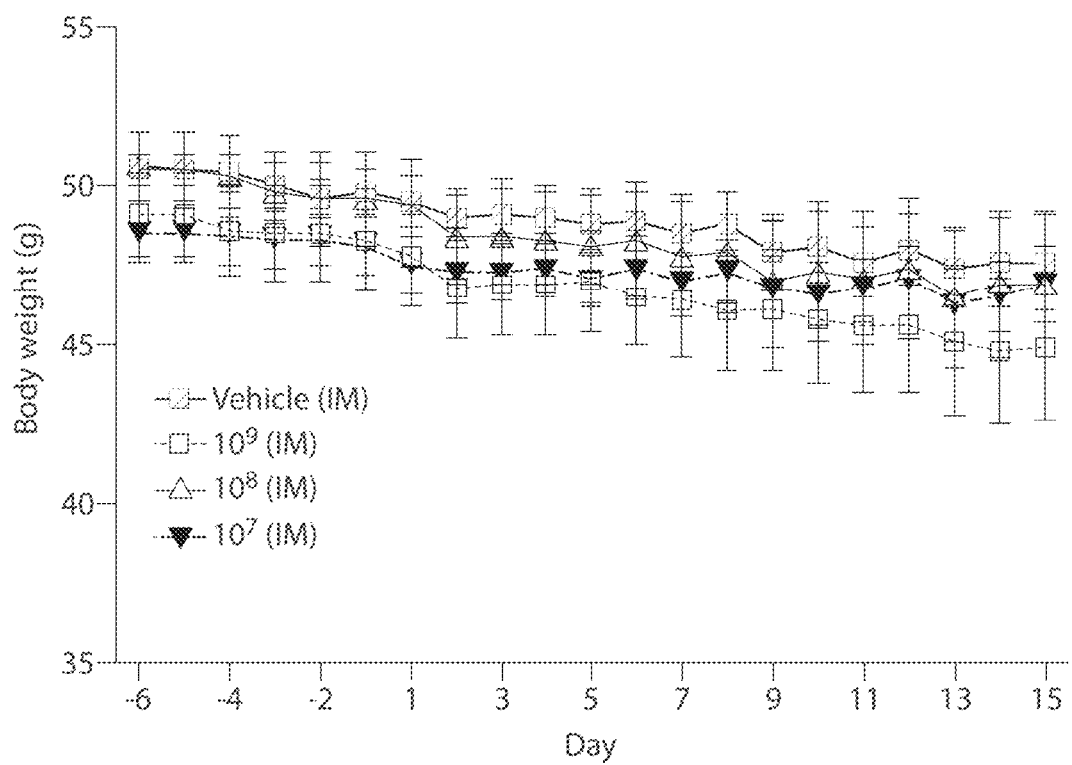
FIG. 5H shows body weight of test subjects over the course of testing.
Figure 5J:
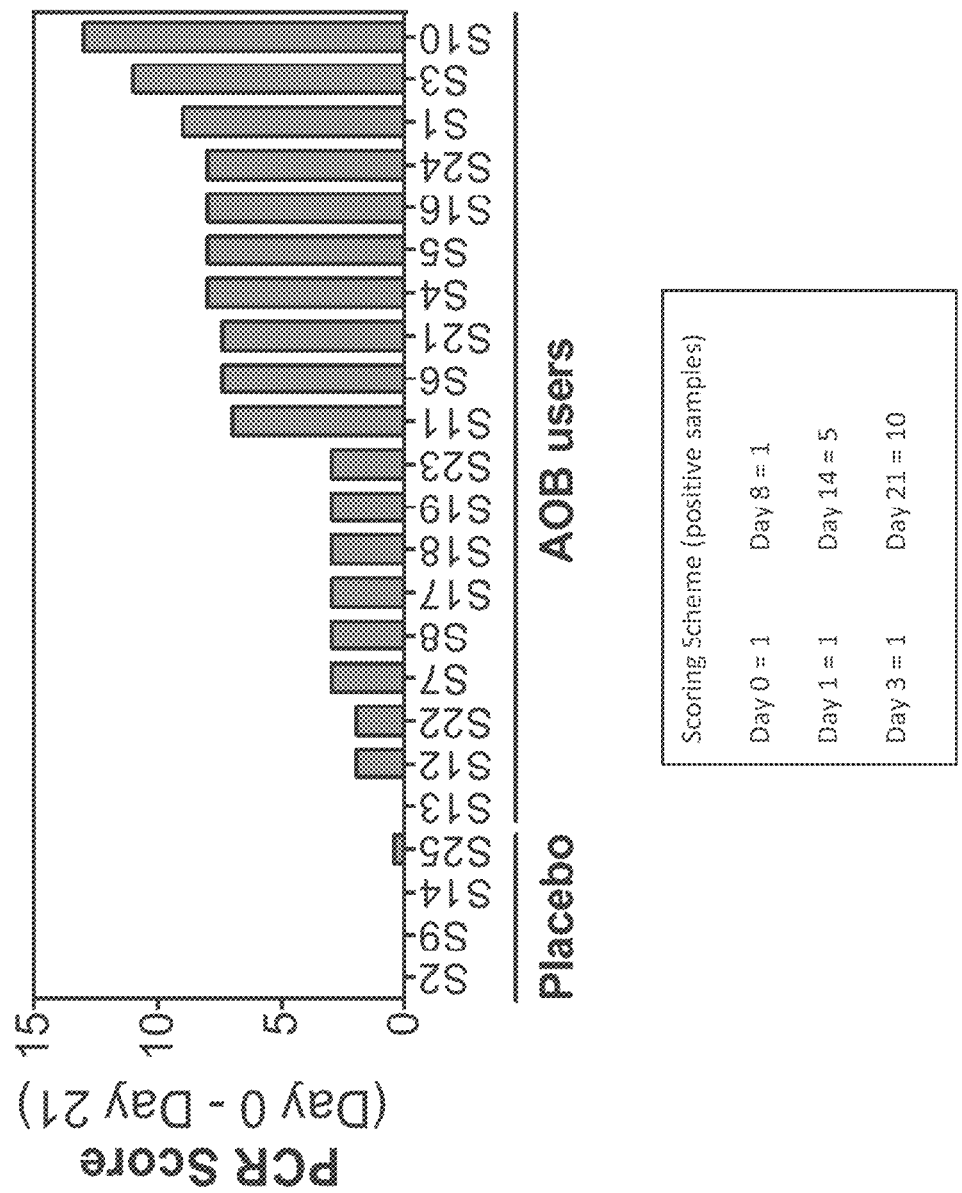
FIG. 5J shows PCR scores for a scalp test of subjects. AOB refers to D23 in this Figure.

FIG. 5G are plots of blood glucose levels in the mice tested for the control (vehicle) and various concentrations of D23. "IM" shown in the x-axis of the right-hand panel plot represents those tests down with an immersion pre-treatment of D23. FIG. 5H is a plot of body weight of the animals used in testing for the study including immersion pre-treatment, over the time of the study. FIG. 5I are plots of body weight of the animals used in testing for the study, including the immersion pre-treatment study, and the study done without immersion pre-treatment, over the time of the studies.

In Study 2, the effect of pretreatment of db/db mice with $10^9$ cells/ml of B244 on wound closure was examined. Groups of seven mice were treated topically with $10^9$ cells/ml of B244 with and without prior body immersion. One additional group of seven mice was treated topically with $10^{10}$ cells/ml of D23 (B244). Corresponding vehicle groups (seven mice) were run in parallel with and without body immersion as negative controls. Wound surface area and photo images of each wound were obtained as before. These studies reproduced the findings of Study 1 suggesting improvement of wound closure with a B244 dose of approximately $10^9$ cells/ml. Moreover, topical treatment alone with $10^9$ cells/ml improved wound closure rates similar to the animals receiving topical treatments with immersion. Additional histopathology analyses by of H & E-stained wound tissue sections recovered on Day 5 did not reveal any differences between vehicle and D23 (B244)-treated wounds.

Cytokine and growth factor expression in D23-treated diabetic animals was investigated using Luminex technology. Specifically, expression of growth-regulated oncogene/keratinocyte chemoattractant (Gro/KC), interleukin-1 (IL-1), interleukin-6 (IL-6), macrophage inflammatory protein-2 (MIP-2), tumor necrosis factor (TNF), and vascular endothelial growth factor (VEGF) was compared between D23-treated and control diabetic animals in serum samples obtained on Day 5 and Day 15 from four mice per group treated with or without prior body immersion. In similar Luminex analyses, lysates of tissues from D23-treated or Vehicle control animals obtained upon completion of the study (Day 15) were also analyzed. Abnormally high and sustained expression of inflammation markers, including MIP-2, TNFα and IL-1β, has been previously associated with a dysregulated inflammatory response and impaired wound healing processes in db/db mice (Wetzler, 2000). Analyses of Day 5 and Day 15 serum samples yielded very low signal for all six cytokines in both D23-treated and vehicle control animals, a result indicating the lack of systemic effects following wound treatment with high D23 doses. In wound tissue lysates obtained on Day 15, MIP-2 levels (1155-1516 pg/100 g total protein) were significantly higher than the remaining five cytokines, with IL-6 and Gro/KC measured at much lower levels (44-48 pg/100 g total protein) and both IL-1 and VEGF being close to undetectable (≥3.8 pg/100 g total protein). Overall, no difference was observed between D23-treated animals and vehicle control animals with or without full-body immersion in D23 suspensions. The levels of all six cytokines or growth factors measured in tissue lysates of all four groups of mice examined are summarized in Table 10 below.

TABLE 10

Cytokine levels measured in wound tissue lysates of D23-treated and vehicle control-treated db/db mice

| Treatment | Animal | Gro/KC (pg/100 g protein) | IL-1β (pg/100 g protein) | IL-6 (pg/100 g protein) | MIP-2 (pg/100 g protein) | TNFα (pg/100 g protein) | VEGF (pg/100 g protein) |
|---|---|---|---|---|---|---|---|
| Vehicle | 1-1 | 49 | 2.4 | 78 | 1089 | 28.7 | 5.8 |
| (with prior | 1-3 | 66 | 2.4 | 134 | 1335 | 31.2 | 4.5 |
| immersion) | 1-5 | 59 | 2.7 | 128 | 1112 | 25.7 | 4.2 |
|  | 1-7 | 76 | 1.2 | 148 | 1013 | 9.4 | 4.1 |
|  | MEAN | 62 | 2.2 | 122 | 1137 | 23.7 | 4.7 |
| D23 | 3-1 | 49 | 2.1 | 66 | 1830 | 24.7 | 4.1 |
| $10^9$cells/ml | 3-3 | 75 | 1.8 | 162 | 1615 | 32.3 | 3.6 |
| (with prior | 3-5 | 50 | 2.4 | 132 | 1896 | 23.9 | 4.3 |
| immersion) | 3-7 | 17 | 1.5 | 28 | 720 | 9.0 | 3.4 |
|  | MEAN | 48 | 1.9 | 97 | 1516 | 22.5 | 3.8 |
| Vehicle | 5-1 | 43 | 1.5 | 90 | 833 | 13.2 | 3.6 |
| (topical | 5-3 | 55 | 2.2 | 104 | 1312 | 18.6 | 3.6 |
| only) | 5-5 | 44 | 1.4 | 59 | 644 | 17.6 | 3.2 |
|  | 5-7 | 100 | 3.8 | 168 | 1308 | 48.6 | 4.0 |
|  | MEAN | 60 | 2.2 | 105 | 1024 | 24.5 | 3.6 |
| D23 | 6-1 | 82 | 2.2 | 105 | 1573 | 28.5 | 2.9 |
| $10^9$cells/ml | 6-3 | 18 | 0.8 | 36 | 943 | 8.0 | 2.5 |
| (topical | 6-5 | 25 | 1.2 | 45 | 1027 | 9.5 | 2.2 |
| only) | 6-7 | 49 | 1.5 | 92 | 1077 | 18.5 | 2.9 |
|  | MEAN | 44 | 1.4 | 69 | 1155 | 16.1 | 2.6 |

Pharmacokinetic evaluation of D23 (B244) in rodents was conducted during a 28-day repeat dose toxicology study as described in the section below. No separate single dose pharmacokinetic studies were run for D23 (B244).

Example 7: Toxicology

28-Day Safety Study of *Nitrosomonas eutropha* D23 (B244) Application on Full-Thickness Wounds of Streptozotocin-Induced Diabetic Sprague-Dawley Rats The objectives of this study were to determine the potential toxicity of *Nitrosomonas eutropha* D23 (B244) in rats when given dermally on wounded skin for a minimum of 28 days, and to evaluate the potential reversibility of any findings. In addition, the toxicokinetic characteristics of D23 (B244) were determined.

Study Design and Methods

The design was based on the study objectives, the overall product development strategy for the test article, and the following study design guidelines: OECD Guidelines 407 and 417, Committee for Human Medicinal Products (CHMP), and ICH Harmonised Tripartite Guidelines M3 (R2), S3a, and S6 (R1). The study design is outlined herein and results are shown in Table 11.

For induction of diabetes, Streptozotocin was administered to Sprague Dawley rats via intraperitoneal injection on Day −4. Animals with blood glucose levels of >200 mg/dL were considered as responders to the Streptozotocin treatment and were used for the dosing phase of the study. Two full-thickness skin wounds were created per animal (1 on each side of the back of each anesthetized animal) using an 8-mm skin biopsy punch. The wounds were left uncovered during administration of the control and test article and also for the duration of the study. The test and control articles were administered to the appropriate animals dermally once daily (for 24 hours±1 hour) from Days 1 to 28. The end points evaluated in this study were the following: clinical signs, dermal findings, body weights, body weight changes, food consumption, ophthalmology, glucose analysis, clinical pathology parameters (hematology, coagulation, clinical chemistry, urinalysis, hemoglobin A1c, and methemoglobin), C-reactive protein and serum ferritin analysis, toxicokinetic parameters, gross necropsy findings, organ weights, and wound histopathology.

Results

The results for the endpoints evaluated in the 28-day GLP toxicology study are outlined below in Table 12.

TABLE 11

28-Day Safety Study design

| Group No. | Test Material | Dose Level (CFU/kg/day) | Dose Volume (mL/kg) Split | Dose Conc. (CFU/mL) | No. of Animals Main Study M | Main Study F | Recovery M | Recovery F |
|---|---|---|---|---|---|---|---|---|
| 1 | Control Article | 0 | 0.8 | 0 | 10 | 10 | 5 | 5 |
| 2 | AOB-D23-100 | $6 \times 10^7$ | 0.8 | $8 \times 10^7$ | 10 | 10 | 0 | 0 |
| 3 | AOB-D23-100 | $6 \times 10^8$ | 0.8 | $8 \times 10^8$ | 10 | 10 | 0 | 0 |
| 4 | AOB-D23-100 | $6 \times 10^9$ | 0.8 | $8 \times 10^9$ | 10 | 10 | 5 | 5 |

M = Male, F = Female, Conc. = Concentration, CFU = Colony Forming Unit.
Control Article = 99.998% Phosphate Buffered Saline, pH 7.4 (PBS), 0.002% 1M NH4Cl

TABLE 12

28-Day Safety Study-Results

| End points | Observations | Comments |
|---|---|---|
| Mortality | No unscheduled deaths during the course of the study were attributed to D23 (B244). One control male was found dead on Day 41; the cause of death due to necrosis in the kidney, liver, pancreas, and spleen | |
| Clinical Observations | No test article D23 (B244)-related clinical signs were observed during the study. Clinical signs including abdominal distension, prominent backbone, fur staining, soft stools and ungroomed appearance were related to the diabetic state of the animals Skin discoloration (red/black) was present in both control and treated animals | Similar clinical signs have been previously associated with an uncontrolled diabetic state in rats and other animal models |
| Dermal Scores | No dermal irritation occurred during the study No erythema or edema was observed following dermal administration of the test article | |
| Body Weights and Body Weight Changes | No D23 (B244)-related effects on body weight or body weight change were noted during the study. Mean weight gain was observed throughout the study interval, with isolated instances of slight loss in individual animals across the dose groups which did not follow specific dose-related trends | |
| Food Consumption | There were no test article-related effects on food consumption. | |
| Ophthalmic Examinations | There were no D23 (B244)-related ophthalmologic changes during the study. The majority of the animals on study developed cataracts and there were no differences among dose groups. | The appearance of cataracts is a known complication of diabetes |
| Hematology, Coagulation, Hemoglobin A1c, and Methemoglobin | No test article-related changes were noted in hematology, coagulation, hemoglobin A1c, and methemoglobin parameters on Day 29 or 43. Isolated statistically significant differences were noted during the study; however, the values were within the historical control ranges and were not considered meaningful | |
| Clinical Chemistry | No test article-related changes were noted on Days 29 or 43. Isolated statistically significant differences were noted during the study; however, the values were within the historical control ranges and not considered meaningful | |
| Urinalysis | No test article-related effects | |
| C-reactive Protein and Serum Ferritin Analysis | No test article-related effects | |
| Gross Pathology | No test article-related gross findings were noted on Day 29 or Day 43 | Any gross findings observed were considered to be related to the diabetic condition of the rats and incidental in nature |
| Organ Weights | There was an increase in adrenal weight in females at $\geq 6 \times 10^8$ CFU/kg/day on Day 29, whereas adrenal weight was decreased in males and there were no associated gross pathology findings making the association of this finding to D23 (B244) administration equivocal Potential D23 (B244)-related organ weight changes noted at the terminal euthanasia (Day 29) were not observed at the end of the recovery period (Day 43) | |
| Histopathology Terminal Euthanasia (Day 29) | No D23 (B244)-related microscopic findings on Day 29. Changes observed in the kidneys, large and small intestine, and urinary bladder were related to the diabetic state of the animals. The incidence and severity of these | |

TABLE 12-continued

28-Day Safety Study-Results

| End points | Observations | Comments |
|---|---|---|
| | findings were similar in all study groups including controls. Changes at the administration/wound sites included epidermal regeneration, fibrosis, and granulomatous inflammation. The incidence and severity of these findings were similar in all groups including controls | |
| Histopathology Recovery Euthanasia (Day 43) | Changes observed on Day 43 were similar to those reported on Day 29 | |

Conclusions
- Once daily application of D23 (B244) on rat wounds was well tolerated at levels of $6 \times 10^7$, $6 \times 10^8$, and $6 \times 10^9$ CFU/kg/day.
- No D23 (B244)-related mortality observed during the study
- Healing of full tissue thickness excisions was similar in all groups
- No D23 (B244)-related clinical signs or dermal irritation were observed
- No effects observed during the study on body weight, food consumption, clinical pathology parameters, c-reactive protein, or serum ferritin
- No test article-related gross necropsy findings or histopathologic findings
- The no-observed-adverse-effect level (NOAEL) was determined to be $6 \times 10^9$ CFU/kg/day ($8 \times 10^9$ cells/ml)
- No specific target organs were identified No D23 related mortality occurred during the study. There were no D23-related clinical signs or dermal irritation, and there were no effects on body weight, body weight changes, food consumption, clinical pathology parameters, C-reactive protein, or serum ferritin during the study. There were no test article-related gross necropsy findings or histopathologic findings. Increases in adrenal weights were noted in the $>6 \times 10^8$ CFU/kg/day females on Day 29; however, association with D23 was considered equivocal based on the lack of a similar effect in the males, the lack of corresponding gross findings, and the lack of microscopic evaluation of this tissue.

All wound sites were completely covered by epidermis and appeared to be in the remodeling/resolution phase, which was characterized by stratification of the epidermis with keratinization and refinement of the dermal collagen (synthesis, bundling, and degradation) and capillaries to restore the normal architecture of the epidermis and dermis. The incidence and severity were similar in all groups, including controls.

Example 8: Antibiotic Susceptibility

The activities of five antibiotics, each representing a different antibiotic class, were tested against *Nitrosomonas eutropha* D23. The antibiotics tested included clindamycin, erythromycin, gentamicin, piperacillin with or without the β-lactamase inhibitor Tazobactam, and tetracycline. These were chosen based on the Clinical and Laboratory Standards Institute (CLSI) recommendations for routine testing and reporting of phylogenetically-related proteobacteria (*Pseudomonas aeruginosa*) listed under Non-fastidious organisms and Non-Enterobacteriaceae in the CLSI 24th Informational Supplement (M100-S24), and also included topical or systemic antimicrobial agents commonly used against acne, such as clindamycin or tetracycline. Studies with clindamycin were included even though this antibiotic was not expected to be very effective at inhibiting *Nitrosomonas*, as is the case for other aerobic Gram-negative bacteria.

Minimal Inhibitory Concentrations (MICs) were determined by culturing *N. eutropha* D23 in decreasing concentrations of each of the five antibiotics. Bacterial growth at 30° C. was monitored for 48-72 hr by determining optical density ($OD_{600}$) values in samples collected at 24 hr intervals. MIC values were identified as the lowest antibiotic concentration from a two-fold dilution series leading to no increase in $OD_{600}$ measurements for the 2 or 3-day incubation period. The *N. eutropha* D23 phenotype in each antibiotic test was determined as Susceptible, Intermediate, or Resistant according to the MIC Interpretive Criteria provided by the CLSI. As summarized in Table 13, these studies demonstrated susceptibility of *N. eutropha* D23 to erythromycin and gentamicin and intermediate resistance to tetracycline and piperacillin suggesting the lack of strong antibiotic-resistance potential by the Drug Substance. Clindamycin resistance observed for *N. eutropha* D23 is in agreement with previous reports for natural resistance of aerobic Gram-negative bacteria to this antibiotic. In addition to testing the β-lactam antibiotic piperacillin alone, the broad range β-lactamase inhibitor Tazobactam was also tested in combination with piperacillin to assess the possible expression of β-lactamase(s) by *N. eutropha* D23. The results from this comparison showed no increase in *N. eutropha* D23 susceptibility, indicating the absence of β-lactamase expression by *N. eutropha* D23, at least under the conditions tested.

TABLE 13

MIC values for five antibiotics tested against
*N. eutropha* D23 cultures in vitro

| Antibiotic | Antibiotic Class | MIC (μg/ml) | MIC Interpretive Criteria* |
|---|---|---|---|
| Clindamycin | Lincosamide | >16 | Resistant (≥4 μg/ml) |
| Erythromycin | Macrolide | 0.16 | Susceptible (≤0.5 μg/ml) |
| Gentamicin | Aminoglycoside | 0.25 | Susceptible (≤4 μg/ml) |
| Piperacillin | β-lactam | 64 | Intermediate (32-64 μg/ml) |

TABLE 13-continued

MIC values for five antibiotics tested against
N. eutropha D23 cultures in vitro

| Antibiotic | Antibiotic Class | MIC (μg/ml) | MIC Interpretive Criteria* |
|---|---|---|---|
| Piperacillin/ Tazobactam | β-lactam/ β-lactamase inhibitor | 64/4 | Intermediate (32/4-64/4 μg/ml) |
| Tetracycline | Tetracycline | 8 | Intermediate (8 μg/ml) |

*as recommended by the Clinical and Laboratory Standards Institute (values in parentheses represent MIC levels for corresponding Susceptible, Intermediate or Resistant outcomes)

Conclusions

These studies demonstrate susceptibility of D23 (B244) to macrolide and aminoglycoside antibiotics and resistance to lincosamides, results that indicate the lack of strong antibiotic-resistance potential by the Drug Substance.

Example 9: Elucidation of Structure of N. eutropha

N. eutropha was defined at the species and the strain level using PCR and gene sequencing methodologies. The species level was defined as N. eutropha by sequencing of the V1-V5 variable regions of the 16S rRNA gene. N. eutropha was defined as a novel N. eutropha strain D23 by identification of a unique gene from whole genome sequence analysis. N. eutropha was defined at the species level as N. eutropha by 16S rRNA gene sequencing using the MicroSeq 500 rDNA Bacterial Identification PCL and sequencing kit.

Strain identity may be determined using custom primers, which correspond to the underlined portions of the following sequence and the D23 1c1355 sequence & primers Table 14 below. While not wishing to be bound by theory, it is believed that gene D23 1c1355 is unique to N. eutropha D23, and thus performing a PCR amplification reaction within gene D23 1c1355 will indicate whether N. eutropha D23 is present in a given sample.

TABLE 14

D23_1c1355 sequence & primers

| Primer | Sequence (5' - 3') | Tm (° C.) | Position | Product size (bp) |
|---|---|---|---|---|
| D23_1c1355-F | AATCTGTCTCCACAGGCAGC (SEQ ID NO: 64) | 54 | 287 - 305 | 595 |
| D23_1c1355-R | TATACCCACCACCCACGCTA (SEQ ID NO: 65) | 54 | 881 - 862 | |

D23_1c1355 outer membrane autotransporter barrel domain-containing protein

```
TTGGTTGGTTTGAAACAGGTAAGGGAGAAGGAGGAAAATCGCCAGAATATCGTCGCCAAA
         10        20        30        40        50        60

GGTTATCGGATCACCATAGCTTATCCACTCAAAGGGGAGATTATCATGAGCAAGGTTCGT
         70        80        90       100       110       120

CGATTAAAAAAGAGTTTATATACGGTTACTGCACTAACTCTCGGTTTCGGACCATTTGTG
        130       140       150       160       170       180

ACAGCGAGTGGACAATCATTCGAAGAAACACCCGTACAAACACCCGGACGAGCTTTTGCA
        190       200       210       220       230       240

GTGGACAATTTAAAGGGTATCTGTGTACAAAACACAAGTGAAGACCCCTCATTAGCAATA
        250       260       270       280       290       300

GCTTGCACCTTCGCACTGGGCGGGATAAATGATATTACCGCGCAGAATCTGTCTCCACAG
        310       320       330       340       350       360

GCAGCGATTCAGGCCGAGTCGATCGCGATTACTTCTCCCTATCAGTTTATTCGCAGCACG
        370       380       390       400       410       420

AATGAAAGCATACAGCGGCTAACAGGTCGCTCTGCTGAGAAACGTCAGCAACAATCCTCT
        430       440       450       460       470       480

TTTTTACTACAAAGCTCAGCGTCGGTAGCAGGCACGCCATCATTTGGCACTTCTGGTTTT
        490       500       510       520       530       540

ATAGGGCCTGTAGGGGTTTCGCTGAGCGGTGGCGGGAGCTTTGGTGAACGCAATACCGCT
        550       560       570       580       590       600

GAAGGGCAGACCGGTTTTCAATTGAATACCCGGCAAACCAGCCTGATGATCGATTATTCA
        610       620       630       640       650       660

TTTAATCAAAAATTGATTGGCGGCTTTTCCTTTAATTATCTGGGGACAGATCGTAATTTG
        670       680       690       700       710       720

AGATTGGCGAGTGGGGACTTGAATTCCGATAGCTATCGGTTTGCACCCTTTGTGCTTTTC
        730       740       750       760       770       780

AGACCAACTACCAATAGCTACTTAACTCTGATGGGAGGGTATGCTTTGGTTAATTATCGT
        790       800       810       820       830       840

TCCACGCGCAGCGTTTCGAGTCAAAATGACATCACGTTTGATAACGCCACAGCCAACTAT
        850       860       870       880       890       900
```

TABLE 14-continued

D23_1c1355 sequence & primers

```
GATGCTAATCAGTTTTTTGCTAGCGTGGGTGGTGGGTATACCTTTACTTTAATGGATGGA
        910       920       930       940       950       960

TGGAATCTGCGAGGATATGGTCGCGGGGACTTTAGTGATATTAGTATCCAGAGCTTTCAG
        970       980       990      1000      1010      1020

GAAAAAGGTGGCGTTGCTCATAGTGGGAACGATAGTTTATCTCTTGCTATGTCTGTGAAT
       1030      1040      1050      1060      1070      1080

AAACAAACCATACGCTCGGTTACCAGTACATTAGGCGTTGAACTTAGTCATGCAATTAGC
       1090      1100      1110      1120      1130      1140

ACCAGAACTTTTATTCCCGTCATTATCCCGAGACTGCGTGCAGAATGGGTGCATGAATTT
       1150      1160      1170      1180      1190      1200

GAAAACAATGCCAGAACTATCACGGCCGGTTTCACTGGCCAGAACTATAGTCCCACTTCT
       1210      1220      1230      1240      1250      1260

GCATCAATGGCAGTTGCAAGCTCAGTGCGTAATTGGGCAAACCTGGGGGTTGGAGTGCAA
       1270      1280      1290      1300      1310      1320

ATGCTGTTTGCCCGCTCGATTATCGGGTACATTAATTACGACAGATTAATTATCAAGCAC
       1330      1340      1350      1360      1370      1380

GCGGAGAACAATATCATTTCTGGTGGGATTCGTATGAATTTCTAA (SEQ ID NO: 66)
```

Example 10: Administering Ammonia Oxidizing Bacteria to the Back of the Head to Change the Skin Microbiome Ammonia oxidizing bacteria (*N. eutropha* D23) was applied topically to the back of the head of a subject for over 2 weeks. The dose was $3 \times 10^{10}$ CFU applied per day. The product concentration was $1 \times 10^9$ CFU/ml (15 ml, two times a day) in a phosphate buffer with magnesium chloride. On each day a skin swab was taken to isolate and sequence all the bacterial DNA that was present, using isolation and sequencing protocols known in the art.

Ammonia oxidizing bacteria of the genus *Nitrosomonas* was not present in the Day 0 sample, and was detected and present in the Day 7, 14, and 16 skin swabs.

As shown in FIGS. 17 and 18, which plots the proportion versus bacterial genus for Day 0, 1, 8, 14, and 16, the application of ammonia oxidizing bacteria led to proportional increases in commensal non-pathogenic *Staphylococcus* (which was at least 98% *Staphylococcus epidermidis*) from close to 0% on day 0 to approximately 50% on day 16. Additionally, application of ammonia oxidizing bacteria led to a proportional reduction in potentially pathogenic or disease associated *Propionibacteria* over the time period tested (from over 75% on day 0 to less than 50% on day 16). Application of ammonia oxidizing bacteria also led to reductions in potentially pathogenic or disease associated *Stenotrophomonas* over the time period tested (from 0.1% on day 0 to less than 0.01% on day 16.)

Some of the data shown in FIGS. 1 and 2 is also presented below in Table 15.

TABLE 15

Genera by Day

| Day | Proportion by genus: *Propionibacteria* | Proportion by genus: *Staphylococci* | Proportion by genus: *Stenotrophomonas* |
|---|---|---|---|
| 0 | 0.78 | 0.01 | 0.13 |
| 1 | 0.79 | 0.1 | 0 |
| 8 | 0.8 | 0.15 | 0 |
| 14 | 0.55 | 0.45 | 0.001 |
| 16 | 0.48 | 0.49 | 0 |

As shown in Table 15, the proportion of *Propionibacteria* was reduced after about 14 days (compare data for Day 0, 1, and 8 with Day 14 and 16 in Table 15). The proportion of Staphylococci increased after about two weeks (compare data for Day 0, 1, and 8 with Day 14 and 16 in Table 15). The proportion of *Stenotrophomonas* decreased after about 1 day (compare data for Day 0 with Day 1, 8, 14, and 16 in Table 15).

These changes in the skin microbiome composition to a less pathogenic state indicate that application of ammonia oxidizing bacteria would be useful in treatment of dermatologic diseases including but not limited to acne, eczema, skin infections, and rosacea.

Example 11: Studies with Ammonia-oxidizing Bacteria for the Human Skin: Cosmetic Effects, Safety, Detection and Skin Metagenomics A blinded, placebo-controlled 24 human volunteer study randomized 4:1 AOB to placebo control was performed. Subjects applied a *Nitrosomonas* suspension ($10^9$ CFU/ml, 2 times per day, for a total of $3 \times 10^{10}$ CFU per day) to their face and scalp twice daily for one week and were followed for two additional weeks post-application. Volunteers were instructed to refrain from using hair products during the one-week AOB application as well as the week following application, then returned to regular shampoo use for the third week. Scalp swabs were obtained on Day 0 as baseline controls and on Day 1, 3, 8, 14 and 21 to assess presence/absence of AOB by PCR and 16S rRNA sequencing analyses.

No serious adverse events were associated with AOB application for one week and the product was deemed safe. AOB users reported a clear improvement in skin condition and quality, as indicated by self-assessment reports completed after the seven-day application period. Using AOB-specific PCR analyses of the skin samples, we could demonstrate presence of the bacteria in 83-100% of AOB users during the application period, whereas no AOB were detected in the placebo control samples. All subjects lacked AOB from baseline swabs obtained prior to study initiation, consistent with the predicted sensitivity of these bacteria to soaps and other commercial products. Amplification of the 16S rRNA gene and sequencing of a subset of samples confirmed presence of AOB in corresponding samples and suggested potential trends in modulating the skin microbiome by topical AOB application. In summary, live AOB-based products are safe and could hold great promise as novel self-regulating topical delivery agents of nitrite and nitric oxide to the human skin.

As shown in Table 16, below, the proportion of *Nitrosomonas* (AOB) went up when comparing Day 0 versus Day 8. The proportion of other bacteria, *Propionibacterium, Enterobacter*, and *Citrobacter* went down, when comparing Day 0 versus Day 8. The p-values indicated in Table 16 demonstrate that the most significant change between Day 0 and Day 8 was observed with *Nitrosomonas* (AOB) followed by *Propionibacterium. Enterobacter* and *Citrobacter* also showed changes between Day 0 and Day 8 to a lesser degree.

TABLE 16

Trends in microbiome composition following AOB application (Day 0 versus Day 8)

| Genus | P-value (unadjusted) | Trend |
|---|---|---|
| *Nitrosomonas* (AOB) | 0.0039 | Up |
| *Propionibacterium* | 0.0078 | Down |
| *Enterobacter* | 0.0346 | Down |
| *Citrobacter* | 0.036 | Down |

Because nitrite and nitric oxide have been implicated in critical physiological functions, such as vasodilation, skin inflammation and wound healing, we have hypothesized that AOB may have beneficial effects on both healthy and immunopathological skin conditions by metabolizing ammonia from sweat while concurrently driving skin acidification. We reasoned that *Nitrosomonas* would be safe for human use because they are slow-growing and incapable of utilizing organic carbon sources, they are sensitive to antibiotics, and they have never been linked to animal or human disease. Here we describe a blinded, placebo-controlled 24 human volunteer study where subjects applied a live *Nitrosomonas* suspension to their face and scalp twice daily for one week and were subsequently followed for two additional weeks. Volunteers did not use hair products during the first and second week, then they returned to their regular routine for the third week. Scalp swabs were obtained on Day 0 as baseline controls and on Day 1, 3, 8, 14 and 21 to assess presence/absence of *Nitrosomonas* and to examine microbial diversity. Importantly, no adverse events were associated with topical application. PCR analyses demonstrated presence of the bacteria in 83%-100% of skin swabs obtained from AOB users during or immediately after completion of the one-week application period (Day 1, 3 or 8) and in 60% of the users on Day 14, but not in any of the placebo control samples. All subjects lacked AOB from baseline swabs obtained prior to study initiation. Increased levels of AOB during the one-week application period correlated with a qualitative improvement in skin condition, in contrast to no improvement reported by placebo control subjects. Sequencing of the 16S rRNA gene amplification product obtained from a subset of subjects verified the presence of AOB in corresponding samples and suggested potential modulation of the skin microbiome composition. In summary, live *Nitrosomonas* are well tolerated and may hold promise as novel self-regulating topical delivery agents of nitrite and nitric oxide to the human skin.

Here, we present the results from preliminary studies in humans where we have begun evaluating topical application of a *Nitrosomonas* suspension to the human skin and the potential of using AOB as natural delivery systems of $NO/NO_2^-$ in vivo. We have explored methodologies for AOB detection in skin specimens and the possible effects of AOB in skin microbial communities, as well as collected important user feedback from the early adopters of our topical cosmetic.

Methods

Culture conditions. *N. eutropha* D23 was propagated in batch culture at 28-30° C. in mineral salt medium supplemented with 20-50 mM $NH_4^+$ and sodium carbonate as the carbon source [Ensign et al, 1993]. For continuous culture, D23 was grown at ~$10^9$ cells/ml in a 1 liter mini-Bioreactor (Applikon Biotechnology) at 28° C. using sodium carbonate for both pH neutralization and the carbon source.

Nitrite quantification. Nitrite concentrations in culture supernatants were determined using the Griess colorimetric assay [Hageman and Kucklesby, 1971] and sodium nitrite as standards.

DNA extraction from skin swabs. Samples were maintained in 1 ml of 10% AssayAssure Bioservative (Thermo Scientific) diluted in PBS. Biomass was centrifuged and cells were lysed using a method developed for skin specimens [Grice, 2009] with modifications to the buffer designed to maintain long DNA integrity. DNA was then purified using the PowerLyzer UltraClean microbial DNA isolation kit (Mo Bio Laboratories). *N. eutropha* D23 was identified using a 3-gene PCR signature amplifying the ammonia monooxygenase encoding locus amoCAB.

PCR and library preparation. Full-length 16S rRNA genes were amplified in duplicate reactions using a cocktail of primers and AccuPrime DNA polymerase SuperMix kit (Life Technologies). All PCR products were directly treated with the SMRTbell Template Prep Kit followed by the DNA/Polymerase Binding Kit P4 (Pacific Biosciences).

16S rDNA sequencing and analysis. PCR products were sequenced using the Pacific Biosciences RS instrument [Eid, 2009]. Raw base calls were transformed to consensus DNA sequences using the Pacific Biosciences Consensus Tools package and then processed with the Whole Biome Microbiome Profiling Platform to obtain phylum-genus and strain-level frequency measures for each sample.

Human volunteer study. A total of 24 male volunteers were included in a blinded, placebo-controlled, study each for a total of three weeks according to a protocol for topical AOB-001 use approved by the Allendale Institutional Review Board (Old Lyme, Connecticut). Written informed consent was obtained from each study participant. Subjects applied 15 ml of an aqueous suspension of *N. eutropha* (AOB-001), or placebo (vehicle), twice daily containing ~$10^9$ cells/ml.

Figure 5K:
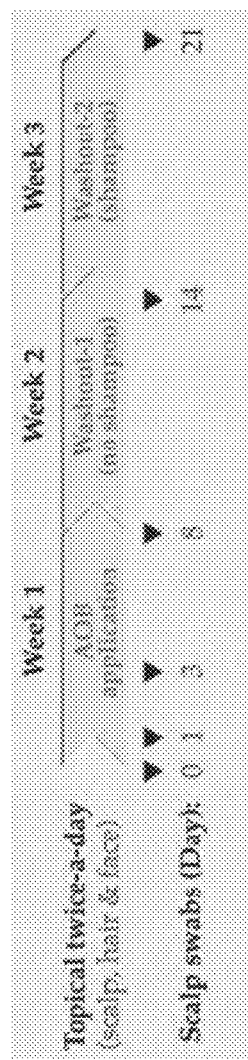
FIG. 5K shows a schematic of a human volunteer study for an evaluation of a *Nitrosomonas*-containing topical suspension (AOB-001).
Figure 5L:
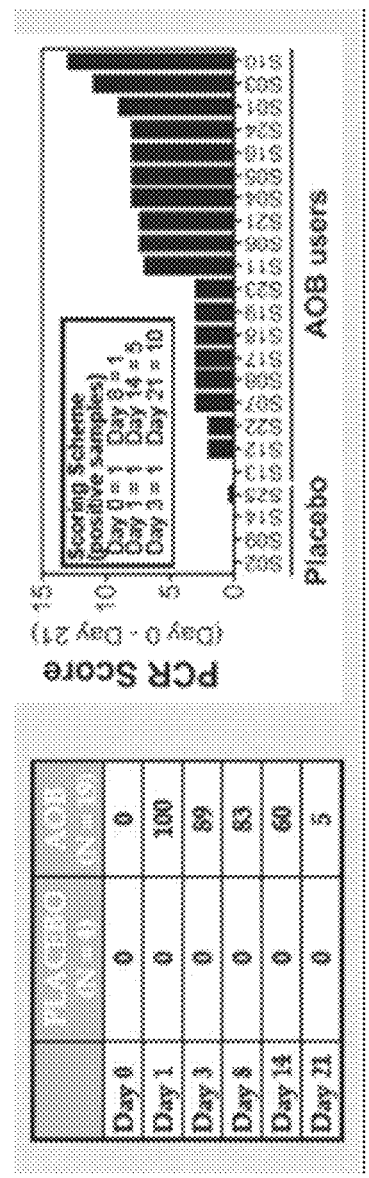
FIG. 5L (left panel) shows PCR analyses of scalp swabs collected during the study. Percent-positive samples for AOB-specific three-gene signature (amoA, amoB, amoC). The right panel shows PCR analyses of scalp swabs collected during the study. Composite PCR scores for a total of six samples collected from each of 23 volunteers. The scoring scheme used for the positive samples collected at each of six sampling points is indicated.

The human volunteer study design for the preliminary evaluation of a *Nitrosomonas*-containing topical suspension (AOB-001) is shown in FIG. 5K. Detection of AOB was performed by PCR in scalp swab samples. FIG. 5L shows PCR analyses of scalp swabs collected during the study. The left panel indicates the percent-positive samples for AOB-specific three-gene signature (amoA, amoB, amoC). The right panel indicates the Composite PCR scores for a total of six samples collected from each of 23 volunteers. The scoring scheme used for the positive samples collected at each of six sampling points is indicated.

Figure 5M:
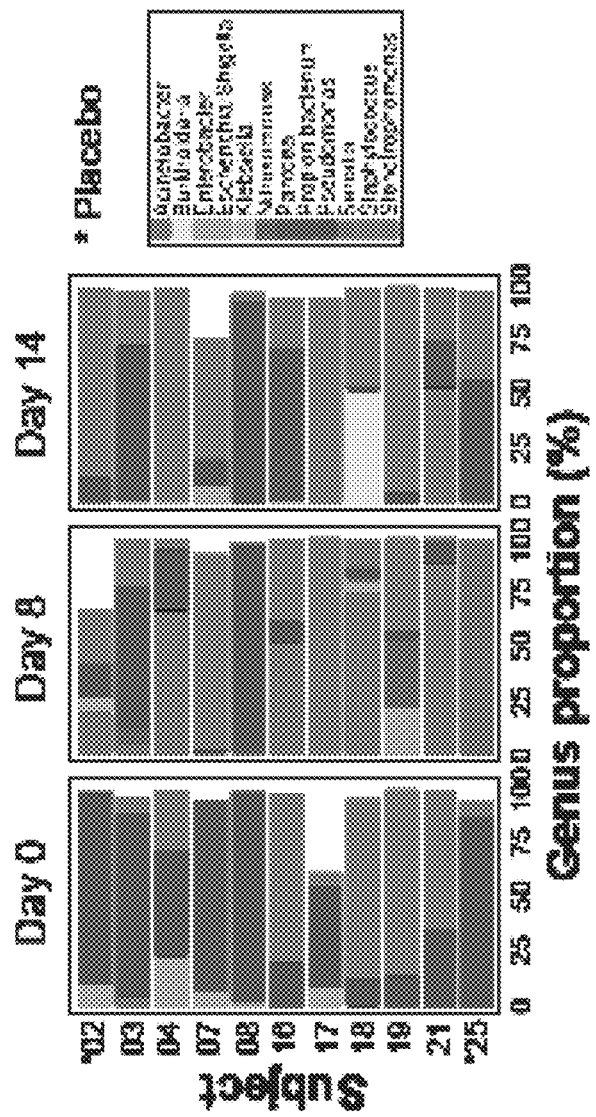
FIG. 5M shows genus-level bacterial diversity as determined by 16S rDNA sequencing in skin swab samples collected before and after topical application of AOB-001. The percentage of the total sequence reads representing each of twelve bacterial genera in samples collected at baseline prior to application (Day 0) and immediately after the one week application (Day 8), or one week after stopping topical application (Day 14), are shown. The proportions of *Acinetobacter, Burkholderia, Enterobacter, Escherichia Shigella, Klebsiella, Nitrosomonas, Pantoea, Propionibacterium, Pseudomonas, Serratia, Staphylococcus*, and *Stenotrophomonas* are shown.

Skin microbiome composition prior and during AOB-001 application were obtained by 16S rDNA sequencing. FIG. 5M indicates that genus-level bacterial diversity as determined by 16S rDNA sequencing in skin swab samples collected before and after topical application of AOB-001.

The percentage of the total sequence reads representing each of twelve bacterial genera in samples collected at baseline prior to application (Day 0) and immediately after the one week application (Day 8), or one week after stopping topical application (Day 14), are shown.

Figure 5N:
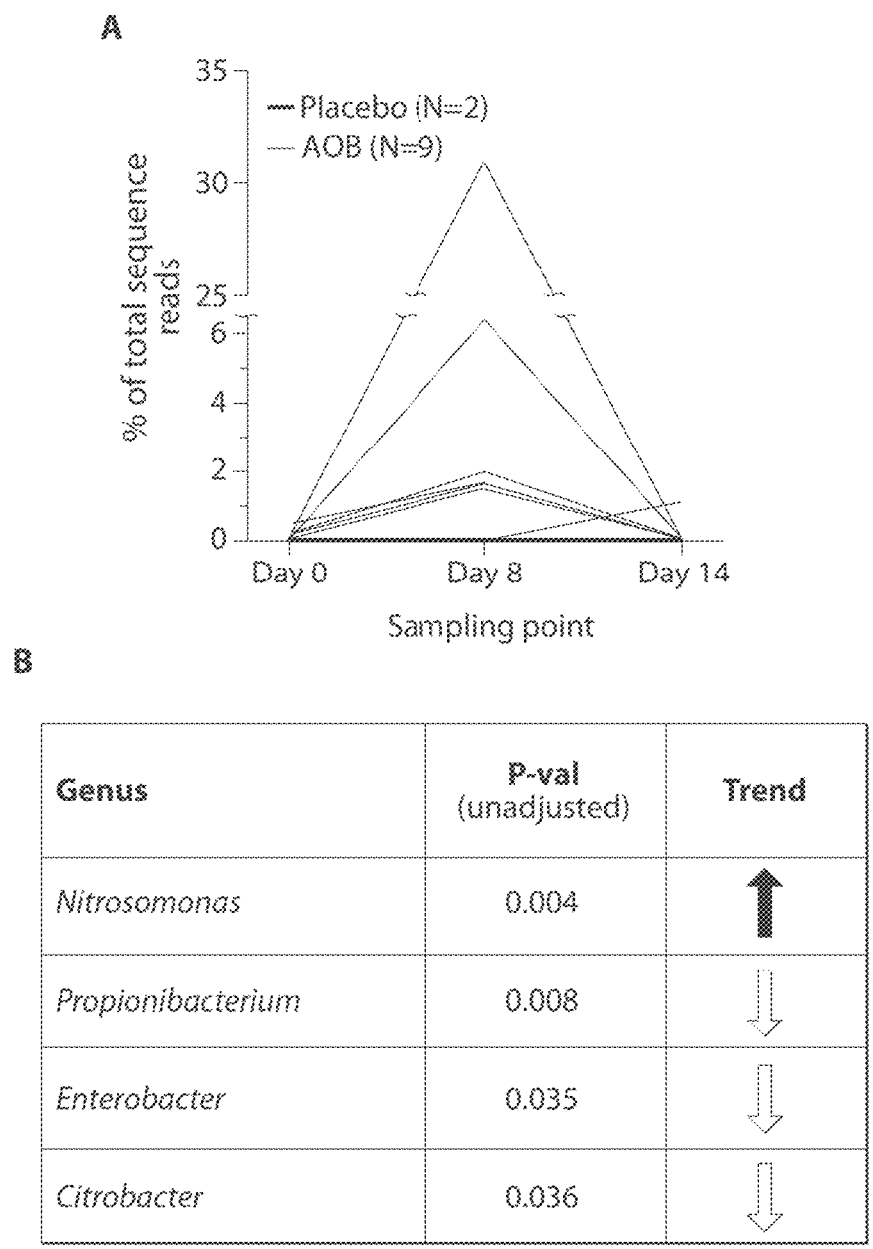
FIG. 5N shows changes in abundance of *Nitrosomonas* and other species in skin samples collected before and after AOB-001 application. The percentages of the total 16S rDNA sequence reads representing *Nitrosomonas* prior to application (Day 0), immediately after the one-week application (Day 8), or one week after terminating application (Day 14) are shown.
Figure 50:
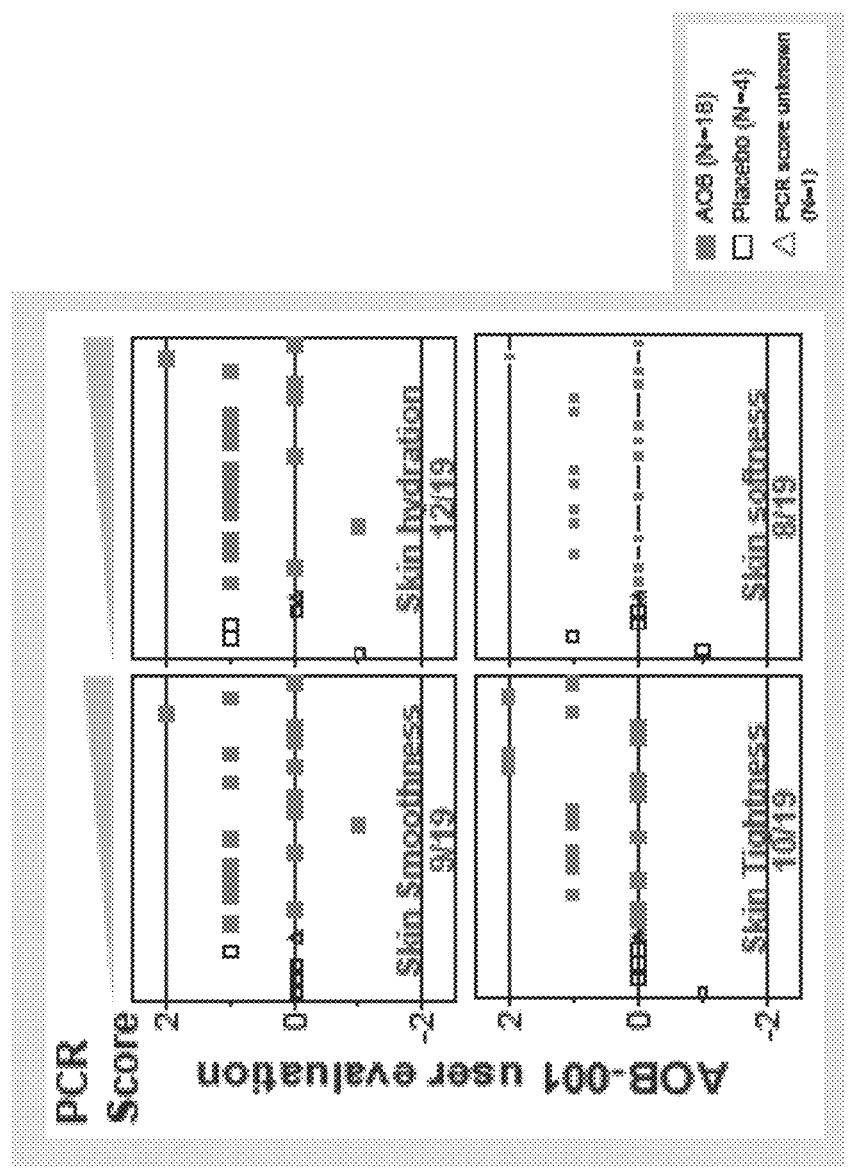

FIG. 5N indicates changes in abundance of *Nitrosomonas* and other species in skin samples collected before and after AOB-001 application. Panel A shows percentages of the total 16S rDNA sequence reads representing *Nitrosomonas* prior to application (Day 0), immediately after the one-week application (Day 8), or one week after terminating application (Day 14) are shown. Panel B shows a change in patterns in abundance of species detected by 16S rDNA sequencing in Day 0 versus Day 8 samples collected from AOB users.

AOB-001 users report an improvement in skin condition. FIG. 5O shows a user evaluation of AOB-001. Assessment of AOB-001 cosmetic effects was provided by 23 volunteers upon completion of the one week application to their scalp and face. Subjects were plotted in order of increasing composite PCR scores. (The responses were categorized as 2=agree strongly; 0=no change; −2=disagree strongly). In summary, AOB-001 is well-tolerated. The user responses in a blind study indicate improved skin/scalp condition. AOB (*Nitrosomonas*) are readily detectable in skin microbiome samples by PCR and 16S rRNA gene sequencing. Preliminary microbiome analyses indicate modulation of skin microbiota by AOB.

Lengthy table referenced here

US12091652-20240917-T00001

Please refer to the end of the specification for access instructions.

Lengthy table referenced here

US12091652-20240917-T00002

Please refer to the end of the specification for access instructions.

INCORPORATION BY REFERENCE

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

Certain embodiments are within the following claims.

LENGTHY TABLES

The patent contains a lengthy table section. A copy of the table is available in electronic form from the USPTO web site (https://seqdata.uspto.gov/?pageRequest=docDetail&DocID=US12091652B2). An electronic copy of the table will also be available from the USPTO upon request and payment of the fee set forth in 37 CFR 1.19(b)(3).

SEQUENCE LISTING

The patent contains a lengthy sequence listing. A copy of the sequence listing is available in electronic form from the USPTO web site (https://seqdata.uspto.gov/?pageRequest=docDetail&DocID=US12091652B2). An electronic copy of the sequence listing will also be available from the USPTO upon request and payment of the fee set forth in 37 CFR 1.19(b)(3).

What is claimed is:

1. A *Nitrosomonas eutropha* bacterium having American Type Culture Collection designation number PTA-121157 or having a genomic DNA comprising the nucleotide sequence of SEQ ID NO: 1 or the full-length complementary nucleotide sequence of SEQ ID NO: 1.

2. A composition comprising the *N. eutropha* bacterium of claim 1.

3. The composition of claim 2, formulated for topical administration.

4. The composition of claim 2, which is provided as or disposed in a cosmetic intended to alter a person's appearance.

5. A method of inhibiting microbial growth on a subject's skin, comprising topically administering to the subject an effective dose of the *N. eutropha* bacterium of claim 1.

6. A method of supplying nitric oxide to a subject, comprising administering an effective dose of the *N. eutropha* bacterium of claim 1 to the subject.

7. A method of reducing body odor, comprising topically administering to a subject in need thereof an effective dose of the *N. eutropha* bacteria bacterium of claim 1.

8. A method of treating a disease associated with low nitrite levels, comprising topically administering to a subject in need thereof a therapeutically effective dose of the *N. eutropha* bacterium of claim 1.

9. The method of claim 8, wherein the disease is HIV dermatitis, infection in a diabetic foot ulcer, atopic dermatitis, contact dermatitis, allergic reaction, skin infections, vascular disease, vaginal yeast infection, a sexually transmitted disease, heart disease, atherosclerosis, baldness, leg ulcers secondary to diabetes or confinement to bed, angina, chronic angina, stable angina pectoris, ischemic diseases, congestive heart failure, myocardial infarction, ischemia reperfusion injury, laminitis, hypertension, hypertrophic organ degeneration, Raynaud's phenomenon, fibrosis, fibrotic organ degeneration, allergies, autoimmune sensitization, end stage renal disease, obesity, impotence, or cancer.

10. A method of treating a skin disorder, comprising topically administering to a subject in need thereof a therapeutically effective dose of the *N. eutropha* bacterium of claim 1, wherein the skin disorder is an ulcer, venous ulcer, leg ulcer, or infection in a diabetic foot ulcer.

11. A method of promoting wound healing or closure, comprising administering to a wound an effective dose of the *N. eutropha* bacterium of claim 1.

12. A method of changing a composition of a skin microbiome of a subject comprising:

administering to the subject a therapeutically effective dose of the *N. eutropha* bacterium of claim 1.

* * * * *